US008530171B2

(12) United States Patent
Retallack et al.

(10) Patent No.: US 8,530,171 B2
(45) Date of Patent: Sep. 10, 2013

(54) HIGH LEVEL EXPRESSION OF RECOMBINANT TOXIN PROTEINS

(75) Inventors: Diane M. Retallack, Poway, CA (US); Lawrence Chew, San Diego, CA (US); Hongfan Jin, San Diego, CA (US); Henry W. Talbot, San Diego, CA (US)

(73) Assignee: Pfenex Inc., San Diego, CA (US)

( * ) Notice: Subject to any disclaimer, the term of this patent is extended or adjusted under 35 U.S.C. 154(b) by 66 days.

(21) Appl. No.: 13/073,955

(22) Filed: Mar. 28, 2011

(65) Prior Publication Data

US 2011/0287443 A1    Nov. 24, 2011

Related U.S. Application Data

(63) Continuation-in-part of application No. PCT/US2010/030573.

(60) Provisional application No. 61/325,235, filed on Apr. 16, 2010, provisional application No. 61/319,152, filed on Mar. 30, 2010.

(51) Int. Cl.
*C07K 14/195* (2006.01)
*C12P 21/00* (2006.01)
*G01N 33/53* (2006.01)

(52) U.S. Cl.
USPC ........................................................ 435/7.1

(58) Field of Classification Search
USPC .......................... 435/7.1, 69.1, 69.7; 530/350
See application file for complete search history.

(56) References Cited

U.S. PATENT DOCUMENTS

| | | | |
|---|---|---|---|
| 4,551,433 A | 11/1985 | DeBoer | |
| 4,695,455 A | 9/1987 | Barnes et al. | |
| 4,709,017 A | 11/1987 | Collier et al. | |
| 4,755,465 A | 7/1988 | Gray et al. | |
| 4,830,962 A | 5/1989 | Gelfand et al. | |
| 4,861,595 A | 8/1989 | Barnes et al. | |
| 4,892,827 A | 1/1990 | Pastan et al. | |
| 4,925,792 A | 5/1990 | Rappuoli | |
| 5,055,294 A | 10/1991 | Gilroy | |
| 5,085,862 A | 2/1992 | Klein et al. | |
| 5,128,130 A | 7/1992 | Gilroy et al. | |
| 5,169,760 A | 12/1992 | Wilcox | |
| 5,281,532 A | 1/1994 | Rammler et al. | |
| 5,389,540 A | 2/1995 | Makoff et al. | |
| 5,427,788 A | 6/1995 | Rappuoli et al. | |
| 5,443,966 A | 8/1995 | Fairweather et al. | |
| 5,571,694 A | 11/1996 | Makoff et al. | |
| 5,614,382 A | 3/1997 | Metcalf | |
| 5,773,600 A | 6/1998 | Burnette, III | |
| 5,785,971 A | 7/1998 | Rappuoli et al. | |
| 5,792,458 A | 8/1998 | Johnson et al. | |
| 5,935,580 A | 8/1999 | Ladant et al. | |
| 6,010,871 A | 1/2000 | Takahara et al. | |
| 6,043,057 A | 3/2000 | Holmgren et al. | |
| 6,140,082 A | 10/2000 | Loosmore et al. | |
| 7,169,399 B2 | 1/2007 | Roberts | |
| 7,226,597 B2 | 6/2007 | Ballard et al. | |
| 7,232,671 B2 | 6/2007 | Cieplak | |
| 7,273,728 B2 | 9/2007 | Wolfe et al. | |
| 7,427,404 B1 | 9/2008 | Pizza et al. | |
| 7,575,891 B2 | 8/2009 | Wolfe et al. | |
| 7,666,436 B1 | 2/2010 | Pizza et al. | |
| 2006/0008877 A1 | 1/2006 | Retallack et al. | |
| 2006/0040352 A1 | 2/2006 | Retallack et al. | |
| 2006/0110747 A1 | 5/2006 | Ramseier et al. | |
| 2006/0246036 A1 | 11/2006 | Francis et al. | |
| 2007/0292918 A1 | 12/2007 | Stelman et al. | |
| 2008/0193974 A1 | 8/2008 | Coleman et al. | |
| 2008/0269070 A1 | 10/2008 | Ramseier et al. | |
| 2009/0081184 A1 | 3/2009 | Margolin et al. | |
| 2009/0325230 A1 | 12/2009 | Schneider et al. | |
| 2010/0048864 A1 | 2/2010 | Coleman et al. | |
| 2010/0137162 A1 | 6/2010 | Retallack | |

FOREIGN PATENT DOCUMENTS

| | | |
|---|---|---|
| WO | WO-90-009444 | 8/1990 |
| WO | WO-2005-000346 A1 | 1/2005 |
| WO | WO-2005-056773 A1 | 6/2005 |
| WO | WO-2006-014899 | 2/2006 |
| WO | WO-2010-008764 | 1/2010 |

OTHER PUBLICATIONS

Allured et al., "Structure of exotoxin a of Pseudomonas aeruginosa at 3.0-Angrstom resolution," PNAS USA 83:1320-1324 (1986).
Anderson et al., "Safety and Immunogenicity of Meningococcal A and C Polysaccharide Conjugate Vaccine in Adults," Infection and Immunity 62(8):3391-3395 (1994).
Barth et al., "Binary Bacterial Toxins: Biochemistry, Biology, and Applications of Common Clostridium and Bacillus Proteins," Microbiol Mol Biol Rev 68(3):373-402 (2004).
Bergey'S Manual of Determinative Bacteriology, R.E. Buchanan and n. E. Gibbons eds., pp. 217-289, 8th ed., The Williams & Wilkins Co., Baltimore, MD, 1974.
Bishai et al., "High-Level Expression of a Proteolytically Sensitive Diphtheria Toxin Fragment in *Escherichia coli*," J Bacteriology 169(11):5140-5151 (1987).
Burnette et al., "Properties of Pertussis Toxin B Oligomer Assembled in Vitro from Recombinant Polypeptides Produced by *Escherichia coli*," Infection and Immunity 60(6):2252-2256 (1992).
Carbonetti et al., "Proteolytic cleavage of pertussis toxin Si subunit is not essential for its activity in mammalian cells," BMC Microbiology 5:7 (2005).
Collier, "Diphtheria Toxin: Mode of Action and Structure," Bacteriological Reviews 39(1):54-85 (1975).
Cryz et al., Isolation and characterization of a Pseudomonas aeruginos a mutant producing a nontoxic, immunologically crossactive toxin a protein, PNAS 77 (12):7199-7203 (1980).

(Continued)

*Primary Examiner* — Chih-Min Kam
(74) *Attorney, Agent, or Firm* — Wilson, Sonsini, Goodrich & Rosati

(57) ABSTRACT

The present invention relates to the field of recombinant toxin protein production in bacterial hosts. In particular, the present invention relates to production processes for obtaining high levels of a recombinant CRM197, Diphtheria Toxin, Pertussis Toxin, Tetanus Toxoid Fragment C, Cholera Toxin B, Cholera holotoxin, and *Pseudomonas* Exotoxin A, from a bacterial host.

36 Claims, 59 Drawing Sheets

(56) References Cited

OTHER PUBLICATIONS

Davis and Mingioli, "Mutants of *Escherichia coli* requiring methionine or Vitamin B12," Bact 60:17-28 (1950).
Eisel et al., "Tetanus toxin: primary structure, expression in *E. coli*, and homology with botulinum toxins," EMBO J 5(10):2495-2502 (1986).
Ellingsworth, "Pseudomonas fluorescens: Expression System for Producing Recombinant Vaccines and Adjuvants," (2006).
Fairweather and Lyness, "The complete nucleotide sequence of tetanus toxin," Nucl Acids Res 14(19):7809-781 2 (1986).
Fattom et al., "Laboratory and Clinical Evaluation of Conjugate Vaccines Composed of Staphylococcus aureus Type 5 and Type 8 Capsular Polysaccharides Bound to Pseudomonas aeruginosa Recombinant Exoprotein A," Infection and Immunity 61(3):1023-1032 (1993).
Frishman et al., "Starts of Bacterial Genes: Estimating the Reliability of Computer Predictions," Gene 234(20):257-265 (1999).
Giannini et al., "The amino acid sequence of two non-toxic mutants of diphtheria toxin: CRM45 and CRM 197," Nucl Acids Res 12(10):4063-4069 (1984).
Greenfield et al., "Nucleotide sequence of the structural gene for diphtheria toxin carried by corynebacteriophage β," PNAS USA 80:6853-6857 (1983).
Gurkin and Ellar, "Recombinant production of bacterial toxins and their derivatives in the methylotrophic yeast Pichia pastoris," Microbial Cell Factories 4:33 (2005).
Haemophilus b Conjugate Vaccine (Diphtheria $CRM_{197}$ Protein Conjugate (HibTiter) Package Insert, 17 pages dated Jan. 2007.
Harakuni et al., "Heteropentameric Cholera Toxin B Subunit Chimeric Molecules Genetically Fused to a Vaccine Antigen Induce Systemic and Mucosal Immune Responses: a Potential New Strategy to Target Recombinant Vaccine Antigens to Mucosal Immune Systems," Infection and Immunity 73(9): 5654-5665 (2005).
Ikehata et al., "Primary structure of nitrile hydratase deduced from the nucleotide sequence of a Rhodococcus species and its expression in *Escherichia coli*," Eur J Biochem 181(3):563-570 (1989).
Jank and Aktories, "Structure and mode of action of clostridial glucosylating toxins: The ABCD model," Trends in Microbiol. 16(5):222-229 (2008).
Kaslow et al., "Structure-Activity Analysis of the Activation of Pertussis Toxin," Biochem 26(1):123-127 (1987).
Kulic et al., "Expression of Recombinant Exoenzyme S of Pseudomonas aeruginosa," Infection and Immunity 63(1): 1-8 (1995).
Lee et al., "Characterization of a Cloned Temperature-Sensitive Construct of the Diphtheria Toxin A Domain," Biochem 44(7):2555-2565 (2005) (Abstract).
Lin et al., "The Efficacy of a Salmonella Typhi Vi Conjugate Vaccine in Two-to-Five Year-Old Children," New England J Med 344(17):1263-1269 (2001).
Lukac et al., "Toxoid of Pseudomonas aeruginosa Exotoxin A Generated by Deletion of an Active-Site Residue," Infection and Immunity 56(12):3095-3098 (1988).
Maunsell et al., "Complex regulation of AprA metalloprotease in Pseudomonas fluorescens M114: evidence for the involvement of iron, the ECF sigma factor, PbrA and pseudobactin M114 siderophore," Microbiol 152(Pt 1):29-42 (2006).
Mccoy et al., "PAR1 and PAR2 couple to overlapping and distinct sets of G proteins and linked signaling pathways to differentially regulate cell physiology," Molecular Pharmacology Fast Forward. Published on Mar. 9, 2010 as doi:10.1124/mo1.109.062018.
Mekada and Uchida, "Binding Properties of Diphtheria Toxin to Cells Are Altered by Mutation in the Fragment a Domain," J Biol Chem 260(22):12148-12153 (1985).
MenACWY-CRM Clinical Trial and Product Overview, Novartis Vaccines 24 Jun. 2009—ACIP Meeting Atlanta.
Menveo product insert Feb. 2010.
Miyaji et al., "Induction of Neutralizing Antibodies against Diphtheria Toxin by Priming with Recombinant Mycobacterium bovis BCG Expressing $CRM_{197}$, a Mutant Diphtheria Toxin," Infection and Immunity 69(2):869-874 (2001).
Mueller-Dieckmann et al., "Structure of mouse ADP-ribosylhydrolase 3 (mARH3)," Acta Cryst F64:156-162 (2008).
Nozoye et al., "Production of Ascaris suum As14 Protein and Its Fusion Protein with Cholera Toxin B Subunit in Rice Seeds," J. Vet. Med. Sci. 71(7):995-1000 (2009).
Orr et al., "Expression and Immunogenicity of a Mutant Diphtheria Toxin Molecule, CRM197, and Its Fragments in Salmonella typhi Vaccine Strain CVD 908-htrA," Infection and Immunity 67(8):4290-4294 (1999).
Pneumococcal 7-valent Conjugate Vaccine (Diphtheria CRM197 Protein) Prevnar Package Insert Wyeth Pharmaceuticals Inc. dated Oct. 2008.
Popoff et al., "Actin-Specific ADP-Ribosyltransferase Produced by a Clostridium difficule Strain," Infection and Immunity 56(9):2299-2306 (1988).
PCT/US10/30573 Search Report and Written Opinion mailed May 27, 2011.
Price et al., "Intranasal Administration of Recombinant Neisseria gonorrhoeae Transferrin Binding Proteins A and B Conjugated to the Cholera Toxin B Subunit Induces Systemic and Vaginal Antibodies in Mice," Infection and Immunity 73(7):3945-3953 (2005).
Qian et al., "Conugating recombinant proteins to Pseudomonas aeruginosa ExoProtein A: a strategy for enhancing immunogenicity of malaria vaccine candidates," Vaccine 25(20):3923-3933 (2007).
Riesenberg et al., "High cell density cultivation of *Escherichia coli* at controlled specific growth rate," J Biotechnol 20(1):17-27 (1991).
Rhodighiero et al., "A Cholera Toxin B-subunit Variant That Binds Ganglioside $G_{M1}$ but Fails to Induce Toxicity," J Biol Chem 276(40):36939-36945 (2001).
Roberts et al., "A Mutant Pertussis Toxin Molecule That Lacks ADP-Ribosyltransferase Activity, PT-9K/129G, is an Effective Mucosal Adjuvant for Intranasally Delivered Proteins," Infection and Immunity 63(6):2100-2108 (1995).
Sakurai et al., Clostridium perfringens Iota-Toxin: Structure and Function, Toxins 1:208-228 (2009).
Sanchez-Romero and V. De Lorenzo, Manual of Industrial Microbiology and Biotechnology, . Demain & J. Davies, eds., pp. 460-474, 1999.
Schweizer, "Vectors to express foreign genes and techniques to monitor gene expression in Pseudomondas," Curr Op Biotech 12:439-445 (2001).
Sekura et al., "Pertussis Toxin. Affinity Purification of a New Adp-Ribosyltransferase," J Biol Chem 258:14647 (1983).
Schirmer et al., "The Adp-ribosylating Mosquitocidal Toxin from Bacillus sphaericus," J Biol Chem 277(14):11941-11948 (2002).
Schmidt and Schmidt, "Inhibition of Pertussis Toxin Binding to Model Receptors by Antipeptide Antibodies Directed at an Antigenic Domain of the S2 Subunit," Infection and Immunity 57(12):3828-3833 (1989).
R. Slater & R. Williams, Molecular Biology and Biotechnology, J. Walker & R. Rapley, eds., pp. 125-154 , the Royal Society of Chemistry, Cambridge, UK, 2000.
Stickings et al., "Transcutaneous Immunization with Cross-Reacting Material $CRM_{197}$ of Diphtheria Toxin Boosts Functional Antibody Levels in Mice Primed Parenterally with Adsorbed Diphtheria Toxoid Vaccine," Infection and Immunity 76(4):1766-1773 (2008).
Su et al., "Pertussis Toxin Inhibits Induction of Tissue-Specific Autoimmune Disease by Disrupting g Protein-Coupled Signals," J Immunol 167:250-256 (2001).
Sullivan et al., "Purification and Characterization of Toxins A and B of Clostridium difficule," Infection and Immunity 35(3):1032-1040 (1982).
Sun et al., "Intransal Administration of a Schistosoma mansoni Glutathione S-Transferase-Cholera Toxoid Conjugate Vaccine Evokes Antiparasitic and Antipathological Immunity in Mice," J Immunol 163:1045-1052 (1999).
Townsend et al., "Tetanus toxin C fragment conjugated nanoparticles for targeted drug delivery to neurons," Biomaterials 28(34):5176-5184 (2007).
Tsuge et al., "Structural basis of actin recognition and arginine Adp-ribosylation by Clostridium perfringens ι— toxin," PNAS 105(21):7399-7404 (2008).

Watkins et al., "Pertussis Toxin Treatment in Vivo is Associated with a Decline in G-protein β-Subunits," J Biol Chem 264(7):4186-4194 (1989).

Yang et al., "Expression of recombinant Clostridium difficile toxin A and B in Bacillus megaterium," Bmc Microbiol 8:192 (2008).

PCT/US2011/030227 International Search Report and Written Opinion dated Dec. 22, 2011.
Schneider et al., Auxotropic markers pyrF and proC can replace antibiotic markers on protein production plasmids in hig-cell-density Pseudomonas fluorescens fermentation. Biotechnol. Progress 21(2) (2005): 343-8.
Schweizer, Herbert P., Vectors to Express Foreign Genes and Techniques to Monitor Gene Expression in Pseudornmads, Current Opinion in Biotechnology, 2001, pp. 439-445, vol. 12, Elsevier Science Ltd.
Suzek, Baris E., et al., "A Probalistic Method for Identifying Start Codons in Bacterial Genomes." Bioinformatics, 2001, pp. 1123-1130, vol. 17, No. 12, Oxford University Press.

A. CRM197 amino acid sequence

```
  1 Gly Ala Asp Asp Val Val Asp Ser Ser Lys Ser Phe Val Met Glu Asn Phe Ser Ser Tyr
 21 His Gly Thr Lys Pro Gly Tyr Val Asp Ser Ile Gln Lys Gly Ile Gln Lys Pro Lys Ser
 41 Gly Thr Gln Gly Asn Tyr Asp Asp Asp Trp Lys Glu Phe Tyr Ser Thr Asp Asn Lys Tyr
 61 Asp Ala Ala Gly Tyr Ser Val Asp Asn Glu Asn Pro Leu Ser Gly Lys Ala Gly Gly Val
 81 Val Lys Val Thr Tyr Pro Gly Leu Thr Lys Val Leu Ala Leu Lys Val Asp Asn Ala Glu
101 Thr Ile Lys Lys Glu Leu Gly Leu Ser Leu Thr Glu Pro Leu Met Glu Gln Val Gly Thr
121 Glu Glu Phe Ile Lys Arg Phe Gly Asp Gly Ala Ser Arg Val Val Leu Ser Leu Pro Phe
141 Ala Glu Gly Ser Ser Ser Val Glu Tyr Ile Asn Asn Trp Glu Gln Ala Lys Ala Leu Ser
161 Val Glu Leu Glu Ile Asn Phe Glu Thr Arg Gly Lys Arg Gly Gln Asp Ala Met Tyr Glu
181 Tyr Met Ala Gln Ala Cys Ala Gly Asn Arg Val Arg Arg Ser Val Gly Ser Ser Leu Ser
201 Cys Ile Asn Leu Asp Trp Asp Val Ile Arg Asp Lys Thr Lys Thr Lys Ile Glu Ser Leu
221 Lys Glu His Gly Pro Ile Lys Asn Lys Met Ser Glu Ser Pro Asn Lys Thr Val Ser Glu
241 Glu Lys Ala Lys Gln Tyr Leu Glu Glu Phe His Gln Thr Ala Leu Glu His Pro Glu Leu
261 Ser Glu Leu Lys Thr Val Thr Gly Thr Asn Pro Val Phe Ala Gly Ala Asn Tyr Ala Ala
281 Trp Ala Val Asn Val Ala Gln Val Ile Asp Ser Glu Thr Ala Asp Asn Leu Glu Lys Thr
301 Thr Ala Ala Leu Ser Ile Leu Pro Gly Ile Gly Ser Val Met Gly Ile Ala Asp Gly Ala
321 Val His His Asn Thr Glu Glu Ile Val Ala Gln Ser Ile Ala Leu Ser Ser Leu Met Val
341 Ala Gln Ala Ile Pro Leu Val Gly Glu Leu Val Asp Ile Gly Phe Ala Ala Tyr Asn Phe
361 Val Glu Ser Ile Ile Asn Leu Phe Gln Val Val His Asn Ser Tyr Asn Arg Pro Ala Tyr
381 Ser Pro Gly His Lys Thr Gln Pro Phe Leu His Asp Gly Tyr Ala Val Ser Trp Asn Thr
401 Val Glu Asp Ser Ile Ile Arg Thr Gly Phe Gln Gly Glu Ser Gly His Asp Ile Lys Ile
421 Thr Ala Glu Asn Thr Pro Leu Pro Ile Ala Gly Val Leu Leu Pro Thr Ile Pro Gly Lys
441 Leu Asp Val Asn Lys Ser Lys Thr His Ile Ser Val Asn Gly Arg Lys Ile Arg Met Arg
461 Cys Arg Ala Ile Asp Gly Asp Val Thr Phe Cys Arg Pro Lys Ser Pro Val Tyr Val Gly
481 Asn Gly Val His Ala Asn Leu His Val Ala Phe His Arg Ser Ser Ser Glu Lys Ile His
501 Ser Asn Glu Ile Ser Ser Asp Ser Ile Gly Val Leu Gly Tyr Gln Lys Thr Val Asp His
521 Thr Lys Val Asn Ser Lys Leu Ser Leu Phe Phe Glu Ile Lys Ser
```

FIGURE 1

B. CRM197 DNA sequence with translation

| | | | | | | | | | | | | | | | | | | | | |
|---|---|---|---|---|---|---|---|---|---|---|---|---|---|---|---|---|---|---|---|---|
| 1 | Gly GGG | Ala GCG | Asp GAC | Asp GAT | Val GTG | Val GTG | Asp GAT | Ser TCC | Ser AAG | Lys TCG | Ser ATG | Phe TTT | Val GTC | Met GAA | Glu AAT | Asn TTC | Phe TCG | Ser TAC | Tyr | |
| 61 | His CAT | Gly GGC | Thr ACT | Lys AAG | Pro CCA | Gly GGC | Tyr TAC | Val GTG | Asp GAT | Ser AGC | Ile ATT | Gln CAA | Lys AAA | Gly GGC | Ile ATC | Gln CAG | Lys AAG | Pro CCC | Lys AAG | Ser AGC |
| 121 | Gly GGT | Thr ACT | Gln CAG | Asn GGG | Gly AAC | Tyr TAT | Asp GAC | Asp GAC | Trp TGG | Lys AAG | Glu GAC | Phe TTT | Tyr TAC | Ser AGC | Thr ACC | Asp ACC | Asn AAT | Lys AAG | Tyr TAC | |
| 181 | Asp GAT | Ala GCT | Ala GCC | Gly GGC | Tyr TAT | Ser AGC | Val GTG | Asp GAC | Asn AAC | Glu GAA | Asn AAC | Pro CCA | Leu TTG | Ser TCG | Gly AAG | Ala GCC | Gly GGT | Gly GGC | Val GTG | |
| 241 | Val GTG | Lys AAG | Val GTG | Thr ACC | Tyr TAT | Pro CCT | Gly GGT | Leu CTG | Ser CTG | Thr ACG | Lys AAA | Val GTT | Leu CTG | Ala GCG | Leu TTG | Lys AAA | Val GAC | Asp GAC | Ala GCC | Glu GAG |
| 301 | Thr ACT | Ile ATC | Lys AAG | Lys AAA | Phe GAA | Ile ATT | Ser AGT | Leu GGC | Leu TTG | Gly AGT | Ser ACC | Thr TTG | Glu GAG | Pro ATG | Leu CAG | Met GTG | Gln GGT | Val ACC | Gly | Thr |
| 361 | Glu GAA | Glu GAA | Phe TTC | Lys AAA | Arg CGT | Phe TTT | Gly GGG | Ala GAC | Ser GGC | Ser TCG | Val GTC | Glu GTC | Tyr GAA | Ile ATC | Asn AAC | Trp TGG | Arg CGG | Arg CGG | Arg CGC | Leu CCG Pro | Phe TTC |
| 421 | Ala GCC | Glu GAA | Gly GGG | Ser TCG | Ser TCG | Val TCG | Glu GTG | Tyr GAA | Ile ATC | Asn AAC | Asn AAC | Arg CGG | Gly GGC | Lys AAA | Val GTG | Arg CGG | Ala GCC | Met ATG | Leu TAC | Ser TCG |
| 481 | Val GTG | Glu GAA | Leu CTG | Gln GAA | Ile ATT | Asn AAC | Phe TTC | Glu GAA | Thr ACG | Arg CGG | Gly GGC | Lys AAA | Gly GGC | Gln CAG | Ala GCC | Ser AGT | Ser TCC | Leu TTG | Ser AGT | |
| 541 | Tyr TAC | Met ATG | Ala GCC | Gln CAG | Ala GCA | Cys TGC | Ala GCC | Gly GGG | Asn AAC | Arg CGG | Val GTG | Arg CGG | Arg CGC | Ser AGC | Lys AAG | Thr ACG | Val GTG | Ile ATC | Glu GAG | Leu CTC |
| 601 | Cys TGC | Ile ATC | Asn AAT | Leu CTG | Asp GAC | Trp TGG | Val GAC | Val GTC | Ile ATC | Arg CGC | Asp GAT | Arg CGC | Lys AAG | Thr ACG | Lys AAG | Pro CCG | Asn AAT | Lys AAA | Ser TCC | Leu TCG Glu |
| 661 | Lys AAA | Glu GAG | His CAC | Gly GGC | Pro CCG | Ile ATC | Lys AAA | Asn AAC | Lys AAA | Met

```
 961  Val His His Asn Thr Glu Glu Ile Val Ala Gln Ser Ile Ala Leu Ser Ser Leu Met Val
      GTG CAT CAC AAC ACC GAA GAG ATC GTC GCG CAG TCG ATC GCA TTG TCC TCC CTG ATG GTC

1021  Ala Gln Ala Ile Pro Leu Val Gly Glu Val Asp Val Leu Phe Gly Ile Phe Ala Tyr Asn Phe
      GCC CAA GCT ATC CCG CTG GTC GGC GAG GTC GAT ATC GGC TTT GCC GCT TAT AAC TTT

1081  Val Glu Ser Ile Ile Asn Leu Phe Gln Val His Val Ser Tyr Asn Ser Arg Pro Ala Tyr
      GTT GAA TCG ATC ATT AAC CTG TTC CAG GTG CAT GTG TAC AAC AGC CGG CCA GCG TAC

1141  Ser Pro Gly His Lys Thr Gln Pro Phe Leu His Asp Gly Tyr Ala Val Ser Trp Asn Thr
      TCG CCC GGT CAC AAG ACC CAG CCC TTT CTC CAC GAC GGC TAT GCC GTG TCG AAC ACC

1201  Val Glu Asp Ser Ile Ile Arg Thr Gly Phe Gln Gly Glu Gly Ser Gly His Asp Ile Lys Ile
      GTG GAG GAC AGC ATC ATC CGC ACC GGT TTC CAG GAG GGC AGC GGC CAT GAC ATC AAA ATT

1261  Thr Ala Glu Asn Thr Pro Leu Pro Ile Ala Gly Val Leu Leu Pro Thr Ile Pro Gly Lys
      ACC GCG GAA AAC ACG CCG CTG CCG ATC GCT GGC GTG CTC CCG ACG ATC CCG GGT AAG

1321  Leu Asp Val Ser Lys Ser Ile Thr His Ile Ser Val Asn Gly Arg Lys Ile Arg Met Arg
      CTC GAC GTC AAG AGC TCC ATC ACC CAT ATC AGC GTC AAT GGC CGC AAG ATC CGC ATG CGC

1381  Cys Arg Ala Ile Asp Gly Asp Val Thr Phe Pro Cys Arg Pro Lys Ser Pro Val Tyr Val Gly
      TGT CGG GCC ATT GAT GGC GAC GTC ACG TTT TGC CGG CCG AAG AGT CCC GTC TAT GTC GGG

1441  Asn Gly Val His Ala Asn Leu His Val Ala Phe His Arg Ser Ser Glu Lys Ile His
      AAC GGT GTC CAT GCC AAC CTG CAC GTC GCA TTC CAC CGG AGC TCG GAA AAG ATC CAC

1501  Ser Asn Glu Ile Ser Ser Asp Ser Ile Gly Tyr Leu Val Gly Tyr Gln Lys Thr Val Asp His
      AGC AAT GAG ATC AGC AGC GAC AGC ATC GGC CTG GGG TAT CAA AAG ACG GTC GAT CAC

1561  Thr Lys Val Asn Ser Lys Leu Ser Leu Phe Phe Glu Ile Lys Ser
      ACC AAG GTG AAC AGT AAA CTG AGC TTG TTC TTT GAA ATC AAG TCG
```

FIGURE 1-3

A. Cholera Toxin B Subunit amino acid sequence

```
  1 Thr Pro Gln Asn Ile Thr Asp Leu Cys Ala Glu Tyr His Asn Thr Gln Ile His Thr Leu
 21 Asn Asp Lys Ile Phe Ser Tyr Thr Glu Leu Ala Gly Lys Arg Glu Met Ala Ile Ile
 41 Thr Phe Lys Asn Gly Ala Thr Phe Gln Val Glu Val Pro Gly Ser Gln His Ile Asp Ser
 61 Gln Lys Lys Ala Ile Glu Arg Met Lys Asp Thr Leu Arg Ile Ala Tyr Leu Thr Glu Ala
 81 Lys Val Glu Lys Leu Cys Val Trp Asn Asn Lys Thr Pro His Ala Ile Ala Ala Ile Ser
101 Met Ala
```

B. Cholera Toxin B Subunit DNA sequence with translation

```
      Thr Pro Gln Asn Ile Thr Asp Leu Cys Ala Glu Tyr His Asn Thr Gln Ile His Thr Leu
  1 ACG CCG CAA AAT ATC ACC GAC CTG TGC GCA GAA TAT CAC AAT ACC CAA ATC CAT ACT CTG
      Asn Asp Lys Ile Phe Ser Tyr Thr Glu Leu Ala Gly Lys Arg Glu Met Ala Ile Ile
 61 AAC GAC AAA ATC TTC AGC TAC ACC GAG CTG GCT GGC AAG CGC GAG ATG GCG ATC ATT
      Thr Phe Lys Asn Gly Ala Thr Phe Gln Val Glu Val Pro Gly Ser Gln His Ile Asp Ser
121 ACG TTC AAA AAC GGT GCG ACC TTT CAG GTG GAA GTC CCC GGC AGT CAG CAC ATC GAT TCC
      Gln Lys Lys Ala Ile Glu Arg Met Lys Asp Thr Leu Arg Ile Ala Tyr Leu Thr Glu Ala
181 CAG AAA AAG GCC ATT GAA CGG ATG AAG GAC ACC CTC CGT ATC GCC TAC TTG ACC GAA GCC
      Lys Val Glu Lys Leu Cys Val Trp Asn Asn Lys Thr Pro His Ala Ile Ala Ala Ile Ser
241 AAG GTG GAG AAG CTG TGC GTT TGG AAC AAC AAA ACC CCG CAC GCC ATC GCG GCC ATC TCG
      Met Ala
301 ATG GCC
```

FIGURE 3

```
                              signal sequence
                         ┌────────────────────────────────────────────────────────────┐
  1  Met Arg Cys Thr Arg Ala Ile Arg Gln Thr Ala Arg Gly Trp Leu Thr Trp Leu Ala
     ATG CGT TGC ACT CGG GCA ATT CGG CAA ACC GCA AGA ACA GGC TGG CTG ACG TGG CTG GCG
                                                   signal sequence
                                                   ─────────── S1
 61  Ile Leu Ala Val Thr Ala Pro Val Thr Ala Pro Ala Trp Ala Asp Asp Pro Pro Ala Thr
     ATT CTT GCC GTC ACG GCG CCC GTG ACT TCG GCA CCG GAT CCT CCC GCC ACC
                                                               S1
121  Val Tyr Lys Tyr Asp Ser Arg Pro Pro Glu Asp Val Phe Gln Asn Gly Phe Thr Ala Trp
     GTA TAC AAA TAT GAC TCC CGC CCG CCG GAG GAC GTT TTC CAG AAC GGA TTC ACG GCG TGG
                                                               S1
181  Gly Asn Asn Asp Asn Val Leu Asp His Leu Thr Gly Arg Ser Gln Val Cys Gly Ser Ser
     GGA AAC AAC GAC AAT GTC CTC CTC ACC CAT CTG ACC GGA CGT TCC CAG GTC TGC GGC AGC
                                                               S1
241  Asn Ser Ala Phe Val Ser Thr Ser Ser Thr Glu Arg Arg Tyr Thr Leu Val Tyr Leu Glu His
     AAC AGC GCT TTC GTC TCC ACC AGC AGC ACC GAA CGC AGG TAT ACC GTC TAT CTC GAA CAT
                                                               S1
301  Arg Met Gln Glu Val Glu Ala Val Glu Ala Arg Ala Gly Ala Gly Thr Gly His Phe Ile Gly
     CGC ATG CAG GAA GCG GTC GAG GCC GAA CGC GCC GGC AGG GGC ACC GGC CAC TTC ATC GGC
                                                               S1
361  Tyr Ile Tyr Glu Val Arg Ala Asp Asn Phe Tyr Gly Ala Ser Ser Tyr Phe Glu
     TAC ATC TAC GAA GTC CGC GCC GAC AAT TTC TAC GGC GCC AGC TCG TAC TTC GAA
                                                               S1
421  Tyr Val Asp Thr Tyr Gly Val Asp Asn Ala Gly Arg Ile Leu Ala Gly Ala Leu Ala Thr Tyr
     TAC GTC GAC ACT TAT GGC GAC AAT GCC GGT ATC CTC GCC GCG CTG GCC ACC TAC
                                                               S1
481  Gln Ser Ala Tyr Leu Ala His Arg Glu Pro Pro Glu Asn Ile Arg Arg Val Thr Arg
     CAG AGC GCA TAT CTG GCA CAC CGG ATT CCG GAA AAC ATC CGC AGG GTA ACG CGG
                                                               S1
541  Val Tyr His Asn Gly Ile Thr Gly Ile Glu Thr Thr Thr Glu Tyr Ser Asn Ala Arg Tyr
     GTC TAT CAC AAC GGC ATC ACC GGC ATC GAG ACC ACG ACC GAG TAT TCC AAC GCT CGC TAC
```

FIGURE 6-1

```
                    S1
     Val Ser Gln Thr Arg Ala Asn Pro Tyr Thr Ser Arg Ser Val Ala Ser
601  GTC AGC CAG ACT CGC GCC AAT CCC TAC ACA TCG CGA AGG TCC GTA GCG TCG
                            S1
     Ile Val Gly Thr Leu Val Arg Met Ala Pro Val Ile Gly Ala Cys Met Ala Arg Gln Ala
661  ATC GTC GGC ACA TTG GTG CGC ATG GCG CCG GTG ATA GGC GCT TGC ATG GCG CGG CAG GCC

Glu Ser Glu Met Ala Ala Trp Ser Glu Arg Ala Gly Glu Ala Met Val Leu Val
721  GAA AGC GAG ATG GCA GCC TGG TCC GAA CGC GCC GGC GAG GCC ATG GTG CTC GTG
                S1
     Tyr Tyr Glu Ser Ile Ala Tyr Ser Phe
781  TAC TAC GAA AGC ATC GCG TAT TCG TTC TAG ACC TGG CCC AGC CCC CAA CTC CGG TAA
                                        signal sequence
                                                                        S2
     Met Pro Ile Asp Arg Lys Thr Leu Cys His Leu Leu Ser Val Leu Pro Leu
841  TTG AAC ACC ATG CCG ATC GAC CGC AAG ACG CTC TGC CAT CTC TCC GTT CTG CCG TTG
                    signal sequence
                                                                    S2
     Ala Leu Leu Gly Ser His Val Ala Arg Ala Ser Thr Pro Gly Ile Val Ile Pro Pro Gln
901  GCC CTG CTC GGA TCT CAC GTG GCG CGG GCC TCC ACG ATC GGC ATT GTC ATT CCG CCG CAG
                                                                        S2
     Glu Gln Ile Thr Gln His Gly Ile Ser Pro Tyr Gly Arg Cys Ala Asn Lys Thr Arg Ala Leu
961  GAA CAG ATT ACC CAG CAT CAG GGC AGC GGC TAT GGA CGC TGC GCG AAC AAG ACC CGT GCC CTG
                                                                        S2
     Thr Val Ala Glu Leu Arg Gly Ser Gly Asp Tyr Leu Gln Gln Tyr Leu Arg His Val Thr Arg
1021 ACC GTG GCG GAA TTG CGC GGC AGC GGC GAT CTG CAG GAG TAC CTC CGT CAT CTG ACG CGC
                                                                        S2
     Gly Trp Ser Ile Phe Ala Leu Tyr Asp Gly Thr Leu Gly Gly Tyr Glu Tyr Gly Gly Val
1081 GGC TGG TCA ATA TTT GCG CTC TAC GAT GGC ACC TAT CTC GGC GGA TAT GGC GGC GTG
                                                                        S2
     Ile Lys Asp Gly Thr Gly Pro Gly Ala Phe Asp Leu Lys Thr Phe Cys Ile Met Thr
1141 ATC AAG GAC GGA ACA CCC GGC GCA TTC GAC CTG AAA ACG TTC TGC ATC ATG ACC
                                                                        S2
     Thr Arg Asn Thr Gly Gln Pro Ala Thr Asp His Tyr Tyr Ser Asn Val Thr Ala Thr Arg
1201 ACG CGC AAT ACG GGT CAA CCC GCA GAT CAC TAC AGC AAC GTC ACC GCC ACT CGC
```

FIGURE 6-2

```
              Leu Ser Ser Thr Asn Ser Arg Leu Cys Ala Val Phe Val Arg Ser Gly Gln Pro Val
1261          CTG CTC TCC AGC ACC AAC AGC AGG CTA TGC GCG GTC TTC GTC AGA AGC GGG CAA CCG GTC
                                                  S2

Ile Gly Ala Cys Thr Ser Pro Tyr Asp Gly Lys Tyr Trp Ser Met Tyr Ser Arg Leu Arg
1321          ATT GGC GCC TGC ACC AGC CCG TAT GAC GGG AAG TAC TGG AGC ATG TAC AGC CGG CTG CGG
                                                  S2

Lys Met Leu Tyr Leu Ile Tyr Val Ala Gly Ile Ser Val Arg Val His Val Ser Lys Glu
1381          AAA ATG CTT TAC CTG ATC TAC GTG GCC GGC ATC TCC GTA CGC GTC CAT GTC AGC AAG GAA
                                                  S2

Glu Gln Tyr Tyr Asp Tyr Glu Asp Ala Thr Phe Glu Thr Phe Tyr Ala Leu Thr Gly Ile Ser
1441          GAA CAG TAT TAC GAC TAT GAG GAC GCA ACG TTC GAG ACT TAC GCC CTT ACC GGC ATC TCC
                                                  S2

Ile Cys Asn Pro Gly Ser Ser Leu Cys
1501          ATC TGC AAT CCT GGA TCA TCC TTA TGC TGA GAC GCT TCC CCA CTC GAA CCA CCG CGG
                                                  signal sequence
                                                       S4

Val Arg Ala Leu Ala Trp Leu Leu Ala Ser Gly
1561          GAC AGG GCG GCG CCC GGC GGT CGC GC GTG CGC GCC CTG GCG TGG TTG CTG GCA TCC GGC
              signal sequence
                                              S4

Ala Met Thr His Leu Ser Pro Ala Leu Ala Asp Val Pro Tyr Val Leu Val Lys Thr Asn
1620          GCG ATG ACG CAT CTT TCC CCC GCC CTG GCC GAC GTT CCT TAT GTG CTG GTG AAG ACC AAT
                                                  S4

Met Val Val Thr Ser Val Ala Met Lys Pro Tyr Glu Val Thr Pro Thr Arg Met Leu Val
1680          ATG GTG GTC ACC AGC GTA GCC ATG AAG CCG TAT GAA GTC ACC CCG ACG CGC ATG CTG GTC
                                                  S4

Cys Gly Ile Ala Ala Lys Leu Leu Gly Ala Ala Ser Ser Pro Met Glu Ala His Val Pro Phe
1740          TGC GGC ATC GCC GCC AAA CTG GGC GCC GCC AGC AGT CCC ATG GAA GTC CAC GTG CCG TTC
                                                  S4

Cys Phe Gly Lys Asp Leu Lys Arg Pro Gly Ser Ser Pro Met Phe Leu Gly Met Leu Arg Ala
1800          TGC TTC GGC AAG GAT CTC AAG CGT CCC GGC AGC AGT CCC ATG TTC CTG GGT ATG TTG CGC GCC
                                                  S4

Val Phe Met Gln Gln Arg Leu Arg Met Phe Leu Gly Pro Lys Gln Leu Thr Phe Glu
1860          GTC TTC ATG CAA CAA CGG CTG CGC ATG TTT CTG GGT CCC AAG CAA CTC ACT TTC GAA
```

FIGURE 6-3

```
                                                                Gly Lys Pro Ala Leu Glu Leu Ile Arg Met Val Glu Cys Ser Gly Lys Gln Asp Cys Pro
1920                                                            GGC AAG CCC GCG CTC GAA CTG ATC CGG ATG GTC GAA TGC AGC GGC AAG CAG GAT TGC CCC T
                                                                                              S4
                                                                                                             signal sequence
                                                                                            Met His Thr Ile Ala Ser Ile Leu Leu Ser Val Leu Gly Ile Tyr Ser·
1981 GAA GGC GAA CCC C ATG CAT ACC ATC GCA TCC ATC CTG TTG TCC GTG CTC GGC ATA TAC AG
     signal sequence
                                                                         S5
     · Pro Ala Asp Val Ala Gly Leu Pro Thr His Leu Tyr Lys Asn Phe Thr Val Gln Glu Leu·
2041 C CCG GCT GAC GTC GCC GGC TTG CCG ACC CAT CTG TAC AAG AAC TTC ACT GTC CAG GAG CT
                                                                         S5
     · Ala Leu Lys Leu Lys Gly Lys Asn Gln Glu Phe Cys Leu Thr Ala Phe Met Ser Gly Arg·
2101 G GCC TTG AAA CTG AAG GGC AAG AAT CAG GAG TTC TGC CTG ACC GCC TTC ATG TCG GGC AG
                                                                         S5
     · Ser Leu Val Arg Ala Cys Leu Ser Asp Ala Gly His Glu His Asp Thr Trp Phe Asp Thr·
2161 A AGC CTG GTC CGG GCG TGC CTG TCC GAC GCG GGA CAC GAG CAC GAC ACG TGG TTC GAC AC
                                                                         S5
     · Met Leu Gly Phe Ala Ile Ser Ala Tyr Ala Leu Lys Ser Arg Ile Ala Leu Thr Val Glu·
2221 C ATG CTT GGC TTT GCC ATA TCC GCC TAT GCG CTC AAG AGC CGG ATC GCG CTG ACG GTG GA
                                                                         S5
     · Asp Ser Pro Tyr Pro Gly Thr Pro Leu Asp Leu Gln Leu Gln Ile Cys Pro Leu Asn·
2281 A GAC TCG CCG TAT CCG GGC ACT CCC GGC GAT CTC GAA CTG CAG ATC TGC CCG CTC AA
                                                                         S5
     · Gly Tyr Cys Glu
2341 C GGA TAT TGC GAA TG AAC CCT TCC GGA GGT TTC GAC GTT TCC GCG CAA TCC GCT TGA GAC
                                                                         signal sequence
                                                                                            S3
                                                                                            Met Leu Ile Asn Asn Lys Lys Leu·
2401 GAT CTT CCG CCC TGG TTC CAT TCC GGG AAC ACC GCA AC ATG CTG ATC AAC AAC AAG AAG C
                         signal sequence
                                   S3
     · Leu His His Ile Leu Pro Ile Leu Val Leu Ala Leu Leu Gly Met Arg Thr Ala Gln Ala·
2461 TG CTT CAT CAC ATT CTG CCC ATC CTG GTG CTC GCC CTG CTG GGC ATG CGC ACG GCC CAG G
```

FIGURE 6-4

```
     signal sequence
      ~~                                                                                                        S3
      |   Val Ala Pro Gly Ile Val Ile Pro Pro Lys Ala Leu Phe Thr Gln Gln Gly Gly Ala Tyr·
2521  CC GTT GCG CCA GGC ATC GTC ATC CCG AAG GCA CTG TTC ACC CAA CAG GGC GGC GCC T
                                                                                       S3
      · Gly Arg Cys Pro Asn Gly Thr Arg Ala Leu Thr Val Ala Glu Leu Arg Gly Asn Ala Glu·
2581  AT GGA CGC TGC CCG AAC GGA ACC CGC GCC TTG ACC GTG GCC GAA CTG CGC GGC AAC GCC G
      · Leu Gln Thr Tyr Leu Arg Gln Ile Thr Pro Gly Trp Ser Ile Tyr Gly Leu Tyr Asp Gly·
2641  AA TTG CAG ACG TAT TTG CGC CAG ATA ACG CCC GGC TGG TCC ATA TAC GGT CTC TAT GAC G
                                                                                       S3
      · Thr Tyr Leu Gly Gln Ala Tyr Gly Ile Ile Lys Asp Ala Pro Pro Gly Ala Gly Phe·
2701  GT ACG TAC CTG GGC CAG GCG TAC GGC ATC ATC AAG GAC GCG CCA GGC GGG GGG T
                                                                                       S3
      · Ile Tyr Arg Glu Thr Phe Cys Ile Thr Thr Ile Tyr Gly Gln Pro Ala Ala Asp·
2761  TC ATT TAT CGC GAA ACT TTC TGC ATC ACG ACC ATA TAC AAG GGG CAA CCG GCT GCG G
      · His Tyr Ser Lys Val Thr Ala Thr Arg Leu Leu Ala Ser Thr Asn Ser Arg Leu Cys·
2821  AT CAC TAC AGC GTC ACG GCC ACG CGC CTG CTC GCC AGC ACC AAC AGC AGG CTG T
                                                                                       S3
      · Ala Val Phe Val Arg Asp Gly Gln Ser Val Ile Gly Ala Cys Ala Ser Pro Tyr Glu Gly·
2881  GC GCG GTA TTC GTC AGG GAC GGG CAA TCG ATC GGA GCC TGC GCC AGC CCC TAT GAA G
      · Arg Tyr Arg Asp Met Tyr Asp Ala Leu Arg Arg Leu Leu Tyr Met Ile Tyr Met Ser Gly·
2941  GC AGG TAC AGA GAC ATG TAC GAC GCC CTG CGG CGC CTG CTG TAC ATG ATC TAT ATG TCC G
                                                                                       S3
      · Leu Ala Val Arg Val His Val Ser Lys Glu Gln Tyr Tyr Asp Tyr Glu Asp Ala Thr·
3001  GC CTT GCC GTA CGC GTC CAC GTC AGC AAG GAG CAG TAT TAC GAC TAC GAG GAC GCC A
      · Phe Gln Thr Tyr Ala Leu Thr Gly Ile Ser Leu Cys Asn Pro Ala Ala Ser Ile Cys
3061  CA TTC CAG ACC TAT GCC CTC ACC GGC ATT TCC CTC TGC AAC CCG GCA GCG TCG ATA TGC
```

```
  1  Met Arg Cys Thr Arg Ala Ile Arg Gln Thr Ala Arg Thr Gly Trp Leu Thr Trp Leu Ala
 21  Ile Leu Ala Val Thr Ala Pro Val Thr Ser Pro Ala Trp Ala Asp Asp Pro Pro Ala Thr
 41  Val Tyr Lys Tyr Asp Ser Arg Pro Pro Glu Asp Val Phe Gln Asn Gly Phe Thr Ala Trp
 61  Gly Asn Asn Asp Asn Val Leu Asp His Leu Thr Gly Arg Ser Cys Gln Val Gly Ser Ser
 81  Asn Ser Ala Phe Val Ser Thr Ser Ser Arg Arg Tyr Thr Glu Val Tyr Leu Glu His
101  Arg Met Gln Glu Ala Val Glu Ala Gly Ala Gly Arg Gly Thr Gly His Phe Ile Gly
121  Tyr Ile Tyr Glu Val Arg Ala Asp Asn Phe Tyr Gly Ala Ala Ser Ser Tyr Phe Glu
141  Tyr Val Asp Thr Tyr Gly Asp Asn Ala Gly Arg Ile Leu Ala Gly Ala Leu Ala Thr Tyr
161  Gln Ser Ala Tyr Leu Ala His Arg Arg Ile Pro Pro Glu Asn Ile Arg Arg Val Thr Arg
181  Val Tyr His Asn Gly Ile Thr Gly Glu Thr Thr Thr Glu Tyr Ser Asn Ala Arg Tyr
201  Val Ser Gln Gln Thr Arg Ala Asn Pro Tyr Thr Ser Arg Arg Ser Val Ala Ser
221  Ile Val Gly Thr Leu Val Arg Met Ala Pro Val Ile Gly Ala Cys Met Ala Arg Gln Ala
241  Glu Ser Ser Glu Ala Met Ala Ala Trp Ser Glu Arg Ala Gly Glu Ala Met Val Leu Val
261  Tyr Tyr Glu Ser Ile Ala Tyr Ser Phe
```

Fig. 7B

```
  1  Met Pro Ile Asp Arg Lys Thr Leu Cys His Leu Leu Ser Val Leu Pro Leu Ala Leu Leu
 21  Gly Ser His Val Ala Arg Ala Ser Thr Pro Gly Ile Val Ile Pro Pro Gln Glu Gln Ile
 41  Thr Gln His Gly Ser Pro Tyr Gly Arg Cys Ala Asn Lys Thr Arg Ala Leu Thr Val Ala
 61  Glu Leu Arg Gly Ser Gly Asp Leu Gln Glu Tyr Leu Arg His Val Thr Arg Gly Trp Ser
 81  Ile Phe Ala Leu Tyr Asp Gly Thr Tyr Leu Gly Gly Glu Tyr Gly Gly Val Ile Lys Asp
101  Gly Thr Pro Gly Gly Ala Phe Asp Leu Lys Thr Thr Phe Cys Ile Met Thr Thr Arg Asn
121  Thr Gly Gln Pro Ala Thr Asp His Tyr Tyr Ser Asn Val Thr Ala Thr Arg Leu Leu Ser
141  Ser Thr Asn Ser Arg Leu Cys Ala Val Phe Val Arg Ser Gly Gln Pro Val Ile Gly Ala
161  Cys Thr Ser Pro Tyr Asp Gly Lys Tyr Tyr Trp Ser Met Tyr Ser Arg Leu Arg Lys Met Leu
181  Tyr Leu Ile Tyr Val Ala Gly Ile Ser Val Arg Val His Val Ser Lys Glu Glu Gln Tyr
201  Tyr Asp Tyr Glu Asp Ala Thr Phe Glu Thr Tyr Ala Leu Thr Gly Ile Ser Ile Cys Asn
221  Pro Gly Ser Ser Leu Cys
```

Fig. 7C

```
  1 Met Leu Ile Asn Asn Lys Lys Leu Leu His His Ile Leu Pro Ile Leu Val Leu Ala Leu
 21 Leu Gly Met Arg Thr Ala Gln Ala Val Ala Pro Gly Ile Val Ile Pro Pro Lys Ala Leu
 41 Phe Thr Gln Gln Gly Gly Ala Tyr Gly Arg Cys Pro Asn Gly Thr Arg Ala Leu Thr Val
 61 Ala Glu Leu Arg Gly Asn Ala Glu Leu Gln Thr Tyr Leu Arg Gln Ile Thr Pro Gly Trp
 81 Ser Ile Tyr Gly Leu Tyr Asp Gly Thr Tyr Leu Gly Gln Ala Tyr Gly Gly Ile Ile Lys
101 Asp Ala Pro Pro Gly Ala Gly Phe Ile Tyr Arg Glu Thr Phe Cys Ile Thr Thr Ile Tyr
121 Lys Thr Gly Gln Pro Ala Ala Asp His Tyr Tyr Ser Lys Val Thr Ala Thr Arg Leu Leu
141 Ala Ser Thr Asn Ser Arg Leu Cys Ala Val Phe Val Arg Asp Gly Gln Ser Val Ile Gly
161 Ala Cys Ala Ser Pro Tyr Glu Gly Arg Tyr Arg Asp Met Tyr Asp Ala Leu Arg Arg Leu
181 Leu Tyr Met Ile Tyr Met Ser Gly Leu Ala Val Arg Val His Val Ser Lys Glu Glu Gln
201 Tyr Tyr Asp Tyr Glu Asp Ala Thr Phe Gln Thr Tyr Ala Leu Thr Gly Ile Ser Leu Cys
221 Asn Pro Ala Ala Ser Ile Cys
```

Fig. 7D

```
  1 Val Arg Ala Leu Ala Trp Leu Leu Ala Ser Gly Ala Met Thr His Leu Ser Pro Ala Leu
 21 Ala Asp Val Pro Tyr Val Leu Val Lys Thr Asn Met Val Thr Ser Val Ala Met Lys
 41 Pro Tyr Glu Val Thr Pro Thr Arg Met Leu Val Cys Gly Ile Ala Ala Lys Leu Gly Ala
 61 Ala Ala Ser Ser Pro Asp Ala His Val Pro Phe Cys Phe Gly Lys Asp Leu Lys Arg Pro
 81 Gly Ser Ser Pro Met Glu Val Met Leu Arg Ala Val Phe Met Gln Gln Arg Pro Leu Arg
101 Met Phe Leu Gly Pro Lys Gln Leu Thr Phe Glu Gly Lys Pro Ala Leu Glu Leu Ile Arg
121 Met Val Glu Cys Ser Gly Lys Gln Asp Cys Pro
```

Fig. 7E

1 Met His Thr Ile Ala Ser Ile Leu Leu Ser Val Leu Gly Ile Tyr Ser Pro Ala Asp Val

21 Ala Gly Leu Pro Thr His Leu Tyr Lys Asn Phe Thr Val Gln Glu Leu Ala Leu Lys Leu

41 Lys Gly Lys Asn Gln Glu Phe Cys Leu Thr Ala Phe Met Ser Gly Arg Ser Leu Val Arg

61 Ala Cys Leu Ser Asp Ala Gly His Glu His Asp Thr Trp Phe Asp Thr Met Leu Gly Phe

81 Ala Ile Ser Ala Tyr Ala Leu Lys Ser Arg Ile Ala Leu Thr Val Glu Asp Ser Pro Tyr

101 Pro Gly Thr Pro Gly Asp Leu Leu Glu Leu Gln Ile Cys Pro Leu Asn Gly Tyr Cys Glu

A. Tetanus Toxin C Fragment Amino Acid Sequence

```
  1 Lys Asn Leu Asp Cys Trp Val Asp Asn Glu Glu Asp Ile Asp Val Ile Leu Lys Lys Ser
 21 Thr Ile Leu Asn Leu Asp Ile Asn Asn Asp Ile Ile Ser Asp Ile Ser Gly Phe Asn Ser
 41 Ser Val Ile Thr Tyr Pro Asp Ala Gln Leu Val Pro Gly Ile Asn Gly Lys Ala Ile His
 61 Leu Val Asn Asn Glu Ser Ser Glu Val Ile Val His Lys Ala Met Asp Ile Glu Tyr Asn
 81 Asp Met Phe Asn Asn Phe Thr Val Ser Phe Trp Leu Arg Val Pro Lys Val Ser Ala Ser
101 His Leu Glu Gln Tyr Gly Thr Asn Glu Tyr Ser Ile Ile Ser Ser Met Lys Lys His Ser
121 Leu Ser Ile Gly Ser Gly Trp Ser Val Ser Leu Lys Gly Asn Asn Leu Ile Trp Thr Leu
141 Lys Asp Ser Ala Gly Glu Val Arg Gln Ile Thr Phe Arg Asp Leu Pro Asp Lys Phe Asn
161 Ala Tyr Leu Ala Asn Lys Trp Val Phe Ile Thr Ile Thr Asn Asp Arg Leu Ser Ser Ala
181 Asn Leu Tyr Ile Asn Gly Val Leu Met Gly Ser Ala Glu Ile Thr Gly Leu Gly Ala Ile
201 Arg Glu Asp Asn Asn Ile Thr Leu Lys Leu Asp Arg Cys Asn Asn Asn Asn Gln Tyr Val
221 Ser Ile Asp Lys Phe Arg Ile Phe Cys Lys Ala Leu Asn Pro Lys Glu Ile Glu Lys Leu
241 Tyr Thr Ser Tyr Leu Ser Ile Thr Phe Leu Arg Asp Phe Trp Gly Asn Pro Leu Arg Tyr
261 Asp Thr Glu Tyr Tyr Leu Ile Pro Val Ala Ser Ser Lys Asp Val Gln Leu Lys Asn Ile
281 Ile Asp Tyr Met Tyr Leu Thr Asn Ala Pro Ser Tyr Thr Asn Gly Lys Leu Asn Ile
301 Tyr Tyr Arg Arg Leu Tyr Asn Gly Leu Lys Phe Ile Ile Lys Arg Tyr Thr Pro Asn Asn
321 Glu Ile Asp Ser Phe Val Lys Ser Gly Asp Phe Ile Lys Leu Tyr Val Ser Tyr Asn Asn
341 Asn Glu His Ile Val Gly Tyr Pro Lys Asp Gly Asn Ala Phe Asn Asn Leu Asp Arg Ile
361 Leu Arg Val Gly Tyr Asn Ala Pro Gly Ile Pro Leu Tyr Lys Lys Met Glu Ala Val Lys
381 Leu Arg Asp Leu Lys Thr Tyr Ser Val Gln Leu Lys Leu Tyr Asp Asp Lys Asn Ala Ser
401 Leu Gly Leu Val Gly Thr His Asn Gly Gln Ile Gly Asn Asp Pro Asn Arg Asp Ile Leu
421 Ile Ala Ser Asn Trp Tyr Phe Asn His Leu Lys Asp Lys Ile Leu Gly Cys Asp Trp Tyr
441 Phe Val Pro Thr Asp Glu Gly Trp Thr Asn Asp
```

FIGURE 9-1

B. Tetanus Toxin C DNA Sequence with Translation

```
      Lys Asn Leu Asp Cys Trp Val Asp Asn Glu Glu Asp Ile Asp Val Ile Leu Lys Lys Ser
  1   AAA AAC CTG GAC TGT TGG GTT GAC AAC GAA GAA GAT ATC GAT GTC ATC CTG AAG AAA TCC

Thr Ile Leu Asn Leu Asp Ile Asn Asn Asp Ile Ile Ser Asp Ile Ser Gly Phe Asn Ser
 61   ACC ATT TTG AAC CTC GAC ATC AAC AAT GAC ATT ATT TCC GAC ATT AGC GGT TTC AAC TCG

Ser Val Ile Thr Tyr Pro Asp Ala Gln Leu Val Pro Gly Ile Asn Gly Lys Ala Ile His
121   TCC GTG ATT ACG TAC CCA GAT GCT CAG CTG GTG CCC GGG ATT AAC GGC AAG GCT ATC CAC

Leu Val Asn Asn Glu Ser Ser Glu Val Ile Val His Lys Ala Met Asp Ile Glu Tyr Asn
181   CTC GTC AAC AAC GAG TCG GAA GTC ATC GTC CAT AAA GCG ATG GAC ATC GAG TAT AAC

Asp Met Phe Asn Asn Phe Thr Val Ser Phe Trp Leu Arg Val Pro Lys Val Ser Ala Ser
241   GAC ATG TTT AAT AAT TTC ACC GTG TCC TTC TGG CTG CGC GTG CCC AAG GTG TCC GCC TCC

His Leu Glu Gln Tyr Gly Thr Asn Glu Tyr Ser Ile Ile Ser Ser Met Lys Lys His Ser
301   CAC CTG GAA CAG TAC GGG ACC AAC GAG TAC AGC ATC ATC AGC TCG ATG AAG AAG CAC TCG

Leu Ser Ile Gly Ser Gly Trp Ser Val Ser Leu Lys Gly Asn Asn Leu Ile Trp Thr Leu
361   TTG AGC ATC GGC AGC GGC TGG TCG GTT AGT CTC AAA GGG AAC AAC CTG ATT TGG ACC CTG

Lys Asp Ser Ala Gly Glu Val Arg Gln Ile Thr Phe Arg Asp Leu Pro Asp Lys Phe Asn
421   AAA GAT AGC GCC GGC GAG GTG CGT GTG CAG ATC ACT TTC CGG GAC CTG CCG GAT AAG TTC AAC

Ala Tyr Leu Ala Asn Lys Trp Val Phe Ile Thr Ile Thr Asn Asp Arg Leu Ser Ser Ala
481   GCC TAC CTG GCA AAC AAA TGG GTG TTC ATT ACC ATC ACG AAC GAC CGC CTG AGT AGC GCG

Asn Leu Tyr Ile Asn Gly Val Leu Met Gly Ser Ala Glu Ile Thr Gly Leu Gly Ala Ile
541   AAT CTC TAC ATC AAT GGC GTG CTG ATG GGC AGC GCG GAA ATC ACG GGT TTG GGT GCC ATC

Arg Glu Asp Asn Asn Ile Thr Leu Lys Leu Asp Arg Cys Asn Asn Asn Asn Gln Tyr Val
601   CGC GAA GAT AAC AAC ATC ACC TTG AAG CTG GAC CGC TGC AAC AAC AAC CAA TAC GTG

Ser Ile Asp Lys Phe Arg Ile Phe Cys Lys Ala Leu Asn Pro Lys Glu Ile Glu Lys Leu
661   TCC ATT GAT AAG TTC CGC ATC TTT TGC AAG GCC CTG AAC CCG AAA GAG ATC GAA AAG CTC

Tyr Thr Ser Tyr Leu Ser Ile Thr Phe Leu Arg Asp Phe Trp Gly Asn Pro Leu Arg Tyr
721   TAC ACC AGC TAC TTG AGT ATC ACC TTC CTG CGC GAC TTT TGG GGT AAT CCG TTG CGT TAT

Asp Thr Glu Tyr Tyr Leu Ile Pro Val Ala Ser Ser Ser Lys Asp Val Gln Leu Lys Asn
781   GAC ACC GAG TAT TAT CTG ATC CCC GTG GCC AGC AGC AGC AAG GAC GTC CAG CTG AAG AAC

Ile Thr Asp Tyr Met Tyr Leu Thr Asn Ala Pro Ser Tyr Thr Asn Gly Lys Leu Asn Ile
841   ATC ACC GAC TAC ATG TAC TTG ACT AAC GCG CCC TCG TAT ACC AAT GGC AAA CTG AAC ATT

Tyr Tyr Arg Arg Leu Tyr Asn Gly Leu Lys Phe Ile Ile Lys Arg Tyr Thr Pro Asn Asn
901   TAC TAC CGC CGG CTC TAC AAC GGG CTC AAG TTC ATC ATC AAA CGC TAT ACG CCG AAT AAT
```

FIGURE 9-2

```
      Glu Ile Asp Ser Phe Val Lys Ser Gly Asp Phe Ile Lys Leu Tyr Val Ser Tyr Asn Asn
 961  GAA ATC GAC AGT TTT GTC AAG AGC GGC GAC TTC ATC AAG TTG TAC GTG AGC TAC AAT AAC

Asn Glu His Ile Val Gly Tyr Pro Lys Asp Leu Asn Ala Phe Asn Asn Leu Asp Arg Ile
1021  AAC GAG CAC ATC GTT GGT TAC CCT AAG GAT GGC AAC AAC GCT TTC AAC AAC CTC GAT CGT ATC

Leu Arg Val Gly Tyr Asn Ala Pro Gly Ile Gly Tyr Leu Pro Leu Tyr Lys Met Glu Ala Val Lys
1081  CTG CGG GTT GGC TAC AAC GCA CCA GGC ATT GGC TAT CCG CTG TAT AAG ATG GAA GCC GTC AAA

Leu Arg Asp Leu Lys Thr Tyr Ser Val Gln Leu Lys Tyr Asp Asp Lys Asn Ala Ser
1141  CTG CGT GAC CTG AAA ACC TAC TCC GTG CAA CTG AAG TAC GAC GAC AAG AAT GCC TCG

Leu Gly Leu Val Gly Thr His Asn Gly Ile Gln Ile Gly Asn Asp Pro Asn Arg Asp Ile Leu
1201  TTG GGT CTG GTC GGC ACG CAT AAT GGT CAG ATT CAG ATT GGC AAC GAC CGG AAC ATC CTG

Ile Ala Ser Asn Trp Tyr Phe Asn His Leu Lys Asp Lys Ile Leu Gly Cys Asp Trp Tyr
1261  ATC GCC AGC AAC TGG TAT TTC AAT CAC CTG AAG GAT AAG ATC TTG GGC TGC GAT TGG TAT

Phe Val Pro Thr Asp Glu Gly Trp Thr Asn Asp
1321  TTC GTC CCT ACC GAT GAG GGC TGG ACT AAT GAC
```

FIGURE 9-3

A. C. difficile VPI TcdB Amino Acid Sequence

```
  1  Met Ser Leu Val Asn Arg Lys Gln Leu Glu Lys Met Ala Asn Val Arg Phe Arg Thr Gln
 21  Glu Asp Glu Tyr Val Ala Ile Leu Asp Ala Leu Glu Glu Tyr His Asn Met Ser Glu Asn
 41  Thr Val Val Glu Lys Tyr Leu Lys Leu Lys Asp Ile Asn Ser Leu Thr Asp Ile Tyr Ile
 61  Asp Thr Tyr Lys Lys Ser Gly Arg Asn Lys Ala Leu Lys Lys Phe Lys Glu Tyr Leu Val
 81  Thr Glu Val Leu Glu Leu Lys Asn Asn Asn Leu Thr Pro Val Glu Lys Asn Leu His Phe
101  Val Trp Ile Gly Gly Gln Ile Asn Asp Thr Ala Ile Asn Tyr Ile Asn Gln Trp Lys Asp
121  Val Asn Ser Asp Tyr Asn Val Asn Val Phe Tyr Asp Ser Asn Ala Phe Leu Ile Asn Thr
141  Leu Lys Lys Thr Val Val Glu Ser Ala Ile Asn Asp Thr Leu Glu Ser Phe Arg Glu Asn
161  Leu Asn Asp Pro Arg Phe Asp Tyr Asn Lys Phe Phe Arg Lys Arg Met Glu Ile Ile Tyr
181  Asp Lys Gln Lys Asn Phe Ile Asn Tyr Tyr Lys Ala Gln Arg Glu Glu Asn Pro Glu Leu
201  Ile Ile Asp Asp Ile Val Lys Thr Tyr Leu Ser Asn Glu Tyr Ser Lys Glu Ile Asp Glu
221  Leu Asn Thr Tyr Ile Glu Gly Ser Leu Asn Lys Ile Thr Gln Asn Ser Gly Asn Asp Val
241  Arg Asn Phe Glu Glu Phe Lys Asn Gly Glu Ser Phe Asn Leu Tyr Glu Gln Glu Leu Val
261  Glu Arg Trp Asn Leu Ala Ala Ala Ser Asp Ile Leu Arg Ile Ser Ala Leu Lys Glu Ile
281  Gly Gly Met Tyr Leu Asp Val Asp Met Leu Pro Gly Ile Gln Pro Asp Leu Phe Glu Ser
301  Ile Glu Lys Pro Ser Ser Val Thr Val Asp Phe Trp Glu Met Thr Lys Leu Glu Ala Ile
321  Met Lys Tyr Lys Glu Tyr Ile Pro Glu Tyr Thr Ser Glu His Phe Asp Met Leu Asp Glu
341  Glu Val Gln Ser Ser Phe Glu Ser Val Leu Ala Ser Lys Ser Asp Lys Ser Glu Ile Phe
361  Ser Ser Leu Gly Asp Met Glu Ala Ser Pro Leu Glu Val Lys Ile Ala Phe Asn Ser Lys
381  Gly Ile Ile Asn Gln Gly Leu Ile Ser Val Lys Asp Ser Tyr Cys Ser Asn Leu Ile Val
```

FIGURE 11-1

| | | | | | | | | | | |
|---|---|---|---|---|---|---|---|---|---|---|
| 401 | Lys | Gln | Ile | Glu | Asn | Arg | Tyr | Lys | Ile | Leu | Asn | Asn | Ser | Leu | Asn | Pro | Ala | Ile | Ser | Glu |
| 421 | Asp | Asn | Asp | Phe | Asn | Thr | Thr | Thr | Asn | Thr | Phe | Ile | Asp | Ser | Ile | Met | Ala | Glu | Ala | Asn |
| 441 | Ala | Asp | Asn | Gly | Arg | Phe | Met | Met | Glu | Leu | Gly | Lys | Tyr | Leu | Arg | Val | Gly | Phe | Phe | Pro |
| 461 | Asp | Val | Lys | Thr | Thr | Ile | Asn | Leu | Ser | Gly | Pro | Glu | Ala | Tyr | Ala | Ala | Tyr | Gln | Arg | Asp |
| 481 | Leu | Leu | Met | Phe | Lys | Glu | Gly | Ser | Met | Asn | Ile | His | Leu | Ile | Glu | Ala | Asp | Leu | Arg | Asn |
| 501 | Phe | Glu | Ile | Ser | Lys | Thr | Asn | Ile | Ser | Gln | Ser | Thr | Glu | Gln | Glu | Met | Ala | Ser | Leu | Trp |
| 521 | Ser | Phe | Asp | Asp | Ala | Arg | Ala | Lys | Ala | Gln | Phe | Glu | Glu | Tyr | Lys | Arg | Asn | Tyr | Phe | Glu |
| 541 | Gly | Ser | Leu | Gly | Glu | Asp | Asp | Asn | Leu | Asp | Phe | Ser | Gln | Asn | Ile | Val | Val | Asp | Lys | Glu |
| 561 | Tyr | Leu | Leu | Glu | Lys | Ile | Ser | Ser | Leu | Ala | Arg | Ser | Ser | Glu | Arg | Gly | Tyr | Ile | His | Tyr |
| 581 | Ile | Val | Gln | Leu | Gln | Gly | Asp | Lys | Ile | Ser | Tyr | Glu | Ala | Ala | Cys | Asn | Leu | Phe | Ala | Lys |
| 601 | Thr | Pro | Tyr | Asp | Ser | Val | Leu | Phe | Gln | Lys | Asn | Ile | Glu | Asp | Ser | Glu | Ile | Ala | Tyr | Tyr |
| 621 | Tyr | Asn | Pro | Gly | Asp | Gly | Glu | Ile | Gln | Glu | Ile | Asp | Lys | Tyr | Lys | Ile | Pro | Ser | Ile | Ile |
| 641 | Ser | Asp | Arg | Pro | Lys | Ile | Lys | Leu | Thr | Phe | Ile | Gly | His | Gly | Lys | Asp | Glu | Phe | Asn | Thr |
| 661 | Asp | Ile | Phe | Ala | Gly | Phe | Asp | Val | Asp | Ser | Leu | Ser | Thr | Glu | Ile | Glu | Ala | Ala | Ile | Asp |
| 681 | Leu | Ala | Lys | Glu | Asp | Ile | Ser | Pro | Lys | Ser | Ile | Glu | Ile | Asn | Leu | Leu | Gly | Cys | Asn | Met |
| 701 | Phe | Ser | Tyr | Ser | Ile | Asn | Val | Glu | Glu | Thr | Tyr | Pro | Gly | Lys | Leu | Leu | Leu | Lys | Val | Lys |
| 721 | Asp | Lys | Ile | Ser | Glu | Leu | Met | Pro | Ser | Ile | Ser | Gln | Asp | Ser | Ile | Ile | Val | Ser | Ala | Asn |
| 741 | Gln | Tyr | Glu | Val | Arg | Ile | Asn | Ser | Glu | Gly | Arg | Arg | Glu | Leu | Leu | Asp | His | Ser | Gly | Glu |
| 761 | Trp | Ile | Asn | Lys | Glu | Ser | Ile | Ile | Lys | Asp | Ile | Ser | Ser | Lys | Glu | Tyr | Ile | Ser | Phe |
| 781 | Asn | Pro | Lys | Glu | Asn | Lys | Ile | Thr | Val | Lys | Ser | Lys | Asn | Leu | Pro | Glu | Leu | Ser | Thr | Leu |
| 801 | Leu | Gln | Glu | Ile | Arg | Asn | Asn | Ser | Asn | Ser | Ser | Asp | Ile | Glu | Leu | Glu | Glu | Lys | Val | Met |

FIGURE 11-2

| | | | | | | | | | |
|---|---|---|---|---|---|---|---|---|---|
| 821 | Leu | Thr | Glu | Cys | Glu | Ile | Asn | Val | Ile | Ser | Asn | Ile | Asp | Thr | Gln | Ile | Val | Glu | Glu | Arg |
| 841 | Ile | Glu | Glu | Ala | Lys | Asn | Leu | Thr | Ser | Asp | Ser | Ile | Asn | Tyr | Ile | Lys | Asp | Glu | Phe | Lys |
| 861 | Leu | Ile | Glu | Ser | Ile | Ser | Asp | Ala | Leu | Cys | Asp | Leu | Lys | Gln | Gln | Asn | Glu | Leu | Glu | Asp |
| 881 | Ser | His | Phe | Ile | Ser | Phe | Glu | Asp | Ile | Ser | Glu | Thr | Asp | Glu | Gly | Phe | Ser | Ile | Arg | Phe |
| 901 | Ile | Asn | Lys | Glu | Thr | Gly | Glu | Ser | Ile | Phe | Val | Glu | Thr | Glu | Lys | Thr | Ile | Phe | Ser | Glu |
| 921 | Tyr | Ala | Asn | His | Ile | Thr | Glu | Glu | Ile | Ser | Lys | Ile | Lys | Gly | Thr | Ile | Phe | Asp | Thr | Val |
| 941 | Asn | Gly | Lys | Leu | Val | Lys | Lys | Val | Asn | Leu | Asp | Thr | Thr | His | Glu | Val | Asn | Thr | Leu | Asn |
| 961 | Ala | Ala | Phe | Phe | Ile | Gln | Ser | Leu | Ile | Glu | Tyr | Asn | Ser | Ser | Lys | Glu | Ser | Leu | Ser | Asn |
| 981 | Leu | Ser | Val | Ala | Met | Lys | Val | Gln | Val | Tyr | Ala | Gln | Leu | Phe | Ser | Thr | Gly | Leu | Asn | Thr |
| 1001 | Ile | Thr | Asp | Ala | Ala | Lys | Val | Val | Glu | Leu | Val | Ser | Thr | Ala | Leu | Asp | Glu | Thr | Ile | Asp |
| 1021 | Leu | Leu | Pro | Thr | Leu | Ser | Glu | Gly | Leu | Pro | Ile | Ile | Ala | Thr | Ile | Ile | Asp | Gly | Val | Ser |
| 1041 | Leu | Gly | Ala | Ala | Ile | Lys | Glu | Leu | Ser | Glu | Thr | Ser | Asp | Pro | Leu | Leu | Arg | Gln | Glu | Ile |
| 1061 | Glu | Ala | Lys | Ile | Gly | Ile | Met | Ala | Val | Asn | Leu | Thr | Thr | Ala | Thr | Thr | Ala | Ile | Ile | Thr |
| 1081 | Ser | Ser | Leu | Gly | Ile | Ala | Ser | Gly | Phe | Ser | Ile | Leu | Leu | Val | Pro | Leu | Ala | Gly | Ile | Ser |
| 1101 | Ala | Gly | Ile | Pro | Ser | Leu | Val | Asn | Asn | Glu | Leu | Val | Leu | Arg | Asp | Lys | Ala | Thr | Lys | Val |
| 1121 | Val | Asp | Tyr | Phe | Lys | His | Val | Ser | Leu | Val | Glu | Thr | Glu | Gly | Val | Phe | Thr | Leu | Leu | Asp |
| 1141 | Asp | Lys | Ile | Met | Met | Pro | Gln | Asp | Asp | Leu | Val | Ile | Ser | Glu | Ile | Asp | Phe | Asn | Asn | Asn |
| 1161 | Ser | Ile | Val | Leu | Gly | Lys | Cys | Glu | Ile | Trp | Arg | Met | Glu | Gly | Gly | Ser | Gly | His | Thr | Val |
| 1181 | Thr | Asp | Asp | Ile | Asp | His | Phe | Phe | Ser | Ala | Pro | Ser | Ile | Thr | Tyr | Arg | Glu | Pro | His | Leu |
| 1201 | Ser | Ile | Tyr | Asp | Val | Leu | Glu | Val | Gln | Lys | Glu | Glu | Leu | Asp | Leu | Ser | Lys | Asp | Leu | Met |
| 1221 | Val | Leu | Pro | Asn | Ala | Pro | Asn | Arg | Val | Phe | Ala | Trp | Glu | Thr | Gly | Trp | Thr | Pro | Gly | Leu |

FIGURE 11-3

| | | | | | | | | | | |
|---|---|---|---|---|---|---|---|---|---|---|
| 1241 | Arg | Ser | Leu | Glu | Asn | Asp | Gly | Thr | Lys | Leu | Leu | Asp | Arg | Ile | Arg | Asp | Asn | Tyr | Glu | Gly |
| 1261 | Glu | Phe | Tyr | Trp | Arg | Tyr | Phe | Ala | Phe | Ile | Ala | Asp | Ala | Leu | Ile | Thr | Thr | Leu | Lys | Pro |
| 1281 | Arg | Tyr | Glu | Asp | Thr | Asn | Ile | Arg | Ile | Asn | Leu | Asp | Ser | Asn | Thr | Arg | Ser | Phe | Ile | Val |
| 1301 | Pro | Ile | Thr | Thr | Glu | Tyr | Ile | Arg | Glu | Lys | Leu | Ser | Tyr | Ser | Phe | Tyr | Gly | Ser | Gly |
| 1321 | Gly | Thr | Tyr | Ala | Leu | Ser | Leu | Ser | Gln | Tyr | Asn | Met | Gly | Ile | Asn | Ile | Glu | Leu | Ser | Glu |
| 1341 | Ser | Asp | Val | Trp | Ile | Ile | Asp | Val | Asp | Asn | Val | Arg | Asp | Val | Thr | Ile | Glu | Ser | Asp |
| 1361 | Lys | Ile | Lys | Gly | Asp | Leu | Ile | Gly | Ile | Leu | Ser | Thr | Leu | Ser | Ile | Ser | Ile | Glu | Glu | Asn |
| 1381 | Lys | Ile | Leu | Asn | Ser | His | Glu | Ile | Asn | Phe | Ser | Gly | Glu | Val | Asn | Gly | Ser | Asn | Gly |
| 1401 | Phe | Val | Ser | Leu | Thr | Phe | Ser | Ile | Leu | Glu | Gly | Ile | Asn | Ala | Ile | Ile | Glu | Val | Asp | Leu |
| 1421 | Leu | Ser | Lys | Ser | Tyr | Lys | Leu | Leu | Ile | Ser | Gly | Glu | Leu | Lys | Ile | Leu | Met | Leu | Asn | Ser |
| 1441 | Asn | His | Ile | Gln | Gln | Lys | Ile | Asp | Tyr | Ile | Gly | Phe | Asn | Ser | Glu | Leu | Gln | Lys | Asn | Ile |
| 1461 | Pro | Tyr | Ser | Phe | Val | Asp | Ser | Glu | Gly | Lys | Glu | Leu | Pro | Asp | Val | Val | Leu | Ile | Ser | Gly | Phe | Ile | Asn | Gly | Ser | Thr | Lys |
| 1481 | Glu | Gly | Leu | Phe | Val | Ser | Glu | Leu | Pro | Asp | Val | Val | Leu | Ile | Ser | Lys | Val | Tyr | Met | Asp |
| 1501 | Asp | Ser | Lys | Pro | Ser | Phe | Gly | Tyr | Tyr | Ser | Asn | Asn | Leu | Lys | Asp | Asp | Ile | Lys | Val | Ile | Thr |
| 1521 | Lys | Asp | Asn | Val | Asn | Ile | Leu | Thr | Gly | Tyr | Tyr | Leu | Lys | Asp | Asp | Ile | Lys | Ile | Ser | Leu |
| 1541 | Ser | Leu | Thr | Leu | Gln | Asp | Glu | Lys | Thr | Ile | Lys | Leu | Asn | Ser | Val | His | Leu | Asp | Glu | Ser |
| 1561 | Gly | Val | Ala | Glu | Ile | Leu | Lys | Phe | Met | Asn | Arg | Lys | Gly | Asn | Thr | Asn | Thr | Ser | Asp | Ser |
| 1581 | Leu | Met | Ser | Phe | Leu | Glu | Ser | Met | Asn | Ile | Lys | Ser | Ile | Phe | Val | Asn | Phe | Leu | Gln | Ser |
| 1601 | Asn | Ile | Lys | Phe | Ile | Leu | Asp | Ala | Asn | Phe | Ile | Ile | Ser | Gly | Thr | Thr | Ser | Ile | Gly | Gln |
| 1621 | Phe | Glu | Phe | Ile | Cys | Asp | Glu | Asn | Asp | Asn | Ile | Gln | Pro | Tyr | Phe | Ile | Lys | Phe | Asn | Thr |
| 1641 | Leu | Glu | Thr | Asn | Tyr | Thr | Leu | Tyr | Val | Gly | Asn | Arg | Gln | Asn | Met | Ile | Val | Glu | Pro | Asn |

FIGURE 11-4

| | | | | | | | | | |
|---|---|---|---|---|---|---|---|---|---|
| 1661 | Tyr | Asp | Leu | Asp | Asp | Ser | Gly | Asp | Ile | Ser | Ser | Thr | Val | Ile | Asn | Phe | Ser | Gln | Lys | Tyr |
| 1681 | Leu | Tyr | Gly | Ile | Asp | Ser | Cys | Val | Asn | Lys | Val | Val | Ile | Ser | Pro | Asn | Ile | Tyr | Thr | Asp |
| 1701 | Glu | Ile | Asn | Ile | Thr | Pro | Val | Tyr | Glu | Thr | Asn | Asn | Thr | Tyr | Pro | Glu | Val | Ile | Val | Leu |
| 1721 | Asp | Ala | Asn | Tyr | Ile | Asn | Glu | Lys | Ile | Ile | Asn | Val | Asn | Ile | Asn | Asp | Leu | Ser | Ile | Arg | Tyr |
| 1741 | Val | Trp | Ser | Asn | Asp | Gly | Asn | Asp | Phe | Ile | Leu | Met | Ser | Thr | Ser | Glu | Glu | Asn | Lys | Val |
| 1761 | Ser | Gln | Val | Lys | Ile | Arg | Phe | Val | Asn | Val | Phe | Lys | Asp | Lys | Leu | Ser | Leu | Ala | Asn | Lys | Leu |
| 1781 | Ser | Phe | Asn | Phe | Ser | Asp | Lys | Gln | Asp | Val | Pro | Val | Ser | Gly | Ile | Ile | Leu | Ser | Phe | Thr |
| 1801 | Pro | Ser | Tyr | Tyr | Glu | Asp | Gly | Leu | Ile | Gly | Tyr | Asp | Leu | Gly | Leu | Val | Ser | Leu | Tyr | Asn |
| 1821 | Gly | Lys | Phe | Tyr | Ile | Asn | Asn | Phe | Gly | Met | Met | Val | Ser | Gly | Leu | Ile | Tyr | Ile | Asn | Asp |
| 1841 | Ser | Leu | Tyr | Tyr | Phe | Lys | Pro | Pro | Val | Asn | Asn | Leu | Ile | Thr | Gly | Phe | Val | Thr | Val | Gly |
| 1861 | Asp | Asp | Lys | Tyr | Phe | Tyr | Asn | Pro | Ile | Asn | Gly | Gly | Ala | Ala | Ser | Ile | Gly | Glu | Thr | Ile |
| 1881 | Ile | Asp | Asp | Lys | Asn | Tyr | Tyr | Phe | Asn | Gln | Ser | Gly | Val | Leu | Gln | Thr | Gly | Val | Phe | Ser |
| 1901 | Thr | Glu | Asp | Gly | Phe | Lys | Tyr | Phe | Ala | Pro | Ala | Asn | Thr | Leu | Asp | Glu | Asn | Leu | Glu | Gly |
| 1921 | Glu | Ala | Ile | Asp | Phe | Thr | Gly | Lys | Leu | Ile | Ile | Asp | Glu | Asn | Ile | Tyr | Tyr | Phe | Asp | Asp |
| 1941 | Asn | Tyr | Arg | Gly | Ala | Val | Glu | Trp | Lys | Glu | Leu | Asp | Gly | Glu | Met | His | Tyr | Phe | Ser | Pro |
| 1961 | Glu | Thr | Gly | Lys | Ala | Phe | Lys | Gly | Leu | Asn | Gln | Ile | Gly | Asp | Tyr | Lys | Tyr | Tyr | Phe | Asn |
| 1981 | Ser | Asp | Gly | Val | Met | Gln | Lys | Gly | Phe | Val | Ser | Ile | Asn | Asp | Asn | Lys | His | Tyr | Phe | Asp |
| 2001 | Asp | Ser | Gly | Val | Met | Lys | Val | Gly | Tyr | Thr | Glu | Ile | Asp | Gly | Lys | His | Phe | Tyr | Phe | Ala |
| 2021 | Glu | Asn | Gly | Glu | Met | Gln | Ile | Gly | Val | Phe | Asn | Thr | Glu | Asp | Gly | Phe | Lys | Tyr | Phe | Ala |
| 2041 | His | His | Asn | Glu | Asp | Leu | Gly | Asn | Glu | Gly | Gly | Glu | Ile | Ser | Tyr | Ser | Gly | Ile | Leu |
| 2061 | Asn | Phe | Asn | Asn | Lys | Ile | Tyr | Tyr | Phe | Asp | Asp | Ser | Phe | Thr | Ala | Val | Val | Gly | Trp | Lys |

FIGURE 11-5

```
2081  Asp Leu Glu Asp Gly Ser Lys Tyr Tyr Phe Asp Glu Asp Thr Ala Glu Ala Tyr Ile Gly
2101  Leu Ser Leu Ile Asn Asp Gly Gln Tyr Tyr Phe Asn Asp Asp Gly Ile Met Gln Val Gly
2121  Phe Val Thr Ile Asn Asp Lys Val Phe Tyr Phe Ser Asp Ser Gly Ile Ile Glu Ser Gly
2141  Val Gln Asn Ile Asp Asp Asn Tyr Phe Tyr Ile Asp Asp Asn Gly Ile Val Gln Ile Gly
2161  Val Phe Asp Thr Ser Asp Gly Tyr Lys Tyr Phe Ala Pro Ala Asn Thr Val Asn Asp Asn
2181  Ile Tyr Gly Gln Ala Val Glu Tyr Ser Gly Leu Val Arg Val Gly Glu Asp Val Tyr Tyr
2201  Phe Gly Glu Thr Tyr Thr Ile Glu Thr Gly Trp Ile Tyr Asp Met Glu Asn Gln Ser Asp
2221  Lys Tyr Tyr Phe Asn Pro Glu Thr Lys Lys Ala Cys Lys Gly Ile Asn Leu Ile Asp Asp
2241  Ile Lys Tyr Tyr Phe Asp Glu Lys Gly Ile Met Arg Thr Gly Leu Ile Ser Phe Glu Asn
2261  Asn Asn Tyr Tyr Phe Asn Glu Asn Gly Asp Met Gln Phe Gly Tyr Ile Asn Ile Glu Asp
2281  Lys Met Phe Tyr Phe Gly Glu Asp Gly Val Met Gln Ile Gly Val Phe Asn Thr Pro Asp
2301  Gly Phe Lys Tyr Phe Ala His Gln Asn Thr Leu Asp Glu Asn Phe Glu Gly Glu Ser Ile
2321  Asn Tyr Thr Gly Trp Leu Asp Leu Asp Glu Lys Arg Tyr Tyr Phe Thr Asp Glu Tyr Ile
2341  Ala Ala Thr Gly Ser Val Ile Ile Asp Gly Glu Glu Tyr Tyr Phe Asp Pro Asp Thr Ala
2361  Gln Leu Val Ile Ser Glu
```

FIGURE 11-6

B. Clostridium difficile VPI TcdB DNA sequence with translation

```
      Met Ser Leu Val Asn Arg Lys Gln Leu Glu Lys Met Ala Asn Val Arg Phe Arg Thr Gln
  1   ATG TCC CTC GTC AAT CGC AAG CAG CTG GAG AAG ATG GCC AAC GTT CGT TTC CGC ACC CAA

Glu Asp Glu Tyr Val Ala Ile Leu Asp Ala Leu Glu Glu Tyr His Asn Met Ser Glu Asn
 61   GAG GAC GAA TAC GTC GCC ATC CTC GAC GCC CTG GAA GAA TAC CAT AAC ATG AGC GAA AAC

Thr Val Val Glu Lys Tyr Leu Lys Leu Lys Asp Ile Asn Ser Leu Thr Asp Ile Tyr Ile
121   ACC GTT GTC GAG AAG TAC CTC AAG CTG AAG GAC ATC AAC AGC CTG ACG GAC ATC TAT ATC

Asp Thr Tyr Lys Lys Ser Gly Arg Asn Lys Ala Leu Lys Lys Phe Lys Glu Tyr Leu Val
181   GAC ACG TAC AAG AAG TCC GGT CGC AAC AAG GCA CTC AAG AAG TTC AAA GAG TAC CTG GTC

Thr Glu Val Leu Glu Leu Lys Asn Asn Asn Leu Thr Pro Val Glu Lys Asn Leu His Phe
241   ACC GAA GTG TTG GAA CTC AAG AAC AAC AAC CTC ACG CCG GTG GAA AAG AAC CTG CAT TTC

Val Trp Ile Gly Gly Gln Ile Asn Asp Thr Ala Ile Asn Tyr Ile Asn Gln Trp Lys Asp
301   GTG TGG ATT GGC GGC CAG ATC AAC GAC ACC GCC ATC AAC TAC ATT AAC CAG TGG AAA GAC

Val Asn Ser Asp Tyr Asn Val Asn Val Phe Tyr Asp Ser Asn Ala Phe Leu Ile Asn Thr
361   GTC AAC TCG GAC TAC AAT GTG AAT GTG TTC TAT GAC TCG AAC GCC TTT TTG ATC AAC ACG

Leu Lys Lys Thr Val Val Glu Ser Ala Ile Asn Asp Thr Leu Glu Ser Phe Arg Glu Asn
421   CTG AAG AAA ACC GTC GTG GAA TCG GCC ATC AAT GAC ACC CTG GAA AGC TTC CGT GAA AAC

Leu Asn Asp Pro Arg Phe Asp Tyr Asn Lys Phe Phe Arg Lys Arg Met Glu Ile Ile Tyr
481   CTC AAC GAT CCT CGG TTT GAC TAC AAC AAG TTT TTC CGC AAG CGC ATG GAG ATC ATC TAT

Asp Lys Gln Lys Asn Phe Ile Asn Tyr Tyr Lys Ala Gln Arg Glu Glu Asn Pro Glu Leu
541   GAC AAG CAG AAA AAC TTT ATC AAC TAC TAC AAA GCG CAG CGC GAA GAG AAC CCG GAG CTG

Ile Ile Asp Asp Ile Val Lys Thr Tyr Leu Ser Asn Glu Tyr Ser Lys Glu Ile Asp Glu
601   ATC ATC GAC GAT ATC GTG AAA ACC TAT CTG TCC AAC GAG TAT AGT AAA GAA ATC GAT GAG

Leu Asn Thr Tyr Ile Glu Glu Ser Leu Asn Lys Ile Thr Gln Asn Ser Gly Asn Asp Val
661   CTG AAC ACG TAT ATC GAA GAG AGT CTG AAC AAG ATC ACT CAG AAC AGC GGT AAC GAC GTC

Arg Asn Phe Glu Glu Phe Lys Asn Gly Glu Ser Phe Asn Leu Tyr Glu Gln Glu Leu Val
721   CGG AAC TTT GAA GAG TTC AAA AAC GGC GAG TCG TTC AAC CTC TAC GAA CAG GAG CTG GTC

Glu Arg Trp Asn Leu Ala Ala Ala Ser Asp Ile Leu Arg Ile Ser Ala Leu Lys Glu Ile
781   GAG CGC TGG AAC CTG GCA GCG GCG TCG GAC ATC CTG CGT ATC AGC GCT CTG AAA GAG ATC

Gly Gly Met Tyr Leu Asp Val Asp Met Leu Pro Gly Ile Gln Pro Asp Leu Phe Glu Ser
841   GGC GGC ATG TAC CTG GAC GTG GAT ATG CTC CCT GGC ATC CAG CCT GAT CTG TTT GAA TCG

Ile Glu Lys Pro Ser Ser Val Thr Val Asp Phe Trp Glu Met Thr Lys Leu Glu Ala Ile
901   ATT GAA AAG CCA TCG AGC GTG ACC GTC GAC TTT TGG GAG ATG ACC AAG CTG GAG GCG ATC

Met Lys Tyr Lys Glu Tyr Ile Pro Glu Tyr Thr Ser Glu His Phe Asp Met Leu Asp Glu
961   ATG AAG TAC AAA GAA TAC ATC CCG GAG TAT ACG AGT GAA CAC TTT GAT ATG CTG GAC GAA
```

FIGURE 11-7

```
     Glu Val Gln Ser Ser Phe Glu Ser Val Leu Ala Ser Lys Ser Asp Lys Ser Glu Ile Phe
1021 GAA GTG CAA TCC TCG TTT GAA AGC GTC CTG GCG AGC AGT GAT AAG AGC GAA ATC TTC

Ser Ser Leu Gly Asp Met Glu Ala Ser Pro Leu Val Lys Ile Ala Phe Asn Ser Lys
1081 TCG TCC TTG GGC GAT ATG GAG GCG TCC CCA CTG GTC AAA ATC GCC TTC AAC AGC AAG

Gly Ile Asn Gln Gly Leu Ile Ser Val Lys Asp Ser Tyr Cys Ser Asn Leu Ile Val
1141 GGC ATT AAT CAG GGC CTG ATT TCG GTC AAG GAT AGC TAC TGC AGC AAC CTG ATC GTC

Lys Gln Ile Glu Asn Arg Tyr Lys Ile Leu Asn Asn Ser Leu Asn Pro Ala Ile Ser Glu
1201 AAG CAG ATC GAG AAC CGT TAC AAG ATC CTG AAC AAC AGT CTG AAC CCC GCC ATC AGC GAA

Asp Asn Asp Phe Asn Thr Thr Asn Thr Phe Ile Asp Ser Ile Met Ala Glu Ala Asn
1261 GAT AAT GAC TTC AAT ACC ACG AAC ACG TTT ATC GAC TCC ATC ATG GCC GAA GCC AAC

Ala Asp Asn Gly Arg Phe Met Met Glu Leu Gly Leu Lys Tyr Leu Arg Val Gly Phe Phe Pro
1321 GCG GAC AAC GGC CGC TTT ATG ATG GAG TTG GGG CTG AAG TAC CTG CGC GTG GGC TTC CCG

Asp Val Lys Thr Thr Ile Asn Leu Ser Gly Pro Glu Ala Tyr Ala Ala Ala Tyr Gln Asp
1381 GAC GTG AAA ACC ACG ATC AAT CTC TCC GGC CCA GAA GCC TAT GCA GCC GCA TAC CAA GAT

Leu Leu Met Phe Lys Gly Gly Ser Met Asn Ile His Leu Ile Glu Ala Asp Leu Arg Asn
1441 CTG CTC ATG TTC AAA GGC TCG ATG AAC ATC CAT CTG ATT GAG GCG GAC TTG CGC AAC

Phe Glu Ile Ser Lys Thr Asn Ile Ser Gln Thr Glu Gln Gly Met Ala Ser Leu Trp
1501 TTC GAA ATC TCG AAA ACG AAC AGC TCG ACG GAG CAG CAG GAA ATG GCG AGC CTG TGG

Ser Phe Asp Ala Arg Ala Lys Ala Gln Phe Glu Gln Tyr Lys Asn Ile Val Arg Tyr Phe Glu
1561 TCC TTC GAC GCT CGC AAG GCC CAA TTT GAA GAG TAC AAA ATC GTC AAC TAC TTC GAA

Gly Ser Leu Gly Lys Glu Leu Lys Asp Asn Leu Ala Arg Ser Glu Ala Ala Cys Lys Glu
1621 GGC TCG CTG GGT GAG AAG CTG GAT GAC TTG GCC AGC TCC AGC CGG GAA GCG AAA GAA

Tyr Leu Leu Glu Leu Gln Leu Lys Ile Ser Tyr Gly Ala Ala Glu Leu Phe Ala Lys
1681 TAC CTG TTG GAA CTG CAA GAT AAG ATC TCG TAT GAA GCG GGG TGC AAT CTC TTC GCC AAG

Ile Val Gln Leu Gln Leu Phe Gln Lys Asn Ile Leu Glu Asp Ser Ile Glu Ala Tyr Tyr
1741 ATT GTT CAG CTG CAA GGG GAT AAG ATC TTG AAG AAC ATC GAG GAC AGT GAA ATC GCC AAG

Thr Pro Tyr Asp Ser Val Leu Phe Gln Lys Ile Asn Glu Ile Ala Pro Ile Ala Tyr Tyr
1801 ACG CCG TAC GAC TCC GTG CTG TTC CAG AAG ATC AAC GAG ATC GAA GAC ATC GCC TAC TAT

Tyr Asn Pro Gly Asp Gly Ile Glu Ile Gln Glu Lys Tyr Lys Ile Pro Ser Ile Ile
1861 TAC AAC CCC GGT GAC GGC GAA ATC CAA GAA ATT GAT AAG AAG TAC AAG ATC CCG TCC ATT ATC

Ser Asp Arg Pro Lys Ile Phe Lys Gly His Gly Lys Asp Phe Glu Asn Thr Ala Lys
1921 TCC GAT CGT CCG AAG ATC TTC AAA GGC CAC GGG AAG GAC TTC GAG AAC ACC

Asp Ile Phe Ala Gly Phe Val Asp Val Asp Ser Leu Asp Ser Thr Glu Ile Ala Ala Ile Asp
1981 GAT ATC TTC GCA GGT TTT GAC GTG GAC AGT CTC GAT AGT ACC TCG GAG ATC GAG GCC ATC GAC
```

| | | | | | | | | | | | | | | | | | | | |
|---|---|---|---|---|---|---|---|---|---|---|---|---|---|---|---|---|---|---|---|
3061 | Leu | Leu | Pro | Thr | Leu | Ser | Glu | Gly | Leu | Pro | Ile | Ile | Ala | Thr | Ile | Ile | Asp | Gly | Val | Ser
 | CTG | CTG | CCG | ACC | CTG | AGC | GAG | GGC | CTG | CCC | ATC | ATC | GCC | ACG | ATC | ATT | GAC | GGG | GTC | AGC
3121 | Leu | Gly | Ala | Ala | Ile | Lys | Glu | Lys | Leu | Ser | Glu | Thr | Ser | Asp | Pro | Leu | Arg | Gln | Glu | Ile
 | CTG | GGC | GCA | GCC | ATC | AAA | GAG | AAG | TTG | AGC | GAG | ACT | TCC | GAC | CCG | CTG | CGC | CAG | GAA | ATC
3181 | Glu | Ala | Lys | Ile | Gly | Ile | Met | Ala | Val | Asn | Leu | Thr | Thr | Ala | Thr | Thr | Ala | Ile | Ile | Thr
 | GAA | GCT | AAG | ATC | GGG | ATC | ATG | GCC | GTG | AAT | CTG | ACC | ACC | GCG | ACC | ACC | GCC | ATC | ATT | ACC
3241 | Ser | Ser | Leu | Gly | Ile | Ala | Ser | Gly | Phe | Ser | Ile | Leu | Val | Pro | Leu | Ala | Gly | Ile | Ser
 | TCC | AGC | CTC | GGC | ATT | GCC | AGC | TTC | GGC | TCC | ATC | CTG | GTC | CCC | TTG | GCG | GGC | ATC | AGC
3301 | Ala | Gly | Ile | Pro | Ser | Leu | Asn | Asn | Glu | Leu | Val | Leu | Arg | Asp | Lys | Ala | Thr | Lys | Val
 | GCC | GGT | ATC | CCT | AGC | TTG | AAC | AAC | GAG | TTG | GTC | CTG | CGT | GAT | AAA | GCC | ACC | AAG | GTT
3361 | Val | Asp | Tyr | Phe | Lys | His | Val | Ser | Leu | Ser | Leu | Glu | Thr | Gly | Val | Phe | Thr | Leu | Leu | Asp
 | GTG | GAT | TAC | TTC | AAG | CAT | GTC | TCC | CTG | TCC | CTG | GAA | ACG | GGG | GTG | TTC | ACC | CTG | CTG | GAC
3421 | Asp | Lys | Met | Met | Pro | Gln | Asp | Asp | Leu | Val | Ile | Glu | Ile | Ser | Gly | Ile | Asp | Phe | Asn | Asn
 | GAT | AAG | ATG | ATG | CCC | CAA | GAC | GAT | CTG | TTG | ATC | GAA | ATT | GAC | AGC | GGT | ATT | GAC | TTT | AAC | AAT
3481 | Ser | Ile | Val | Leu | Gly | Lys | Cys | Glu | Ile | Trp | Arg | Met | Gly | Gly | Ser | Gly | His | Thr | Val
 | TCG | ATC | GTC | CTC | GGG | AAG | TGT | GAA | ATC | TGG | CGG | ATG | GAG | GGT | TCG | GGC | CAC | ACC | GTG
3541 | Thr | Asp | Asp | Ile | Asp | Ala | Pro | Ser | Ala | Pro | Ser | Ile | Thr | Arg | Glu | Lys | Leu | Met
 | ACC | GAT | GAT | ATC | GAC | GCT | CCC | AAT | AGT | GCG | CCC | TCC | ATC | ACG | CGC | GAG | AAA | CTG | ATG
3601 | Ser | Ile | Tyr | Asp | Val | Leu | Glu | Glu | Lys | Val | Gln | Lys | Met | Gly | Gly | Tyr | Arg | Trp | Pro | Gly | Leu
 | AGC | GTC | GAC | GTG | CTC | GAG | GTG | CAG | AAA | GAA | ATG | GGT | TCG | TAC | CGG | ACG | GAG | TGG | CCA | GGC | CTC
3661 | Val | Leu | Pro | Asn | Ala | Pro | Arg | Val | Phe | Ala | Trp | Leu | Leu | Ala | Asp | Ala | Asn | Tyr | Glu | Gly
 | GTT | CTG | CCC | AAC | GCT | CCC | CGG | GTG | TTC | GCT | TGG | CTG | CTG | GCC | GAT | GCC | AAT | TAC | GAA | GGC
3721 | Arg | Ser | Leu | Glu | Asn | Ala | Gly | Thr | Phe | Ala | Ile | Leu | Asn | Asp | Ala | Ile | Arg | Asp | Ile | Thr | Arg | Ile | Glu | Lys | Pro
 | CGC | TCG | GAG | AAC | GAC | GGG | ACT | AAG | GCG | ATT | ATC | AAT | ATC | GCC | GAT | GCC | ATT | CGC | GAC | ATT | ACC | CGC | ATC | GAG | AAG | CCG
3781 | Glu | Phe | Tyr | Arg | Tyr | Asp | Phe | Ala | Ile | Arg | Ile | Asn | Asp | Ala | Ile | Asn | Thr | Arg | Ser | Phe | Ile | Val
 | GAA | TTC | TAC | CGC | TAC | GAT | TTT | GCG | ATT | CGC | TAC | GAT | GCC | ATT | AAT | ACT | CGC | AGC | TTC | ATT | GTC
3841 | Arg | Tyr | Ile | Thr | Thr | Glu | Thr | Ile | Ser | Tyr | Leu | Lys | Ser | Tyr | Phe | Tyr | Ser | Gly
 | CGG | TAC | ATC | ACC | ACT | GAA | ACT | ATA | TCC | TAC | CTG | AAG | AGC | TAT | TTT | TAC | AGC | GGT
3901 | Pro | Ile | Thr | Leu | Ser | Leu | Ser | Thr | Glu | Lys | Tyr | Ile | Arg | Met | Gly | Ile | Asn | Ile | Glu | Ile | Ser | Glu
 | CCG | ATC | ACC | CTG | AGC | CTG | TCC | ACT | GAA | AAG | TAC | ATT | CGC | ATG | GGC | ATC | AAC | ATT | GAA | ATT | TCG | CAG
3961 | Gly | Thr | Tyr | Ala | Leu | Ser | Leu | Asp | Ser | Gln | Tyr | Asn | Met | Val | Val | Arg | Asp | Val | Thr | Ile | Glu | Ser | Glu
 | GGT | ACC | TAT | GCC | CTG | AGC | CTG | GAC | AGC | CAG | TAC | AAT | ATG | GTC | GTC | CGC | GAT | GTG | ACC | ATT | GAA | TTG | TCG | CAG
4021 | Ser | Asp | Val | Trp | Ile | Ile | Asp | Ala | Ile | Thr | Arg | Asn | Val | Asn | Asp | Val | Thr | Gly | Ile | Glu | Ser | Asp
 | AGC | GAT | GTG | TGG | ATC | ATT | GAC | GCT | ATT | ACC | CGC | AAC | GTG | AAT | GAT | GTG | ACC | GTC | ACC | ATT | CAG | AGC | GAC

```
5101  Glu Ile Asn Ile Thr Pro Val Tyr Glu Thr Asn Thr Tyr Pro Glu Val Ile Leu
      GAA ATC AAT ATC ACT CCC GTC TAT GAA ACC AAC ACC TAC CCC GAG GTG ATT GTC TTG

5161  Asp Ala Asn Tyr Ile Asn Glu Lys Ile Asn Val Asn Ile Thr Asp Leu Ser Ile Arg Tyr
      GAT GCC AAC TAC ATT AAC GAA AAG ATT AAC GTG AAC ATT GAC CTG AGC ATC CGG TAT

5221  Val Trp Ser Asn Asp Gly Asn Asp Phe Ile Leu Met Ser Thr Ser Glu Glu Asn Lys Val
      GTG TGG AGT GAT AAT GAC GGG AAC GAC TTC ATT CTG ATG AGC ACC TCC GAA GAA AAA GTC

5281  Ser Gln Val Lys Ile Arg Ile Phe Val Asn Val Phe Lys Asp Lys Thr Leu Ala Asn Leu
      TCG CAA GTC AAG ATC CGC TTC GTT AAC GTT TTC AAA GAC AAG ACC TTG GCC AAC CTC

5341  Ser Phe Asn Phe Ser Asp Lys Gln Asp Val Pro Val Ser Glu Ile Ile Leu Ser Phe Thr
      AGC TTC AAT TTC TCG GAC AAA CAG GAC GTG CCT GTG TCG GAG ATC ATT CTC AGT TTC ACC

5401  Pro Ser Tyr Glu Ile Asp Lys Leu Gly Ile Gly Tyr Asp Leu Gly Leu Val Ser Leu Tyr Asn
      CCG AGC TAC GAG ATC GAC GGC ATC GGT TAC GAC CTG GGC CTG GTT AGC CTC TAC AAC

5461  Glu Lys Phe Tyr Ile Asn Asn Phe Gly Met Met Val Ser Gly Leu Ile Tyr Ile Asn Asp
      GAA AAG TTC TAT ATC AAC AAT TTC GGG ATG ATG GTT TCG GGT CTG ATC TAT ATC AAT GAC

5521  Ser Leu Tyr Tyr Tyr Phe Lys Pro Pro Val Asn Leu Ile Thr Gly Phe Val Thr Val Gly
      AGC TTG TAC TAC TAC TTC AAA CCT CCG GTG AAC TTG ATC ACC GGC TTC GTG ACC GTG GGC

5581  Asp Asp Lys Asn Tyr Phe Tyr Phe Asn Pro Ile Phe Ala Ser Ala Gln Gly Ile Phe Ile
      GAT GAC AAG AAC TAC TAT TTC AAC CCG GCC GCT GCG TCG ATT GGC GAA ACC ATC

5641  Ile Asp Lys Asp Tyr Asn Lys Leu Gln Thr Leu Asp Asn Gly Asn Leu Glu Gly
      ATC GAT AAG GAC TAC AAC AAA CAG CTG CTG CAA ACC GAC CTG GAC AAT TTG GAG GGC

5701  Thr Glu Asp Phe Phe Tyr Gly Phe Phe Lys Lys Ile Ile Ile Asp Pro Ala Pro Ile Leu Ile Asp Asp
      ACG GAG GAT TTT TAC GGC TTC TTC AAG AAA ATC ATC ATC GAC CCT GCC CCG ATT ATC GAT GAT

5761  Glu Ala Ile Asp Phe Ala Val Ala Phe Gly Leu Ile Leu Glu Ile Asp Asn Ile Tyr Tyr Phe Asp Asp
      GAA GCC ATT GAC TTC GCC GCC TTC GGC AAA CTG ATT GAC GAA AAC GAC ATC TAC TAT GAT

5821  Asn Tyr Arg Gly Ala Val Glu Trp Lys Leu Asp Gly Ile Met Tyr Tyr His Lys Phe Phe Ser Pro
      AAC TAC CGC GGT GCC GTC GAA TGG AAA GAG GAC GGG GAG ATG TAT AAG CAC TTC TCG CCA

5881  Glu Thr Gly Lys Ala Phe Gln Ile Gly Leu Asn Gln Ile Ser Tyr Lys Asn Phe Asn
      GAG ACT GGT AAG GCC TTC CAG ATC GGC CTG AAC CAG ATC AGC TAC AAG AAC TTC AAT

5941  Ser Asp Gly Val Met Gly Lys Val Gly Tyr Thr Glu Ile Lys His Phe Tyr Phe Asp
      AGC GAC GGC GTT ATG AAG GTC GGC TAT ACT GAG AAG CAT TTC TAC TTC GAC

6001  Asp Ser Gly Val Met Gln Met Lys Gln Ile Ile Asp Gly Lys His Phe Tyr Phe Ala
      GAT AGC GGC GTT ATG CAA ATG AAG CAA ATC GAC GGC AAG CAC TTC TAT TTC GCC

6061  Glu Asn Gly Asn Thr Asn Phe Val Phe Glu Thr Asp Gly Phe Lys Tyr Phe Ala
      GAG AAC GGC AAC ACC AAC TTC GTG GGC GAG GAC TTC AAA TAC TTC GCT
```

FIGURE 11-12

```
6121  His His Asn Glu Asp Leu Gly Asn Glu Glu Gly Glu Ile Ser Tyr Ser Gly Ile Leu
      CAT CAC AAC GAA GAT CTC GGT AAT GAA GAA GGT GAG ATT TCC TAT TCG ATC CTG

6181  Asn Phe Asn Lys Ile Tyr Tyr Asp Ser Phe Thr Ala Val Gly Trp Lys
      AAC TTC AAC AAG ATC TAC TAC GAC TCG TTC ACC GCC GTG GGT TGG AAG

6241  Asp Leu Glu Asp Gly Ser Lys Tyr Phe Asp Glu Asp Thr Ala Glu Ala Tyr Ile Gly
      GAC TTG GAG GAC GGG AGC AAG TAT TTC GAC GAA GAT ACC GCA GCA TAC ATC GGC

6301  Leu Ser Leu Ile Asn Asp Gly Gln Tyr Tyr Phe Asn Asp Asn Ser Gly Ile Met Gln Val Gly
      TTG TCG CTC ATC AAC GAC GGT CAG TAC TAC TTC AAC GAC AAC AGT GGC ATC ATG CAG GTG GGC

6361  Phe Val Thr Ile Asn Asp Lys Val Phe Tyr Phe Ser Asp Asn Gly Ile Ile Glu Ser Gly
      TTC GTG ACT ATC AAC GAC AAG GTG TTC TAC TTC AGT GAC AAT GGC ATC ATT GAG TCG GGC

6421  Val Gln Asn Ile Asp Asp Asn Tyr Phe Tyr Ile Asp Asp Asn Gly Ile Val Gln Ile Gly
      GTG CAG AAT ATC GAC GAT AAT TAC TTC TAT ATC GAT GAT AAT GGC ATT GTG CAG ATC GGC

6481  Val Phe Asp Thr Ser Asp Glu Tyr Phe Tyr Ile Phe Ala Pro Ala Asn Thr Val Asn Asp Asn
      GTG TTT GAT ACC TCC GAT GAG TAT TTC TAT ATC TTC GCA CCA AAT ACC GTC AAT GAC AAC

6541  Ile Tyr Gly Gln Ala Val Glu Leu Val Arg Val Gly Asp Val Tyr Tyr
      ATC TAC CAG GCC GTC GAG CTG CGT CGT GTT GGC GAC GTT TAC TAT

6601  Phe Gly Glu Thr Thr Ile Glu Gly Trp Ile Tyr Asp Met Glu Asn Glu Ser Asp
      TTC GGC GAG ACT TAT ACT ATC GGG ATC TAT GAT ATG GAA AAC GAA TCG GAT

6661  Lys Tyr Phe Asn Pro Glu Thr Lys Ala Cys Lys Gly Lys Asp Val Gly Ile Asn Leu Ile Asp Asp
      AAG TAC TTT AAC CCA GAA ACG AAA GCC TGC AAG GGG ACC ATC AAC CTC ATT GAT GAC

6721  Ile Lys Tyr Tyr Tyr Phe Asp Glu Met Arg Thr Gly Met Phe Gln Ile Leu Ile Ser Phe Glu Asn
      ATC AAG TAC TAT TAC TTT GAC ATG CGC ACC GGG TAC TTT CAG ATT CTC ATC TCG TTT GAG AAC

6781  Asn Asn Tyr Tyr Phe Asn Asp Asn Gly Met Gln Val Met Asn Gln Ile Gln Val Phe Asn Thr Pro Asp
      AAC AAC TAC TAT TTC AAC GAC AAT GGC ATG GTC ATG CAG ATT GGT CTG TTT AAC ACC CCG GAT

6841  Lys Met Phe Tyr Phe Gly Ala His Gln Asn Thr Leu Asp Gln Ile Asp Phe Gln Gly Glu Ser Ile
      AAG ATG TTC TAC TTC GGG GCC CAT CAG AAC ACT CTG GAC CAG ATT GGT CTG TTT AAC ACC

6901  Gly Phe Phe Lys Tyr Phe Leu Asp Asn Leu Asp Glu Lys Asp Tyr Phe Thr Phe Asp Glu Tyr Ile
      GGC TTC AAG TAC TTC CTC GAC CAT CAG AAC ACT CTG GAC CAG ATT GGC GGC GAA AGC ATC

6961  Asn Tyr Thr Gly Trp Leu Asp Leu Asp Lys Asp Asn Gly Glu Tyr Tyr Phe Asp Pro Asp Thr Ile
      AAT TAC ACT GGC TGG CTG GAC CTG GAT AAG GAC AAC GGC GAA TAC TAC TTC GAT CCC GAC ACC ATT

7021  Ala Ala Thr Gly Ser Val Ile Ile Asp Gly Gly Glu Tyr Tyr Phe Asp Pro Asp Thr Ala
      GCC GCC ACG GGC TCC GTG ATT ATC GAC GGC GGC GAA TAC TAC TTC GAT CCC GAC ACC GCC

7081  Gln Leu Val Ile Ser Glu
      CAG TTG GTC ATT AGC GAA
```

FIGURE 11-13

Pseudomonas Exotoxin A Amino Acid Sequence

```
  1  Ala Glu Glu Ala Phe Asp Leu Trp Asn Glu Cys Ala Lys Ala Cys Val Leu Asp Leu Lys
 21  Asp Gly Val Arg Ser Ser Arg Met Ser Val Asp Pro Ala Ile Ala Asp Thr Asn Gly Gln
 41  Gly Val Leu His Tyr Ser Met Val Leu Glu Gly Gly Asn Asp Ala Leu Lys Leu Ala Ile
 61  Asp Asn Ala Leu Ser Ile Thr Ser Asp Gly Leu Thr Ile Arg Leu Glu Gly Gly Val Glu
 81  Pro Asn Lys Pro Val Arg Tyr Ser Tyr Thr Arg Gln Ala Arg Gly Ser Trp Ser Leu Asn
101  Trp Leu Val Pro Ile Gly His Glu Lys Pro Ser Asn Ile Lys Val Phe Ile His Glu Leu
121  Asn Ala Gly Asn Gln Leu Ser His Met Ser Pro Ile Tyr Thr Ile Glu Met Gly Asp Glu
141  Leu Leu Ala Lys Leu Ala Arg Asp Ala Thr Phe Phe Val Arg Ala His Glu Ser Asn Glu
161  Met Gln Pro Thr Leu Ala Ile Ser His Ala Gly Val Ser Val Val Met Ala Gln Ala Gln
181  Pro Arg Arg Glu Lys Arg Trp Ser Glu Trp Ala Ser Gly Lys Val Leu Cys Leu Leu Asp
201  Pro Leu Asp Gly Val Tyr Asn Tyr Leu Ala Gln Gln Arg Cys Asn Leu Asp Asp Thr Trp
221  Glu Gly Lys Ile Tyr Arg Val Leu Ala Gly Asn Pro Ala Lys His Asp Leu Asp Ile Lys
241  Pro Thr Val Ile Ser His Arg Leu His Phe Pro Glu Gly Gly Ser Leu Ala Ala Leu Thr
261  Ala His Gln Ala Cys His Leu Pro Leu Glu Thr Phe Thr Arg His Arg Gln Pro Arg Gly
281  Trp Glu Gln Leu Glu Gln Cys Gly Tyr Pro Val Gln Arg Leu Val Ala Leu Tyr Leu Ala
301  Ala Arg Leu Ser Trp Asn Gln Val Asp Gln Val Ile Arg Asn Ala Leu Ala Ser Pro Gly
321  Ser Gly Gly Asp Leu Gly Glu Ala Ile Arg Glu Gln Pro Glu Gln Ala Arg Leu Ala Leu
341  Thr Leu Ala Ala Ala Glu Ser Glu Arg Phe Val Arg Gln Gly Thr Gly Asn Asp Glu Ala
361  Gly Ala Ala Ser Ala Asp Val Val Ser Leu Thr Cys Pro Val Ala Ala Gly Glu Cys Ala
```

FIGURE 13-1

```
381  Gly Pro Ala Asp Ser Gly Asp Ala Leu Leu Glu Arg Asn Tyr Pro Thr Gly Ala Glu Phe
401  Leu Gly Asp Gly Gly Asp Ile Ser Phe Ser Thr Arg Gly Thr Arg Gln Asn Trp Thr Val Glu
                    Tyr - CRM66
421  Arg Leu Leu Gln Ala His Arg Gln Leu Glu Glu Arg Gly Tyr Val Phe Val Gly Tyr His
441  Gly Thr Phe Leu Glu Ala Ala Ala Gln Ser Ile Val Phe Gly Gly Val Arg Ala Arg Ser Gln
461  Asp Leu Asp Ala Ile Trp Arg Gly Phe Tyr Ile Ala Gly Asp Pro Ala Leu Ala Tyr Gly
481  Tyr Ala Gln Asp Gln Glu Pro Asp Ala Arg Gly Arg Ile Arg Asn Gly Ala Leu Leu Arg
501  Val Tyr Val Pro Arg Ser Ser Leu Pro Gly Phe Tyr Arg Thr Gly Leu Thr Leu Ala Ala
521  Pro Glu Ala Gly Glu Val Glu Arg Leu Ile Gly His Pro Leu Pro Leu Arg Leu Asp
                                                      Δ - rEPA
541  Ala Ile Thr Gly Pro Glu Glu Glu Gly Gly Arg Leu Glu Thr Ile Leu Gly Trp Pro Leu
561  Ala Glu Arg Thr Val Val Ile Pro Ser Ala Ile Pro Thr Asp Pro Arg Asn Val Gly Gly
581  Asp Leu Asp Pro Ser Ser Ile Pro Asp Lys Glu Gln Ala Ile Ser Ala Leu Pro Asp Tyr
601  Ala Ser Gln Pro Gly Lys Pro Pro Arg Glu Asp Leu Lys
```

FIGURE 13-2 signal sequence

1   Met Arg Cys Thr Arg Ala Ile Arg Gln Thr Ala Arg Thr Gly Trp Leu Thr Trp Leu Ala
    ATG CGT TGC ACT CGG GCA ATT CGG CAA ACC GCA AGA ACA GGC TGG ACG TGG CTG GCG signal sequence
                   51

61  Ile Leu Ala Val Thr Ala Pro Val Thr Ser Pro Ala Trp Ala Asp Asp Pro Ala Thr
    ATT CTT GCC GTC ACG GCG CCC GTG ACT TCG CCA GCC GAC GAT CCT CCC GCC ACC
                                          51

121 Val Tyr Arg Tyr Asp Ser Arg Pro Arg Pro Glu Asp Val Phe Gln Asn Gly Phe Ala Trp
    GTA TAC CGC TAT GAC TCC CGC CCG CCG GAG GAC GTT TTC CAG AAC GGA TTC GCG TGG signal sequence
                                       51

181 Gly Asn Asp Asn Val Leu Asp His Leu Thr Gly Arg Ser Cys Gln Val Gly Ser Ser
    GGA AAC GAC AAT GTG CTC GAC CAT CTG ACC GGA CGT TCC TGC CAG GTC GGC AGC AGC
                                                                              51

241 Asn Ser Ala Phe Val Ser Thr Ser Ser Arg Arg Tyr Thr Glu Val Tyr Leu Glu His
    AAC AGC GCT TTC GTC TCC ACC AGC AGC CGC AGG CGC TAT ACC GAG GTC TAT CTC GAA CAT

301 Arg Met Gln Glu Val Glu Ala Val Glu Ala Arg Ala Gly Ala Gly Thr His Phe Ile Gly
    CGC ATG CAG GAA GTC GAA GCG GTC GAG GCC CGC GCC GGC ACC GGC CAC TTC ATC GGC
                                          51

361 Tyr Ile Tyr Glu Val Arg Ala Asp Asn Phe Tyr Gly Ala Ala Ser Ser Tyr Phe Glu
    TAC ATC TAC GAA GTC CGC GCC GAC AAT TTC TAC GGC GCC AGC TCG TAC TTC GAA

421 Tyr Val Asp Thr Tyr Gly Asn Ala Gly Arg Ile Leu Ala Gly Ala Leu Ala Thr Tyr
    TAC GTC GAC ACT TAT GGC AAT GCC GGC CGT ATC CTC GCC GGG CTG GCC ACC TAC
                                          51

481 Gln Ser Tyr Leu Ala His Arg Arg Ile Pro Pro Glu Asn Ile Arg Arg Val Thr Arg
    CAG AGC TAT CTG GCA CAC CGG CGG ATT CCG CCC GAA AAC ATC CGC AGG GTA ACG CGG
                                          51

541 Val Tyr His Asn Gly Ile Thr Gly Glu Thr Thr Thr Thr Glu Tyr Ser Asn Ala Arg Tyr
    GTC TAT CAC AAC GGC ATC ACC GGC GAG ACG ACC ACG ACG GAG TAT TCC AAC GCT CGC TAC

FIGURE 17-1

```
     Val Ser Gln Gln Thr Arg Ala Asn Pro Tyr Thr Ser Arg Arg Ser Val Ala Ser
601  GTC AGC CAG CAG ACT CGC GCC AAT CCC TAC ACA TCG CGA AGG TCC GTA GCG TCG
                                     S1
     Ile Val Gly Thr Leu Val Arg Met Ala Pro Val Ile Gly Ala Cys Met Ala Arg Gln Ala
661  ATC GTC GGC ACA TTG GTG CGG ATG GCG CCG GTG ATA GGC GCT TGC ATG GCG CGG CAG GCC
                                     S1
     Glu Ser Ser Glu Ala Met Ala Ala Trp Ser Glu Arg Ala Gly Glu Ala Met Val Leu Val
721  GAA AGC TCC GAG GCC ATG GCC GCA TGG TCC GAA CGC GCC GAG GCG ATG GTT CTC GTG
                                     S1
     Tyr Tyr Glu Ser Ile Ala Tyr Phe
781  TAC TAC GAA AGC ATC GCG TAT TCG TTC TAG ACC TGG CCC AGC CCC GCC CAA CTC CGG TAA
                                signal sequence
                                                                     S2
     Met Pro Ile Asp Arg Lys Thr Leu Cys His Leu Leu Ser Val Leu Pro Leu
841  TTG AAC AGC ATG CCG ATC GAC CGC AAG ACG CTC TGC CAT CTC TCC GTT CTG CCG TTG
                                signal sequence
                                         S2
     Ala Leu Leu Gly Ser His Val Ala Arg Ala Ser Thr Pro Gly Ile Val Ile Pro Pro Gln
901  GCC CTC CTC GGA TCT CAC GTG GCG CGG GCC TCC ACG CCA GGC ATC GTC ATT CCG CCG CAG
                                         S2
     Glu Gln Ile Thr Gln His Gly Ser Pro Tyr Gly Arg Cys Ala Asn Lys Thr Arg Ala Leu
961  GAA CAG ATT ACC CAG CAT GGC AGC CCC TAT GGA CGC TGC GCG AAC AAG ACC CGT GCC CTG
                                         S2
     Thr Val Ala Glu Leu Arg Gly Ser Gly Asp Leu Gln Glu Tyr Leu Arg His Val Thr Arg
1021 ACC GTG GCG GAA TTG CGC GGC AGC GGC GAT CTG CAG GAG TAC CTG CGT CAT GTG ACG CGC
                                         S2
     Gly Trp Ser Ile Phe Ala Leu Tyr Asp Gly Thr Leu Tyr Leu Gly Gly Tyr Gly Gly Val
1081 GGC TGG TCA ATA TTT GCC CTC TAC GAT GGC ACC CTC GGC GGC GAA TAT GGC GGC GTG
                                         S2
     Ile Lys Asp Gly Thr Gly Gly Ala Phe Asp Leu Lys Thr Thr Phe Cys Ile Met Thr
1141 ATC AAG GAC GGA ACA CCC GGC GGC GCA TTC GAC CTG AAA ACG ACG TTC TGC ATC ATG ACC
                                         S2
     Thr Arg Asn Thr Gly Gln Pro Ala Thr His Asp Tyr Tyr Ser Asn Val Thr Ala Thr Arg
1201 ACG CGC AAT ACG GGT CAA CCC GCA ACG CAC GAT TAC TAC AGC AAC GTC ACC GCC ACT CGC
```

FIGURE 17-2

```
                                                          S2
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
      Leu Leu Ser Thr Asn Ser Arg Leu Cys Ala Val Phe Val Arg Ser Gly Gln Pro Val
1261  CTG CTC TCC AGC AAC AGC AGG CTA TGC GCG GTC TTC GTC AGA AGC GGG CAA CCG GTC
                                                   S2
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
      Ile Gly Ala Cys Thr Ser Pro Tyr Asp Gly Lys Tyr Trp Ser Met Tyr Ser Arg Leu Arg
1321  ATT GGC GCC TGC ACC AGC CCG TAT GAC GGG AAG TAC TGG AGC ATG TAC AGC CGG CTG CGG
                                                   S2
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
      Lys Met Leu Tyr Leu Tyr Ile Tyr Val Ala Gly Ile Ser Val Arg Val His Val Ser Lys Glu
1381  AAA ATG CTT TAC CTG TAC ATC TAC GTG GCC GGC ATC TCC GTC CGC GTC CAT GTC AGC AAG GAA
                                                   S2
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
      Glu Gln Tyr Tyr Asp Tyr Glu Asp Ala Thr Phe Glu Thr Tyr Ala Leu Thr Gly Ile Ser
1441  GAA CAG TAT TAC GAC TAT GAG GAC GCA ACG TTC GAG ACT TAC GCC CTT ACC GGC ATC TCC
                                                   S2
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
      Ile Cys Asn Pro Gly Ser Ser Leu Cys
1501  ATC TGC AAT CCT GGA TCA TCC TTA TGC TGA GAC GCT TCC CCA CTC GAA CCA CCG CCC CGG
                                          signal sequence
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                                                              Val Arg Ala Leu Ala Trp Leu Ala Ser Gly
1561  GAC AGG GCG GGG CCC GGC GGT CGC GC GTG CGC GCC CTG GCG TGG TTG CTG GCA TCC GGC
                    signal sequence                S4
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
      Ala Met Thr His Leu Ser Pro Ala Leu Ala Asp Val Pro Tyr Val Leu Val Lys Thr Asn
1620  GCG ATG ACG CAT CTT TCC CCC GCC CTG GCC GAC GTT CCT TAT GTG CTG GTG AAG ACC AAT
                                                   S4
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
      Met Val Val Thr Ser Val Ala Met Lys Pro Tyr Glu Val Thr Pro Thr Arg Met Leu Val
1680  ATG GTC GTC ACC AGC GTA GCC ATG AAG CCG TAT GAA GTC ACC CCG ACG CGC ATG CTG GTC
                                                   S4
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
      Cys Gly Ile Ala Ala Lys Leu Gly Ala Ala Ala Ser Ser Pro Ala His Val Pro Phe
1740  TGC GGC ATC GCC AAA CTG GGC GCC GCG GCC AGC CCG GAC AGC CAC GTG CCG TTC
                                                   S4
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
      Cys Phe Gly Lys Asp Leu Lys Arg Pro Gly Ser Ser Pro Met Glu Val Met Leu Arg Ala
1800  TGC TTC GGC AAG GAT CTC AAG CGT CCC GGC AGT CCC ATG GAA GTC ATG TTG CGC GCC
                                                   S4
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
      Val Phe Met Gln Gln Arg Pro Leu Arg Met Phe Leu Gly Pro Lys Gln Leu Thr Phe Glu
1860  GTC TTC ATG CAA CAA CGG CCG CTG TTT CTG GGT CCC AAG CAA CTC ACT TTC GAA
```

FIGURE 17-3

```
                    S4
     Gly Lys Pro Ala Leu Ile Leu Glu Arg Met Val Glu Cys Ser Gly Lys Gln Asp Cys Pro
1920 GGC AAG CCC GCG CTC ATC CTG GAA CTG ATC CGG ATG GTC GAA TGC AGC GGC AAG CAG GAT TGC CCC T
                                                       signal sequence
                                                              S5

Met His Thr Ile Ala Ser Ile Leu Leu Ser Val Leu Gly Ile Tyr Ser
1981 GAA GGC GAA CCC C ATG CAT ACC ATC GCA TCC ATC CTG TTG TCC GTG CTC GGC ATA TAC AG
     signal sequence
                       S5

. Pro Ala Asp Val Ala Gly Leu Pro Thr His Leu Tyr Lys Asn Phe Thr Val Gln Glu Leu·
2041 C CCG GCT GAC GTC GCC GGC TTG CCG ACC CAT CTG TAC AAG AAC TTC ACT GTC CAG GAG CT
                                                                                S5

· Ala Leu Lys Leu Gly Lys Lys Asn Gln Glu Phe Cys Leu Thr Ala Phe Met Ser Gly Arg·
2101 G GCC TTG AAA CTG GGC AAG AAG AAT CAG GAG TTC TGC CTG ACC GCC TTC ATG TCG GGC AG
                                                                                S5

· Ser Leu Val Arg Ala Cys Leu Ser Asp Ala Gly His Glu His Asp Thr Trp Phe Asp Thr·
2161 A AGC CTG GTC CGG GCG TGC CTG TCC GAT GCC GGA CAC GAG CAC GAC ACG TGG TTC GAC AC
                                                                                S5

· Met Leu Gly Phe Ala Ile Ser Ala Tyr Ala Leu Lys Ser Arg Ile Ala Leu Thr Val Glu·
2221 C ATG CTT GGC TTT GCC ATA TCC GCG TAT GCG CTC AAG AGC CGG ATC GCG CTG ACG GTG GA
                                                                                S5

· Asp Ser Pro Tyr Pro Gly Thr Pro Gly Asp Leu Glu Leu Gln Ile Cys Pro Leu Asn·
2281 A GAC TCG CCG TAT CCG GGC ACT CCC GGC GAT CTG CTG GAA CTG CAG ATC TGC CCG CTC AA
                                                                                S5

· Gly Tyr Cys Glu
2341 C GGA TAT TGC GAA TG AAC CCT TCC GGA GGT TTC GAC GTT TCC GCG GAA TCC GCT TGA GAC
                                                                    signal sequence
                                                                           S3

Met Leu Ile Asn Lys Leu·
2401 GAT CTT CCG CCC TGG TTC CAT TCC AAC ACC GCA AC ATG CTG ATC AAC AAG CTG AAG C
                signal sequence
                       S3

· Leu His His Ile Leu Pro Ile Leu Val Leu Ala Leu Leu Gly Met Arg Thr Ala Gln Ala·
2461 TG CTT CAT CAC ATT CTG CCC ATC CTG GTG CTC GCC CTG CTG GGC ATG CGC ACG GCC CAG G
```

FIGURE 17-4 signal sequence

```
        Val Ala Pro Gly Ile Val Ile Pro Pro Lys Ala Leu Phe Thr Gln Gln Gly Gly Ala Tyr·
2521 CC GTT GCG CCA GGC ATC GTC ATC CCG AAG GCA CTG TTC ACC CAA CAG GGC GGC GCC T
                                                  S3

· Gly Arg Cys Pro Asn Gly Thr Arg Ala Leu Thr Val Ala Glu Leu Arg Gly Asn Ala Glu·
2581 AT GGA CGC TGC CCG AAC GGA ACC CGC GCC TTG ACC GTG GCC GAA CTG CGC GGC AAC GCC G
                                                  S3

; Leu Gln Thr Tyr Leu Arg Gln Ile Thr Pro Gly Trp Ser Ile Tyr Gly Leu Tyr Asp Gly·
2641 AA TTG CAG ACG TAT TTG CGC CAG ATA ACG CCC GGC TGG TCC ATA TAC GGT CTC TAT GAC G
                                                  S3

Thr Tyr Leu Gly Gln Ala Tyr Gly Gly Ile Ile Lys Asp Ala Pro Pro Gly Ala Gly Phe·
2701 GT ACG TAC CTG GGC CAG GCG TAC GGC GGC ATC ATC AAG GAC GCG CCG CCA GGC GCG GGG T
                                                  S3

Ile Tyr Arg Glu Thr Phe Cys Ile Thr Thr Ile Thr Lys Thr Gly Gln Pro Ala Ala Asp·
2761 TC ATT TAT CGC GAA ACT TTC TGC ATC ACG ACC ATA ACC AAG ACC GGG CAA CCG GCT GCG G
                                                  S3

· His Tyr Ser Lys Val Thr Ala Thr Arg Leu Leu Ala Ser Thr Asn Ser Arg Arg Leu Cys·
2821 AT CAC TAC TCC AAG GTC ACG GCC ACG CGC CTG CTC GCC AGC ACC AAC AGC AGG CTG T
                                                  S3

Ala Val Phe Val Arg Asp Gly Gln Ser Val Ile Gly Ala Cys Ala Ser Pro Tyr Glu Gly·
2881 GC GCG GTA TTC GTC AGG GAC CAG GGG CAA TCG GTC ATC GGA GCC TGC GCC AGC CCG TAT GAA G
                                                  S3

Arg Tyr Asp Met Tyr Asp Ala Leu Arg Arg Leu Tyr Met Ile Tyr Met Ser Gly·
2941 GC AGG TAC GAC ATG TAC GAC GCG CTG CGG CGC CTG TAC ATG ATC TAT ATG TCC G
                                                  S3

· Leu Ala Val Arg Val His Val Ser Lys Glu Glu Gln Tyr Tyr Asp Tyr Glu Asp Ala Thr·
3001 GC CTT GCC GTA CGC GTC CAC GTC AGC AAG GAG GAA CAG TAT TAC GAC TAC GAG GAC GCC A
                                                  S3

Phe Gln Thr Tyr Ala Leu Thr Gly Ile Ser Leu Cys Asn Pro Ala Ala Ser Ile Cys
3061 CA TTC CAG ACC TAT GCC CTC ACC GGC ATT TCC CTC TGC AAC CCG GCA GCG TCG ATA TGC
```

FIGURE 17-5

A. Diptheria Toxin amino acid sequence

```
  1 Gly Ala Asp Asp Val Val Asp Ser Ser Lys Ser Phe Val Met Glu Asn Phe Ser Ser Tyr
 21 His Gly Thr Lys Pro Gly Tyr Val Asp Ser Ile Gln Lys Gly Ile Gln Lys Pro Lys Ser
 41 Gly Thr Gln Gly Asn Tyr Asp Asp Asp Trp Lys Gly Phe Tyr Ser Thr Asp Asn Lys Tyr
 61 Asp Ala Ala Gly Tyr Ser Val Asp Asn Glu Asn Pro Leu Ser Gly Lys Ala Gly Gly Val
 81 Val Lys Val Thr Tyr Pro Gly Leu Thr Lys Val Leu Ala Leu Lys Val Asp Asn Ala Glu
101 Thr Ile Lys Lys Glu Leu Gly Leu Ser Leu Thr Glu Pro Leu Met Glu Gln Val Gly Thr
121 Glu Glu Phe Ile Lys Arg Phe Gly Asp Gly Ala Ser Arg Val Val Leu Ser Leu Pro Phe
141 Ala Glu Gly Ser Ser Ser Val Glu Tyr Ile Asn Asn Trp Glu Gln Ala Lys Ala Leu Ser
161 Val Glu Leu Glu Ile Asn Phe Glu Thr Arg Gly Lys Arg Gly Gln Asp Ala Met Tyr Glu
181 Tyr Met Ala Gln Ala Cys Ala Gly Asn Arg Val Arg Arg Ser Val Gly Ser Ser Leu Ser
201 Cys Ile Asn Leu Asp Trp Asp Val Ile Arg Asp Lys Thr Lys Thr Lys Ile Glu Ser Leu
221 Lys Glu His Gly Pro Ile Lys Asn Lys Met Ser Glu Ser Pro Asn Lys Thr Val Ser Glu
241 Glu Lys Ala Lys Gln Tyr Leu Glu Glu Phe His Gln Thr Ala Leu Glu His Pro Glu Leu
261 Ser Glu Leu Lys Thr Val Thr Gly Thr Asn Pro Val Phe Ala Gly Ala Asn Tyr Ala Ala
281 Trp Ala Val Asn Val Ala Gln Val Ile Asp Ser Glu Thr Ala Asp Asn Leu Glu Lys Thr
301 Thr Ala Ala Leu Ser Ile Leu Pro Gly Ile Gly Ser Val Met Gly Ile Ala Asp Gly Ala
321 Val His His Asn Thr Glu Glu Ile Val Ala Gln Ser Ile Ala Leu Ser Ser Leu Met Val
341 Ala Gln Ala Ile Pro Leu Val Gly Glu Leu Val Asp Ile Gly Phe Ala Ala Tyr Asn Phe
361 Val Glu Ser Ile Ile Asn Leu Phe Gln Val Val His Asn Ser Tyr Asn Arg Pro Ala Tyr
381 Ser Pro Gly His Lys Thr Gln Pro Phe Leu His Asp Gly Tyr Ala Val Ser Trp Asn Thr
401 Val Glu Asp Ser Ile Ile Arg Thr Gly Phe Gln Gly Glu Ser Gly His Asp Ile Lys Ile
421 Thr Ala Glu Asn Thr Pro Leu Pro Ile Ala Gly Val Leu Leu Pro Thr Ile Pro Gly Lys
441 Leu Asp Val Asn Lys Ser Lys Thr His Ile Ser Val Asn Gly Arg Lys Ile Arg Met Arg
461 Cys Arg Ala Ile Asp Gly Asp Val Thr Phe Cys Arg Pro Lys Ser Pro Val Tyr Val Gly
481 Asn Gly Val His Ala Asn Leu His Val Ala Phe His Arg Ser Ser Ser Glu Lys Ile His
501 Ser Asn Glu Ile Ser Ser Asp Ser Ile Gly Val Leu Gly Tyr Gln Lys Thr Val Asp His
521 Thr Lys Val Asn Ser Lys Leu Ser Leu Phe Phe Glu Ile Lys Ser
```

FIGURE 18-1

B. Diphtheria Toxin DNA sequence with translation

```
  1  Gly Ala As

A. Cholera Toxin A Subunit (AE003852; Protein ID AAF94614.1) with secretion leader underlined

```
  1  Met Val Lys Ile Ile Phe Val Phe Phe Ile Phe Leu Ser Ser Phe Ser Tyr Ala Asn Asp
 21  Asp Lys Leu Tyr Arg Ala Asp Ser Arg Pro Pro Asp Glu Ile Lys Gln Ser Gly Gly Leu
 41  Met Pro Arg Gly Gln Ser Glu Tyr Phe Asp Arg Gly Thr Gln Met Asn Ile Asn Leu Tyr
 61  Asp His Ala Arg Gly Thr Gln Thr Gly Phe Val Arg His Asp Asp Gly Tyr Val Ser Thr
 81  Ser Ile Ser Leu Arg Ser Ala His Leu Val Gly Gln Thr Ile Leu Ser Gly His Ser Thr
101  Tyr Tyr Ile Tyr Val Ile Ala Thr Ala Pro Asn Met Phe Asn Val Asn Asp Val Leu Gly
121  Ala Tyr Ser Pro His Pro Asp Glu Gln Glu Val Ser Ala Leu Gly Gly Ile Pro Tyr Ser
141  Gln Ile Tyr Gly Trp Tyr Arg Val His Phe Gly Val Leu Asp Glu Gln Leu His Arg Asn
161  Arg Gly Tyr Arg Asp Arg Tyr Tyr Ser Asn Leu Asp Ile Ala Pro Ala Ala Asp Gly Tyr
181  Gly Leu Ala Gly Phe Pro Pro Glu His Arg Ala Trp Arg Glu Glu Pro Trp Ile His His
201  Ala Pro Pro Gly Cys Gly Asn Ala Pro Arg Ser Ser Met Ser Asn Thr Cys Asp Glu Lys
221  Thr Gln Ser Leu Gly Val Lys Phe Leu Asp Glu Tyr Gln Ser Lys Val Lys Arg Gln Ile
241  Phe Ser Gly Tyr Gln Ser Asp Ile Asp Thr His Asn Arg Ile Lys Asp Glu Leu
```

FIGURE 19-1

B. Cholera Toxin B Amino Acid Sequence with secretion leader underlined (AE003852; Protein ID AAF94613.1)

```
  1  Met Ile Lys Leu Lys Phe Gly Val Phe Phe Thr Val Leu Leu Ser Ser Ala Tyr Ala His
 21  Gly Thr Pro Gln Asn Ile Thr Asp Leu Cys Ala Glu Tyr His Asn Thr Gln Ile Tyr Thr
 41  Leu Asn Asp Lys Ile Phe Ser Tyr Thr Glu Ser Leu Ala Gly Lys Arg Glu Met Ala Ile
 61  Ile Thr Phe Lys Asn Gly Ala Ile Phe Gln Val Glu Val Pro Gly Ser Gln His Ile Asp
 81  Ser Gln Lys Lys Ala Ile Glu Arg Met Lys Asp Thr Leu Arg Ile Ala Tyr Leu Thr Glu
101  Ala Lys Val Glu Lys Leu Cys Val Trp Asn Asn Lys Thr Pro His Ala Ile Ala Ala Ile
121  Ser Met Ala Asn
```

FIGURE 19-2

C. Cholera Toxin DNA Sequences (A and B subunit coding regions Genbank AE003852)

```
                                   Secretion Leader
       ~~~~~~~~~~~~~~~~~~~~~~~~~~~~~~~~~~~~~~~~~~~~~~~~~~~~~~~~~~~~~~~~~~~~~~~~~~~~
                                   CTA
       ~~~~~~~~~~~~~~~~~~~~~~~~~~~~~~~~~~~~~~~~~~~~~~~~~~~~~~~~~~~~~~~~~~~~~~~~~~~~~~~
       Met Val Lys Ile Ile Phe Val Phe Phe Ile Phe Leu Ser Ser Phe Ser Tyr Ala Asn Asp
    1  ATG GTA AAG ATA ATA TTT GTG TTT TTT ATT TTC TTA TCA TCA TTT TCA TAT GCA AAT GAT
                                   CTA
       ~~~~~~~~~~~~~~~~~~~~~~~~~~~~~~~~~~~~~~~~~~~~~~~~~~~~~~~~~~~~~~~~~~~~~~~~~~~~~~~
       Asp Lys Leu Tyr Arg Ala Asp Ser Arg Pro Pro Asp Glu Ile Lys Gln Ser Gly Gly Leu
   61  GAT AAG TTA TAT CGG GCA GAT TCT AGA CCT CCT GAT GAA ATA AAG CAG TCA GGT GGT CTT
                                   CTA
       ~~~~~~~~~~~~~~~~~~~~~~~~~~~~~~~~~~~~~~~~~~~~~~~~~~~~~~~~~~~~~~~~~~~~~~~~~~~~~~~
       Met Pro Arg Gly Gln Ser Glu Tyr Phe Asp Arg Gly Thr Gln Met Asn Ile Asn Leu Tyr
  121  ATG CCA AGA GGA CAG AGT GAG TAC TTT GAC CGA GGT ACT CAA ATG AAT ATC AAC CTT TAT
                                   CTA
       ~~~~~~~~~~~~~~~~~~~~~~~~~~~~~~~~~~~~~~~~~~~~~~~~~~~~~~~~~~~~~~~~~~~~~~~~~~~~~~~
       Asp His Ala Arg Gly Thr Gln Thr Gly Phe Val Arg His Asp Asp Gly Tyr Val Ser Thr
  181  GAT CAT GCA AGA GGA ACT CAG ACG GGA TTT GTT AGG CAC GAT GAT GGA TAT GTT TCC ACC
                                   CTA
       ~~~~~~~~~~~~~~~~~~~~~~~~~~~~~~~~~~~~~~~~~~~~~~~~~~~~~~~~~~~~~~~~~~~~~~~~~~~~~~~
       Ser Ile Ser Leu Arg Ser Ala His Leu Val Gly Gln Thr Ile Leu Ser Gly His Ser Thr
  241  TCA ATT AGT TTG AGA AGT GCC CAC TTA GTG GGT CAA ACT ATA TTG TCT GGT CAT TCT ACT
                                   CTA
       ~~~~~~~~~~~~~~~~~~~~~~~~~~~~~~~~~~~~~~~~~~~~~~~~~~~~~~~~~~~~~~~~~~~~~~~~~~~~~~~
       Tyr Tyr Ile Tyr Val Ile Ala Thr Ala Pro Asn Met Phe Asn Val Asn Asp Val Leu Gly
  301  TAT TAT ATA TAT GTT ATA GCC ACT GCA CCC AAC ATG TTT AAC GTT AAT GAT GTA TTA GGG
                                   CTA
       ~~~~~~~~~~~~~~~~~~~~~~~~~~~~~~~~~~~~~~~~~~~~~~~~~~~~~~~~~~~~~~~~~~~~~~~~~~~~~~~
       Ala Tyr Ser Pro His Pro Asp Glu Gln Glu Val Ser Ala Leu Gly Gly Ile Pro Tyr Ser
  361  GCA TAC AGT CCT CAT CCA GAT GAA CAA GAA GTT TCT GCT TTA GGT GGG ATT CCA TAC TCC
                                   CTA
       ~~~~~~~~~~~~~~~~~~~~~~~~~~~~~~~~~~~~~~~~~~~~~~~~~~~~~~~~~~~~~~~~~~~~~~~~~~~~~~~
       Gln Ile Tyr Gly Trp Tyr Arg Val His Phe Gly Val Leu Asp Glu Gln Leu His Arg Asn
  421  CAA ATA TAT GGA TGG TAT CGA GTT CAT TTT GGG GTG CTT GAT GAA CAA TTA CAT CGT AAT
                                   CTA
       ~~~~~~~~~~~~~~~~~~~~~~~~~~~~~~~~~~~~~~~~~~~~~~~~~~~~~~~~~~~~~~~~~~~~~~~~~~~~~~~
       Arg Gly Tyr Arg Asp Arg Tyr Tyr Ser Asn Leu Asp Ile Ala Pro Ala Ala Asp Gly Tyr
  481  AGG GGC TAC AGA GAT AGA TAT TAC AGT AAC TTA GAT ATT GCT CCA GCA GCA GAT GGT TAT
                                   CTA
       ~~~~~~~~~~~~~~~~~~~~~~~~~~~~~~~~~~~~~~~~~~~~~~~~~~~~~~~~~~~~~~~~~~~~~~~~~~~~~~~
       Gly Leu Ala Gly Phe Pro Pro Glu His Arg Ala Trp Arg Glu Glu Pro Trp Ile His His
  541  GGA TTG GCA GGT TTC CCT CCG GAG CAT AGA GCT TGG AGG GAA GAG CCG TGG ATT CAT CAT
                                   CTA
       ~~~~~~~~~~~~~~~~~~~~~~~~~~~~~~~~~~~~~~~~~~~~~~~~~~~~~~~~~~~~~~~~~~~~~~~~~~~~~~~
       Ala Pro Pro Gly Cys Gly Asn Ala Pro Arg Ser Ser Met Ser Asn Thr Cys Asp Glu Lys
  601  GCA CCG CCG GGT TGT GGG AAT GCT CCA AGA TCA TCG ATG AGT AAT ACT TGC GAT GAA AAA
```

FIGURE 19-3

```
           Thr Gln Ser Leu Gly Val Lys Phe Leu Asp Glu Tyr Gln Ser Lys Val Lys Arg Gln Ile
    661    ACC CAA AGT CTA GGT GTA AAA TTC CTT GAC GAA TAC CAA TCT AAA GTT AAA AGA CAA ATA
                                    CTA                                             CDS_1

Secretion Leader
                                    CTA
                                                                                      CTB
                                                                                   Met Ile Lys.
           Phe Ser Gly Tyr Gln Ser Asp Ile Asp Thr His Asn Arg Ile Lys Asp Glu Leu ***
    721    TTT TCA GGC TAT CAA TCT GAT ATT GAT ACA CAT AAT AGA ATT AAG GAT GAA TTA TGA TTA
                                Secretion Leader
                                                   CTB
          ·lLeu Lys Phe Gly Val Phe Phe Thr Val Leu Leu Ser Ala Tyr Ala His Gly Thr Pro·
    781    AAT TAA AAT TTG GTG TTT TTT TTA CTG ATT CTT TTA TAC TAT GCA CAT GGA ACA CCA
                                                   CTB
          ·PGln Asn Ile Thr Asp Leu Cys Ala Glu Tyr His Asn Thr Gln Ile Tyr Thr Leu Asn Asp·
    841    CTC AAA ATA TTA CTG ATT TGT GCT GAA TAC CAC AAA ACA CAA ATA TAT ACA TTG AAC GAT
                                                   CTB
          ·Alys Ile Phe Ser Tyr Glu Ser Leu Ala Gly Lys Arg Glu Met Ala Ile Ile Thr Phe·
    901    GCA ATA TTT AGT TAT GAA TCT CTA GCT GGA AAA AGA GAG ATG GCT ATA ATA ACA TTT TTT
                                                   CTB
          ·PLys Asn Gly Ala Ile Phe Gln Val Glu Val Pro Gly Ser Gln His Ile Asp Ser Gln Lys·
    961    AAA AAT GGT GCA ATT TTC CAA GTA GAA GTA CCA GGA TCA CAA CAT ATA GAT TCA CAA AAG
                                                   CTB
          ·lLys Ala Ile Glu Arg Met Lys Asp Thr Leu Arg Ile Ala Tyr Leu Thr Glu Ala Lys Val·
   1021    TTA GCT ATA GAA CGT ATG AAA GAT ACA TTA AGG ATA GCC TAT TTA ACA GAA GCT AAA GTT
                                                   CTB
          ·vGlu Lys Leu Cys Val Trp Asn Asn Lys Thr Pro His Ala Ile Ala Ile Ser Met Ala·
   1081    GAA AAA TTA TGT GTA TGG AAT AAT AAA ACT CCA CAT GCA ATA GCA ATA TCA ATG GCA
                                                   CTB
                                                  ·AAsn·
   1141    AAT ATT AA
```

FIGURE 19-4

HIGH LEVEL EXPRESSION OF RECOMBINANT TOXIN PROTEINS

CLAIM OF PRIORITY

This application claims priority under 35 U.S.C. §119(e) to U.S. Provisional Application Ser. No. 61/325,235 filed on Apr. 16, 2010, PCT/US10/30573 filed on Apr. 9, 2010, and U.S. Provisional Application Ser. No. 61/319,152 filed on Mar. 30, 2010, and is a continuation-in-part of PCT/US10/30573, filed on Apr. 9, 2010, which claims priority to U.S. Provisional Application Ser. No. 61/319,152 filed on Mar. 30, 2010. The contents of these applications are hereby incorporated by reference in their entirety.

SEQUENCE LISTING

The instant application contains a Sequence Listing which has been submitted in ASCII format via EFS-Web and is hereby incorporated by reference in its entirety. Said ASCII copy, created on Mar. 16, 2011, is named 38194201.txt and is 156,975 bytes in size.

BACKGROUND OF THE INVENTION

Microbial toxin proteins are used in medicine, as immunogens for vaccination against the toxin-producing microbe and as carrier proteins and adjuvants for other vaccines, and in scientific research as tools for studying molecular pathways.

Diphtheria toxin (DT) is a proteinaceous toxin that is synthesized and secreted by toxigenic strains of *Corynebacterium diphtheriae*. Toxigenic strains contain a bacteriophage lysogen carrying the toxin gene. DT is synthesized as a 535-amino-acid polypeptide, which undergoes proteolysis to form the mature toxin. The mature toxin comprises two subunits, A and B, joined by a disulfide bridge. The B subunit, formed from the C-terminal portion of intact DT, enables binding and entry of DT through the cell membrane and into the cytoplasm. Upon cell entry, the enzymatic A subunit, formed from the N terminal portion of intact DT, catalyzes ADP ribosylation of Elongation Factor 2 (EF-2). As a result, EF-2 is inactivated, protein synthesis stops, and the cell dies. Diphtheria toxin is highly cytotoxic; a single molecule can be lethal to a cell, and a dose of 10 ng/kg can kill animals and humans.

The CRM197 protein is a nontoxic, immunologically cross-reacting form of DT. It has been studied for its potential use as a DT booster or vaccine antigen. CRM197 is produced by *C. diphtheriae* that has been infected by the nontoxigenic phage β197tox-created by nitrosoguanidine mutagenesis of the toxigenic corynephage β. The CRM197 protein has the same molecular weight as DT but differs by a single base change (guanine to adenine) in the A subunit. This single base change results in an amino acid substitution (glutamic acid for glycine) and eliminates the toxic properties of DT.

Conjugated polysaccharide vaccines that use CRM197 as a carrier protein have been approved for human use. Vaccines include: Menveo® (Novartis Vaccines and Diagnostics), a vaccine indicated for preventing invasive meningococcal disease caused by *Neisseria meningitidis* subgroups A, C, Y, and W-135; Menjugate (Novartis Vaccines), a meningococcal group C conjugate vaccine; and Prevnar® (Wyeth Pharmaceuticals, Inc.), a childhood pneumonia vaccine that targets seven serotypes of *Streptococcus pneumoniae*, and HibTITER® (Wyeth), a *Haemophilus influenzae* type b vaccine. In addition, CRM197 has potential use as a boosting antigen for

*C. diphtheria* vaccination and is being investigated as a carrier protein for use in other vaccines.

A method for high-level expression of CRM197 for approved therapeutics and investigational use has not been reported. CRM197 has been expressed in, e.g., *C. diphtheriae, B. subtilis*, and *E. coli*, at levels that range in the tens of mg/L. A single dose of the Prevnar conjugate vaccine contains about 20 μg of CRM197. Therefore, a method for economically producing CRM197 at levels of about 1 g/L or more would greatly facilitate vaccine research and manufacture.

Cholera Toxin (CTX), produced by *Vibrio cholera*, a bacterial pathogen that causes an infection characterized by diarrhea and vomiting, is also an ADP-ribosylating toxin. CTX is an oligomeric complex made up of six protein subunits: a single copy of the Cholera toxin A subunit (CTA), and five copies of the Cholera Toxin B subunit (CTB). The five B subunits, each weighing 12 kDa, form a five-membered ring. The A subunit has an A1 portion, CTA1, a globular enzyme that ADP-ribosylates G proteins, and an A2 chain, CTA2, that forms an extended alpha helix which sits snugly in the central pore of the B subunit ring. This ring binds to GM1 ganglioside receptors on the host cell surface, resulting in internalization of the entire complex. Once internalized, the CTA1 chain is released by reduction of a disulfide bridge. CTA1 is then activated and catalyzes ADP ribosylation of adenylate cyclase. The resulting increase in adenylate cyclase activity increases cyclic AMP synthesis, which causes massive fluid and electrolyte efflux and results in diarrhea.

The B subunit of CTX, though relatively harmless, retains its ability to bind to the GM1 ganglioside receptor. CTB therefore finds use in facilitating mucosal uptake of chemically or genetically conjugated foreign antigens. It has been demonstrated to induce both mucosal and systemic immunity, and is a candidate for use in edible vaccine production. Because of its binding preference, CTB also finds use as a neuronal tracer.

Pertussis toxin (PTX) is an exotoxin and virulence factor produced by *Bordetella pertussis*, a bacterial pathogen of the human respiratory tract that causes the disease whooping cough. The pertussis holotoxin is a multi-subunit complex with an AB 5 structure. The enzymatically active A subunit (S1) is an ADP-ribosyltransferase that modifies the alpha subunit of several heterotrimeric G proteins in mammalian cells, and the B oligomer (S2, S3, two copies of S4, and S5) binds glycoconjugate receptors on cells. The five subunits of the toxin are expressed from the Pertussis Toxoid operon.

Nontoxic variants of Pertussis toxin have been explored for use in protective vaccines and as a vaccine adjuvant. There is also a need for Pertussis toxin protein to use in research, e.g., for studies of G protein signaling pathways.

Tetanus Toxin, produced by *Clostridium tetani*, is a neurotoxin having a molecular weight of 150 kDa. It is made up of two parts: a 100 kDa heavy or B-chain and a 50 kDa light or A-chain. The chains are connected by a disulfide bond. The B-chain binds to disialogangliosides (GD2 and GD1b) on the neuronal membrane. The A-chain, a zinc endopeptidase, attacks the vesicle-associated membrane protein (VAMP).

The action of the A-chain stops the affected neurons from releasing the inhibitory neurotransmitters GABA (gamma-aminobutyric acid) and glycine by degrading the protein synaptobrevin. The consequence of this is dangerous overactivity in the muscles from the smallest stimulus—the failure of inhibition of motor reflexes by sensory stimulation. This causes generalized contractions of the agonist and antagonist musculature, termed a tetanic spasm.

Tetanus Toxin Fragment C (Tet C or TTC) is a 50 kD polypeptide generated by protease cleavage (e.g., with papain) of Tetanus toxin, or through recombinant expression of the fragment. It corresponds to the 451 amino acids at the C-terminus (amino acid positions 865-1315).

Fragment C has been shown to be non-toxic. Because it binds to neurons with high specificity and affinity, TTC finds use as a targeting molecule for neuronal drug delivery or for research purposes. TTC protein is also potentially useful as a vaccine carrier protein and for use in a vaccine to protect against *C. tetani* infection.

*Clostridium difficile* Toxin B (TcdB) is a virulence factor produced by *Clostridium difficile*, which causes hospital acquired diarrhea and pseudomembranous colitis. TcdB, and a second large clostridial toxin, TcdA, are involved in the development of pseudomembranous colitis.

TcdB is a glucosylating toxin of about 270 kD, and can be divided into enzymatic, translocation and receptor binding domains. The first 546 amino acids of TcdB contain the enzymatic region, which is followed by a putative translocation and receptor-binding domain. TcdB has potential use as a protective vaccine for *C. difficile* infection, as well as in diagnostic tests and their development.

Exotoxin A (ETA or PE) of *Pseudomonas aeruginosa* is a Type II ADPRT. Like its family members Diphtheria toxin and Cholera Toxin, it inhibits protein synthesis by the ADP-ribosylation of cellular elongation factor 2. *P. aeruginosa* Exotoxin A exists as a monomer, consisting of a single polypeptide chain of 613 amino acids (66 Kd).

ETA is potentially useful as a vaccine conjugate. Nontoxic mutants of ETA have been studied as vaccine conjugates for vaccinations that protect against *Staphylococcus aureus*, malaria, and *Salmonella Typhi*.

Producing these toxins in amounts sufficient to meet expanding needs has presented significant challenges. When made in conventional protein overexpression systems, the toxin proteins are recovered in active form only at very low concentration due to degradation, improper folding, or both, depending on the specific characteristics, e.g., size and secondary structure, of the toxin. Therefore, methods for producing large amounts of these toxins, in soluble and/or active form, and at low cost is needed.

SUMMARY OF THE INVENTION

The present invention relates to a method for producing a recombinant toxin protein in a Pseudomonad host cell, said method comprising: ligating into an expression vector a nucleotide sequence encoding a toxin protein; transforming the *Pseudomonas* host cell with the expression vector; and culturing the transformed *Pseudomonas* host cell in a culture media suitable for the expression of the recombinant toxin protein; wherein the recombinant toxin protein is CRM197, Diphtheria Toxin, Cholera holotoxin, Cholera Toxin B, Pertussis toxin, Tetanus Toxin Fragment C, *C. difficile* Toxin B, or *P. aeruginosa* Exotoxin A.

In embodiments, the recombinant toxin protein is Cholera Toxin B, Cholera holotoxin, Pertussis toxin, Tetanus Toxin Fragment C, *C. difficile* Toxin B, or *P. aeruginosa* Exotoxin A.

In other embodiments, the recombinant toxin protein is Cholera Toxin B, Cholera holotoxin, Pertussis toxin, Tetanus Toxin Fragment C, or *C. difficile* Toxin B.

In other embodiments, the recombinant toxin protein is CRM197, Diphtheria Toxin, Cholera holotoxin, Cholera Toxin B, Pertussis toxin, Tetanus Toxin Fragment C, or *C. difficile* Toxin B.

In certain embodiments, the recombinant protein is produced at a yield of soluble and/or active toxin protein of about 0.2 grams per liter to about 12 grams per liter. In specific embodiments, the yield of soluble and/or active toxin protein is about 0.2 g/L, about 0.3 g/L, about 0.4 g/L, about 0.5 g/L, about 0.6 g/L, about 0.7 g/L, about 0.8 g/L, about 0.9 g/L, about 1 g/L, about 1.5 g/L, about 2 g/L, about 2.5 g/L, about 3 g/L, about 3.5 g/L, about 4 g/L, about 4.5 g/L, about 5 g/L, about 5.5 g/L, about 6 g/L, about 6.5 g/L, about 7 g/L, about 7.5 g/L, about 8 g/L, about 8.5 g/L, about 9 g/L, about 9.5 g/L, about 10 g/L, about 10.5 g/L, about 11 g/L, about 12 g/L, about 0.2 g/L to about 0.5 g/L, about 0.2 g/L to about 1 g/L, about 0.2 to about 2 g/L, about 0.3 g/L to about 0.6 g/L, about 0.3 g/L to about 1 g/L, about 0.3 to about 2 g/L, about 0.4 to about 0.7 g/L, about 0.4 to about 1 g/L about 0.4 to about 2 g/L, about 0.4 to about 3 g/L, about 0.5 g/L to about 1 g/L, about 0.5 g/L to about 2 g/L, about 0.5 g/L to about 3 g/L, about 0.5 g/L to about 4 g/L, about 0.5 g/L to about 5 g/L, about 0.5 g/L to about 6 g/L, about 0.5 g/L to about 7 g/L, about 0.5 g/L to about 8 g/L, about 0.5 g/L to about 9 g/L, about 0.5 g/L to about 10 g/L, about 0.5 g/L to about 11 g/L, about 0.5 g/L to about 12 g/L, about 1 g/L to about 2 g/L, about 1 g/L to about 3 g/L, about 1 g/L to about 4 g/L, about 1 g/L to about 5 g/L, about 1 g/L to about 6 g/L, about 1 g/L to about 7 g/L, about 1 g/L to about 8 g/L, about 1 g/L to about 9 g/L, about 1 g/L to about 10 g/L, about 1 g/L to about 11 g/L, about 1 g/L to about 12 g/L, about 2 g/L to about 3 g/L, about 2 g/L to about 4 g/L, about 2 g/L to about 5 g/L, about 2 g/L to about 6 g/L, about 2 g/L to about 7 g/L, about 2 g/L to about 8 g/L, about 2 g/L to about 9 g/L, about 2 g/L to about 10 g/L, about 2 g/L to about 11 g/L, about 2 g/L to about 12 g/L, about 3 g/L to about 4 g/L, about 3 g/L to about 5 g/L, about 3 g/L to about 6 g/L, about 3 g/L to about 7 g/L, about 3 g/L to about 8 g/L, about 3 g/L to about 9 g/L, about 3 g/L to about 10 g/L, about 3 g/L to about 11 g/L, about 3 g/L to about 12 g/L, about 4 g/L to about 5 g/L, about 4 g/L to about 6 g/L, about 4 g/L to about 7 g/L, about 4 g/L to about 8 g/L, about 4 g/L to about 9 g/L, about 4 g/L to about 10 g/L, about 4 g/L to about 11 g/L, about 4 g/L to about 12 g/L, about 5 g/L to about 6 g/L, about 5 g/L to about 7 g/L, about 5 g/L to about 8 g/L, about 5 g/L to about 9 g/L, about 5 g/L to about 10 g/L, about 5 g/L to about 11 g/L, about 5 g/L to about 12 g/L, about 6 g/L to about 7 g/L, about 6 g/L to about 8 g/L, about 6 g/L to about 9 g/L, about 6 g/L to about 10 g/L, about 6 g/L to about 11 g/L, about 6 g/L to about 12 g/L, about 7 g/L to about 8 g/L, about 7 g/L to about 9 g/L, about 7 g/L to about 10 g/L, about 7 g/L to about 11 g/L, about 7 g/L to about 12 g/L, about 8 g/L to about 9 g/L, about 8 g/L to about 10 g/L, about 8 g/L to about 11 g/L, about 8 g/L to about 12 g/L, about 9 g/L to about 10 g/L, about 9 g/L to about 11 g/L, about 9 g/L to about 12 g/L, about 10 g/L to about 11 g/L, about 10 g/L to about 12 g/L, or about 11 g/L to about 12 g/L.

In embodiments, the nucleotide sequence encoding the toxin protein is fused to a secretion signal coding sequence that when expressed directs transfer of the toxin protein to the periplasm. In embodiments, the host cell is defective in the expression of at least one protease or the host cell overexpresses at least one folding modulator, or a combination thereof.

In embodiments, the recombinant toxin protein is CRM197 and the host cell is defective in the expression of HslU, HslV, Prc1, DegP1, DegP2, and AprA. In related embodiments, the recombinant toxin protein is fused to a secretion leader that is Azu, IbpS31A, CupA2, PbpA20V, or Pbp. In embodiments, the recombinant toxin protein is CRM197 and the host cell is defective in the expression of HslU and HslV, or Prc1, or DegP1, or DegP2, or AprA. In specific embodiments, the recombinant toxin protein is CRM197 and the host cell is defective in the expression of Serralysin, HslU, HslV, Prc1, DegP1, DegP2, or AprA, or the host cell overexpresses DsbA, DsbB, DsbC, and DsbD. In embodiments, the host cell overexpresses DsbA, DsbB, DsbC, and DsbD, and the recombinant toxin protein is fused to the secretion leader Azu. In embodiments, the host cell is defective in the expression of Serralysin, and the recombinant toxin protein is fused to the secretion leader Pbp or Azu. In embodiments, the host cell is defective in the expression of HslU and HslV, and the recombinant toxin protein is fused to the secretion leader Pbp or Azu. In embodiments, the recombinant toxin protein is CRM197, the host cell is wild-type and wherein the recombinant toxin protein is fused to the secretion leader Pbp or Azu. In embodiments, the recombinant toxin protein is CRM197 and the recombinant toxin protein is fused to the secretion leader Azu, Pbp, IbpS31A, CupA2, or PbpA20V.

In other embodiments, the recombinant toxin protein is Cholera Toxin B and the host cell is defective in the expression of Lon, La, and AprA, or the host cell is defective in the expression of HslU, HslV, Prc1, DegP1, DegP2, and AprA. In related embodiments, the host cell is defective in the expression of Lon, La, and AprA and wherein the recombinant toxin protein is fused to the secretion leader Pbp A20V.

In other embodiments, the recombinant toxin protein is Pertussis toxin S1 E129A R9K and the host cell is defective in the expression of Lon, La, and AprA; GrpE, DnaK, and DnaJ; HtpX; RXF01590; or ppiB (RXF05345). In related embodiments, the recombinant toxin protein is fused to its native secretion leader.

In other embodiments, the recombinant toxin protein is Tetanus Toxin C and the host cell is defective in the expression of HslU, HslV, Prc1, DegP1, DegP2, and AprA. In related embodiments, the recombinant toxin protein is fused to the secretion leader DsbC, Pbp A20V, or CupA2.

In other embodiments, the recombinant toxin protein is Tetanus Toxin C and the host cell is defective in the expression of Lon, La, and AprA. In related embodiments, the recombinant toxin protein is fused to the secretion leader DsbA.

In other embodiments, the recombinant toxin protein is Tetanus Toxin C and the host cell is defective in the expression of GrpE, DnaK, and DnaJ. In related embodiments, the recombinant toxin protein is fused to the secretion leader NikA.

In other embodiments, the recombinant toxin protein is *C. difficile* Toxin B and the host cell is defective in the expression of: HtpX; DegP1; HslU, HslV, Prc1 and Prc2; or Lon and DegP2, or the host cell is both defective in the expression of Lon, Prc1, DegP2, AprA and overexpresses DegP2 S219A.

In embodiments, the activity of the recombinant toxin protein is measured in an activity assay, wherein about 40% to about 100% of the soluble toxin protein produced is determined to be active. In related embodiments, the activity assay is an immunological assay, a receptor-binding assay, or an enzyme assay.

In embodiments of the invention, the expression vector comprises a lac derivative promoter operatively linked to the protein coding sequence, and wherein the culturing comprises induction of the promoter using IPTG at a concentration of about 0.02 to about 1.0 mM, the cell density at induction is an optical density of about 40 to about 200 absorbance units (AU), the pH of the culture is from about 6 to about 7.5, and the growth temperature is about 20 to about 35° C.

In embodiments, the host cell is a *Pseudomonas* cell. In related embodiments, the host cell is *Pseudomonas fluorescens*.

In embodiments of the invention, the nucleotide sequence has been optimized for expression in the Pseudomonad host cell. In related embodiments, the nucleotide sequence has been optimized for expression in the *Pseudomonas* host cell. In other related embodiments, the nucleotide sequence has been optimized for expression in the *Pseudomonas fluorescens* host cell.

In embodiments, the Pertussis toxin is wild-type or S1 E129A R9K. In embodiments, the *P. aeruginosa* Exotoxin A is wild-type, CRM66, or rEPA.

In embodiments of the invention, the expression vector further comprises a tag sequence adjacent to the coding sequence for the secretion signal. In embodiments, the expression vector further comprises a tag sequence adjacent to the coding sequence for the toxin protein.

The present invention also provides a recombinant toxin protein produced according to the methods described herein. In embodiments, the recombinant toxin protein is CRM197, Diphtheria Toxin, Cholera holotoxin, Cholera Toxin B, Pertussis Toxin, Tetanus Toxin fragment C, *C. difficile* Toxin B, or *P. aeruginosa* Exotoxin A. In embodiments, the Exotoxin A is wild-type, CRM66, or rEPA. In certain embodiments, the recombinant toxin protein is produced in a strain of *P. fluorescens* identified herein as producing a high yield of the toxin or producing high quality toxin. In certain embodiments, the recombinant toxin protein is produced in a strain of *P. fluorescens* described herein as producing the highest yield of the toxin protein. In other embodiments, the recombinant toxin protein is produced in a strain described herein as one used for fermentation production of the toxin.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings.

FIG. 1. CRM197 Amino Acid and DNA Sequences. A. Amino acid sequence (SEQ ID NO: 1). B. An optimized DNA sequence (SEQ ID NO:2) encoding the CRM197 protein, with translation shown. This optimized sequence is a non-limiting example of an optimized sequence useful in the methods of the present invention.

FIG. 3. Cholera Toxin B Amino Acid and DNA Sequences. A. Amino acid sequence (SEQ ID NO: 22). B. An optimized DNA sequence (SEQ ID NO: 23) encoding the CTB protein, with translation. This optimized sequence is a non-limiting example of an optimized sequence useful in the methods of the present invention.

FIG. 6. DNA Sequence of the Pertussis Toxoid. The Pertussis toxin S1 R9K E129A DNA sequence with translation is shown (SEQ ID NO:24). The sequence is derived from Genebank entry M13223. Subunits S1-S5 and signal sequences are indicated above the sequences. The R9K and E129A mutations in 51 are underlined. Encoded proteins are disclosed as SEQ ID NOS 25, 26, 28, 29, and 27, respectively, in order of appearance.

FIG. 7. Amino Acid Sequences of Pertussis Toxoid Subunits. Secretion signals are underlined. FIG. 7A. S1 subunit (R9K E129A) (SEQ ID NO:25). FIG. 7B. S2 subunit (SEQ ID NO:26). FIG. 7C. S3 subunit (SEQ ID NO:27). FIG. 7D. S4 subunit (SEQ ID NO:28). FIG. 7E. S5 subunit (SEQ ID NO:29).

FIG. 9. Tetanus Toxin C Amino Acid and DNA Sequences. A. Amino acid sequence (SEQ ID NO:30). B. An optimized DNA sequence encoding the Tetanus Toxin C protein, with translation (SEQ ID NO:31). This optimized sequence is a non-limiting example of an optimized sequence useful in the methods of the present invention.

FIG. 11. TcdB Amino Acid and DNA Sequences. A. Amino acid sequence (SEQ ID NO:32). B. An optimized DNA sequence encoding the TcdB protein, with translation (SEQ ID NO:33). This optimized sequence is a non-limiting example of an optimized sequence useful in the methods of the present invention.

FIG. 13. Exotoxin A Amino Acid Sequence. The amino acid sequence of P. aeruginosa Exotoxin A is shown (SEQ ID NO:34). Three Exotoxin A proteins are indicated by the drawing: wild-type, CRM66, and rEPA. In variant CRM66, His 426 (bold, underlined text) is replaced by a Tyr as indicated above the sequence. In rEPA, Glu 553 (bold, underlined text) is deleted as indicated above the sequence.

FIG. 17. DNA Sequence of Wild-Type Pertussis Toxoid. The wild-type Pertussis toxin DNA sequence with translation is shown (SEQ ID NO:35). The sequence is from Genebank entry M13223. Subunits S1-S5 and signal sequences are indicated above the sequences. The encoded proteins are disclosed as SEQ ID NOS 41-45, respectively, in order of appearance.

FIG. 18. Amino Acid and DNA Sequence of Wild-Type Diphtheria toxin. A. Amino acid sequence (SEQ ID NO: 36). B. An optimized DNA sequence (SEQ ID NO:37) encoding the DT protein, with translation shown. This optimized sequence is a non-limiting example of an optimized sequence useful in the methods of the present invention. The encoded protein is disclosed as residues 1-320 of SEQ ID NO: 36.

FIG. 19. Amino Acid and DNA Sequence of Cholera Holotoxin. A. CTA amino acid sequence (SEQ ID NO: 38), with secretion leader (underlined) (AE003852; Protein ID AAF94614.1). B. CTB amino acid sequence (SEQ ID NO: 39), with secretion leader (underlined) (GenBank AE003852;

Protein ID AAF94613.1). C. CTX DNA sequence (SEQ ID NO:40) indicating the A and B subunits, with translation shown (Genbank AE003852). The encoded proteins are disclosed as SEQ ID NOS 38 and 39, respectively, in order of appearance.

Figure 20:
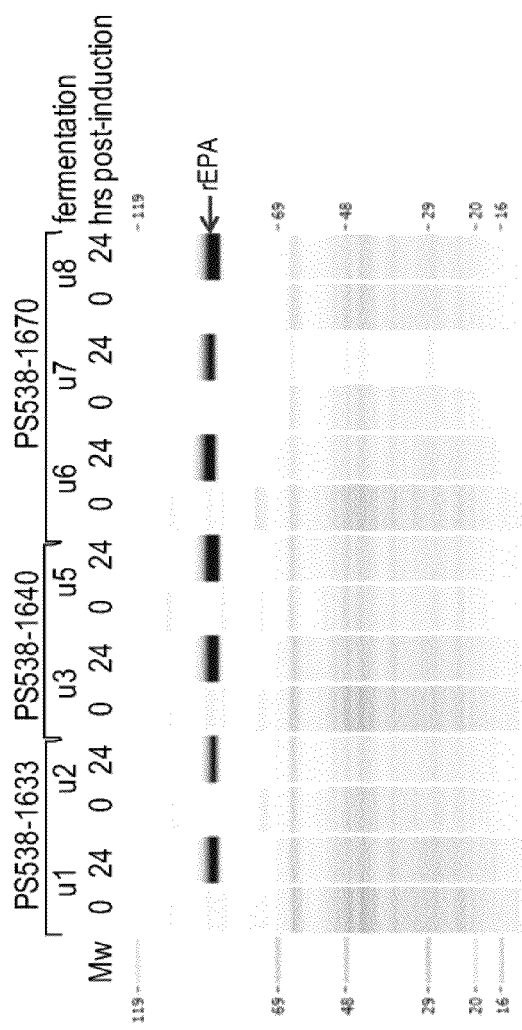

FIG. 20. SDS-CGE Gel-like Image of Soluble rEPA Production in *P. fluorescens* Fermentation Cultures. Soluble rEPA expressed in fermentation cultures of *P. fluorescens* was analyzed using capillary gel electrophoresis (SDS-CGE). Soluble fractions from fermentations of expression strains PS538-1633 (u1 and u2), PS538-1640 (u3 and u5) and PS538-1670 (u6, u7 and u8) at 0 and 24 hours post-induction tested are shown in a gel-like image generated from the SDS-CGE data. Mw=molecular weight standards (16, 20, 29, 48, and 69 kilodaltons).

FIG. 21. Soluble rEPA Production Trends in *P. fluorescens* Fermentation Cultures. Soluble rEPA expression levels, as determined by SDS-CGE analysis of strains (PS538-1633, PS538-1640 and PS538-1670) in their respective fermentations (u1, u2, u3, u6, u7 and u8), are plotted against post-induction times.

FIG. 22. Western Blot of Soluble rEPA Production in *P. fluorescens* Fermentation Cultures. Soluble rEPA expressed in fermentation cultures of *P. fluorescens* were analyzed using Western blot analysis. Soluble fractions from fermentations of expression strains PS538-1633 (u1), PS538-1640 (u3 and u5) and PS538-1670 (u6 and u8) at 0 and 24 hours post-induction are shown in a Western blot analysis using an antibody specific for *P. aeruginosa* Exotoxin A. Mw=molecular weight standards. std=rEPA standard.

FIG. 23. SDS-CGE Gel-like Image of Soluble CRM197 Production in *P. fluorescens* Fermentation Cultures. CRM197 expressed in fermentation cultures of *P. fluorescens* was analyzed using capillary gel electrophoresis (SDS-CGE). Soluble fractions from various fermentations of expression strains PS538-772 (u1 and u2), PS538-776 (u3 and u5) and PS538-782 (u6 and u7) at various times post-induction (0, 16, 21 and 23 hours) tested are shown in a gel-like image generated from the SDS-CGE data. Mw=molecular weight standards (16, 20, 29, 48, 68, and 119 kilodaltons).

FIG. 24. Soluble CRM197 Production Trends in *P. fluorescens* Fermentation Cultures. Soluble CRM197 expression levels as determined by SDS-CGE from the different strains (PS538-772, PS538-776 and PS538-782) in their respective fermentations (u1, u2, u3, u6 and u7) are plotted against post-induction times.

FIG. 25. Western Blot of Soluble CRM197 Production in *P. fluorescens* Fermentation Cultures. CRM197 expressed in fermentation cultures of *P. fluorescens* were analyzed using Western blot analysis. Soluble fractions from various fermentations of expression strains PS538-772 (u1 and u2), PS538-776 (u3 and u5) and PS538-782 (u6 and u7) at various times post-induction (0, 16, 21 and 23 hours) tested are shown in a Western blot analysis using a diphtheria toxin specific antibody. Mw=molecular weight standards (37, 50, 75, 100, 150, and 250 kilodaltons). STD=CRM197 standard.

DETAILED DESCRIPTION OF THE INVENTION

Toxins

ADP-Ribosylating Toxins

ADP-ribosylating toxins (ADPRTs) facilitate scission of the N-glycosyl bond between nicotinamide and the N-ribose of NAD and transfer the ADP-ribose moiety to target proteins. ADPRTs are classified into four families based on their respective targets. Type I ADPRTs target heteromeric GTP-binding proteins. They include Cholera Toxin (CTX), Pertussis toxin (PTX), and *Escherichia coli* heat-labile enterotoxin (LT). Type II ADPRTs (Diphtheria toxin and *Pseudomonas* Exotoxin A) modify elongation factor 2 (EF2). Type III ADPRTs (*Clostridium botulinum* C3 exoenzyme) ADP-ribosylate small GTP-binding proteins. Type IV ADPRTs ADP-ribosylate actin. These actin-specific ADPRTs include a family of binary toxins comprising *C. botulinum* C2 toxin, *C. perfringens* l-toxin, *C. difficile* toxin (a toxin distinct from TcdA and TcdB, described by Popoff, et al., 1988, "Actin-specific ADP-ribosyltransferase produced by a *Clostridium difficile* strain," Infection and Immunity 56(9):2299-2306, incorporated herein by reference), *C. spiroforme* toxin, and *Bacillus cereus* vegetative insecticidal protein (VIP).

The structures of several enzymatic components from each type of ADPRT have been determined with or without NAD, and are discussed by, e.g., Tsuge, et al., 2008, "Structural basis of actin recognition and arginine ADP-ribosylation by *Clostridium perfringens*-toxin," PNAS 105(21):7399-7404, incorporated herein by reference. Typical actin-specific ADPRTs possess two similar domains: the C domain, which is essential for catalytic activity; and the N domain, which is important for the interaction with the binding and translocation subunit. By contrast, SpvB from *Salmonella* and the type III ADPRT C3 have only one ADP-ribosyltransferase domain and lack the N-terminal adaptor domain. In all type IV ADPRTs, the EXE motif, including two key glutamate residues, is present at the catalytic center. The former glutamate of the EXE motif is thought to be a key residue for ADP-ribosyltransferase, which is deprotonated from Arg-177 in actin. The latter glutamate forms a hydrogen bond with the O'2 on N-ribose, which is thought to stabilize the oxocarbenium cation.

ADPRTs are further described by Barth, et al., 2004, "Binary Bacterial Toxins: Biochemistry, Biology, and Application of Common *Clostridium* and *Bacillus* Proteins," Microbiology and Molecular Biology Reviews 68(3):373-402; Mueller-Dieckmann, et al., "Structure of mouse ADP-ribosylhydrolase 3 (mARH3)," Acta Cryst F64:156-162; Kulich, et al., 1995, "Expression of Recombinant Exoenzyme S of *Pseudomonas aeruginosa*," Infection and Immunity 63(1):1-8; Sakurai, et al., 2009, "*Clostridium perfringens* Iota-Toxin: Structure and Function," Toxins 1:208-228; and Schirmer, et al., 2002, "The ADP-ribosylating Mosquitocidal Toxin from *Bacillus sphaericus*," The Journal of Biological Chemistry 277(14): 11941-11948, all incorporated herein by reference.

In embodiments of the present invention, a recombinant toxin protein selected from a group including ADPRTs is produced. In embodiments, the group of ADPRTs consists of CTX (CTA and/or CTB), PTX, DT (CRM197 and/or WT), and *Pseudomonas* Exotoxin A. In embodiments, the group of ADPRTs consists of CTX(CTA and/or CTB), PTX, and *Pseudomonas* Exotoxin A. In other embodiments, a recombinant toxin protein selected from a group including Type I ADPRTs is produced. In embodiments, the group of Type I ADPRTs consists of CTX (CTA and/or CTB), and PTX. In other embodiments, a recombinant toxin protein selected from a group including Type II ADPRTs is produced. In embodiments, the group of Type II ADPRTs consists of DT (CRM197 and/or WT), and *Pseudomonas* Exotoxin A. In other embodiments, a recombinant toxin protein selected from a group including Type IV ADPRTs is produced. In embodiments, the Type IV ADPRT is TcdB.

CRM197 and DT

Cross-reacting material 197 (CRM197) is a Diphtheria toxin (DT) variant produced from a DT gene having a missense mutation. DT is an ADP-ribosylating toxin; CRM197 lacks the ADP-ribosyltransferase (ADPRT) activity of DT, and is thus nontoxic. The gene for CRM197 has a single base substitution, resulting in the incorporation of glutamic acid instead of glycine at residue 52. (See, e.g., Bishai, et al., 1987, "High-Level Expression of a Proteolytically Sensitive Diphtheria toxin Fragment in *Escherichia coli*," J. Bact. 169(11): 5140-51, Giannini, et al., 1984, "The Amino-Acid Sequence of Two Non-Toxic Mutants of Diphtheria toxin: CRM45 and CRM197," Nucleic Acids Research 12(10): 4063-9, and GenBank Acc. No. 1007216A, all incorporated herein by reference.)

CRM197 protein may be prepared at low levels by methods known in the art or by expression in *C. diphtheriae* or other microorganisms. The naturally occurring, or wild-type, Diphtheria toxin may be obtained from toxin producing strains available from a variety of public sources including the American Type Culture Collection. A plasmid system for producing CRM197 protein in *C. diphtheriae* is described by, e.g., U.S. Pat. No. 5,614,382, "Plasmid for Production of CRM Protein and Diphtheria toxin," incorporated herein by reference in its entirety.

The nucleotide sequence may be prepared using the techniques of recombinant DNA technology (described by, e.g., Sambrook et al, Molecular Cloning, a Laboratory Manual, Cold Spring Harbor Laboratory Press, 1989), and also by site-directed mutagenesis, based on the known DT nucleotide sequence of the wild type structural gene for Diphtheria toxin carried by corynebacteriophage β. (See, e.g., Greenfield, et al., 1993, "Nucleotide Sequence of the Structural Gene for Diphtheria toxin Carried by Corynebacteriophage 18," Proc Nat Acad Sci 80:6953-7, incorporated herein by reference.) The nucleotide sequence can be optimized as described elsewhere herein.

In embodiments of the present invention, CRM197 or DT are produced using any of the host strains described herein in Example 1, in combination with any of the expression vectors (plasmids) described in Example 1. In embodiments, the nucleic acid sequence is optimized for expression in the Pseudomonad host cell. In embodiments, the expression vectors used contain constructs expressing any of the secretion leaders described in Table 8 and Table 3 fused to the recombinant CRM197 or DT protein. In embodiments, the native secretion leader is used. In certain embodiments, the CRM197 or DT protein is expressed with a tag, e.g., a purification tag. In embodiments, the methods of the invention are used to produce CRM197 or DT at a yield of about 0.5 g/L to at least about 12 g/L.

Cholera Toxin

Cholera toxin (CTX), produced by *Vibrio cholera*, is also an ADP-ribosylating toxin. The Cholera toxin (CTX) is an oligomeric complex made up of six protein subunits: a single copy of the Cholera toxin A subunit (CTA), and five copies of the Cholera toxin B subunit (CTB). The five B subunits, each weighing 12 kDa, form a five-membered ring. The A subunit has an A1 portion, CTA1, a globular enzyme that ADP-ribosylates G proteins, and an A2 chain, CTA2, that forms an extended alpha helix which sits snugly in the central pore of the B subunit ring. This ring binds to GM1 ganglioside receptors on the host cell surface, resulting in internalization of the entire complex. Once internalized, the CTA1 chain is released by reduction of a disulfide bridge. CTA1 is then activated and catalyzes ADP ribosylation of adenylate cyclase. The resulting increase in adenylate cyclase activity increases cyclic AMP synthesis, which causes massive fluid and electrolyte efflux and results in diarrhea.

The B subunit of CTX, though relatively harmless, retains its ability to bind to the GM1 ganglioside receptor. CTB therefore finds use in facilitating mucosal uptake of chemically or genetically conjugated foreign antigens. It has been demonstrated to induce both mucosal and systemic immunity, and is a candidate for use in edible vaccine production. Because of its binding preference, CTB also finds use as a neuronal tracer.

The use of CTB, as well as its structural features, have been described, e.g., by: Nozoye, et al., 2009, "Production of *Ascaris suum* As14 Protein and Its Fusion Protein with Cholera Toxin B Subunit in Rice Seeds," Parasitology 995-1000; Harakuni, et al., 2005, "Heteropentameric Cholera Toxin B Subunit Chimeric Molecules Genetically Fused to a Vaccine Antigen Induce Systemic and Mucosal Immune Responses: a Potential New Strategy to Target Recombinant Vaccine Antigens to Mucosal Immune Systems," Infection and Immunity 73(9):5654-5665; Price, et al., 2005, "Intranasal Administration of Recombinant *Neisseria gonorrhoeae* Transferrin Binding Proteins A and B Conjugated to the Cholera Toxin B Subunit Induces Systemic and Vaginal Antibodies in Mice," Infection and Immunity 73(7):3945-3953; and Sun, et al., 1999, "Intranasal Administration of a *Schistosoma mansoni* Glutathione S-Transferase-Cholera Toxoid Conjugate Vaccine Evokes Antiparasitic and Antipathological Immunity in Mice," J. Immunol. 163:1045-1052, all incorporated herein by reference.

In embodiments of the present invention, CTB or CTX is produced using any of the host strains described herein in Example 1, in combination with any of the expression vectors described in Example 3. In embodiments, the nucleic acid sequence is optimized for expression in the Pseudomonad host cell. In embodiments, the expression vectors used contain constructs expressing any of the secretion leaders described in Table 8 and Table 3 fused to the recombinant CTB or CTX protein. In embodiments, the native secretion leader is used. In certain embodiments, the CTB or CTX protein is expressed with a tag, e.g., a purification tag. In embodiments, the methods of the invention are used to produce CTB or CTX at a yield of about 0.2 g/L to at least about 5 g/L.

Pertussis Toxin

Pertussis toxin is an exotoxin and virulence factor produced by *Bordetella pertussis*, a bacterial pathogen of the human respiratory tract that causes the disease whooping cough. The pertussis holotoxin is a multi-subunit complex with an AB 5 structure. The enzymatically active A subunit (S1) is an ADP-ribosyltransferase that modifies the alpha subunit of several heterotrimeric G proteins (primarily G i proteins) in mammalian cells, and the B oligomer (S2, S3, 2 copies of S4, and S5) binds glycoconjugate receptors on cells. S1 is proteolytically processed after cell entry. Carbonetti, et al., 2005, "Proteolytic Cleavage of Pertussis Toxin S1 Subunit is Not Essential for Its Activity in Mammalian Cells," BMC Microbiology 5:7, incorporated herein by reference, reported that processing of S1 is not essential for its cytotoxic activity in mammalian cells.

Nontoxic variants of Pertussis toxin have been explored for use in vaccines. Pertussis toxin protein produced using the methods of the present invention is contemplated for use in a vaccine to protect against pertussis. Pertussis toxin has also been tested as a vaccine adjuvant, e.g., as described by Roberts, et al., 1995, "A Mutant Pertussis Toxin Molecule That Lacks ADP-Ribosyltransferase Activity, PT-9K/129G, Is an Effective Mucosal Adjuvant for Intranasally Delivered Proteins," Infection and Immunity 63(6):2100-2108, incorporated herein by reference. Further, Pertussis toxin is also useful for research purposes, e.g., for studies of G protein signaling pathways (e.g., McCoy, et al., 2010, "PAR1 and PAR2 couple to overlapping and distinct sets of G proteins and linked signaling pathways to differentially regulate cell physiology," Molecular Pharmacology Fast Forward MOL 62018, incorporated herein by reference) and as an adjuvant to enhance induction of autoimmune diseases, e.g., experimental autoimmune encephalomyelitis (EAE), experimental autoimmune orchitis, experimental autoimmune uveitis, etc. (Su, et al., 2001, "Pertussis Toxin Inhibits Induction of Tissue-Specific Autoimmune Disease by Disrupting G Protein-Coupled Signals," J Immunol 167:250-256. incorporated herein by reference).

Figure 5:
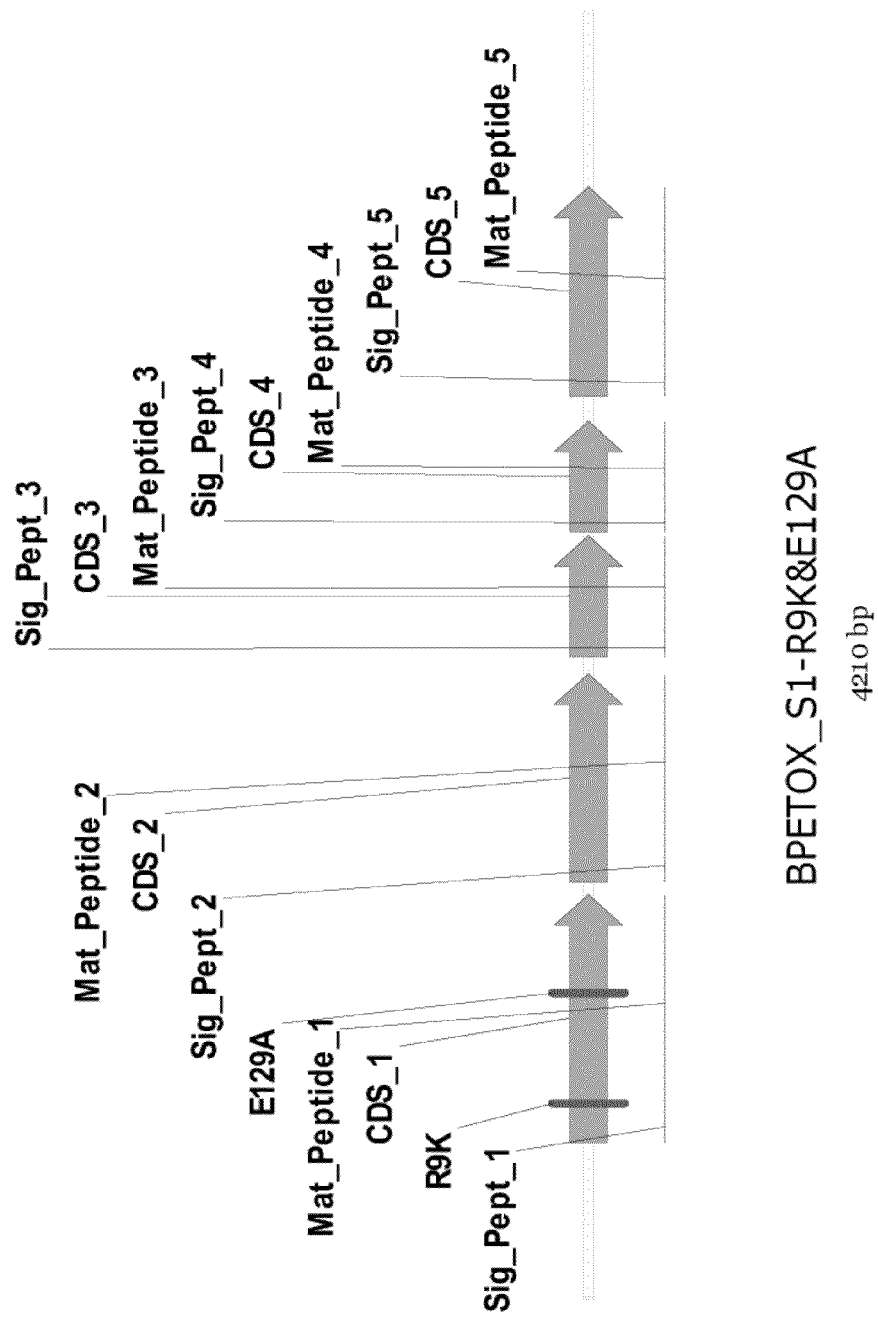
FIG. 5. Pertussis Toxoid Operon. BPETOX_S1-R9K & E129A, having 4210 basepairs, is shown.

The five subunits of the toxin are expressed from the Pertussis Toxoid operon, shown in FIG. 5. The expression and structure of Pertussis toxin proteins, including certain variants, are described by above-cited reports, as well as by Burnette, et al., 1992, "Properties of Pertussis Toxin B Oligomer Assembled In Vitro from Recombinant Polypeptides Produced by *Escherichia coli*," Infection and Immunity 60(6):2252-2256; U.S. Pat. No. 5,085,862, "Genetic detoxification of pertussis toxin;" and Kaslow, et al., 1987, "Structure-Activity Analysis of the Activation of Pertussis Toxin," Biochemistry 26(1):123-7; all incorporated by reference herein in their entirety.

Pertussis Toxin or PTX as used herein refers to Pertussis Toxin mutant S1 R9K E129A or the wild-type protein. Wild-type Pertussis toxin and Pertussis toxin mutant S1 R9K E129A are described by, e.g.: Roberts, et al., 1995 (cited above); U.S. Pat. No. 7,427,404 and U.S. Pat. No. 7,666,436, both titled, "Pertussis Toxin Mutants, *Bordetella* Strains Capable of Producing Such Mutants and Their Use in the Development of Antipertussis Vaccines;" U.S. Pat. No. 5,935, 580, "Recombinant Mutants for Inducing Specific Immune Responses;" U.S. Pat. No. 7,169,399, "Non-Toxic Double Mutant Forms of Pertussis Toxin as Adjuvants;" U.S. Pat. No. 5,785,971 and U.S. Pat. No. 5,427,788, both titled, "Pertussis Toxin and Use in Vaccines;" and U.S. Pat. No. 5,773,600, "DNA Encoding Pertussis Toxin Muteins," all incorporated herein by reference in their entirety.

In embodiments of the present invention, Pertussis toxin mutant S1 E129A or wild-type Pertussis toxin is produced using any of the host strains described herein in Example 1, 5 and 7. In embodiments, the expression vectors used contain constructs expressing any of the secretion leaders described in Table 8 and Table 3 fused to the recombinant PTX protein. In embodiments, the native secretion leader is used. In embodiments, any or all of the subunit encoding sequences are optimized for expression in the Pseudomonad host selected, as described elsewhere herein. In certain embodiments, the subunits are expressed from two or more constructs, for example, by subcloning the individual sequences according to methods well-known in the art. In certain embodiments, the PTX protein is expressed with a tag, e.g., a purification tag. In embodiments, the methods of the invention are used to produce PTX or each individual subunit of PTX at a yield of about 0.2 g/L to at least about 5 g/L.

Tetanus Toxin Fragment C

Tetanus Toxin, produced by *Clostridium tetani*, is a neurotoxin having a molecular weight of 150 kDa. It is made up of two parts: a 100 kDa heavy or B-chain and a 50 kDa light or A-chain. The chains are connected by a disulfide bond. The B-chain binds to disialogangliosides (GD2 and GD1b) on the neuronal membrane. The A-chain, a zinc endopeptidase, attacks the vesicle-associated membrane protein (VAMP).

The action of the A-chain stops the affected neurons from releasing the inhibitory neurotransmitters GABA (gamma-aminobutyric acid) and glycine by degrading the protein synaptobrevin. The consequence of this is dangerous overactivity in the muscles from the smallest stimulus—the failure of inhibition of motor reflexes by sensory stimulation. This causes generalized contractions of the agonist and antagonist musculature, termed a tetanic spasm.

Tetanus Toxin Fragment C (Tet C or TTC) is a 50 kD polypeptide generated by protease cleavage (e.g., with papain) of Tetanus toxin, or through recombinant expression of the fragment. It corresponds to the 451 amino acids at the C-terminus (amino acid positions 865-1315). Recombinant expression of Fragment C is disclosed in, e.g., U.S. Pat. No. 5,443,966, "Expression of Tetanus Toxin Fragment C," WO/2005/000346, "Carrier Proteins for Vaccines," and U.S. Pat. No. 6,010,871, "Modification of Peptide and Protein," all incorporated herein by reference in their entirety.

Fragment C has been shown to be non-toxic and capable of stimulating a protective immune response in mice and guinea pigs. U.S. Pat. No. 5,443,966 describes the sequence of Tetanus Toxin and production of Fragment C in *E. coli*. Expression of recombinant TTC in yeast has been described, e.g., in U.S. Pat. No. 5,571,694, "Expression of Tetanus Toxin Fragment C in Yeast," incorporated herein by reference in its entirety.

Because it binds to neurons with high specificity and affinity, TTC finds use as a targeting molecule for neuronal drug delivery or for research purposes. Such use is described by, e.g., Townsend, et al., 2007, "Tetanus toxin C fragment conjugated nanoparticles for targeted drug delivery to neurons," Biomaterials 28(34):5176-5184, incorporated herein by reference.

TTC protein is also potentially useful as a vaccine carrier protein, as described in, e.g., WO/2005/000346, and has been explored for use in a vaccine to protect against *C. tetani* infection.

In embodiments of the present invention, TTC is produced using any of the host strains described herein in Example 1, in combination with any of the expression vectors described in Example 8. In embodiments, the nucleic acid sequence is optimized for expression in the Pseudomonad host cell. In embodiments, the expression vectors used have constructs expressing any of the secretion leaders described in Table 8 and Table 3 fused to the recombinant TTC protein. In certain embodiments, the TTC protein is expressed with a tag, e.g., a purification tag. In embodiments, the native secretion leader is used. In embodiments, the methods of the invention are used to produce TTC at a yield of about 0.5 g/L to at least about 12 g/L.

*C. difficile* Toxin B

*Clostridium difficile* Toxin B (TcdB) is a virulence factor produced by *Clostridium difficile*, which causes hospital acquired diarrhea and pseudomembranous colitis. TcdB, and a second large clostridial toxin, TcdA, are involved in the development of pseudomembranous colitis.

TcdB, a glucosylating toxin of about 270 kD, can be divided into enzymatic, translocation and receptor binding domains. The first 546 amino acids of TcdB contain the enzymatic region, which is followed by a putative translocation and receptor-binding domain. Enzymatic activity has been reported to require the amino-terminal 546 residues, as amino or carboxy-terminal deletions of this fragment decrease activity. Within the enzymatic region, tryptophan 102 has been shown to be essential for UDP-glucose binding. A conserved DXD motif within LCTs is essential for LCT glucosyltransferase activity. Studies involving analysis of chimeras of the TcdB and TcsL enzymatic domain suggest that residues 364 to 516 confer substrate specificity.

The structure of TcdB and its expression and potential use as a protective vaccine for *C. difficile* infection are discussed in, e.g.: U.S. Pat. No. 7,226,597, "Mutants of *Clostridium Difficile* Toxin B and Methods of Use;" Jank, et al., 2008, "Structure and mode of action of clostridial glucosylating toxins: the ABCD model," Trends in Microbiology 16(5): 222-229; Sullivan, et al., 1982, "Purification and Characterization of Toxins A and B of *Clostridium difficile*," Infection and Immunity 35(3):1032-1040; and Yang, et al., 2008, "Expression of recombinant *Clostridium difficile* toxin A and B in *Bacillus megaterium*," BMC Microbiology 8:192, all incorporated herein by reference in their entirety.

In embodiments of the present invention, TcdB is produced using any of the host strains described herein in Examples 1, 5 and 7. In embodiments, the nucleic acid sequence is optimized for expression in the Pseudomonad host cell. In embodiments, the expression vectors used contain constructs expressing any of the secretion leaders described in Table 8 and Table 3 fused to the recombinant TcdB protein. In embodiments, the native secretion leader is used. In certain embodiments, the TcdB protein is expressed with a tag, e.g., a purification tag. In embodiments, the methods of the invention are used to produce TcdB at a yield of about 0.5 g/L to at least about 10 g/L.

*Pseudomonas Aeruginosa* Exotoxin A

Exotoxin A (ETA or PE) of *Pseudomonas aeruginosa* is a Type II ADPRT. It is one member of a family of secreted bacterial toxins capable of translocating a catalytic domain into mammalian cells and inhibiting protein synthesis by the ADP-ribosylation of cellular elongation factor 2. The protein exists as a monomer, consisting of a single polypeptide chain of 613 amino acids (66 Kd). The x-ray crystallographic structure of exotoxin A, determined to 3.0-A resolution, shows an amino-terminal domain, composed primarily of antiparallel beta-structure and comprising approximately half of the molecule; a middle domain composed of alpha-helices; and a carboxyl-terminal domain comprising approximately one-third of the molecule. The carboxyl-terminal domain is the ADP-ribosyltransferase of the toxin. The other two domains are presumably involved in cell receptor binding and membrane translocation.

The toxin binds to cells through a specific receptor on the cell surface, then the toxin-receptor complex is internalized into the cell. Finally, ETA is transferred to the cytosol where it enzymatically inhibits protein synthesis. The transfer process is believed to occur from an acidic compartment, since cellular intoxication is prevented by weak bases such as NH4+, which raises the pH in acidic vesicles. Upon exposure to acidic conditions, the hydrophobic domain of PE enters into the membrane, resulting in the formation of a channel through which the enzymatic domain, in extended form, passes into the cytosol. The activity of PE and mutants having reduced toxicity are described in, e.g., U.S. Pat. No. 4,892,827, "Recombinant *Pseudomonas* Exotoxins: Construction of an Active Immunotoxin with Low Side Effects," and by Lukac, et al., 1988, "Toxoid of *Pseudomonas aeruginosa* Exotoxin A Generated by Deletion of an Active-Site Residue," Infection and Immunity 56(12): 3095-3098, both incorporated herein by reference in their entirety.

Use of Exotoxin A mutant rEPA as a vaccine conjugate is described by, e.g.: Fattom, et al., 1993, "Laboratory and Clinical Evaluation of Conjugate Vaccines Composed of *Staphylococcus aureus* Type 5 and Type 8 Capsular Polysaccharides Bound to *Pseudomonas aeruginosa* Recombinant Exoprotein A," Infection and Immunity 61(3):1023-1032; Qian, et al., 2007, "Conjugating recombinant proteins to *Pseudomonas aeruginosa* ExoProtein A: a strategy for enhancing immunogenicity of malaria vaccine candidates," Vaccine 25(20):3923-3933; and Lin, et al., 2001. "The Efficacy of a *Salmonella Typhi* Vi Conjugate Vaccine in Two-To-Five-Year-Old Children," N Engl J Med 344(17): 1263-1269, both incorporated herein by reference.

*Pseudomonas aeruginosa* Exotoxin A as used herein refers to *Pseudomonas aeruginosa* Exotoxin A mutant CRM66, deletion rEPA, or the wild-type protein. In embodiments of the present invention, Exotoxin A is produced using any of the host strains described herein in Examples 1, 5 and 7, and using expression vectors having constructs expressing any of the secretion leaders described in Table 8 and Table 3 fused to the recombinant Exotoxin A protein. In embodiments, the nucleic acid sequence is optimized for expression in the Pseudomonad host cell. In embodiments, the native secretion leader is used. In certain embodiments, the ETA protein is expressed with a tag, e.g., a purification tag. In embodiments, the methods of the invention are used to produce Exotoxin A at a yield of about 0.5 g/L to at least about 12 g/L.

Exemplary toxin proteins produced using the methods of the invention are listed in Table 1. It is understood that this list is not limiting. In embodiments of the invention, any of the nucleic acid sequences of the toxins described herein for production using the methods of the invention can be optimized for expression in the Pseudomonad host cell selected. As described elsewhere herein, there are multiple options for optimization of any given sequence. Any of the options as described are contemplated for use in optimizing the sequences of the toxins produced using the methods of the present invention. The optimized sequences provided herein are non-limiting examples of optimized sequences useful in the methods of the present invention.

TABLE 1

Exemplary Toxin Proteins

| Target | Exemplary Sequence Source/Reference | Origin |
|---|---|---|
| CRM197 | GenBank Acc. No. 1007216A | *Corynebacterium diphtheriae* NCTC 13129 |
| Diphtheria toxin (WT) | GenBank NC_002935.2 GenBank CAA00374.1 | *Corynebacterium diphtheriae* |
| Cholera Holotoxin | GenBank NC_002505.1; NP231099.1 and NP23110.1 | *Vibrio cholerae* |
| Cholera Toxin B | GenBank ACH70471 (E1 Tor strain) | *Vibrio cholerae* O1 biovar E1 tor |
| Pertussis Toxin | GenBank M13223.1 with mutations in S1 | *Bordetella pertussis* |
| Tetanus Toxin C Fragment | GenBank 1A8D_A | *Clostridium tetani* |
| *C. difficile* Tox B VPI (TcdB) | GenBank CAA63562 | *Clostridium difficile* |
| *P. aeruginosa* Exotoxin A | GenBank NP_249839 | *Pseudomonas aeruginosa* PAO1 |

Codon Optimization

In heterologous expression systems, optimization steps may improve the ability of the host to produce the foreign protein. Protein expression is governed by a host of factors including those that affect transcription, mRNA processing, and stability and initiation of translation. The polynucleotide optimization steps may include steps to improve the ability of the host to produce the foreign protein as well as steps to assist the researcher in efficiently designing expression constructs. Optimization strategies may include, for example, the modification of translation initiation regions, alteration of mRNA structural elements, and the use of different codon biases. Methods for optimizing the nucleic acid sequence of to improve expression of a heterologous protein in a bacterial host are known in the art and described in the literature. For example, optimization of codons for expression in a *Pseudomonas* host strain is described, e.g., in U.S. Pat. App. Pub. No. 2007/0292918, "Codon Optimization Method," incorporated herein by reference in its entirety.

Optimization can thus address any of a number of sequence features of the heterologous gene. As a specific example, a rare codon-induced translational pause can result in reduced heterologous protein expression. A rare codon-induced translational pause includes the presence of codons in the polynucleotide of interest that are rarely used in the host organism may have a negative effect on protein translation due to their scarcity in the available tRNA pool. One method of improving optimal translation in the host organism includes performing codon optimization which can result in rare host codons being removed from the synthetic polynucleotide sequence.

Alternate translational initiation also can result in reduced heterologous protein expression. Alternate translational initiation can include a synthetic polynucleotide sequence inadvertently containing motifs capable of functioning as a ribosome binding site (RBS). These sites can result in initiating translation of a truncated protein from a gene-internal site. One method of reducing the possibility of producing a truncated protein, which can be difficult to remove during purification, includes eliminating putative internal RBS sequences from an optimized polynucleotide sequence.

Repeat-induced polymerase slippage can result in reduced heterologous protein expression. Repeat-induced polymerase slippage involves nucleotide sequence repeats that have been shown to cause slippage or stuttering of DNA polymerase which can result in frameshift mutations. Such repeats can also cause slippage of RNA polymerase. In an organism with a high G+C content bias, there can be a higher degree of repeats composed of G or C nucleotide repeats. Therefore, one method of reducing the possibility of inducing RNA polymerase slippage, includes altering extended repeats of G or C nucleotides.

Interfering secondary structures also can result in reduced heterologous protein expression. Secondary structures can sequester the RBS sequence or initiation codon and have been correlated to a reduction in protein expression. Stemloop structures can also be involved in transcriptional pausing and attenuation. An optimized polynucleotide sequence can contain minimal secondary structures in the RBS and gene coding regions of the nucleotide sequence to allow for improved transcription and translation.

Another feature that can effect heterologous protein expression is the presence of restriction sites. By removing restriction sites that could interfere with subsequent subcloning of transcription units into host expression vectors a polynucleotide sequence can be optimized.

For example, the optimization process can begin by identifying the desired amino acid sequence to be heterologously expressed by the host. From the amino acid sequence a candidate polynucleotide or DNA sequence can be designed. During the design of the synthetic DNA sequence, the frequency of codon usage can be compared to the codon usage of the host expression organism and rare host codons can be removed from the synthetic sequence. Additionally, the synthetic candidate DNA sequence can be modified in order to remove undesirable enzyme restriction sites and add or remove any desired signal sequences, linkers or untranslated regions. The synthetic DNA sequence can be analyzed for the presence of secondary structure that may interfere with the translation process, such as G/C repeats and stem-loop structures. Before the candidate DNA sequence is synthesized, the optimized sequence design can be checked to verify that the sequence correctly encodes the desired amino acid sequence. Finally, the candidate DNA sequence can be synthesized using DNA synthesis techniques, such as those known in the art.

In another embodiment of the invention, the general codon usage in a host organism, such as *P. fluorescens*, can be utilized to optimize the expression of the heterologous polynucleotide sequence. The percentage and distribution of codons that rarely would be considered as preferred for a particular amino acid in the host expression system can be evaluated. Values of 5% and 10% usage can be used as cutoff values for the determination of rare codons. For example, the codons listed in Table 2 have a calculated occurrence of less than 5% in the *P. fluorescens* MB214 genome and would be generally avoided in an optimized gene expressed in a *P. fluorescens* host.

TABLE 2

| Codons occurring at less than 5% in *P. fluorescens* MB214 | | |
|---|---|---|
| Amino Acid(s) | Codon(s) Used | % Occurrence |
| G Gly | GGA | 3.26 |
| I Ile | ATA | 3.05 |
| L Leu | CTA | 1.78 |
|  | CTT | 4.57 |
|  | TTA | 1.89 |
| R Arg | AGA | 1.39 |
|  | AGG | 2.72 |
|  | CGA | 4.99 |
| S Ser | TCT | 4.28 |

The present invention contemplates the use of any coding sequence for the toxins produced, including any sequence that has been optimized for expression in the *Pseudomonas* host cell being used. Sequences contemplated for use can be optimized to any degree as desired, including, but not limited to, optimization to eliminate: codons occurring at less than 5% in the *Pseudomonas* host cell, codons occurring at less than 10% in the *Pseudomonas* host cell, a rare codon-induced translational pause, a putative internal RBS sequence, an extended repeat of G or C nucleotides, an interfering secondary structure, a restriction site, or combinations thereof.

Furthermore, the amino acid sequence of any secretion leader useful in practicing the methods of the present invention can be encoded by any appropriate nucleic acid sequence.

Expression Systems

Methods for expressing heterologous proteins, including useful regulatory sequences (e.g., promoters, secretion leaders, and ribosome binding sites), in *Pseudomonas* host cells, as well as host cells useful in the methods of the present invention, are described, e.g., in U.S. Pat. App. Pub. No. 2008/0269070 and U.S. patent application Ser. No. 12/610,207, both titled "Method for Rapidly Screening Microbial Hosts to Identify Certain Strains with Improved Yield and/or Quality in the Expression of Heterologous Proteins," U.S. Pat. App. Pub. No. 2006/0040352, "Expression of Mammalian Proteins in *Pseudomonas Fluorescens*," and U.S. Pat. App. Pub. No. 2006/0110747, "Process for Improved Protein Expression by Strain Engineering," all incorporated herein by reference in their entirety. These publications also describe bacterial host strains useful in practicing the methods of the invention, that have been engineered to overexpress folding modulators or wherein protease mutations, including deletions, have been introduced, in order to increase heterologous protein expression.

Leaders

Sequence leaders are described in detail in U.S. Patent App. Pub. Nos. 2008/0193974 and 2010/0048864, both titled, "Bacterial Leader Sequences for Increased Expression," and U.S. Pat. App. Pub. No. 2006/0008877, "Expression systems with Sec-secretion," all incorporated herein by reference in their entirety, as well as in U.S. Pat. App. Pub. No. 2008/0269070 and U.S. patent application Ser. No. 12/610,207.

In embodiments, a sequence encoding a secretion leader is fused to the sequence encoding the toxin protein. In embodiments, the secretion leader is a periplasmic secretion leader. In embodiments, the secretion leader is the native secretion leader.

TABLE 3

Exemplary Secretion Leader Sequences

| Secretion Leader | Amino Acid Sequence | SEQ ID NO: |
|---|---|---|
| DsbA | MRNLILSAALVTASLFGMTAQA | 3 |
| Azu | MFAKLVAVSLLTLASGQLLA | 4 |
| Ibp-S31A | MIRDNRLKTSLLRGLTLTLLSLTLLSPAAHA | 5 |
| Tpr | MNRSSALLLAFVFLSGCQAMA | 6 |
| CupB2 | MLFRTLLASLTFAVIAGLPSTAHA | 7 |
| CupA2 | MSCTRAFKPLLLIGLATLMCSHAFA | 8 |
| NikA | MRLAALPLLLAPLFIAPMAVA | 9 |
| Pbp A20V | MKLKRLMAAMTFVAAGVATVNAVA | 10 |
| DsbC | MRLTQIIAAAAIALVSTFALA | 11 |
| TolB | MRNLLRGMLVVICCMAGIAAA | 12 |
| Pbp | MKLKRLMAAMTFVAAGVATANAVA | 13 |
| Lao | MQNYKKFLLAAAVSMAFSATAMA | 14 |
| CupC2 | MPPRSIAACLGLLGLLMATQAAA | 15 |
| PorE | MKKSTLAVAVTLGAIAQQAGA | 16 |
| Pbp | MKLKRLMAAMTFVAAGVATANAVA | 17 |
| FlgI | MKFKQLMAMALLLALSAVAQA | 18 |
| ttg2C | MQNRTVEIGVGLFLLAGILALLLLALRVSGLSA | 19 |
| CRM197 native leader | MSRKLFASXLIGALLGIGAPPSAHA | 20 |

It is understood that the secretion leaders useful in the methods of the present invention are not limited to those disclosed in Table 3.

In embodiments, the secretion leader is Azu, IbpS31A, CupA2, or PbpA20V. In other embodiments, the secretion leader is Azu, IbpS31A, CupA2, PbpA20V, or Pbp.

Native CRM197 is transported from *C. diptheriae* to the extracellular space via a secretion leader that is cleaved, leaving an amino terminal sequence of GADD (SEQ ID NO: 21). In order to preserve the natural amino terminus of CRM197 following expression in *P. fluorescens* and ensure disulfide bond formation, the protein is targeted to the periplasmic space.

Promoters

The promoters used in accordance with the present invention may be constitutive promoters or regulated promoters. Common examples of useful regulated promoters include those of the family derived from the lac promoter (i.e. the lacZ promoter), especially the tac and trc promoters described in U.S. Pat. No. 4,551,433 to DeBoer, as well as Ptac16, Ptac17, PtacII, PlacUV5, and the T7lac promoter. In one embodiment, the promoter is not derived from the host cell organism. In certain embodiments, the promoter is derived from an *E. coli* organism.

Inducible promoter sequences can be used to regulate expression of the toxins in accordance with the methods of the invention. In embodiments, inducible promoters useful in the methods of the present invention include those of the family derived from the lac promoter (i.e. the lacZ promoter), especially the tac and trc promoters described in U.S. Pat. No. 4,551,433 to DeBoer, as well as Ptac16, Ptac17, PtacII, PlacUV5, and the T7lac promoter. In one embodiment, the promoter is not derived from the host cell organism. In certain embodiments, the promoter is derived from an *E. coli* organism.

Common examples of non-lac-type promoters useful in expression systems according to the present invention include, e.g., those listed in Table 4.

TABLE 4

Examples of non-lac Promoters

| Promoter | Inducer |
|---|---|
| $P_R$ | High temperature |
| $P_L$ | High temperature |
| Pm | Alkyl- or halo-benzoates |
| Pu | Alkyl- or halo-toluenes |
| Psal | Salicylates |

See, e.g.: J. Sanchez-Romero & V. De Lorenzo (1999) Manual of Industrial Microbiology and Biotechnology (A. Demain & J. Davies, eds.) pp. 460-74 (ASM Press, Washington, D.C.); H. Schweizer (2001) Current Opinion in Biotechnology, 12:439-445; and R. Slater & R. Williams (2000 Molecular Biology and Biotechnology (J. Walker & R. Rapley, eds.) pp. 125-54 (The Royal Society of Chemistry, Cambridge, UK)). A promoter having the nucleotide sequence of a promoter native to the selected bacterial host cell also may be used to control expression of the transgene encoding the target polypeptide, e.g, a *Pseudomonas* anthranilate or benzoate operon promoter (Pant, Pben). Tandem promoters may also be used in which more than one promoter is covalently attached to another, whether the same or different in sequence, e.g., a Pant-Pben tandem promoter (interpromoter hybrid) or a Plac-Plac tandem promoter, or whether derived from the same or different organisms.

Regulated promoters utilize promoter regulatory proteins in order to control transcription of the gene of which the promoter is a part. Where a regulated promoter is used herein, a corresponding promoter regulatory protein will also be part of an expression system according to the present invention. Examples of promoter regulatory proteins include: activator proteins, e.g., *E. coli* catabolite activator protein, MalT protein; AraC family transcriptional activators; repressor proteins, e.g., *E. coli* Lad proteins; and dual-function regulatory proteins, e.g., *E. coli* NagC protein. Many regulated-promoter/promoter-regulatory-protein pairs are known in the art. In one embodiment, the expression construct for the target protein(s) and the heterologous protein of interest are under the control of the same regulatory element.

Promoter regulatory proteins interact with an effector compound, i.e., a compound that reversibly or irreversibly associates with the regulatory protein so as to enable the protein to either release or bind to at least one DNA transcription regulatory region of the gene that is under the control of the promoter, thereby permitting or blocking the action of a transcriptase enzyme in initiating transcription of the gene. Effector compounds are classified as either inducers or co-repressors, and these compounds include native effector compounds and gratuitous inducer compounds. Many regulated-promoter/promoter-regulatory-protein/effector-compound trios are known in the art. Although an effector compound can be used throughout the cell culture or fermentation, in a preferred embodiment in which a regulated promoter is used, after growth of a desired quantity or density of host cell biomass, an appropriate effector compound is added to the culture to directly or indirectly result in expression of the desired gene(s) encoding the protein or polypeptide of interest.

In embodiments wherein a lac family promoter is utilized, a lad gene can also be present in the system. The lad gene, which is normally a constitutively expressed gene, encodes the Lac repressor protein Lad protein, which binds to the lac operator of lac family promoters. Thus, where a lac family promoter is utilized, the lad gene can also be included and expressed in the expression system.

Promoter systems useful in *Pseudomonas* are described in the literature, e.g., in U.S. Pat. App. Pub. No. 2008/0269070, also referenced above.

Other Regulatory Elements

In embodiments, soluble proteins are present in either the cytoplasm or periplasm of the cell during production. Secretion leaders useful for targeting proteins are described elsewhere herein, and in U.S. Pat. App. Pub. No. 2008/0193974, U.S. Pat. App. Pub. No. 2006/0008877, and in U.S. patent application Ser. No. 12/610,207.

Other elements include, but are not limited to, transcriptional enhancer sequences, translational enhancer sequences, other promoters, activators, translational start and stop signals, transcription terminators, cistronic regulators, polycistronic regulators, tag sequences, such as nucleotide sequence "tags" and "tag" polypeptide coding sequences, which facilitates identification, separation, purification, and/or isolation of an expressed polypeptide.

In embodiments, the expression vector further comprises a tag sequence adjacent to the coding sequence for the secretion signal or to the coding sequence for the protein or polypeptide of interest. In one embodiment, this tag sequence allows for purification of the protein. The tag sequence can be an affinity tag, such as a hexa-histidine affinity tag (SEQ ID NO: 46). In another embodiment, the affinity tag can be a glutathione-S-transferase molecule. The tag can also be a fluorescent molecule, such as YFP or GFP, or analogs of such fluorescent proteins. The tag can also be a portion of an antibody molecule, or a known antigen or ligand for a known binding partner useful for purification.

An expression construct useful in practicing the methods of the present invention can include, in addition to the protein coding sequence, the following regulatory elements operably linked thereto: a promoter, a ribosome binding site (RBS), a transcription terminator, and translational start and stop signals. Useful RBSs can be obtained from any of the species useful as host cells in expression systems according to, e.g., U.S. Pat. App. Pub. No. 2008/0269070 and U.S. patent application Ser. No. 12/610,207. Many specific and a variety of consensus RBSs are known, e.g., those described in and referenced by D. Frishman et al., Gene 234(2):257-65 (8 Jul. 1999); and B. E. Suzek et al., Bioinformatics 17(12):1123-30 (December 2001). In addition, either native or synthetic RBSs may be used, e.g., those described in: EP 0207459 (synthetic RBSs); O. Ikehata et al., Eur. J. Biochem. 181(3):563-70 (1989) (native RBS sequence of AAGGAAG). Further examples of methods, vectors, and translation and transcription elements, and other elements useful in the present invention are well known in the art and described in, e.g.: U.S. Pat. No. 5,055,294 to Gilroy and U.S. Pat. No. 5,128,130 to Gilroy et al.; U.S. Pat. No. 5,281,532 to Rammler et al.; U.S. Pat. Nos. 4,695,455 and 4,861,595 to Barnes et al.; U.S. Pat. No. 4,755,465 to Gray et al.; and U.S. Pat. No. 5,169,760 to Wilcox, all incorporated herein by reference, as well as in many of the other publications incorporated herein by reference.

Host Strains

Bacterial hosts, including Pseudomonads, and closely related bacterial organisms are contemplated for use in practicing the methods of the invention. In certain embodiments, the Pseudomonad host cell is *Pseudomonas fluorescens*. The host cell can also be an *E. coli* cell.

Host cells and constructs useful in practicing the methods of the invention can be identified or made using reagents and methods known in the art and described in the literature, e.g., in U.S. Pat. App. Pub. No. 2009/0325230, "Protein Expression Systems," incorporated herein by reference in its entirety. This publication describes production of a recombinant polypeptide by introduction of a nucleic acid construct into an auxotrophic *Pseudomonas fluorescens* host cell comprising a chromosomal lacI gene insert. The nucleic acid construct comprises a nucleotide sequence encoding the recombinant polypeptide operably linked to a promoter capable of directing expression of the nucleic acid in the host cell, and also comprises a nucleotide sequence encoding an auxotrophic selection marker. The auxotrophic selection marker is a polypeptide that restores prototrophy to the auxotrophic host cell. In embodiments, the cell is auxotrophic for proline, uracil, or combinations thereof. In embodiments, the host cell is derived from MB101 (ATCC deposit PTA-7841). U.S. Pat. App. Pub. No. 2009/0325230, "Protein Expression Systems," and in Schneider, et al., 2005, "Auxotrophic markers pyrF and proC can replace antibiotic markers on protein production plasmids in high-cell-density *Pseudomonas fluorescens* fermentation," Biotechnol. Progress 21(2): 343-8, both incorporated herein by reference in their entirety, describe a production host strain auxotrophic for uracil that was constructed by deleting the pyrF gene in strain MB101. The pyrF gene was cloned from strain MB214 (ATCC deposit PTA-7840) to generate a plasmid that can complement the pyrF deletion to restore prototropy. In particular embodiments, a dual pyrF-proC dual auxotrophic selection marker system in a *P. fluorescens* host cell is used. A PyrF production host strain as described can be used as the background for introducing other desired genomic changes, including those described herein as useful in practicing the methods of the invention.

In embodiments, the host cell is of the order Pseudomonadales. Where the host cell is of the order Pseudomonadales, it may be a member of the family Pseudomonadaceae, including the genus *Pseudomonas*. Gamma Proteobacterial hosts include members of the species *Escherichia coli* and members of the species *Pseudomonas fluorescens*.

Other *Pseudomonas* organisms may also be useful. Pseudomonads and closely related species include Gram-negative Proteobacteria Subgroup 1, which include the group of Proteobacteria belonging to the families and/or genera described as "Gram-Negative Aerobic Rods and Cocci" by R. E. Buchanan and N. E. Gibbons (eds.), Bergey's Manual of Determinative Bacteriology, pp. 217-289 (8th ed., 1974) (The Williams & Wilkins Co., Baltimore, Md., USA) (hereinafter "Bergey (1974)"). Table 5 presents these families and genera of organisms.

TABLE 5

Families and Genera Listed in the Part, "Gram-Negative Aerobic Rods and Cocci" (Bergey, 1974)

| Family | Genera |
|---|---|
| Family I. Pseudomonaceae | Gluconobacter |
| | Pseudomonas |
| | Xanthomonas |
| | Zoogloea |
| Family II. Azotobacteraceae | Azomonas |
| | Azotobacter |
| | Beijerinckia |
| | Derxia |
| Family III. Rhizobiaceae | Agrobacterium |
| | Rhizobium |
| Family IV. Methylomonadaceae | Methylococcus |
| | Methylomonas |
| Family V. Halobacteriaceae | Halobacterium |
| | Halococcus |
| Other Genera | Acetobacter |
| | Alcaligenes |
| | Bordetella |
| | Brucella |
| | Francisella |
| | Thermus |

*Pseudomonas* and closely related bacteria are generally part of the group defined as "Gram(−) Proteobacteria Subgroup 1" or "Gram-Negative Aerobic Rods and Cocci" (Buchanan and Gibbons (eds.) (1974) Bergey's Manual of Determinative Bacteriology, pp. 217-289). *Pseudomonas* host strains are described in the literature, e.g., in U.S. Pat. App. Pub. No. 2006/0040352, cited above.

"Gram-negative Proteobacteria Subgroup 1" also includes Proteobacteria that would be classified in this heading according to the criteria used in the classification. The heading also includes groups that were previously classified in this section but are no longer, such as the genera *Acidovorax, Brevundimonas, Burkholderia, Hydrogenophaga, Oceanimonas, Ralstonia,* and *Stenotrophomonas,* the genus *Sphingomonas* (and the genus *Blastomonas,* derived therefrom), which was created by regrouping organisms belonging to (and previously called species of) the genus *Xanthomonas,* the genus *Acidomonas,* which was created by regrouping organisms belonging to the genus *Acetobacter* as defined in Bergey (1974). In addition hosts can include cells from the genus *Pseudomonas, Pseudomonas enalia* (ATCC 14393), *Pseudomonas nigrifaciensi* (ATCC 19375), and *Pseudomonas putrefaciens* (ATCC 8071), which have been reclassified respectively as *Alteromonas haloplanktis, Alteromonas nigrifaciens,* and *Alteromonas putrefaciens.* Similarly, e.g., *Pseudomonas acidovorans* (ATCC 15668) and *Pseudomonas testosteroni* (ATCC 11996) have since been reclassified as *Comamonas acidovorans* and *Comamonas testosteroni,* respectively; and *Pseudomonas nigrifaciens* (ATCC 19375) and *Pseudomonas piscicida* (ATCC 15057) have been reclassified respectively as *Pseudoalteromonas nigrifaciens* and *Pseudoalteromonas piscicida.* "Gram-negative Proteobacteria Subgroup 1" also includes Proteobacteria classified as belonging to any of the families: Pseudomonadaceae, Azotobacteraceae (now often called by the synonym, the "*Azotobacter* group" of Pseudomonadaceae), Rhizobiaceae, and Methylomonadaceae (now often called by the synonym, "Methylococcaceae"). Consequently, in addition to those genera otherwise described herein, further Proteobacterial genera falling within "Gram-negative Proteobacteria Subgroup 1" include: 1) *Azotobacter* group bacteria of the genus *Azorhizophilus;* 2) Pseudomonadaceae family bacteria of the genera *Cellvibrio, Oligella,* and *Teredinibacter;* 3) Rhizobiaceae family bacteria of the genera *Chelatobacter, Ensifer, Liberibacter* (also called "*Candidatus Liberibacter*"), and *Sinorhizobium;* and 4) Methylococcaceae family bacteria of the genera *Methylobacter, Methylocaldum, Methylomicrobium, Methylosarcina,* and *Methylosphaera.*

The host cell can be selected from "Gram-negative Proteobacteria Subgroup 16." "Gram-negative Proteobacteria Subgroup 16" is defined as the group of Proteobacteria of the following *Pseudomonas* species (with the ATCC or other deposit numbers of exemplary strain(s) shown in parenthesis): *Pseudomonas abietaniphila* (ATCC 700689); *Pseudomonas aeruginosa* (ATCC 10145); *Pseudomonas alcaligenes* (ATCC 14909); *Pseudomonas anguilliseptica* (ATCC 33660); *Pseudomonas citronellolis* (ATCC 13674); *Pseudomonas flavescens* (ATCC 51555); *Pseudomonas mendocina* (ATCC 25411); *Pseudomonas nitroreducens* (ATCC 33634); *Pseudomonas oleovorans* (ATCC 8062); *Pseudomonas pseudoalcaligenes* (ATCC 17440); *Pseudomonas resinovorans* (ATCC 14235); *Pseudomonas straminea* (ATCC 33636); *Pseudomonas agarici* (ATCC 25941); *Pseudomonas alcaliphila; Pseudomonas alginovora; Pseudomonas andersonii; Pseudomonas asplenii* (ATCC 23835); *Pseudomonas azelaica* (ATCC 27162); *Pseudomonas beyerinckii* (ATCC 19372); *Pseudomonas borealis; Pseudomonas boreopolis* (ATCC 33662); *Pseudomonas brassicacearum; Pseudomonas butanovora* (ATCC 43655); *Pseudomonas cellulosa* (ATCC 55703); *Pseudomonas aurantiaca* (ATCC 33663); *Pseudomonas chlororaphis* (ATCC 9446, ATCC 13985, ATCC 17418, ATCC 17461); *Pseudomonas fragi* (ATCC 4973); *Pseudomonas lundensis* (ATCC 49968); *Pseudomonas taetrolens* (ATCC 4683); *Pseudomonas cissicola* (ATCC 33616); *Pseudomonas coronafaciens; Pseudomonas diterpeniphila; Pseudomonas elongata* (ATCC 10144); *Pseudomonas flectens* (ATCC 12775); *Pseudomonas azotoformans; Pseudomonas brenneri; Pseudomonas cedrella; Pseudomonas corrugata* (ATCC 29736); *Pseudomonas extremorientalis; Pseudomonas fluorescens* (ATCC 35858); *Pseudomonas gessardii; Pseudomonas libanensis; Pseudomonas mandelii* (ATCC 700871); *Pseudomonas marginalis* (ATCC 10844); *Pseudomonas migulae; Pseudomonas mucidolens* (ATCC 4685); *Pseudomonas orientalis; Pseudomonas rhodesiae; Pseudomonas synxantha* (ATCC 9890); *Pseudomonas tolaasii* (ATCC 33618); *Pseudomonas veronii* (ATCC 700474); *Pseudomonas frederiksbergensis; Pseudomonas geniculata* (ATCC 19374); *Pseudomonas gingeri; Pseudomonas graminis; Pseudomonas grimontii; Pseudomonas halodenitrificans; Pseudomonas halophila; Pseudomonas hibiscicola* (ATCC 19867); *Pseudomonas huttiensis* (ATCC 14670); *Pseudomonas hydrogenovora; Pseudomonas jessenii* (ATCC 700870); *Pseudomonas kilonensis; Pseudomonas lanceolata* (ATCC 14669); *Pseudomonas lini; Pseudomonas marginate* (ATCC 25417); *Pseudomonas mephitica* (ATCC 33665); *Pseudomonas denitrificans* (ATCC 19244); *Pseudomonas pertucinogena* (ATCC 190); *Pseudomonas pictorum* (ATCC 23328); *Pseudomonas psychrophila; Pseudomonas filva* (ATCC 31418); *Pseudomonas monteilii* (ATCC 700476); *Pseudomonas mosselii; Pseudomonas oryzihabitans* (ATCC 43272); *Pseudomonas plecoglossicida* (ATCC 700383); *Pseudomonas putida* (ATCC 12633); *Pseudomonas reactans; Pseudomonas spinosa* (ATCC 14606); *Pseudomonas bale-* arica; *Pseudomonas luteola* (ATCC 43273); *Pseudomonas stutzeri* (ATCC 17588); *Pseudomonas amygdali* (ATCC 33614); *Pseudomonas avellanae* (ATCC 700331); *Pseudomonas caricapapayae* (ATCC 33615); *Pseudomonas cichorii* (ATCC 10857); *Pseudomonas ficuserectae* (ATCC 35104); *Pseudomonas fuscovaginae; Pseudomonas meliae* (ATCC 33050); *Pseudomonas syringae* (ATCC 19310); *Pseudomonas viridiflava* (ATCC 13223); *Pseudomonas thermocarboxydovorans* (ATCC 35961); *Pseudomonas thermotolerans; Pseudomonas thivervalensis; Pseudomonas vancouverensis* (ATCC 700688); *Pseudomonas wisconsinensis*; and *Pseudomonas xiamenensis*. In one embodiment, the host cell is *Pseudomonas fluorescens*.

The host cell can also be selected from "Gram-negative Proteobacteria Subgroup 17." "Gram-negative Proteobacteria Subgroup 17" is defined as the group of Proteobacteria known in the art as the "fluorescent Pseudomonads" including those belonging, e.g., to the following *Pseudomonas* species: *Pseudomonas azotoformans; Pseudomonas brenneri; Pseudomonas cedrella; Pseudomonas corrugata; Pseudomonas extremorientalis; Pseudomonas fluorescens; Pseudomonas gessardii; Pseudomonas libanensis; Pseudomonas mandelii; Pseudomonas marginalis; Pseudomonas migulae; Pseudomonas mucidolens; Pseudomonas orientalis; Pseudomonas rhodesiae; Pseudomonas synxantha; Pseudomonas tolaasii*; and *Pseudomonas veronii*.

In embodiments, the *Pseudomonas* host cell is defective in the expression of HslU, HslV, Prc1, DegP1, DegP2, AprA, or a combination thereof. In embodiments, the host cell is defective in proteases HslU, HslV, Prc1, DegP1, DegP2, and AprA, and overexpresses DegP2 S219A. An example of such a strain is disclosed herein as Host Strain 2. These proteases are known in the art and described in, e.g., U.S. Pat. App. Pub. No. 2006/0110747. AprA, an extracellular serralysin-type metalloprotease metalloproteinase, is described by, e.g., Maunsell, et al., 2006, "Complex regulation of AprA metalloprotease in *Pseudomonas fluorescens* M114: evidence for the involvement of iron, the ECF sigma factor, PbrA and pseudobactin M114 siderophore, Microbiology 152(Pt 1):29-42, incorporated herein by reference, and in U.S. Patent App. Pub. Nos. 2008/0193974 and 2010/0048864.

In other embodiments, the *Pseudomonas* host cell overexpresses DsbA, DsbB, DsbC, and DsbD. DsbA, B, C, and D are disulfide bond isomerases, described, e.g., in U.S. Pat. App. Pub. No. 2008/0269070 and U.S. patent application Ser. No. 12/610,207.

In other embodiments, the *Pseudomonas* host cell is wild-type, i.e., having no protease expression defects and not overexpressing any folding modulator.

A host cell that is defective in the expression of a protease can have any modification that results in a decrease in the normal activity or expression level of that protease relative to a wild-type host. For example, a missense or nonsense mutation can lead to expression of protein that not active, and a gene deletion can result in no protein expression at all. A change in the upstream regulatory region of the gene can result in reduced or no protein expression. Other gene defects can affect translation of the protein. The expression of a protease can also be defective if the activity of a protein needed for processing the protease is defective.

Examples of proteases and folding modulators useful in the methods of the present invention are shown in Tables 6 and 7, respectively. RXF numbers refer to the open reading frame. (See, e.g., U.S. Pat. App. Pub. No. 2008/0269070 and U.S. patent application Ser. No. 12/610,207.)

TABLE 6

*P. fluorescens* strain MB214 proteases

| Class | Family | RXF | Gene | Curated Function | Location |
|---|---|---|---|---|---|
| Aspartic Peptidases | A8 (signal peptidase II family) | RXF05383.2 | | Lipoprotein signal peptidase (ec 3.4.23.36) | Cytoplasmic Membrane |
| | A24 (type IV prepilin peptidase family) | RXF05379.1 | | type 4 prepilin peptidase pild (ec 3.4.99.—) | Cytoplasmic Membrane |
| Cysteine Peptidases | C15 (pyroglutamyl peptidase I family) | RXF02161.1 | | Pyrrolidone-carboxylate peptidase (ec 3.4.19.3) | Cytoplasmic |
| | C40 | RXF01968.1 | | invasion-associated protein, P60 | Signal peptide |
| | | RXF04920.1 | | invasion-associated protein, P60 | Cytoplasmic |
| | | RXF04923.1 | | phosphatase-associated protein papq | Signal peptide |
| | C56 (PfpI endopeptidase family) | RXF01816.1 | | protease I (ec 3.4.—.—) | Non-secretory |
| Metallopeptidases | M1 | RXF08773.1 | | Membrane alanine aminopeptidase (ec 3.4.11.2) | Non-secretory |
| | M3 | RXF00561.2 | prlC | Oligopeptidase A (ec 3.4.24.70) | Cytoplasmic |
| | | RXF04631.2 | | Zn-dependent oligopeptidases | Cytoplasmic |
| | M4 (thermolysin family) | RXF05113.2 | | Extracellular metalloprotease precursor (ec 3.4.24.—) | Extracellular |
| | M41 (FtsH endopeptidase family) | RXF05400.2 | | Cell division protein ftsH (ec 3.4.24.—) | Cytoplasmic Membrane |
| | M10 | RXF04304.1 | | Serralysin (ec 3.4.24.40) | Extracellular |
| | | RXF04500.1 | | Serralysin (ec 3.4.24.40) | Extracellular |
| | | RXF01590.2 | | Serralysin (ec 3.4.24.40) | Extracellular |
| | | RXF04497.2 | | Serralysin (ec 3.4.24.40) | Extracellular |
| | | RXF04495.2 | | Serralysin (ec 3.4.24.40) | Extracellular |
| | | RXF02796.1 | | Serralysin (ec 3.4.24.40) | Extracellular |
| | M14 (carboxypeptidase A family) | RXF09091.1 | | Zinc-carboxypeptidase precursor (ec 3.4.17.—) | Cytoplasmic |
| | M16 (pitrilysin family) | RXF03441.1 | | Coenzyme pqq synthesis protein F (ec 3.4.99.—) | Non-secretory |
| | | RXF01918.1 | | zinc protease (ec 3.4.99.—) | Signal peptide |
| | | RXF01919.1 | | zinc protease (ec 3.4.99.—) | Periplasmic |
| | | RXF03699.2 | | processing peptidase (ec 3.4.24.64) | Signal peptide |

TABLE 6-continued

*P. fluorescens* strain MB214 proteases

| Class | Family | RXF | Gene | Curated Function | Location |
|---|---|---|---|---|---|
| | M17 (leucyl aminopeptidase family) | RXF00285.2 | | Cytosol aminopeptidase (ec 3.4.11.1) | Non-secretory |
| | M18 | RXF07879.1 | | Aspartyl aminopeptidase (ec 3.4.11.21) | Cytoplasmic |
| | M20 | RXF00811.1 | dapE | Succinyl-diaminopimelate desuccinylase (ec 3.5.1.18) | Cytoplasmic |
| | | RXF04052.2 | | Xaa-His dipeptidase (ec 3.4.13.3) | Signal peptide |
| | | RXF01822.2 | | Carboxypeptidase G2 precursor (ec 3.4.17.11) | Signal peptide |
| | | RXF09831.2:: RXF04892.1 | | N-acyl-L-amino acid amidohydrolase (ec 3.5.1.14) | Signal peptide |
| | M28 (aminopeptidase Y family) | RXF03488.2 | | Alkaline phosphatase isozyme conversion protein precursor (ec 3.4.11.—) | OuterMembrane |
| | M42 (glutamyl aminopeptidase family) | RXF05615.1 | | Deblocking aminopeptidase (ec 3.4.11.—) | Non-secretory |
| | M22 | RXF05817.1 | | O-sialoglycoprotein endopeptidase (ec 3.4.24.57) | Extracellular |
| | | RXF03065.2 | | Glycoprotease protein family | Non-secretory |
| | M23 | RXF01291.2 | | Cell wall endopeptidase, family M23/M37 | Signal peptide |
| | | RXF03916.1 | | Membrane proteins related to metalloendopeptidases | Signal peptide |
| | | RXF09147.2 | | Cell wall endopeptidase, family M23/M37 | Signal peptide |
| | M24 | RXF04693.1 | | Methionine aminopeptidase (ec 3.4.11.18) | Cytoplasmic |
| | | RXF03364.1 | | Methionine aminopeptidase (ec 3.4.11.18) | Non-secretory |
| | | RXF02980.1 | | Xaa-Pro aminopeptidase (ec 3.4.11.9) | Cytoplasmic |
| | | RXF06564.1 | | Xaa-Pro aminopeptidase (ec 3.4.11.9) | Cytoplasmic |
| | M48 (Ste24 endopeptidase family) | RXF05137.1 | | Heat shock protein HtpX | Cytoplasmic Membrane |
| | | RXF05081.1 | | Zinc metalloprotease (ec 3.4.24.—) | Signal peptide |
| | M50 (S2P protease family) | RXF04692.1 | | Membrane metalloprotease | Cytoplasmic Membrane |
| Serine Peptidases | S1 (chymotrypsin family) | RXF01250.2 | | protease do (ec 3.4.21.—) | Periplasmic |
| | | RXF07210.1 | | protease do (ec 3.4.21.—) | Periplasmic |
| | S8 (subtilisin family) | RXF06755.2 | | serine protease (ec 3.4.21.—) | Non-secretory |
| | | RXF08517.1 | | serine protease (ec 3.4.21.—) | Extracellular |
| | | RXF08627.2 | | extracellular serine protease (ec 3.4.21.—) | Signal peptide |
| | | RXF06281.1 | | Extracellular serine protease precursor (ec 3.4.21.—) | Non-secretory |
| | | RXF08978.1 | | extracellular serine protease (ec 3.4.21.—) | OuterMembrane |
| | | RXF06451.1 | | serine protease (ec 3.4.21.—) | Signal peptide |
| | S9 (prolyl oligopeptidase family) | RXF02003.2 | | Protease ii (ec 3.4.21.83) | Periplasmic |
| | | RXF00458.2 | | Hydrolase | Non-secretory |
| | S11 (D-Ala-D-Ala carboxypeptidase A family) | RXF04657.2 | | D-alanyl-D-alanine-endopeptidase (ec 3.4.99.—) | Periplasmic |
| | | RXF00670.1 | | D-alanyl-D-alanine carboxypeptidase (ec 3.4.16.4) | Cytoplasmic Membrane |
| | S13 (D-Ala-D-Ala peptidase C family) | RXF00133.1 | | D-alanyl-meso-diaminopimelate endopeptidase (ec 3.4.—.—) | OuterMembrane |
| | | RXF04960.2 | | D-alanyl-meso-diaminopimelate endopeptidase (ec 3.4.—.—) | Signal peptide |
| | S14 (ClpP endopeptidase family) | RXF04567.1 | clpP | atp-dependent Clp protease proteolytic subunit (ec 3.4.21.92) | Non-secretory |
| | | RXF04663.1 | clpP | atp-dependent Clp protease proteolytic subunit (ec 3.4.21.92) | Cytoplasmic |
| | S16 (lon protease family) | RXF04653.2 | | atp-dependent protease La (ec 3.4.21.53) | Cytoplasmic |
| | | RXF08653.1 | | atp-dependent protease La (ec 3.4.21.53) | Cytoplasmic |
| | | RXF05943.1 | | atp-dependent protease La (ec 3.4.21.53) | Cytoplasmic |
| | S24 (LexA family) | RXF00449.1 | | LexA repressor (ec 3.4.21.88) | Non-secretory |
| | | RXF03397.1 | | LexA repressor (ec 3.4.21.88) | Cytoplasmic |
| | S26 (signal peptidase I family) | RXF01181.1 | | Signal peptidase I (ec 3.4.21.89) | Cytoplasmic Membrane |

TABLE 6-continued

*P. fluorescens* strain MB214 proteases

| Class | Family | RXF | Gene | Curated Function | Location |
|---|---|---|---|---|---|
| | S33 | RXF05236.1 | pip3 | Proline iminopeptidase (ec 3.4.11.5) | Non-secretory |
| | | RXF04802.1 | pip1 | Proline iminopeptidase (ec 3.4.11.5) | Non-secretory |
| | | RXF04808.2 | pip2 | Proline iminopeptidase (ec 3.4.11.5) | Cytoplasmic |
| | S41 (C-terminal processing peptidase family) | RXF06586.1 | | Tail-specific protease (ec 3.4.21.—) | Signal peptide |
| | | RXF01037.1 | | Tail-specific protease (ec 3.4.21.—) | Signal peptide |
| | S45 | RXF07170.1 | pacB2 | Penicillin acylase (ec 3.5.1.11) | Signal peptide |
| | | RXF06399.2 | pacB1 | Penicillin acylase ii (ec 3.5.1.11) | Signal peptide |
| | S49 (protease IV family) | RXF06993.2 | | possible protease sohb (ec 3.4.—.—) | Non-secretory |
| | | RXF01418.1 | | protease iv (ec 3.4.—.—) | Non-secretory |
| | S58 (DmpA aminopeptidase family) | RXF06308.2 | | D-aminopeptidase (ec 3.4.11.19) | Cytoplasmic Membrane |
| Threonine Peptidases | T1 (proteasome family) | RXF01961.2 | hslV | atp-dependent protease hslV (ec 3.4.25.—) | Cytoplasmic |
| | T3 (gamma-glutamyltransferase family) | RXF02342.1 | ggt1 | Gamma-glutamyltranspeptidase (ec 2.3.2.2) | Periplasmic |
| | | RXF04424.2 | ggt2 | Gamma-glutamyltranspeptidase (ec 2.3.2.2) | Periplasmic |
| Unclassified Peptidases | U32 | RXF00428.1 | | protease (ec 3.4.—.—) | Cytoplasmic |
| | | RXF02151.2 | | protease (ec 3.4.—.—) | Cytoplasmic |
| | U61 | RXF04715.1 | | Muramoyltetrapeptide carboxypeptidase (ec 3.4.17.13) | Non-secretory |
| | U62 | RXF04971.2 | pmbA | PmbA protein | Cytoplasmic |
| | | RXF04968.2 | | TldD protein | Cytoplasmic |
| Non MEROPS Proteases | | RXF00325.1 | | Repressor protein C2 | Non-secretory |
| | | RXF02689.2 | | Microsomal dipeptidase (ec 3.4.13.19) | Cytoplasmic |
| | | RXF02739.1 | | membrane dipeptidase (3.4.13.19) | Signal peptide |
| | | RXF03329.2 | | Hypothetical Cytosolic Protein | Cytoplasmic |
| | | RXF02492.1 | | Xaa-Pro dipeptidase (ec 3.4.13.9) | Cytoplasmic |
| | | RXF04047.2 | | caax amino terminal protease family | Cytoplasmic Membrane |
| | | RXF08136.2 | | protease (transglutaminase-like protein) | Cytoplasmic |
| | | RXF09487.1 | | Zinc metalloprotease (ec 3.4.24.—) | Non-secretory |

Certain proteases can have both protease and chaperone-like activity. When these proteases are negatively affecting protein yield and/or quality it can be useful to delete them, and they can be overexpressed when their chaperone activity may positively affect protein yield and/or quality. These proteases include, but are not limited to: Hsp100(Clp/Hsl) family members RXF04587.1 (clpA), RXF08347.1, RXF04654.2 (clpX), RXF04663.1, RXF01957.2 (hslU), RXF01961.2 (hslV); Peptidyl-prolyl cis-trans isomerase family member RXF05345.2 (ppiB); Metallopeptidase M20 family member RXF04892.1 (aminohydrolase); Metallopeptidase M24 family members RXF04693.1 (methionine aminopeptidase) and RXF03364.1 (methionine aminopeptidase); and Serine Peptidase S26 signal peptidase I family member RXF01181.1 (signal peptidase).

TABLE 7

*P. fluorescens* strain MB214 protein folding modulators

| ORF ID | GENE | FUNCTION | FAMILY | LOCATION |
|---|---|---|---|---|
| GroES/EL | | | | |
| RXF02095.1 | groES | Chaperone | Hsp10 | Cytoplasmic |
| RXF06767.1::Rxf02090 | groEL | Chaperone | Hsp60 | Cytoplasmic |
| RXF01748.1 | ibpA | Small heat-shock protein (sHSP) IbpA PA3126; Acts as a holder for GroESL folding | Hsp20 | Cytoplasmic |
| RXF03385.1 | hscB | Chaperone protein hscB | Hsp20 | Cytoplasmic |
| Hsp70 (DnaK/J) | | | | |
| RXF05399.1 | dnaK | Chaperone | Hsp70 | Periplasmic |
| RXF06954.1 | dnaK | Chaperone | Hsp70 | Cytoplasmic |
| RXF03376.1 | hscA | Chaperone | Hsp70 | Cytoplasmic |
| RXF03987.2 | cbpA | Curved dna-binding protein, dnaJ like activity | Hsp40 | Cytoplasmic |
| RXF05406.2 | dnaJ | Chaperone protein dnaJ | Hsp40 | Cytoplasmic |
| RXF03346.2 | dnaJ | Molecular chaperones (DnaJ family) | Hsp40 | Non-secretory |
| RXF05413.1 | grpE | heat shock protein GrpE PA4762 | GrpE | Cytoplasmic |
| Hsp100 (Clp/Hsl) | | | | |
| RXF04587.1 | clpA | atp-dependent clp protease atp-binding subunit clpA | Hsp100 | Cytoplasmic |
| RXF08347.1 | clpB | ClpB protein | Hsp100 | Cytoplasmic |

TABLE 7-continued

*P. fluorescens* strain MB214 protein folding modulators

| ORF ID | GENE | FUNCTION | FAMILY | LOCATION |
|---|---|---|---|---|
| RXF04654.2 | clpX | atp-dependent clp protease atp-binding subunit clpX | Hsp100 | Cytoplasmic |
| RXF04663.1 | clpP | atp-dependent Clp protease proteolytic subunit (ec 3.4.21.92) | MEROPS peptidase family S14 | Cytoplasmic |
| RXF01957.2 | hslU | atp-dependent hsl protease atp-binding subunit hslU | Hsp100 | Cytoplasmic |
| RXF01961.2 | hslV | atp-dependent hsl protease proteolytic subunit | MEROPS peptidase subfamily T1B | Cytoplasmic |
| Hsp33 | | | | |
| RXF04254.2 | yrfI | 33 kDa chaperonin (Heat shock protein 33 homolog) (HSP33). | Hsp33 | Cytoplasmic |
| Hsp90 | | | | |
| RXF05455.2 | htpG | Chaperone protein htpG | Hsp90 | Cytoplasmic |
| SecB | | | | |
| RXF02231.1 | secB | secretion specific chaperone SecB | SecB | Non-secretory |
| Disulfide Bond Isomerases | | | | |
| RXF07017.2 | dsbA | disulfide isomerase | DSBA oxido-reductase | Cytoplasmic |
| RXF08657.2 | dsbA/ dsbC/ dsbG/ fernA | disulfide isomerase | DSBA oxido-reductase | Cytoplasmic |
| RXF01002.1 | dsbA/ dsbC | disulfide isomerase | DSBA oxido-reductase/ Thioredoxin | Periplasmic |
| RXF03307.1 | dsbC | disulfide isomerase | Glutaredoxin/ Thioredoxin | Periplasmic |
| RXF04890.2 | dsbG | disulfide isomerase | Glutaredoxin/ Thioredoxin | Periplasmic |
| RXF03204.1 | dsbB | Disulfide bond formation protein B (Disulfide oxidoreductase). | DSBA oxido-reductase | Periplasmic |
| RXF04886.2 | dsbD | Thiol:disulfide interchange protein dsbD | DSBA oxido-reductase | Periplasmic |
| Peptidyl-prolyl cis-trans isomerases | | | | |
| RXF03768.1 | ppiA | Peptidyl-prolyl cis-trans isomerase A (ec 5.2.1.8) | PPIase: cyclophilin type | Periplasmic |
| RXF05345.2 | ppiB | Peptidyl-prolyl cis-trans isomerase B. | PPIase: cyclophilin type | Cytoplasmic |
| RXF06034.2 | fklB | Peptidyl-prolyl cis-trans isomerase FklB. | PPIase: FKBP type | OuterMembrane |
| RXF06591.1 | fklB/ fkbP | fk506 binding protein Peptidyl-prolyl cis-trans isomerase (EC 5.2.1.8) | PPIase: FKBP type | Periplasmic |
| RXF05753.2 | fklB; fkbP | Peptidyl-prolyl cis-trans isomerase (ec 5.2.1.8) | PPIase: FKBP type | OuterMembrane |
| RXF01833.2 | slyD | Peptidyl-prolyl cis-trans isomerase SlyD. | PPIase: FKBP type | Non-secretory |
| RXF04655.2 | tig | Trigger factor, ppiase (ec 5.2.1.8) | PPIase: FKBP type | Cytoplasmic |
| RXF05385.1 | yaad | Probable FKBP-type 16 kDa peptidyl-prolyl cis-trans isomerase (EC 5.2.1.8) (PPiase) (Rotamase). | PPIase: FKBP type | Non-secretory |
| RXF00271.1 | | Peptidyl-prolyl cis-trans isomerase (ec 5.2.1.8) | PPIase: FKBP type | Non-secretory |
| pili assembly chaperones (papD like) | | | | |
| RXF06068.1 | cup | Chaperone protein cup | pili assembly papD | Periplasmic |
| RXF05719.1 | ecpD | Chaperone protein ecpD | pili assembly papD | Signal peptide |
| RXF05319.1 | ecpD | Hnr protein | pili assembly chaperone | Periplasmic |
| RXF03406.2 | ecpD; csuC | Chaperone protein ecpD | pili assembly papD | Signal peptide |

TABLE 7-continued

P. fluorescens strain MB214 protein folding modulators

| ORF ID | GENE | FUNCTION | FAMILY | LOCATION |
|---|---|---|---|---|
| RXF04296.1 | ecpD; cup | Chaperone protein ecpD | pili assembly papD | Periplasmic |
| RXF04553.1 | ecpD; cup | Chaperone protein ecpD | pili assembly papD | Periplasmic |
| RXF04554.2 | ecpD; cup | Chaperone protein ecpD | pili assembly papD | Periplasmic |
| RXF05310.2 | ecpD; cup | Chaperone protein ecpD | pili assembly papD | Periplasmic |
| RXF05304.1 | ecpD; cup | Chaperone protein ecpD | pili assembly papD | Periplasmic |
| RXF05073.1 | gltF | Gram-negative pili assembly chaperone periplasmic function | pili assembly papD | Signal peptide |
| Type II Secretion Complex | | | | |
| RXF05445.1 | YacJ | Histidinol-phosphate aminotransferase (ec 2.6.1.9) | Class-II pyridoxal-phosphate-dependent aminotransferase family. Histidinol-phosphate amino-transferase subfamily. | Membrane |
| RXF05426.1 | SecD | Protein translocase subunit secd | Type II secretion complex | Membrane |
| RXF05432.1 | SecF | protein translocase subunit secf | Type II secretion complex | Membrane |
| Disulfide Bond Reductases | | | | |
| RXF08122.2 | trxC | Thioredoxin 2 | Disulfide Bond Reductase | Cytoplasmic |
| RXF06751.1 | Gor | Glutathione reductase (EC 1.8.1.7) (GR) (GRase) PA2025 | Disulfide Bond Reductase | Cytoplasmic |
| RXF00922.1 | gshA | Glutamate--cysteine ligase (ec 6.3.2.2) PA5203 | Disulfide Bond Reductase | Cytoplasmic |

High Throughput Screens

In some embodiments, a high throughput screen can be conducted to determine optimal conditions for expressing a soluble recombinant toxin protein. The conditions that be varied in the screen include, for example, the host cell, genetic background of the host cell (e.g., deletions of different proteases), type of promoter in an expression construct, type of secretion leader fused to the sequence encoding the recombinant protein, growth temperature, OD at induction when an inducible promoter is used, concentration of IPTG used for induction when a lacZ promoter is used, duration of protein induction, growth temperature following addition of an inducing agent to a culture, rate of agitation of culture, method of selection for plasmid maintenance, volume of culture in a vessel, and method of cell lysing.

In some embodiments, a library (or "array") of host strains is provided, wherein each strain (or "population of host cells") in the library has been genetically modified to modulate the expression of one or more target genes in the host cell. An "optimal host strain" or "optimal expression system" can be identified or selected based on the quantity, quality, and/or location of the expressed protein of interest compared to other populations of phenotypically distinct host cells in the array. Thus, an optimal host strain is the strain that produces the polypeptide of interest according to a desired specification. While the desired specification will vary depending on the polypeptide being produced, the specification includes the quality and/or quantity of protein, e.g., whether the protein is sequestered or secreted, and in what quantities, whether the protein is properly or desirably processed and/or folded, and the like. In embodiments, improved or desirable quality can be production of toxin protein with high fidelity cleavage of the secretion leader and low levels of degradation. In embodiments, the optimal host strain or optimal expression system produces a yield, characterized by the amount or quantity of soluble heterologous protein, the amount or quantity of recoverable heterologous protein, the amount or quantity of properly processed heterologous protein, the amount or quantity of properly folded heterologous protein, the amount or quantity of active heterologous protein, and/or the total amount or quantity of heterologous protein, of a certain absolute level or a certain level relative to that produced by an indicator strain, i.e., a strain used for comparison.

Methods of screening microbial hosts to identify strains with improved yield and/or quality in the expression of heterologous proteins are described, for example, in U.S. Patent Application Publication No. 20080269070.

Fermentation Format

The expression system according to the present invention can be cultured in any fermentation format. For example, batch, fed-batch, semi-continuous, and continuous fermentation modes may be employed herein.

In embodiments, the fermentation medium may be selected from among rich media, minimal media, and mineral salts media. In other embodiments either a minimal medium or a mineral salts medium is selected. In certain embodiments, a mineral salts medium is selected.

Mineral salts media consists of mineral salts and a carbon source such as, e.g., glucose, sucrose, or glycerol. Examples of mineral salts media include, e.g., M9 medium, Pseudomonas medium (ATCC 179), and Davis and Mingioli medium (see, B D Davis & E S Mingioli (1950) J. Bact. 60:17-28). The mineral salts used to make mineral salts media include those selected from among, e.g., potassium phosphates, ammonium sulfate or chloride, magnesium sulfate or chloride, and trace minerals such as calcium chloride, borate, and sulfates of iron, copper, manganese, and zinc. Typically, no organic nitrogen source, such as peptone, tryptone, amino acids, or a yeast extract, is included in a mineral salts medium. Instead, an inorganic nitrogen source is used and this may be selected from among, e.g., ammonium salts, aqueous ammonia, and gaseous ammonia. A mineral salts medium will typically contain glucose or glycerol as the carbon source. In comparison to mineral salts media, minimal media can also contain mineral salts and a carbon source, but can be supplemented with, e.g., low levels of amino acids, vitamins, peptones, or other ingredients, though these are added at very minimal levels. Media can be prepared using the methods described in the art, e.g., in U.S. Pat. App. Pub. No. 2006/0040352, referenced and incorporated by reference above. Details of cultivation procedures and mineral salts media useful in the methods of the present invention are described by Riesenberg, D et al., 1991, "High cell density cultivation of *Escherichia coli* at controlled specific growth rate," J. Biotechnol. 20 (1):17-27.

In embodiments, production can be achieved in bioreactor cultures. Cultures can be grown in, e.g., up to 2 liter bioreactors containing a mineral salts medium, and maintained at 32° C. and pH 6.5 through the addition of ammonia. Dissolved oxygen can be maintained in excess through increases in agitation and flow of sparged air and oxygen into the fermentor. Glycerol can be delivered to the culture throughout the fermentation to maintain excess levels. In embodiments, these conditions are maintained until a target culture cell density, e.g., optical density at 575 nm (A575), for induction is reached, at which time IPTG is added to initiate the target protein production. It is understood that the cell density at induction, the concentration of IPTG, pH and temperature each can be varied to determine optimal conditions for expression. In embodiments, cell density at induction can be varied from A575 of 40 to 200 absorbance units (AU). IPTG concentrations can be varied in the range from 0.02 to 1.0 mM, pH from 6 to 7.5, and temperature from 20 to 35° C. After 16-24 hours, the culture from each bioreactor can be harvested by centrifugation and the cell pellet frozen at –80° C. Samples can then be analyzed, e.g., by SDS-CGE, for product formation.

Fermentation may be performed at any scale. The expression systems according to the present invention are useful for recombinant protein expression at any scale. Thus, e.g., microliter-scale, milliliter scale, centiliter scale, and deciliter scale fermentation volumes may be used, and 1 Liter scale and larger fermentation volumes can be used.

In embodiments, the fermentation volume is at or above about 1 Liter. In embodiments, the fermentation volume is about 1 liter to about 100 liters. In embodiments, the fermentation volume is about 1 liter, about 2 liters, about 3 liters, about 4 liters, about 5 liters, about 6 liters, about 7 liters, about 8 liters, about 9 liters, or about 10 liters. In embodiments, the fermentation volume is about 1 liter to about 5 liters, about 1 liter to about 10 liters, about 1 liter to about 25 liters, about 1 liter to about 50 liters, about 1 liter to about 75 liters, about 10 liters to about 25 liters, about 25 liters to about 50 liters, or about 50 liters to about 100 liters In other embodiments, the fermentation volume is at or above 5 Liters, 10 Liters, 15 Liters, 20 Liters, 25 Liters, 50 Liters, 75 Liters, 100 Liters, 200 Liters, 500 Liters, 1,000 Liters, 2,000 Liters, 5,000 Liters, 10,000 Liters, or 50,000 Liters.

Bacterial Growth Conditions

Growth conditions useful in the methods of the provided invention can comprise a temperature of about 4° C. to about 42° C. and a pH of about 5.7 to about 8.8. When an expression construct with a lacZ promoter is used, expression can be induced by adding IPTG to a culture at a final concentration of about 0.01 mM to about 1.0 mM.

The pH of the culture can be maintained using pH buffers and methods known to those of skill in the art. Control of pH during culturing also can be achieved using aqueous ammonia. In embodiments, the pH of the culture is about 5.7 to about 8.8. In certain embodiments, the pH is about 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, or 8.8 In other embodiments, the pH is about 5.7 to 5.9, 5.8 to 6.0, 5.9 to 6.1, 6.0 to 6.2, 6.1 to 6.3, 6.2 to 6.5, 6.4 to 6.7, 6.5 to 6.8, 6.6 to 6.9, 6.7 to 7.0, 6.8 to 7.1, 6.9 to 7.2, 7.0 to 7.3, 7.1 to 7.4, 7.2 to 7.5, 7.3 to 7.6, 7.4 to 7.7, 7.5 to 7.8, 7.6 to 7.9, 7.7 to 8.0, 7.8 to 8.1, 7.9 to 8.2, 8.0 to 8.3, 8.1 to 8.4, 8.2 to 8.5, 8.3 to 8.6, 8.4 to 8.7, or 8.5 to 8.8. In yet other embodiments, the pH is about 5.7 to 6.0, 5.8 to 6.1, 5.9 to 6.2, 6.0 to 6.3, 6.1 to 6.4, or 6.2 to 6.5. In certain embodiments, the pH is about 5.7 to about 6.25.

In embodiments, the growth temperature is maintained at about 4° C. to about 42° C. In certain embodiments, the growth temperature is about 4° C., about 5° C., about 6° C., about 7° C., about 8° C., about 9° C., about 10° C., about 11° C., about 12° C., about 13° C., about 14° C., about 15° C., about 16° C., about 17° C., about 18° C., about 19° C., about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., or about 42° C. In other embodiments, the growth temperature is maintained at about 25° C. to about 27° C., about 25° C. to about 28° C., about 25° C. to about 29° C., about 25° C. to about 30° C., about 25° C. to about 31° C., about 25° C. to about 32° C., about 25° C. to about 33° C., about 26° C. to about 28° C., about 26° C. to about 29° C., about 26° C. to about 30° C., about 26° C. to about 31° C., about 26° C. to about 32° C., about 27° C. to about 29° C., about 27° C. to about 30° C., about 27° C. to about 31° C., about 27° C. to about 32° C., about 26° C. to about 33° C., about 28° C. to about 30° C., about 28° C. to about 31° C., about 28° C. to about 32° C., about 29° C. to about 31° C., about 29° C. to about 32° C., about 29° C. to about 33° C., about 30° C. to about 32° C., about 30° C. to about 33° C., about 31° C. to about 33° C., about 31° C. to about 32° C., about 30° C. to about 33° C., or about 32° C. to about 33° C. In other embodiments, the temperature is changed during culturing. In one embodiment, the temperature is maintained at about 30° C. before an agent to induce expression from the construct, e.g., IPTG, is added to the culture. After adding the induction agent, the temperature is reduced to about 25° C.

Induction

As described elsewhere herein, inducible promoters can be used in the expression construct to control expression of the recombinant toxin protein, e.g., a lac promoter. In the case of the lac promoter derivatives or family members, e.g., the tac promoter, the effector compound is an inducer, such as a gratuitous inducer like IPTG (isopropyl-β-D-1-thiogalactopyranoside, also called "isopropylthiogalactoside"). In embodiments, a lac promoter derivative is used, and recombinant protein expression is induced by the addition of IPTG to a final concentration of about 0.01 mM to about 1.0 mM, when the cell density has reached a level identified by an OD575 of about 80 to about 160. In embodiments, the OD575 at the time of culture induction for the recombinant protein can be about 80, about 90, about 100, about 110, about 120, about 130, about 140, about 150, about 160, about 170 about 180. In other embodiments, the OD575 is about 80 to about 100, about 100 to about 120, about 120 to about 140, about 140 to about 160. In other embodiments, the OD575 is about 80 to about 120, about 100 to about 140, or about 120 to about 160. In other embodiments, the OD575 is about 80 to about 140, or about 100 to 160. The cell density can be measured by other methods and expressed in other units, e.g., in cells per unit volume. For example, an OD575 of about 80 to about 160 of a *Pseudomonas fluorescens* culture is equivalent to approximately $8 \times 10^{10}$ to about $1.6 \times 10^{11}$ colony forming units per mL or 35 to 70 g/L dry cell weight. In embodiments, the cell density at the time of culture induction is equivalent to the cell density as specified herein by the absorbance at OD575, regardless of the method used for determining cell density or the units of measurement. One of skill in the art will know how to make the appropriate conversion for any cell culture.

In embodiments, the final IPTG concentration of the culture is about 0.01 mM, about 0.02 mM, about 0.03 mM, about 0.04 mM, about 0.05 mM, about 0.06 mM, about 0.07 mM, about 0.08 mM, about 0.09 mM, about 0.1 mM, about 0.2 mM, about 0.3 mM, about 0.4 mM, about 0.5 mM, about 0.6 mM, about 0.7 mM, about 0.8 mM, about 0.9 mM, or about 1 mM. In other embodiments, the final IPTG concentration of the culture is about 0.08 mM to about 0.1 mM, about 0.1 mM to about 0.2 mM, about 0.2 mM to about 0.3 mM, about 0.3 mM to about 0.4 mM, about 0.2 mM to about 0.4 mM, about 0.08 to about 0.2 mM, or about 0.1 to 1 mM.

In embodiments wherein a non-lac type promoter is used, as described herein and in the literature, other inducers or effectors can be used. In one embodiment, the promoter is a constitutive promoter.

After adding and inducing agent, cultures can be grown for a period of time, for example about 24 hours, during which time the recombinant protein is expressed. After adding an inducing agent, a culture can be grown for about 1 hr, about 2 hr, about 3 hr, about 4 hr, about 5 hr, about 6 hr, about 7 hr, about 8 hr, about 9 hr, about 10 hr, about 11 hr, about 12 hr, about 13 hr, about 14 hr, about 15 hr, about 16 hr, about 17 hr, about 18 hr, about 19 hr, about 20 hr, about 21 hr, about 22 hr, about 23 hr, about 24 hr, about 36 hr, or about 48 hr. After an inducing agent is added to a culture, the culture can be grown for about 1 to 48 hrs, about 1 to 24 hrs, about 10 to 24 hrs, about 15 to 24 hrs, or about 20 to 24 hrs. Cell cultures can be concentrated by centrifugation, and the culture pellet resuspended in a buffer or solution appropriate for the subsequent lysis procedure.

In embodiments, cells are disrupted using equipment for high pressure mechanical cell disruption (which are available commercially, e.g., Microfluidics Micro fluidizer, Constant Cell Disruptor, Niro-Soavi homogenizer or APV-Gaulin homogenizer). Cells expressing the recombinant protein can be disrupted, for example, using sonication. Any appropriate method known in the art for lysing cells can be used to release the soluble fraction. For example, in embodiments, chemical and/or enzymatic cell lysis reagents, such as cell-wall lytic enzyme and EDTA, can be used. Use of frozen or previously stored cultures is also contemplated in the methods of the invention. Cultures can be OD-normalized prior to lysis. For example, cells can be normalized to an OD600 of about 10, about 11, about 12, about 13, about 14, about 15, about 16, about 17, about 18, about 19, or about 20.

Centrifugation can be performed using any appropriate equipment and method. Centrifugation of cell culture or lysate for the purposes of separating a soluble fraction from an insoluble fraction is well-known in the art. For example, lysed cells can be centrifuged at 20,800×g for 20 minutes (at 4° C.), and the supernatants removed using manual or automated liquid handling. The pellet (insoluble) fraction is resuspended in a buffered solution, e.g., phosphate buffered saline (PBS), pH 7.4. Resuspension can be carried out using, e.g., equipment such as impellers connected to an overhead mixer, magnetic stir-bars, rocking shakers, etc.

A "soluble fraction," i.e., the soluble supernatant obtained after centrifugation of a lysate, and an "insoluble fraction," i.e., the pellet obtained after centrifugation of a lysate, result from lysing and centrifuging the cultures. These two fractions also can be referred to as a "first soluble fraction" and a "first insoluble fraction," respectively.

Evaluation of Product

Numerous assay methods are known in the art for characterizing proteins. Use of any appropriate method for characterizing the yield or quality of the recombinant toxin protein is contemplated herein.

Protein Yield

Protein yield in any purification fraction as described herein can be determined by methods known to those of skill in the art, for example, by capillary gel electrophoresis (CGE), and Western blot analysis. Activity assays, as described herein and known in the art, also can provide information regarding protein yield. In embodiments, these or any other methods known in the art are used to evaluate proper processing of a protein, e.g., proper secretion leader cleavage.

Useful measures of protein yield include, e.g., the amount of recombinant protein per culture volume (e.g., grams or milligrams of protein/liter of culture), percent or fraction of recombinant protein measured in the insoluble pellet obtained after cell lysis (e.g., amount of recombinant protein in extract supernatant/amount of protein in insoluble fraction), percent or fraction of active protein (e.g., amount of active protein/amount protein used in the assay), percent or fraction of total cell protein (tcp), amount of protein/cell, and percent or proportion of dry biomass. In embodiments, the measure of protein yield as described herein is based on the amount of soluble protein or the amount of active protein, or both, obtained.

In embodiments wherein yield is expressed in terms of culture volume the culture cell density may be taken into account, particularly when yields between different cultures are being compared.

In embodiments, the methods of the present invention can be used to obtain a soluble and/or active and/or properly processed (e.g., having the secretion leader cleaved properly) recombinant toxin protein or subunit protein yield of about 0.2 grams per liter to about 12 grams per liter. In embodiments, the yield is about 0.5 grams per liter to about 12 grams per liter. In certain embodiments, the recombinant protein or subunit protein yield is about 0.2 g/L, about 0.3 g/L, about 0.4 g/L, about 0.5 g/L, about 0.6 g/L, about 0.7 g/L, about 0.8 g/L, about 0.9 g/L, about 1 g/L, about 1.5 g/L, about 2 g/L, about 2.5 g/L, about 3 g/L, about 3.5 g/L, about 4 g/L, about 4.5 g/L, about 5 g/L, about 5.5 g/L, about 6 g/L, about 6.5 g/L, about 7 g/L, about 7.5 g/L, about 8 g/L, about 8.5 g/L, about 9 g/L, about 9.5 g/L, about 10 g/L, about 10.5 g/L, about 11 g/L, about 12 g/L, about 0.2 g/L to about 0.5 g/L, about 0.2 g/L to about 1 g/L, about 0.2 to about 2 g/L, about 0.2 g/L to about 0.6 g/L, about 0.3 g/L to about 1 g/L, about 0.3 to about 2 g/L, about 0.4 to about 0.7 g/L, about 0.4 to about 1 g/L about 0.4 to about 2 g/L, about 0.4 to about 3 g/L, about 0.5 g/L to about 1 g/L, about 0.5 g/L to about 1 g/L, about 0.5 g/L to about 2 g/L, about 0.5 g/L to about 3 g/L, about 0.5 g/L to about 4 g/L, about 0.5 g/L to about 5 g/L, about 0.5 g/L to about 6 g/L, about 0.5 g/L to about 7 g/L, about 0.5 g/L to about 8 g/L, about 0.5 g/L to about 9 g/L, about 0.5 g/L to about 10 g/L, about 0.5 g/L to about 11 g/L, about 0.5 g/L to about 12 g/L, about 1 g/L to about 2 g/L, about 1 g/L to about 3 g/L, about 1 g/L to about 4 g/L, about 1 g/L to about 5 g/L, about 1 g/L to about 6 g/L, about 1 g/L to about 7 g/L, about 1 g/L to about 8 g/L, about 1 g/L to about 9 g/L, about 1 g/L to about 10 g/L, about 1 g/L to about 11 g/L, about 1 g/L to about 12 g/L, about 2 g/L to about 3 g/L, about 2 g/L to about 4 g/L, about 2 g/L to about 5 g/L, about 2 g/L to about 6 g/L, about 2 g/L to about 7 g/L, about 2 g/L to about 8 g/L, about 2 g/L to about 9 g/L, about 2 g/L to about 10 g/L, about 2 g/L to about 11 g/L, about 2 g/L to about 12 g/L, about 3 g/L to about 4 g/L, about 3 g/L to about 5 g/L, about 3 g/L to about 6 g/L, about 3 g/L to about 7 g/L, about 3 g/L to about 8 g/L, about 3 g/L to about 9 g/L, about 3 g/L to about 10 g/L, about 3 g/L to about 11 g/L, about 3 g/L to about 12 g/L, about 4 g/L to about 5 g/L, about 4 g/L to about 6 g/L, about 4 g/L to about 7 g/L, about 4 g/L to about 8 g/L, about 4 g/L to about 9 g/L, about 4 g/L to about 10 g/L, about 4 g/L to about 11 g/L, about 4 g/L to about 12 g/L, about 5 g/L to about 6 g/L, about 5 g/L to about 7 g/L, about 5 g/L to about 8 g/L, about 5 g/L to about 9 g/L, about 5 g/L to about 10 g/L, about 5 g/L to about 11 g/L, about 5 g/L to about 12 g/L, about 6 g/L to about 7 g/L, about 6 g/L to about 8 g/L, about 6 g/L to about 9 g/L, about 6 g/L to about 10 g/L, about 6 g/L to about 11 g/L, about 6 g/L to about 12 g/L, about 7 g/L to about 8 g/L, about 7 g/L to about 9 g/L, about 7 g/L to about 10 g/L, about 7 g/L to about 11 g/L, about 7 g/L to about 12 g/L, about 8 g/L to about 9 g/L, about 8 g/L to about 10 g/L, about 8 g/L to about 11 g/L, about 8 g/L to about 12 g/L, about 9 g/L to about 10 g/L, about 9 g/L to about 11 g/L, about 9 g/L to about 12 g/L, about 10 g/L to about 11 g/L, about 10 g/L to about 12 g/L, or about 11 g/L to about 12 g/L.

In embodiments, the amount of recombinant toxin protein or subunit protein produced is about 1% to 75% of the total cell protein. In certain embodiments, the amount of toxin protein or subunit protein produced is about 1%, about 2%, about 3%, about 4%, about 5%, about 10%, about 15%, about 20%, about 25%, about 30%, about 35%, about 40%, about 45%, about 50%, about 55%, about 60%, about 65%, about 70%, about 75%, about 1% to about 5%, about 1% to about 10%, about 1% to about 20%, about 1% to about 30%, about 1% to about 40%, about 1% to about 50%, about 1% to about 60%, about 1% to about 75%, about 2% to about 5%, about 2% to about 10%, about 2% to about 20%, about 2% to about 30%, about 2% to about 40%, about 2% to about 50%, about 2% to about 60%, about 2% to about 75%, about 3% to about 5%, about 3% to about 10%, about 3% to about 20%, about 3% to about 30%, about 3% to about 40%, about 3% to about 50%, about 3% to about 60%, about 3% to about 75%, about 4% to about 10%, about 4% to about 20%, about 4% to about 30%, about 4% to about 40%, about 4% to about 50%, about 4% to about 60%, about 4% to about 75%, about 5% to about 10%, about 5% to about 20%, about 5% to about 30%, about 5% to about 40%, about 5% to about 50%, about 5% to about 60%, about 5% to about 75%, about 10% to about 20%, about 10% to about 30%, about 10% to about 40%, about 10% to about 50%, about 10% to about 60%, about 10% to about 75%, about 20% to about 30%, about 20% to about 40%, about 20% to about 50%, about 20% to about 60%, about 20% to about 75%, about 30% to about 40%, about 30% to about 50%, about 30% to about 60%, about 30% to about 75%, about 40% to about 50%, about 40% to about 60%, about 40% to about 75%, about 50% to about 60%, about 50% to about 75%, about 60% to about 75%, or about 70% to about 75%, of the total cell protein.

In certain embodiments, multiple proteins are produced from the same host cell. For example, in embodiments, all five subunits of Pertussis toxin are made from the same host cell grown in a single culture. In such embodiments the concentration, % total cell protein, or activity observed is that for each individual toxin subunit or for all the subunits taken together. That is, in embodiments, the methods of the invention are used to obtain a yield of the S1, S2, S3, S4, or S5 subunit of Pertussis toxin protein of about 1 gram per liter to about 12 grams per liter. In embodiments, the amount of S1, S2, S3, S4, or S5 subunit protein produced is 1% to 75% of the total cell protein. Alternatively, the methods of the invention are used to obtain a yield of S1, S2, S3, S4, and S5 subunit protein of about 1 gram per liter to about 12 grams per liter. In embodiments, the amount of S1, S2, S3, S4, and S5 subunit protein produced is 1% to 75% of the total cell protein. In certain embodiments, the amount of each subunit obtained, in grams per liter or % total cell protein, is approximately the same.

The "solubility" and "activity" of a protein, though related qualities, are generally determined by different means. The solubility of a protein, particularly a hydrophobic protein, typically relates to the folding of a protein; insolubility indicates that hydrophobic amino acid residues are improperly located on the outside of the folded protein. Protein activity, which can be evaluated using methods, e.g., those described below, is another indicator of proper protein conformation. "Soluble, active, or both," or "soluble and/or active," as used herein, refers to protein that is determined to be soluble, active, or both soluble and active, by methods known to those of skill in the art and described herein. The "activity" of a given protein can include binding activity, e.g., that represented by binding to a receptor, a specific antibody, or to another known substrate, or by enzymatic activity if relevant. Activity levels can be described, e.g., in absolute terms or in relative terms, as when compared with the activity of a standard or control sample, or any sample used as a reference.

Activity assays for evaluating toxins are known in the art and described in the literature. Activity assays include immunological or antibody binding assays, e.g., Western Blot analysis and ELISA, as well as receptor binding assays, e.g., CRM197 can be evaluated by Diptheria toxin receptor (proHB-EGF) binding assay. Antibodies useful in these assays are commercially available. Activity assays also include enzyme activity assays. Wild-type DT can be assayed immunologically and also by ADP-ribosylation activity, using methods known in the art and described elsewhere herein for *P. aeruginosa* Exotoxin A.

For example, Western blot analysis of CTB can be performed as described, e.g., in U.S. Pat. No. 6,140,082, "Expression of Gene Products from Genetically Manipulated Strains of *Bordetella*," incorporated herein by reference. This patent describes expression of CTB in *Bordetella*. The proteins from culture supernatants were resolved by SDS-PAGE or boiled before being resolved to convert the CTB pentamer to the monomeric form. The proteins were transferred onto nylon membranes and probed with goat anti-choleragenoid IgG antibody (anti-CTB, List Biologicals #GAC-01C). Detection was performed with alkaline phosphatase-conjugated donkey anti-goat IgG, using dig chemiluminescence (Boehringer Mannheim). A Cholera toxin standard (Sigma) containing both CTA and CTB was used for comparison.

Western blot analysis of PTX can be performed, e.g., as described herein in the Examples, using commercially available antibodies. Monoclonal antibodies are available from, e.g., Abcam, Cambridge, Mass.

Tetanus Toxin C Fragment can be evaluated by Western Blot analysis, or by ELISA as described in, e.g., U.S. Pat. No. 5,443,966, "Expression of tetanus toxin fragment C," incorporated herein by reference. Antibodies are available from multiple commercial sources, e.g., Abcam, Cambridge, Mass.

TcdB activity can be evaluated by Western Blot or other detection analysis, as described in the art. Enzymatic activity can be assayed, e.g., using glucosylhydrolase/glucosylation assay methods described in the art, for example in U.S. Pat. No. 7,226,597, incorporated herein by reference in its entirety. Specifically, glucosylation reactions can be carried out in a reaction mix containing 50 mM n-2hydroxyethylpiperazine-n'-2-ethane sulfonic acid, 100 mM KCl, 1 mM MnCl2, 1 mM MgCl2, 100 µgram/ml BSA, 0.2 mM GDP, 40 µM[14C]UDP-glucose (303 Ci/mol; ICN Pharmaceuticals), 100 µM UDP-glucose and 3 pmol of TcdB or 10 pmol of each fusion protein. The assay is allowed to incubate overnight at 37° C. and the cleaved glucose is separated using AG1-X2 anion exchange resin and counted in a liquid scintillation counter.

*P. aeruginosa* Exotoxin A activity can be evaluated using immunological methods, e.g., Western Blot analysis. Since ETA is an ADP-ribosylating toxin, it can be assayed for ADP-ribosylation activity, e.g., as described in U.S. Pat. No. 4,892,827, incorporated herein by reference. Specifically, rabbit reticulocyte preparations or wheat germ extracts enriched with elongation factor 2 (EF-2) are used as a source of EF-2. Assays (500 µl total volume) contain about 10 pmole of EF-2, 37 pmole of 14C-NAD (0.06 µCi), 0.25 to 1.25 µg of ETA and buffer (40 mM DTT, 1 mM EDTA, and 50 mM Tris, pH 8.1). Activity is measured as pmoles of NAD transferred to EF-2 in 30 minutes. A standard curve of known concentrations of PE is established and used to determine the activity of PE in extracts from *E. coli*. After incubation for 30 minutes at 37° C., 0.5 ml 12% TCA is added to each assay mixture. The assay mixtures are then set in an ice bath for 15 minutes, followed by centrifugation at 4° C., 3,000×g for 10 minutes. The pellet is washed with 1 ml 6% TCA and centrifuged as above. The pellet is then measured for 14C radioactivity in a liquid scintillation counter as the index of the ADP-ribosylation activity.

Therefore, a measure of activity can represent, e.g., antibody or receptor binding capacity, substrate binding capacity (as to a column material), or enzyme activity.

In embodiments, activity is represented by the % active recombinant toxin protein in the extract supernatant as compared with the total amount assayed. This is based on the amount of recombinant toxin protein determined to be active by the assay relative to the total amount of recombinant toxin protein used in the assay. In other embodiments, activity is represented by the % activity level of the protein compared to a standard, e.g., native protein. This is based on the amount of active recombinant toxin protein in supernatant extract sample relative to the amount of active protein in a standard sample (where the same amount of protein from each sample is used in assay).

In embodiments, about 40% to about 100% of the toxin protein or subunit is determined to be active. In embodiments, about 40%, about 50%, about 60%, about 70%, about 80%, about 90%, or about 100% of the recombinant toxin protein or protein subunit is determined to be active. In embodiments, about 40% to about 50%, about 50% to about 60%, about 60% to about 70%, about 70% to about 80%, about 80% to about 90%, about 90% to about 100%, about 50% to about 100%, about 60% to about 100%, about 70% to about 100%, about 80% to about 100%, about 40% to about 90%, about 40% to about 95%, about 50% to about 90%, about 50% to about 95%, about 50% to about 100%, about 60% to about 90%, about 60% to about 95%, about 60% to about 100%, about 70% to about 90%, about 70% to about 95%, about 70% to about 100%, or about 70% to about 100% of the recombinant toxin protein or subunit is determined to be active.

In other embodiments, about 75% to about 100% of the recombinant toxin protein or protein subunit is determined to be active. In embodiments, about 75% to about 80%, about 75% to about 85%, about 75% to about 90%, about 75% to about 95%, about 80% to about 85%, about 80% to about 90%, about 80% to about 95%, about 80% to about 100%, about 85% to about 90%, about 85% to about 95%, about 85% to about 100%, about 90% to about 95%, about 90% to about 100%, or about 95% to about 100% of the recombinant toxin protein or subunit is determined to be active.

Means of confirming the identity of the induced protein are also known in the art. For example, a protein can analyzed by peptide mass fingerprint using MALDI-TOF mass spectrometry, N-terminal sequencing analysis, or peptide mapping.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

Example 1

High Throughput Expression of a Recombinant CRM197 Protein

CRM197 expression strains were constructed and the amount of soluble CRM197 protein produced in the strains was analyzed using capillary gel electrophoresis (SDS-CGE). Based on the resulting data, certain strains were selected for use in large-scale expression.

Construction and Growth of CRM197 Expression Strains

The CRM197 coding sequence was constructed using *P. fluorescens* preferred codons to encode the CRM197 amino acid sequence. FIG. 1 shows the amino acid and DNA sequences of the expressed synthetic CRM197 gene.

Plasmids carrying the optimized CRM197 sequence, fused to ten *P. fluorescens* secretion leaders as shown in Table 8, were constructed. The CRM197 coding sequence was fused in frame with that of *P. fluorescens* secretion leaders to target the protein to the periplasm for recovery in the properly folded and active form.

TABLE 8

Secretion leaders used for CRM197 expression screen

| | Secretion Leader |
|---|---|
| 1 | DsbA |
| 2 | Azu |

TABLE 8-continued Secretion leaders used for CRM197 expression screen

| | Secretion Leader |
|---|---|
| 3 | Ibp-S31A |
| 4 | Tpr |
| 5 | CupB2 |
| 6 | CupA2 |
| 7 | NikA |
| 8 | Pbp A20V |
| 9 | DsbC |
| 10 | TolB |

Constructs containing the ten secretion leaders fused to the recombinant CRM197 coding sequence were tested in *P. fluorescens* hosts. Four hosts, listed in Table 9, were tested with each expression plasmid. Host cells were electroporated with the indicated plasmids, resuspended in HTP growth medium with trace minerals and 5% glycerol and then transferred to 96-well deep well plate with 400 µl M9 salts 1% glucose medium and trace elements. The 96-well plates were incubated at 30° C. with shaking for 48 hours. Ten microliters of each of the forty seed cultures were transferred into triplicate 96-well deep-well plates, each well containing 500 µl of HTP medium supplemented with trace elements and 5% glycerol, and incubated as before for 24 hours.

TABLE 9

Host strains used for CRM197 expression screen

| Host Strain | Genotype | Type |
|---|---|---|
| 1 | lon, la, aprA | PD |
| 2 | hslUV prc1 degP1 degP2 aprA deletions; overexpresses DegP2 S219A | PD + FMO |
| 3 | dsbABCD | FMO |
| 4 | grpE, dnaKJ | FMO |

PD = Protease Deletion (listed proteases are deleted);
FMO = Folding Modulator Overexpressor (listed folding modulators are overexpressed.

Isopropyl-β-D-1-thiogalactopyranoside (IPTG) was added to each well to a final concentration of 0.3 mM to induce the expression of target proteins. Mannitol (Sigma, M1902) was added to each well to a final concentration of 1% to induce the expression of folding modulators in folding modulator over-expressing strains, and the temperature was reduced to 25° C. Twenty four hours after induction, cells were normalized to OD600=15 using PBS in a volume of 400 µl. Samples were frozen for later processing by sonication and centrifugation to generate soluble and insoluble fractions.

Sample Preparation and SDS-CGE Analysis

Soluble and insoluble cellular fractions were prepared by sonication of the normalized cultures followed by centrifugation. Frozen, normalized culture broth (400 µL) was thawed and sonicated for 3.5 minutes. The lysates were centrifuged at 20,800×g for 20 minutes (4° C.) and the supernatants removed using manual or automated liquid handling (soluble fraction). The pellets (insoluble fraction) were frozen and then thawed for re-centrifugation at 20,080×g for 20 minutes at 4 C, to remove residual supernatant. The pellets were then resuspended in 400 µL of 1× phosphate buffered saline (PBS), pH 7.4. Further dilutions of soluble and insoluble samples for SDS-CGE analysis were performed in 1× phosphate buffered saline (PBS), pH 7.4. Soluble and insoluble samples were prepared for SDS capillary gel electrophoresis (CGE) (Caliper Life Sciences, Protein Express LabChip Kit, Part 760301), in the presence of dithiothreitol (DTT).

Figure 2:
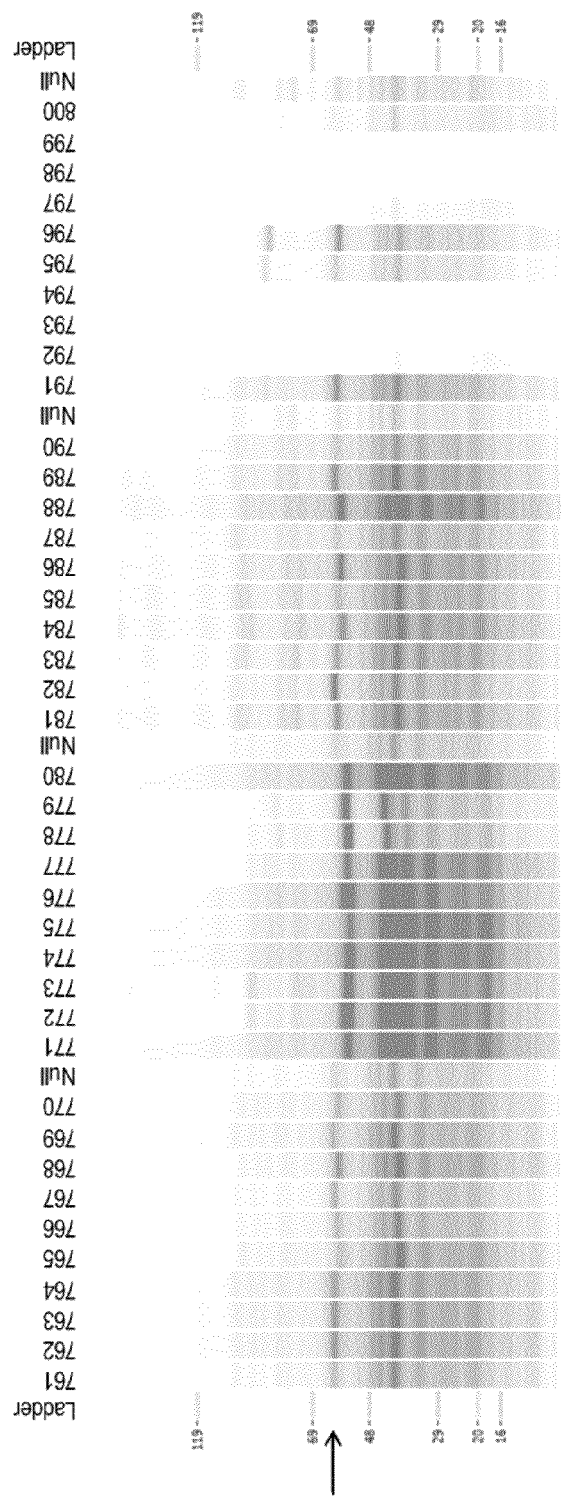
FIG. 2. High Throughput Expression Analysis of CRM197. CRM197 protein expressed using the DNA sequence shown in FIG. 1B was analyzed using capillary gel electrophoresis (SDS-CGE). Soluble fractions of 40 CRM197-expression strains tested are shown in a gel-like image generated from the SDS-CGE data. Strain names as described in Table 10 are listed above each lane. *P. fluorescens*-expressed CRM197 migrated as a single band at ~58 kDa on SDS-CGE (arrow at left). Molecular weight markers in first and last lanes are 16, 20, 29, 48, 69 and 119 kDa.

Representative gel-like images showing the results of the reducing SDS-CGE analysis of the soluble fraction from each strain are shown in FIG. 2. Table 10 shows the mean soluble CRM197 yield and standard deviation of 3 replicates for each of the CRM197-expression strains constructed. The host strain and secretion leader screened for each strain are also indicated.

Both secretion leader and host strain showed a significant impact on CRM197 expression. Expression ranged from no detectable yield to more than 1.2 g/L at the 0.5 mL scale, with the highest expression levels observed in the Host Strain 2 background. The yield observed in PS538-776 was 1263 mg/L, and that in PS538-772 was 1241 mg/L, both well over the average yield of 340 mg/L. Both high and low yields were observed in the same host strain depending on the leader used, and both high and low yields were observed using the same leader in different host strains.

PS538-772, PS538-773, PS538-776, PS538-778, PS538-782 were selected for evaluation in large-scale fermentation.

TABLE 10

Mean CRM197 yield for CRM197-expression strains

| Strain Number | Corresponding Strain Number in U.S. patent application Ser. No. 61/325,235 | Host | Leader | Mean Yield (mg/L) | Std Dev (3 replicates) |
|---|---|---|---|---|---|
| PS538-761 | PS538-731 | 1 | DsbA | 205 | 162 |
| PS538-762 | PS538-732 | 1 | Azu | 427 | 186 |
| PS538-763 | PS538-733 | 1 | Ibp-S31A | 361 | 183 |
| PS538-764 | PS538-734 | 1 | Tpr | 298 | 106 |
| PS538-765 | PS538-735 | 1 | CupB2 | 105 | 109 |
| PS538-766 | PS538-736 | 1 | CupA2 | 175 | 99 |
| PS538-767 | PS538-737 | 1 | NikA | 314 | 85 |
| PS538-768 | PS538-738 | 1 | Pbp A20V | 291 | 204 |
| PS538-769 | PS538-739 | 1 | DsbC | 148 | 91 |
| PS538-770 | PS538-740 | 1 | TolB | 213 | 36 |
| PS538-771 | PS538-741 | 2 | DsbA | 407 | 218 |
| PS538-772 | PS538-742 | 2 | Azu | 1241 | 372 |
| PS538-773 | PS538-743 | 2 | Ibp-S31A | 1107 | 219 |
| PS538-774 | PS538-744 | 2 | Tpr | 280 | 285 |
| PS538-775 | PS538-745 | 2 | CupB2 | 192 | 219 |
| PS538-776 | PS538-746 | 2 | CupA2 | 1263 | 474 |
| PS538-777 | PS538-747 | 2 | NikA | 699 | 259 |
| PS538-778 | PS538-748 | 2 | Pbp A20V | 914 | 416 |
| PS538-779 | PS538-749 | 2 | DsbC | 567 | 141 |
| PS538-780 | PS538-750 | 2 | TolB | 382 | 217 |
| PS538-781 | PS538-751 | 3 | DsbA | 591 | 230 |
| PS538-782 | PS538-752 | 3 | Azu | 1094 | 543 |
| PS538-783 | PS538-753 | 3 | Ibp-S31A | 323 | 143 |
| PS538-784 | PS538-754 | 3 | Tpr | 419 | 70 |
| PS538-785 | PS538-755 | 3 | CupB2 | 75 | 74 |
| PS538-786 | PS538-756 | 3 | CupA2 | 309 | 214 |
| PS538-787 | PS538-757 | 3 | NikA | 52 | 73 |
| PS538-788 | PS538-758 | 3 | Pbp A20V | 356 | 295 |
| PS538-789 | PS538-759 | 3 | DsbC | 319 | 117 |
| PS538-790 | PS538-760 | 3 | TolB | 69 | 88 |
| PS538-791 | PS538-761 | 4 | DsbA | 270 | 106 |
| PS538-792 | PS538-762 | 4 | Azu | 0 | 14 |
| PS538-793 | PS538-763 | 4 | Ibp-S31A | 0 | 6 |
| PS538-794 | PS538-764 | 4 | Tpr | 0 | 0 |
| PS538-795 | PS538-765 | 4 | CupB2 | 18 | 39 |
| PS538-796 | PS538-766 | 4 | CupA2 | 118 | 134 |
| PS538-797 | PS538-767 | 4 | NikA | 0 | 9 |
| PS538-798 | PS538-768 | 4 | Pbp A20V | 0 | 0 |
| PS538-799 | PS538-769 | 4 | DsbC | 0 | 0 |
| PS538-800 | PS538-770 | 4 | TolB | 0 | 0 |

Example 2

Large-Scale Expression of a Recombinant Crm197 Protein

Recombinant CRM197 protein was produced in *Pseudomonas fluorescens* strains PS538-772, PS538-776, and PS538-782 in 2 liter fermentors. Cultures were grown in 2 liter fermentors containing a mineral salts medium as described herein and also by, e.g., Riesenberg, D., et al., 1991, and maintained at 32° C. and pH 6.5 through the addition of ammonia. Dissolved oxygen was maintained in excess through increases in agitation and flow of sparged air and oxygen into the fermentor. Glycerol was delivered to the culture throughout the fermentation to maintain excess levels. These conditions were maintained until a target culture cell density (optical density at 575 nm (A575)) for induction is reached, at which time IPTG is added to initiate CRM197 production. Cell density at induction could be varied from A575 of 40 to 200 absorbance units (AU). IPTG concentrations could be varied in the range from 0.02 to 0.4 mM. pH from 6 to 7.5 and temperature 20 to 35° C. After 16-24 hours, the culture from each bioreactor was harvested by centrifugation and the cell pellet frozen at −80° C. Samples were analyzed by SDS-CGE for product formation.

Figure 23:
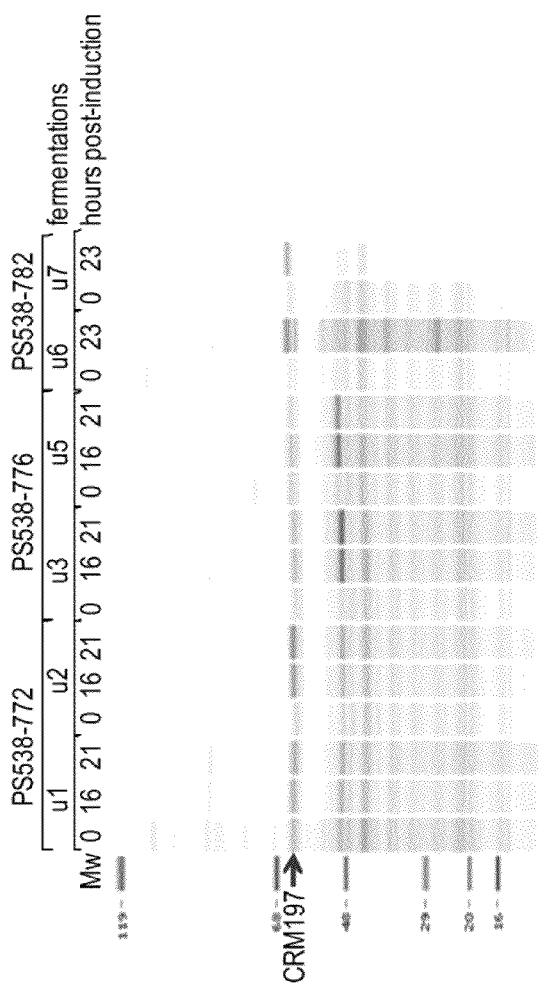
Figure 24:
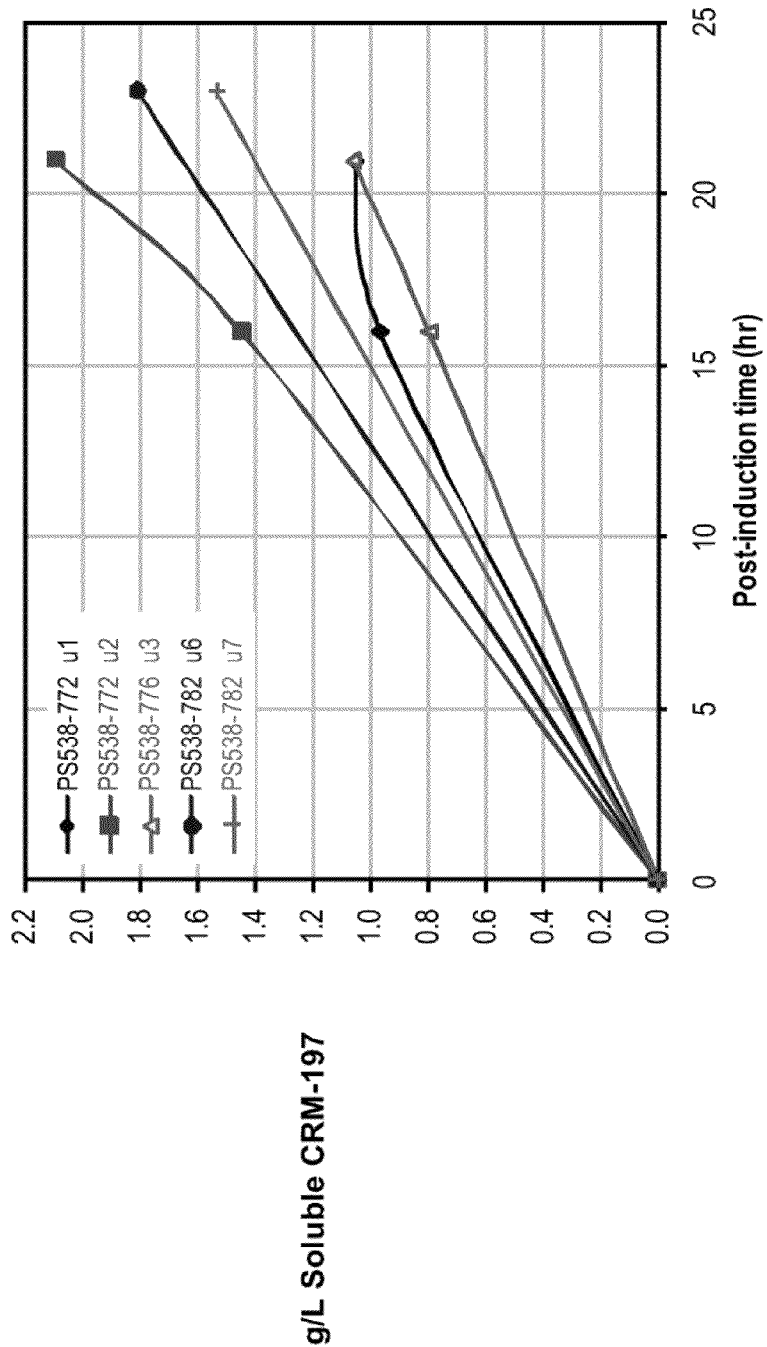
Figure 25:
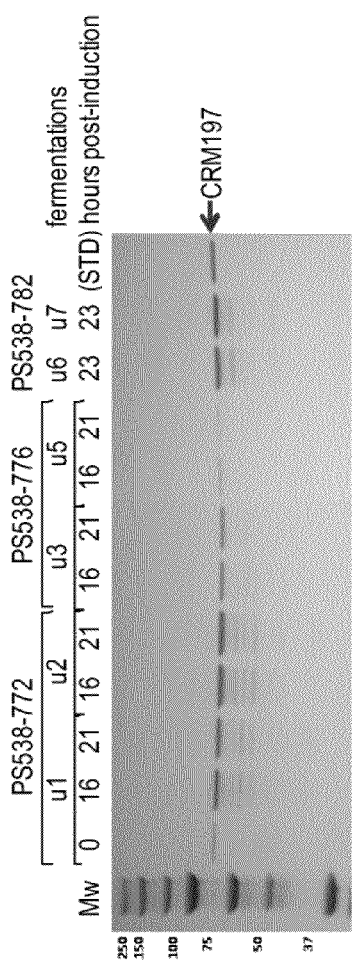

Multiple fermentation conditions were evaluated resulting in top CRM197 expression as determined by SDS-CGE of 1 to 2 g/L (see FIGS. 23 and 24). The identities of the induced proteins were confirmed by Western blot analysis using a diphtheria toxin specific antibody (FIG. 25).

Example 3

High Throughput Expression of a Recombinant Cholera Toxin B Protein

Construction and Growth of Cholera Toxin B Expression Strains

The Cholera Toxin B coding sequence was constructed using *P. fluorescens* preferred codons to encode the Cholera Toxin B amino acid sequence. FIG. 3 shows the amino acid and DNA sequences of the expressed synthetic Cholera Toxin B gene.

Plasmids carrying the optimized Cholera Toxin B sequence, fused to the same ten *P. fluorescens* secretion leader coding sequences used with CRM197 (shown in Table 8) were constructed. The secretion leaders were included to target the protein to the periplasm for recovery in the properly folded and active form.

Constructs expressing the ten secretion leaders fused to the recombinant Cholera Toxin B protein were tested in *P. fluorescens* hosts. The four hosts listed in Table 9 were tested with each expression plasmid. Host cells were electroporated with the indicated plasmids, and grown and induced in 96-well format as described above for the CRM197 high throughput expression. Samples were prepared and analyzed by SDS-CGE as described above for the CRM197 high throughput expression samples.

Figure 4:
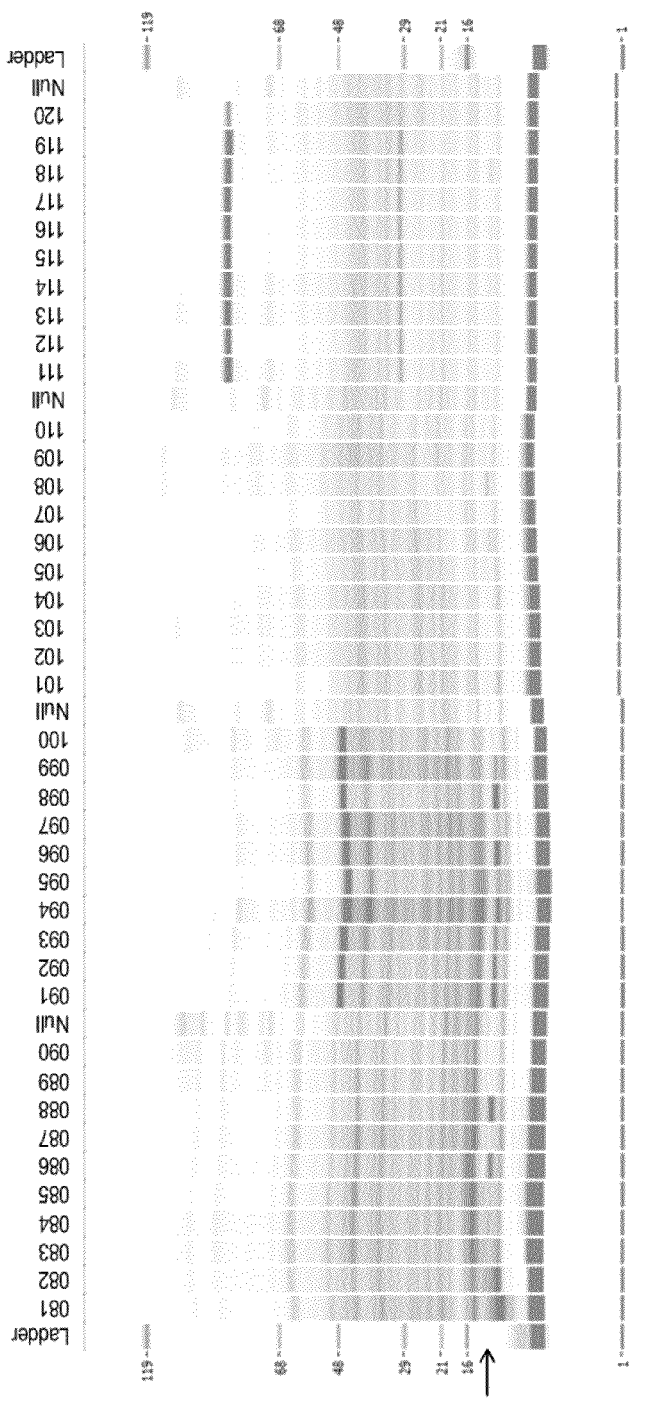
FIG. 4. High Throughput Expression Analysis of Cholera Toxin B. Cholera Toxin B protein expressed using the DNA sequence shown in FIG. 3B was analyzed using capillary gel electrophoresis (SDS-CGE). Soluble fractions from 40 cholera toxin-expression strains tested are shown in a gel-like image generated from the SDS-CGE data. Strain names as described in Table 11 are listed above each lane. Induced CTB migrated as a single band at ~11.5 kDa on SDS-CGE (arrow at left). Molecular weight markers in first and last lanes are 16, 20, 29, 48, 69 and 119 kDa.

Representative gel-like images showing the results of the reducing SDS-CGE analysis of the soluble fraction from each strain are shown in FIG. 4. Table 11 shows the mean soluble Cholera Toxin B yield and standard deviation of 3 replicates for each of the Cholera Toxin B-expression strains constructed.

Both secretion leader and host strain showed a significant impact on Cholera Toxin B expression. Expression ranged from no detectable yield to more than 0.2 g/L at the 0.5 mL scale, with the highest expression levels observed in the hslUV prc1 degP1 degP2 aprA deletion/DegP2 S219A overexpression host background. Expression of Cholera Toxin B fused to leaders 6 (CupA2) and 8 (PbpA20V) appeared to be consistently high in all four strains.

TABLE 11

Cholera Toxin B Expression Summary

| Strain Number | Host Strain | Plasmid | Leader | Mean Yield (mg/L) | Std Dev (3 replicates) |
|---|---|---|---|---|---|
| PS538-081 | 1 | p538-021 | DsbA | 25 | 8 |
| PS538-082 | 1 | p538-022 | Azu | 1 | 8 |
| PS538-083 | 1 | p538-023 | Ibp-S31A | 0 | 5 |
| PS538-084 | 1 | p538-024 | Tpr | 35 | 14 |
| PS538-085 | 1 | p538-025 | CupB2 | 10 | 9 |
| PS538-086 | 1 | p538-026 | CupA2 | 138 | 18 |
| PS538-087 | 1 | p538-027 | NikA | 0 | 5 |
| PS538-088 | 1 | p538-028 | Pbp A20V | 213 | 23 |
| PS538-089 | 1 | p538-029 | DsbC | 0 | 6 |
| PS538-090 | 1 | p538-030 | TolB | 0 | 4 |
| PS538-091 | 2 | p538-021 | DsbA | 133 | 62 |
| PS538-092 | 2 | p538-022 | Azu | 83 | 56 |
| PS538-093 | 2 | p538-023 | Ibp-S31A | 50 | 44 |
| PS538-094 | 2 | p538-024 | Tpr | 61 | 55 |
| PS538-095 | 2 | p538-025 | CupB2 | 62 | 19 |
| PS538-096 | 2 | p538-026 | CupA2 | 147 | 57 |
| PS538-097 | 2 | p538-027 | NikA | 31 | 28 |
| PS538-098 | 2 | p538-028 | Pbp A20V | 223 | 78 |
| PS538-099 | 2 | p538-029 | DsbC | 41 | 24 |
| PS538-100 | 2 | p538-030 | TolB | 6 | 5 |
| PS538-101 | 3 | p538-021 | DsbA | 1 | 7 |
| PS538-102 | 3 | p538-022 | Azu | 1 | 2 |
| PS538-103 | 3 | p538-023 | Ibp-S31A | 19 | 17 |
| PS538-104 | 3 | p538-024 | Tpr | 28 | 36 |
| PS538-105 | 3 | p538-025 | CupB2 | 5 | 9 |
| PS538-106 | 3 | p538-026 | CupA2 | 40 | 12 |
| PS538-107 | 3 | p538-027 | NikA | 5 | 10 |
| PS538-108 | 3 | p538-028 | Pbp A20V | 45 | 19 |
| PS538-109 | 3 | p538-029 | DsbC | 0 | 6 |
| PS538-110 | 3 | p538-030 | TolB | 0 | 3 |
| PS538-111 | 4 | p538-021 | DsbA | 0 | 5 |
| PS538-112 | 4 | p538-022 | Azu | 0 | 3 |
| PS538-113 | 4 | p538-023 | Ibp-S31A | 0 | 2 |
| PS538-114 | 4 | p538-024 | Tpr | 13 | 3 |
| PS538-115 | 4 | p538-025 | CupB2 | 2 | 4 |
| PS538-116 | 4 | p538-026 | CupA2 | 15 | 16 |
| PS538-117 | 4 | p538-027 | NikA | 0 | 2 |
| PS538-118 | 4 | p538-028 | Pbp A20V | 35 | 15 |
| PS538-119 | 4 | p538-029 | DsbC | 0 | 2 |
| PS538-120 | 4 | p538-030 | TolB | 0 | 2 |

Example 4

Large-Scale Expression of a Recombinant Cholera Toxin B Protein

Recombinant Cholera Toxin B protein was produced in *Pseudomonas fluorescens* Pfēnex Expression Technology™ strains PS538-088 and PS538-091. The selected strain was grown in 2 liter fermentors containing a mineral salts medium as described herein and also by, e.g., Riesenberg, D., et al., 1991, and maintained at 32° C. and pH 6.5 through the addition of ammonia. Dissolved oxygen was maintained in excess through increases in agitation and flow of sparged air and oxygen into the fermentor. Glycerol was delivered to the culture throughout the fermentation to maintain excess levels. These conditions were maintained until a target culture cell density (optical density at 575 nm (A575)) for induction was reached, at which time IPTG was added to initiate the target protein production. IPTG was added to initiate CTB production. After 16-24 hours, the culture from each bioreactor was harvested by centrifugation and the cell pellet was frozen at −80° C.

Multiple fermentation conditions were evaluated resulting in top CTB expression as determined by SDS-CGE of 0.6 to 1.0 g/L. The top performing fermentation cultures were induced at approximately 80-160 OD with 0.2 mM IPTG at pH 6.5-7.2 and 32° C. Soluble CTB concentrations were determined by SDS-CGE (see FIG. 14 and Table 12). The identities of the induced proteins were confirmed by peptide mass fingerprint using MALDI-TOF mass spectrometry.

TABLE 12

Soluble Cholera Toxin B Titers

| Strain | Fermentation | Product | Product concentration (g/L) |
|---|---|---|---|
| PS538-088 | U5 | CTB | 0.94 ± 0.03 |
| PS538-088 | U6 | CTB | 0.59 ± 0.01 |
| PS538-091 | U3 | CTB | 0.81 ± 0.09 |

Example 5

High Throughput Expression of a Recombinant Pertussis Toxin Protein

Construction and Growth of Pertussis Toxoid S1 E129A R9K Expression Strains

The sequence of the Pertussis toxin operon encoding subunits S1, S2, S3, S4 and S5, with S1 mutations E129A and R9K was used for expression of recombinant Pertussis toxin. FIG. 5 shows a map of the operon. FIG. 6 shows the DNA sequence of the operon, with translation (SEQ ID NO:24). FIG. 7 shows the individual amino acid sequences of S1, S2, S3, S4 and S5.

The construct was expressed in eight *P. fluorescens* hosts, shown in Table 13. Host cells were electroporated with p538-081, and grown and induced in 96-well format as described above for CRM197 high throughput expression. Samples were prepared and analyzed by SDS-CGE as described above for the CRM197 high throughput expression samples.

TABLE 13

Pertussis Toxin S1 E129A R9K Expression Strains

| Strain Number | Host | Genotype | Plasmid | Type |
|---|---|---|---|---|
| PS538-321 | 1 | lon, la, aprA | p538-081 | PD |
| PS538-322 | 2 | hslUV, prc1, degP1, degP2 and aprA | p538-081 | PD |
| PS538-323 | 3 | dsbABCD | p538-081 | FMO |
| PS538-324 | 4 | grpE, dnaKJ | p538-081 | FMO |
| PS538-325 | 5 | htpX | p538-081 | PD |
| PS538-326 | 6 | RXF01590 | p538-081 | PD |
| PS538-327 | 7 | lon, la, aprA deletions; overexpresses grpE and dnaKJ | p538-081 | PD + FMO |
| PS538-328 | 8 | ppiB (RXF05345) | p538-081 | FMO |

PD = Protease Deletion (listed proteases are deleted);
FMO = Folding Modulator Overexpressor (listed folding modulators are overexpressed.

Western Blot Analysis of Expressed Pertussis Toxin

Figure 8:
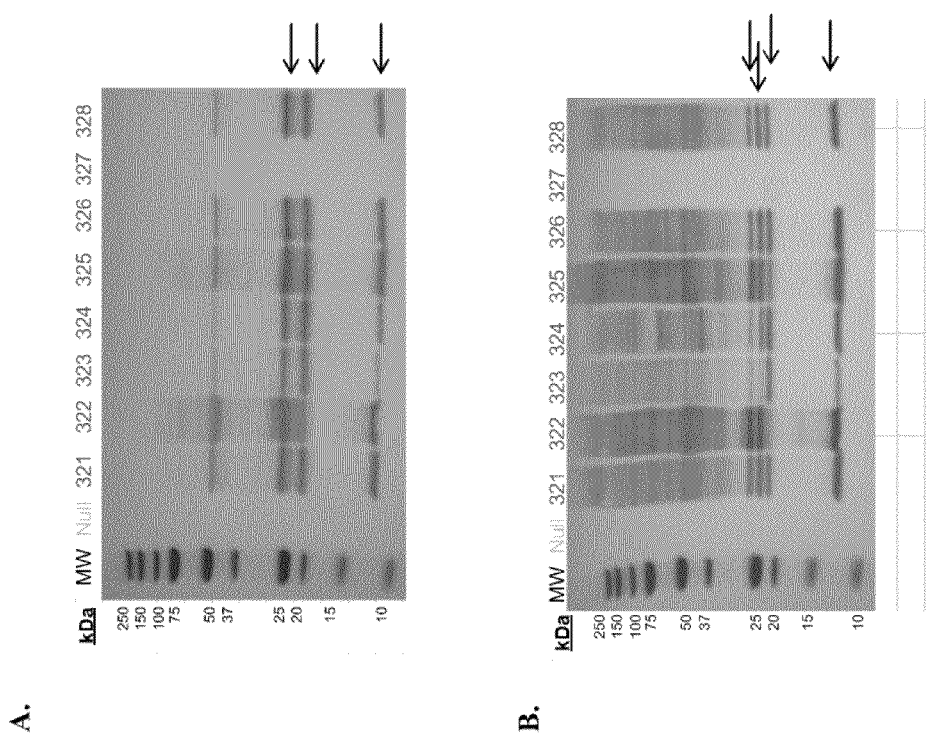
FIG. 8. Western blot analysis of Pertussis Toxoid expression samples. Strain names are listed above each lane. Induced Ptx migrated as multiple bands range from 11 to 26 kDa (S1: 26.1 Kda, S2: 20.9 Kda, S3: 21.8 KDa, S4 (2×): 12 KDa, S5: 11 KDa) A. Reduced samples. B. Non-reduced samples. Both panels: Lane 1—molecular weight markers (10, 15, 20, 25, 37, 50, 75, 100, 150, 250 kDa); Lane 2—Null; Lane 3—strain 321; Lane 4—strain 322; Lane 5—strain 323; Lane 6—strain 324; Lane 7—strain 325; Lane 8—strain 326; Lane 9—strain 327; Lane 10—strain 328.

Soluble fractions from the eight cultures described above were analyzed by Western blot to evaluate Pertussis Toxoid expression. Twenty microliters of the soluble fractions (2× diluted, reduced and non-reduced) were run on Bio-Rad 12% Bis-Tris Gel in 1× Bio_Rad MES running buffer. For reduced Western analysis, 1× XT reducing agent was added. Proteins were transferred from SDS-PAGE at 100V for 60 minutes onto a 0.2 μm nitrocellulose membrane (Bio Rad, 162 0232) using 1× NuPAGE Transfer Buffer (Invitrogen, NP0006-1) with 20% methanol. Membranes were blocked for 1 hour at room temperature in Blocker™ 1% Casein in PBS (Pierce, 37528). For detection, the diluents were poured off and more was added containing the combination of 1:1000 dilution each of monoclonal antibodies directed against *Bordetella pertussis* toxin S4 and S1 (Abcam, cat# ab37686 and #37547). The blots were incubated with rocking overnight at 4° C. The blots were washed three times with PBS-Tween for 5 minutes each, and were then incubated in more diluent containing a 1:5,000 dilution of anti-Mouse IgG-Peroxidase derived in goat (Sigma, Cat#A4416) at room temperature for 1 hour. The blots were washed three times with PBS-Tween (Sigma, P3563) for 5 minutes each, before color development using Immunopure Metal Enhanced DAB substrate (Pierce, 34065). Multiple subunits were detected by the anti-S1 and anti-S4 antibodies under both reducing and non reducing conditions (FIG. 8). The banding pattern of reduced and nonreduced samples of the expressed toxoid observed was consistent with that observed for purified Pertussis toxin from strain 165 as reported by Sekura, et al. (J. Biological Chemistry 258: 14647, 1983).

Example 6

Large-Scale Expression of Recombinant Pertussis Toxin Protein

Recombinant Pertussis toxin protein is produced in *Pseudomonas fluorescens* Pfēnex Expression Technology™ strains PS538-321, PS538-324, PS538-325, PS538-326, and PS538-328. The selected strain is grown in 2 liter fermentors, induced with IPTG, and samples prepared for analysis, as described above for CTB large-scale expression. The samples are analyzed by SDS-CGE, for product formation and their activity analyzed by Western Blot.

Example 7

High Throughput Expression of Recombinant Wild-Type Pertussis Toxoid

Construction and Growth of Pertussis Toxoid Expression Strains

The sequence of the wild-type Pertussis toxin operon encoding subunits S1, S2, S3, S4 and S5, with S1 is used for expression of recombinant Pertussis Toxoid. FIG. 17 shows the DNA sequence of the operon, with translation (SEQ ID NO:35).

The construct is expressed in the *P. fluorescens* hosts shown in Table 14. Each strain listed that does not have an overexpression plasmid is tested a) as described (having no overexpression plasmid); b) including a GrpE DnaKJ overexpression plasmid, and c) including a DsbABCD overexpression plasmid. Host cells are electroporated with the PTX WT expression plasmid, and grown and induced in 96-well format as described above for PTX S1 R9K E129A high-throughput expression. Samples are prepared and analyzed by SDS-CGE also as described above.

TABLE 14

Pertussis Toxoid Wild-Type Expression Strains

| Host* | Genotype | Type |
|---|---|---|
| 9 | hslUV prc2 | PD |
| 10 | hslUV degP1 | PD |
| 11 | la | PD |
| 12 | hslUV prc1 prc2 | PD |
| 13 | lon la prc1 prc2 | PD |
| 14 | RXF01590 | PD |
| 1 | lon la aprA | PD |
| 7 | lon prc1 degP2 aprA; overexpresses GrpE DnaKJ | PD + FMO |
| 15 | RXF02151 RXF00428 | PD |
| 16 | lon la degP2 | PD |
| 17 | overexpresses DsbAB | FMO |
| 18 | overexpresses DsbCD | FMO |
| 19 | prc1 degP2; overexpresses degP2 S219A | PD + FMO |
| 20 | prc1 degP2 clp1 aprA; overexpresses degP2 S219A | PD + FMO |
| 21 | prc1 degP2 lon aprA; overexpresses degP2 S219A | PD + FMO |
| 22 | prc1 degP2 degP1 aprA; overexpresses degP2 S219A | PD + FMO |
| 23 | lon prc1 degP2 degP1 aprA; overexpresses degP2 S219A | PD + FMO |
| 2 | hslUV prc1 degP2 degP1 aprA; overexpresses degP2 S219A | PD + FMO |
| 25 | lon la degP2 prc1 aprA; overexpresses degP2 S219A | PD + FMO |
| 26 | degP2; overexpresses SecB | PD + FMO |
| 27 | degP2; overexpresses FkbP | PD + FMO |
| 28 | degP2; overexpresses GroELES | PD + FMO |
| 29 | lon la aprA; overexpresses SecB | PD + FMO |
| 30 | lon la aprA; overexpresses FkbP | PD + FMO |
| 31 | lon la aprA; overexpresses GroELES | PD + FMO |
| 32 | dsbC | PD |
| 33 | dsbC; ovrexpresses DsbAB | PD + FMO |
| 3 | overexpresses DsbABCD | FMO |
| 35 | lexA aprA | PD |
| 36 | overexpresses SlyD | FMO |
| 37 | lon hslUV | PD |
| 38 | Wt | — |
| 39 | aprA | PD |
| 4 | overexpresses GrpE DnaKJ | FMO |
| 5 | htpX | PD |
| 40 | lon | PD |
| 41 | prc1 | PD |
| 42 | hslUV | PD |
| 43 | degP2 | PD |
| 44 | degP1 | PD |
| 45 | prc2 | PD |
| 46 | RXF6451 | PD |
| 6 | RXF1590 | PD |
| 48 | RXF4692 | PD |
| 49 | hslUV mic | PD |
| 50 | RXF2161 | PD |
| 51 | RXF00133 | PD |
| 52 | RXF2796 | PD |
| 53 | RXF4968 | PD |
| 54 | overexpresses DsbC | FMO |
| 55 | overexpresses DsbAC | FMO |
| 56 | overexpresses LepB | FMO |
| 57 | overexpresses SecB | FMO |
| 58 | overexpresses ClpA | FMO |
| 59 | overexpresses FklB2 | FMO |
| 60 | overexpresses DnaK-like | FMO |
| 61 | overexpresses FkbP | FMO |
| 62 | overexpresses PpiA | FMO |
| 8 | overexpresses PpiB | FMO |
| 63 | overexpresses HscA | FMO |
| 64 | overexpresses GshA | FMO |
| 65 | overexpresses Gor | FMO |
| 66 | overexpresses TrxC | FMO |
| 67 | overexpresses DsbG | FMO |
| 68 | overexpresses Ppi | FMO |
| 69 | overexpresses GroELES | FMO |
| 70 | prc1 aprA; overexpresses GrpE DnaKJ | PD +FMO |
| 71 | hypersecretion | |
| 72 | overexpresses DsbD | FMO |
| 73 | hypersecretion | |
| 74 | hypersecretion | |
| 75 | prc1 prc2 | PD |
| 76 | hslUV clpA | PD |

*Each strain listed that does not have an overexpression plasmid is tested a) as described (having no overexpression plasmid); b) including a GrpE DnaKJ overexpression plasmid, and c) including a DsbABCD overexpression plasmid. PD = Protease Deletion (listed proteases are deleted); FMO = Folding Modulator Overexpressor (listed folding modulators are overexpressed.

Hypersecretion strains, also known as hyper-vesiculating strains, are described, e.g., in WO2010/008764, "*Pseudomonas Fluorescens* Strains for Production of Extracellular Recombinant Protein," incorporated herein by reference in its entirety.

Example 8

High Throughput Expression of a Recombinant Tetanus Toxin Fragment C Protein Construction and Growth of Tetanus Toxin C Expression Strains The Tetanus Toxin C coding sequence was constructed using *P. fluorescens* preferred codons to encode the Tetanus Toxin C amino acid sequence. FIG. 9 shows the amino acid and DNA sequences of the expressed synthetic Tetanus Toxin C gene.

Plasmids carrying the optimized Tetanus Toxin C sequence, fused to the same ten *P. fluorescens* secretion leader coding sequences used with CRM197 (shown in Table 8) were constructed. The secretion leaders were included to target the protein to the periplasm for recovery in the properly folded and active form.

Constructs expressing the ten secretion leaders fused to the recombinant Tetanus Toxin C protein were tested in *P. fluorescens* hosts. The four hosts listed in Table 9 were tested with each leader. Host cells were electroporated with the indicated plasmids, and grown and induced in 96-well format as described above for the CRM197 high throughput expression. Samples were prepared and analyzed by SDS-CGE as described above for the CRM197 high throughput expression samples.

Figure 10:
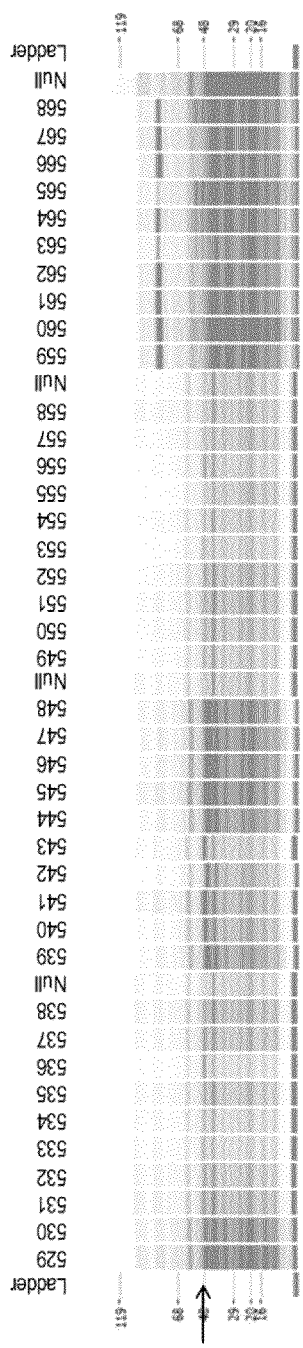
FIG. 10. Tetanus Toxin C Fragment Expression. Tetanus Toxin C Fragment expressed in P. fluorescens was analyzed using capillary gel electrophoresis (SDS-CGE). Soluble fractions from 40 tetanus toxin-expression strains tested are shown in a gel-like image generated from the SDS-CGE data. Strain names as described in Table 15 are listed above each lane. Induced Tetanus Toxin C Fragment migrated as a single band at ~51.6 kDa on SDS-CGE (arrow at left). Molecular weight markers in first and last lanes are 16, 20, 29, 48, 69 and 119 kDa.

Representative gel-like images showing the results of the reducing SDS-CGE analysis of the soluble fraction from each strain are shown in FIG. 10. Table 15 shows the mean soluble Tetanus Toxin C yield and standard deviation of 3 replicates for each of the Tetanus Toxin C-expression strains constructed. Tetanus Toxin C fragment appeared to be expressed well in most strains tested, with highest yields ranging up to 600 mg/L in the hslUV prc1 degP1 degP2 aprA deletion/ DegP2 S219A overexpression expression host. Strains PS538-529, PS538-538, PS538-544, PS538-546, PS538-547, PS538-548, PS538-558, PS538-565 and PS538-568 were selected for further evaluation.

TABLE 15

Tetanus Toxin C Expression Summary.

| Strain Number | Host | Plasmid | Leader | Mean Yield (mg/L) | Std Dev (3 replicates) |
|---|---|---|---|---|---|
| PS538-529 | 1 | p538-132 | DsbA | 261 | 75 |
| PS538-530 | 1 | p538-133 | Azu | 200 | 82 |
| PS538-531 | 1 | p538-134 | Ibp-531A | 165 | 64 |

TABLE 15-continued

Tetanus Toxin C Expression Summary.

| Strain Number | Host | Plasmid | Leader | Mean Yield (mg/L) | Std Dev (3 replicates) |
|---|---|---|---|---|---|
| PS538-532 | 1 | p538-135 | Tpr | 207 | 107 |
| PS538-533 | 1 | p538-136 | CupB2 | 205 | 128 |
| PS538-534 | 1 | p538-137 | CupA2 | 200 | 117 |
| PS538-535 | 1 | p538-138 | NikA | 174 | 96 |
| PS538-536 | 1 | p538-139 | Pbp A20V | 311 | 156 |
| PS538-537 | 1 | p538-140 | DsbC | 188 | 97 |
| PS538-538 | 1 | p538-141 | TolB | 129 | 63 |
| PS538-539 | 2 | p538-132 | DsbA | 486 | 89 |
| PS538-540 | 2 | p538-133 | Azu | 495 | 93 |
| PS538-541 | 2 | p538-134 | Ibp-531A | 568 | 68 |
| PS538-542 | 2 | p538-135 | Tpr | 589 | 364 |
| PS538-543 | 2 | p538-136 | CupB2 | 534 | 318 |
| PS538-544 | 2 | p538-137 | CupA2 | 504 | 134 |
| PS538-545 | 2 | p538-138 | NikA | 444 | 145 |
| PS538-546 | 2 | p538-139 | Pbp A20V | 637 | 280 |
| PS538-547 | 2 | p538-140 | DsbC | 574 | 68 |
| PS538-548 | 2 | p538-141 | TolB | 438 | 61 |
| PS538-549 | 3 | p538-132 | DsbA | 174 | 37 |
| PS538-550 | 3 | p538-133 | Azu | 180 | 58 |
| PS538-551 | 3 | p538-134 | Ibp-S31A | 88 | 58 |
| PS538-552 | 3 | p538-135 | Tpr | 247 | 134 |
| PS538-553 | 3 | p538-136 | CupB2 | 199 | 39 |
| PS538-554 | 3 | p538-137 | CupA2 | 165 | 69 |
| PS538-555 | 3 | p538-138 | NikA | 97 | 90 |
| PS538-556 | 3 | p538-139 | Pbp A20V | 297 | 112 |
| PS538-557 | 3 | p538-140 | DsbC | 151 | 52 |
| PS538-558 | 3 | p538-141 | TolB | 35 | 13 |
| PS538-559 | 4 | p538-132 | DsbA | 39 | 39 |
| PS538-560 | 4 | p538-133 | Azu | 40 | 43 |
| PS538-561 | 4 | p538-134 | Ibp-S31A | 36 | 40 |
| PS538-562 | 4 | p538-135 | Tpr | 35 | 39 |
| PS538-563 | 4 | p538-136 | CupB2 | 54 | 26 |
| PS538-564 | 4 | p538-137 | CupA2 | 42 | 36 |
| PS538-565 | 4 | p538-138 | NikA | 44 | 37 |
| PS538-566 | 4 | p538-139 | Pbp A20V | 37 | 40 |
| PS538-567 | 4 | p538-140 | DsbC | 39 | 43 |
| PS538-568 | 4 | p538-141 | TolB | 45 | 38 |

Example 9

Large-Scale Expression of a Recombinant Tetanus Toxin Fragment C Protein

Recombinant Tetanus Toxin C protein was produced in *Pseudomonas fluorescens* Pfenex Expression Technology™ strains PS538-529, PS538-538, PS538-544, PS538-546, PS538-547, PS538-548, PS538-558, PS538-565 and PS538-568. The selected strains were grown in 2 liter fermentors containing a mineral salts medium as described above for CRM197.

Figure 15A:
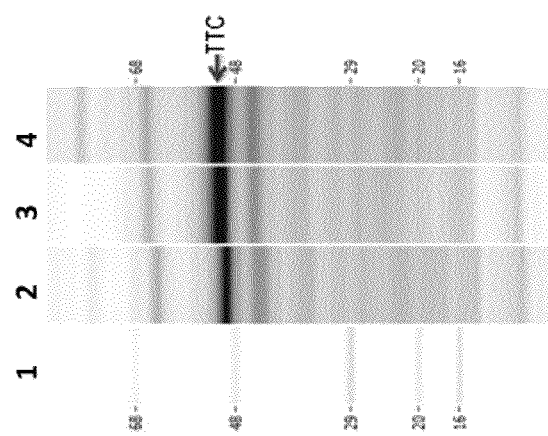
FIG. 15. Soluble Tetanus Toxin Fragment C Production in P. fluorescens Fermentation Cultures. A. SDS-CGE Analysis. Lane 1-16, 20, 29, 48, 69 and 119 kDa molecular markers. Lanes 2, 3 and 4 are post-induction samples of PS538-529 U1 PS538-546 U5 and PS538-547 U7 fermentations, respectively, expressing Tetanus Toxin Fragment C, indicated by arrow at right. B. Western Blot Analysis. Fermentation samples from strains PS538-538 (U1 and U2), PS538-548 (U3 and U4), PS538-558 (U5 and U6) and PS538-568 (U7 and U8) were evaluated by Westen blot. Fermentation unit and hours post induction (I0, I8, I24) are indicated above each lane. Molecular weight (MW) standards are shown on the left of the blot and Tetanus Toxin C reference standard (Std; List Biological, Cat#193) is shown on the right. Blots were probed with Polyclonal Anti-Tetanus Toxin C Fragment, derived in Rabbit (Abcam, Cat#: ab34890) followed by Anti-Rabbit IgG Peroxidase, derived in Goat (Pierce, Cat#: 31460). Immunopure Metal Enhanced DAB (Pierce 34065) was used for detection.
Figure 15B:
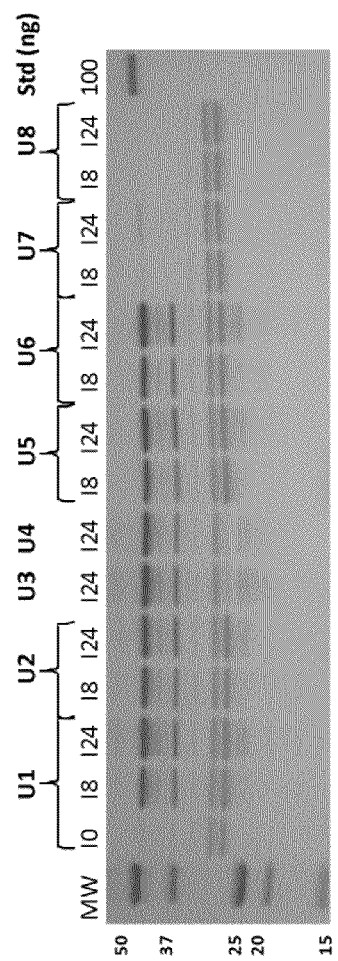
Figure 16:
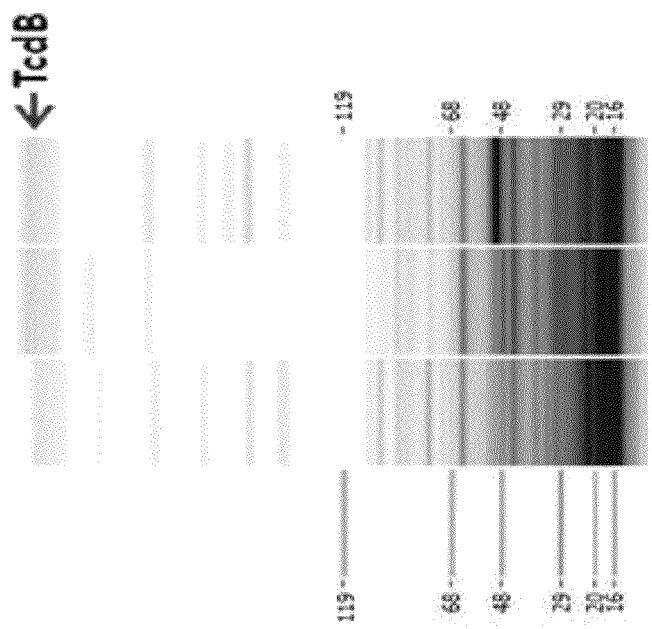
FIG. 16. Soluble C. difficile B Toxin Protein Production in P. fluorescens Fermentation Cultures. Lane 1-16, 20, 29, 48, 69 and 119 kDa molecular weight markers. The marker sizes are also indicated in their respective positions at the right, based on migration in Lane 1. Lanes 2, 3 and 4 are post-induction samples of PS538-671 U5 and U6, and PS538-674 U7 fermentations, respectively, expressing C. difficile B Toxin Protein, indicated by arrow at right.

Multiple fermentation conditions were evaluated resulting in top soluble TTC expression from strains PS538-529, PS538-546, and PS538-547 of 6 to 10 g/L as determined by SDS-CGE (see FIG. 15 and Table 16). The top performing fermentation culture was induced at approximately 160 OD with 0.2 mM IPTG at pH 7.2 and 32° C. The identities of the induced proteins were confirmed by peptide mass fingerprint using MALDI-TOF mass spectrometry and Western Blot. Mass spectrometry and Western blot analyses indicated that the secretion leaders of PS538-529, PS538-546 and PS538-547 (DsbA, Pbp A20V and DsbC, respectively) were not processed from 100% of the expressed protein under these expression conditions. However, the TolB leader was identified as being precisely cleaved from the secreted protein (data not shown). TolB-TTC expression strains PS538-538, PS538-548, PS538-558 and PS538-568 were screened at the 2 L fermentation scale, using the conditions outlined above, to identify a strain that enabled production of TTC with high fidelity cleavage of the secretion leader and low levels of degradation. Strains PS538-538, PS538-548 and PS538-558 were observed to produce similar quality and yield of material by Western blot analysis (FIG. 15B).

TABLE 16

Soluble Tetanus Toxin C (TTC) Titers

| Strain | Fermentation | Product | Product concentration (g/L) |
|---|---|---|---|
| PS538-529 | U1 - FIG. 15A | TTC | 5.7 ± 1.3 |
| PS538-546 | U7 - FIG. 15A | TTC | 9.5 ± 1.1 |
| PS538-547 | U5 - FIG. 15A | TTC | 6.2 ± 1.9 |
| PS538-538 | U1 - FIG. 15B | TTC | 2.5 ± 0.09 |
| PS538-538 | U2 - FIG. 15B | TTC | 1.8 ± 0.2 |
| PS538-548 | U3 - FIG. 15B | TTC | 5.3 ± 0.6 |
| PS538-548 | U4 - FIG. 15B | TTC | 4.5 ± 0.2 |
| PS538-558 | U5 - FIG. 15B | TTC | 1.1 ± 0.8 |
| PS538-558 | U6 - FIG. 15B | TTC | 1.9 ± 0.1 |
| PS538-568 | U7 - FIG. 15B | TTC | 0.2 ± 0.01 |
| PS538-568 | U8 - FIG. 15B | TTC | 0.2 ± 0.01 |

Example 10

High Throughput Expression of a Recombinant C. Difficile B Protein Construction and Growth of TcdB Expression Strains The TcdB coding sequence was constructed using *P. fluorescens* preferred codons to encode the TcdB amino acid sequence. FIG. 11 shows the amino acid and DNA sequences of the expressed synthetic TcdB gene.

Plasmids carrying the optimized TcdB sequence were tested in the *P. fluorescens* hosts having genotypes listed in Table 17. Host cells were electroporated with the cytoplasmic expression plasmid p538-211, and grown and induced in 96-well format as described above for the CRM197 high throughput expression. Samples were prepared and analyzed by SDS-CGE as described above for the CRM197 high throughput expression samples.

TABLE 17

TcdB Host Strains

| Host Strain | Genotype | Type |
|---|---|---|
| 37 | hslUV lon | PD |
| 38 |  | WT |
| 4 | dnaKJ grpE | FMO |
| 5 | htpX | PD |
| 40 | lon | PD |
| 41 | prc1 | PD |
| 42 | hslUV | PD |
| 43 | degP2 | PD |
| 44 | degP1 | PD |
| 45 | prc2 | PD |
| 47 | RXF01590 | PD |
| 49 | hslUV mic | PD |
| 53 | RXF04968 | PD |
| 55 | dsbAC | FMO |
| 61 | fkbP | FMO |
| 66 | trxC | FMO |
| 72 | dsbD | FMO |
| 76 | hslUV clpA | PD |
| 12 | hslUV prc1 prc2 | PD |
| 1 | lon la aprA | PD |

TABLE 17-continued

| TcdB Host Strains | | |
|---|---|---|
| Host Strain | Genotype | Type |
| 16 | lon la degP2 | PD |
| 2 | hslUV prc1 degP1 degP2 aprA deletions; overexpresses degP2 S219A | PD + FMO |
| 3 | dsbABCD | FMO |
| 21 | lon prc1 degP2 aprA deletions with degP2 S219A overexpression | PD + FMO |

Figure 12:
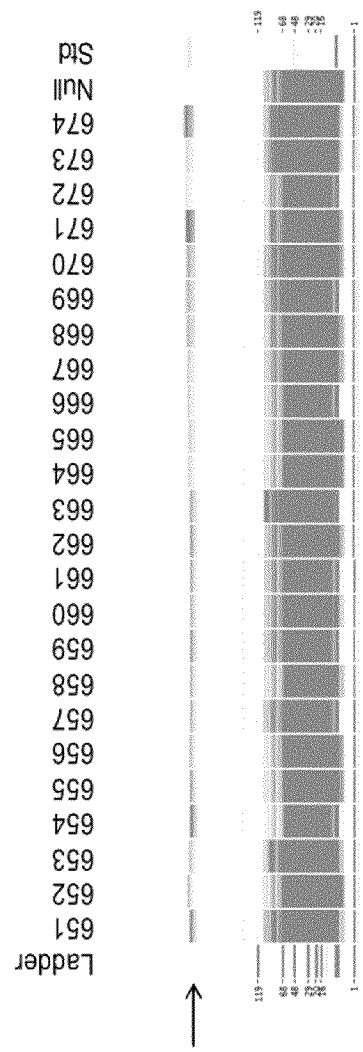
FIG. 12. TcdB Expression. TcdB expressed in P. fluorescens was analyzed using capillary gel electrophoresis (SDS-CGE). Soluble fractions from 24 TcdB-expression strains tested are shown in a gel-like image generated from the SDS-CGE data. Strain names as described in Table 18 as well as null extract and reference standard (List Biologicals) are listed above each lane. Induced TcdB migrated as a single band at ~300 kDa on SDS-CGE (arrow at left). Molecular weight markers in first and last lanes are 16, 20, 29, 48, 69 and 119 kDa.

Representative gel-like images showing the results of the reducing SDS-CGE analysis of the soluble fraction from each of the 24 strains tested are shown in FIG. 12. Table 18 shows the mean soluble TcdB yield and standard deviation of 3 replicates for each of the TcdB-expression strains constructed. Strains PS538-654, PS538-659, PS538-669, PS538-671, and PS538-674 were selected for further evaluation.

TABLE 18

| TcdB Expression Summary | | | | |
|---|---|---|---|---|
| Strain Number | Host | Plasmid | Mean Yield (mg/L) | St Dev (3 replicates) |
| PS538-651 | 37 | p538-211 | 103 | 7 |
| PS538-652 | 38 | p538-211 | 55 | 4 |
| PS538-653 | 4 | p538-211 | 57 | 1 |
| PS538-654 | 5 | p538-211 | 166 | 13 |
| PS538-655 | 40 | p538-211 | 88 | 3 |
| PS538-656 | 41 | p538-211 | 68 | 5 |
| PS538-657 | 42 | p538-211 | 90 | 14 |
| PS538-658 | 43 | p538-211 | 68 | 2 |
| PS538-659 | 44 | p538-211 | 109 | 8 |
| PS538-660 | 45 | p538-211 | 78 | 4 |
| PS538-661 | 6 | p538-211 | 98 | 15 |
| PS538-662 | 49 | p538-211 | 106 | 10 |
| PS538-663 | 53 | p538-211 | 91 | 6 |
| PS538-664 | 55 | p538-211 | 45 | 4 |
| PS538-665 | 61 | p538-211 | 63 | 6 |
| PS538-666 | 66 | p538-211 | 56 | 8 |
| PS538-667 | 72 | p538-211 | 70 | 8 |
| PS538-668 | 76 | p538-211 | 80 | 6 |
| PS538-669 | 12 | p538-211 | 117 | 39 |
| PS538-670 | 1 | p538-211 | 108 | 18 |
| PS538-671 | 16 | p538-211 | 247 | 65 |
| PS538-672 | 2 | p538-211 | 32 | 6 |
| PS538-673 | 3 | p538-211 | 52 | 2 |
| PS538-674 | 21 | p538-211 | 145 | 12 |

Example 11

Large-Scale Expression of Recombinant *C. Difficile* Toxin B Protein

Recombinant *C. difficile* toxin B protein was produced in *Pseudomonas fluorescens* Pfēnex Expression Technology™ strain PS538-654, PS538-659, PS538-669, PS538-671, and PS538-674. The selected strains were grown in 2 liter fermentors, induced with IPTG, and samples prepared for analysis, as described above for CTB large-scale expression.

Multiple fermentation conditions were evaluated resulting in top *C. difficile* B Toxin expression as determined by SDS-CGE of approximately 2 g/L. The top performing fermentation culture was induced at approximately 160 OD with 0.08 mM IPTG at pH 6.5 and 32° C. Soluble *C. difficile* B Toxin concentrations were determined by SDS-CGE (see FIG. 16 and Table 19). The identities of the induced proteins were confirmed by Western blot.

TABLE 19

| Soluble *C. difficile* B Toxin (TcdB) Titers | | | |
|---|---|---|---|
| Strain | Fermentation | Product | Product concentration (g/L) |
| PS538-671 | U5 | TcdB | 1.6 ± 0.4 |
| PS538-671 | U6 | TcdB | 2.1 ± 0.2 |
| PS538-674 | U7 | TcdB | 1.8 ± 0.2 |

Example 12

High Throughput Expression of a Recombinant Exotoxin A Protein

Construction and Growth of *P. Aeruginosa* Exotoxin a Expression Strains

The *P. aeruginosa* Exotoxin A mutant rEPA coding sequence was constructed using *P. fluorescens* preferred codons to encode the rEPA amino acid sequence. FIG. 13 shows the amino acid and DNA sequences of the expressed synthetic rEPA gene.

Plasmids carrying the optimized sequences encoding either the deletion mutant rEPA, as indicated in FIG. 13, fused to the same ten *P. fluorescens* secretion leader coding sequences used with CRM197 (shown in Table 8) were constructed. The secretion leader coding sequences were included to target the protein to the periplasm for recovery in the properly folded and active form.

Constructs expressing the ten secretion leaders fused to the rEPA proteins were tested in eight *P. fluorescens* hosts, listed in Table 20. Host cells were electroporated with the indicated plasmids, and grown and induced in 96-well format as described above for the CRM197 high throughput expression. Samples were prepared and analyzed by SDS-CGE as described above for the CRM197 high throughput expression samples. The highest yields ranged from 4.7-6.7 g/L of soluble rEPA.

TABLE 20

| Exotoxin A Host Strains | | |
|---|---|---|
| Host Strain | Genotype | Type |
| 5 | htpX | PD |
| 6 | serralysin | PD |
| 7 | Lon La1 aprA ; with grpE dnaKJ overexpression | PD/FMO |
| 8 | ppiB | PD |
| 1 | Lon-, La-, aprA- | PD |
| 2 | hslUV-, prc1-, degP1-, degP2-, aprA- with degP2 S219A overexpression | PD + FMO |
| 3 | dsbABCD overexpression | FMO |
| 4 | grpE, dnaKJ overexpression | FMO |

Host cells were electroporated with the indicated plasmids, and grown and induced in 96-well format as described above for the CRM197 high throughput expression. Samples were prepared and analyzed by SDS-CGE as described above for the CRM197 high throughput expression samples. The highest yields ranged from 1.6 to 2.2 g/L of soluble Exotoxin A protein. Table 21 shows the soluble rEPA yield for each of the expression strains selected for further testing.

TABLE 21 rEPA HTP Expression Summary

| Strain Number | Host | Plasmid | Secretion Leader | Volumetric Yield (g/L) |
|---|---|---|---|---|
| PS538-1670 | 3 | p538-250 | DsbC | 6.7 |
| PS538-1663 | 3 | p538-243 | Ibp-s31a | 5.7 |
| PS538-1633 | 1 | p538-243 | Ibp-s31a | 5.7 |
| PS538-1640 | 1 | p538-249 | Pbp-A20V | 4.7 |
| PS538-1662 | 3 | p538-242 | Azu | 4.2 |
| PS538-1632 | 1 | p538-242 | Azu | 3.2 |
| PS538-1671 | 4 | p538-241 | DsbA | 2.9 |
| PS538-1665 | 3 | p538-245 | Tpr | 2.7 |
| PS538-1667 | 3 | p538-247 | CupA2 | 2.6 |
| PS538-1674 | 4 | p538-244 | TolB | 2.3 |
| PS538-1672 | 4 | p538-242 | Azu | 2.2 |
| PS538-1676 | 4 | p538-246 | CupB2 | 2.2 |
| PS538-1677 | 4 | p538-247 | CupA2 | 2.1 |
| PS538-1635 | 1 | p538-245 | Tpr | 2.0 |
| PS538-1675 | 4 | p538-245 | Tpr | 2.0 |
| PS538-1673 | 4 | p538-243 | Ibp-s31a | 2.0 |
| PS538-1680 | 4 | p538-250 | DsbC | 1.9 |
| PS538-1679 | 4 | p538-249 | Pbp-A20V | 1.7 |
| PS538-1669 | 3 | p538-249 | Pbp-A20V | 1.6 |
| PS538-1678 | 4 | p538-248 | NikA | 1.5 |
| PS538-1652 | 2 | p538-242 | Azu | 1.5 |
| PS538-1653 | 2 | p538-243 | Ibp-s31a | 1.4 |
| PS538-1660 | 2 | p538-250 | DsbC | 1.4 |
| PS538-1637 | 1 | p538-247 | CupA2 | 1.3 |
| PS538-1666 | 3 | p538-246 | CupB2 | 1.1 |
| PS538-1636 | 1 | p538-246 | CupB2 | 1.0 |
| PS538-1634 | 1 | p538-244 | TolB | 1.0 |
| PS538-1627 | 8 | p538-247 | CupA2 | 0.8 |
| PS538-1631 | 1 | p538-241 | DsbA | 0.8 |
| PS538-1622 | 8 | p538-242 | Azu | 0.8 |
| PS538-1661 | 3 | p538-241 | DsbA | 0.7 |
| PS538-1603 | 5 | p538-243 | Ibp-s31a | 0.6 |
| PS538-1630 | 8 | p538-250 | DsbC | 0.6 |
| PS538-1602 | 5 | p538-242 | Azu | 0.6 |
| PS538-1605 | 5 | p538-245 | Tpr | 0.6 |
| PS538-1623 | 8 | p538-243 | Ibp-s31a | 0.6 |
| PS538-1664 | 3 | p538-244 | TolB | 0.5 |
| PS538-1668 | 3 | p538-248 | NikA | 0.5 |
| PS538-1610 | 5 | p538-250 | DsbC | 0.5 |
| PS538-1606 | 5 | p538-246 | CupB2 | 0.4 |
| PS538-1659 | 2 | p538-249 | Pbp-A20V | 0.4 |
| PS538-1607 | 5 | p538-247 | CupA2 | 0.4 |
| PS538-1626 | 8 | p538-246 | CupB2 | 0.4 |
| PS538-1625 | 8 | p538-245 | Tpr | 0.4 |
| PS538-1638 | 1 | p538-248 | NikA | 0.3 |
| PS538-1609 | 5 | p538-249 | Pbp-A20V | 0.3 |
| PS538-1604 | 5 | p538-244 | TolB | 0.3 |
| PS538-1629 | 8 | p538-249 | Pbp-A20V | 0.3 |
| PS538-1657 | 2 | p538-247 | CupA2 | 0.2 |
| PS538-1651 | 2 | p538-241 | DsbA | 0.2 |
| PS538-1601 | 5 | p538-241 | DsbA | 0.2 |
| PS538-1624 | 8 | p538-244 | TolB | 0.2 |
| PS538-1621 | 5 | p538-241 | DsbA | 0.2 |
| PS538-1608 | 5 | p538-248 | NikA | 0.2 |
| PS538-1654 | 2 | p538-244 | TolB | 0.2 |
| PS538-1628 | 8 | p538-248 | NikA | 0.1 |
| PS538-1658 | 2 | p538-248 | NikA | 0.1 |
| PS538-1655 | 2 | p538-245 | Tpr | 0.1 |
| PS538-1641 | 7 | p538-241 | DsbA | 0.1 |
| PS538-1611 | 6 | p538-241 | DsbA | NQ |
| PS538-1612 | 6 | p538-242 | Azu | NQ |
| PS538-1613 | 6 | p538-243 | Ibp-s31a | NQ |
| PS538-1614 | 6 | p538-244 | TolB | NQ |
| PS538-1615 | 6 | p538-245 | Tpr | NQ |
| PS538-1616 | 6 | p538-246 | CupB2 | NQ |
| PS538-1617 | 6 | p538-247 | CupA2 | NQ |
| PS538-1618 | 6 | p538-248 | NikA | NQ |
| PS538-1619 | 6 | p538-249 | Pbp-A20V | NQ |
| PS538-1620 | 6 | p538-250 | DsbC | NQ |
| PS538-1642 | 7 | p538-242 | Azu | NQ |
| PS538-1643 | 7 | p538-243 | Ibp-s31a | NQ |
| PS538-1644 | 7 | p538-244 | TolB | NQ |
| PS538-1645 | 7 | p538-245 | Tpr | NQ |
| PS538-1646 | 7 | p538-246 | CupB2 | NQ |
| PS538-1647 | 7 | p538-247 | CupA2 | NQ |
| PS538-1648 | 7 | p538-248 | NikA | NQ |
| PS538-1649 | 7 | p538-249 | Pbp-A20V | NQ |
| PS538-1650 | 7 | p538-250 | DsbC | NQ |
| PS538-1656 | 2 | p538-246 | CupB2 | NQ |

NQ = not quantifiable

Example 13

Large-Scale Expression of a Recombinant Pseudomonas aeruginosa Exotoxin A Protein Recombinant P. aeruginosa exotoxin A protein (rEPA) was produced in Pseudomonas fluorescens strains PS538-1633, PS538-1640 and PS538-1670 in 2 liter fermentors. Cultures were grown in 2 liter fermentors containing a mineral salts medium as described herein and also by, e.g., Riesenberg, D., et al., 1991, and maintained at 32° C. and pH 6.5 through the addition of ammonia. Dissolved oxygen was maintained in excess through increases in agitation and flow of sparged air and oxygen into the fermentor. Glycerol is delivered to the culture throughout the fermentation to maintain excess levels. These conditions were maintained until a target culture cell density (optical density at 575 nm (A575)) for induction is reached, at which time IPTG was added to initiate rEPA production. Cell density at induction can be varied from A575 of 40 to 200 absorbance units (AU). IPTG concentrations can be varied in the range from 0.02 to 0.4 mM. pH from 6 to 7.5 and temperature 20 to 35° C. After 16-24 hours, the culture from each bioreactor was harvested by centrifugation and the cell pellet frozen at −80° C. Samples were analyzed by SDS-CGE for product formation.

Figure 21:
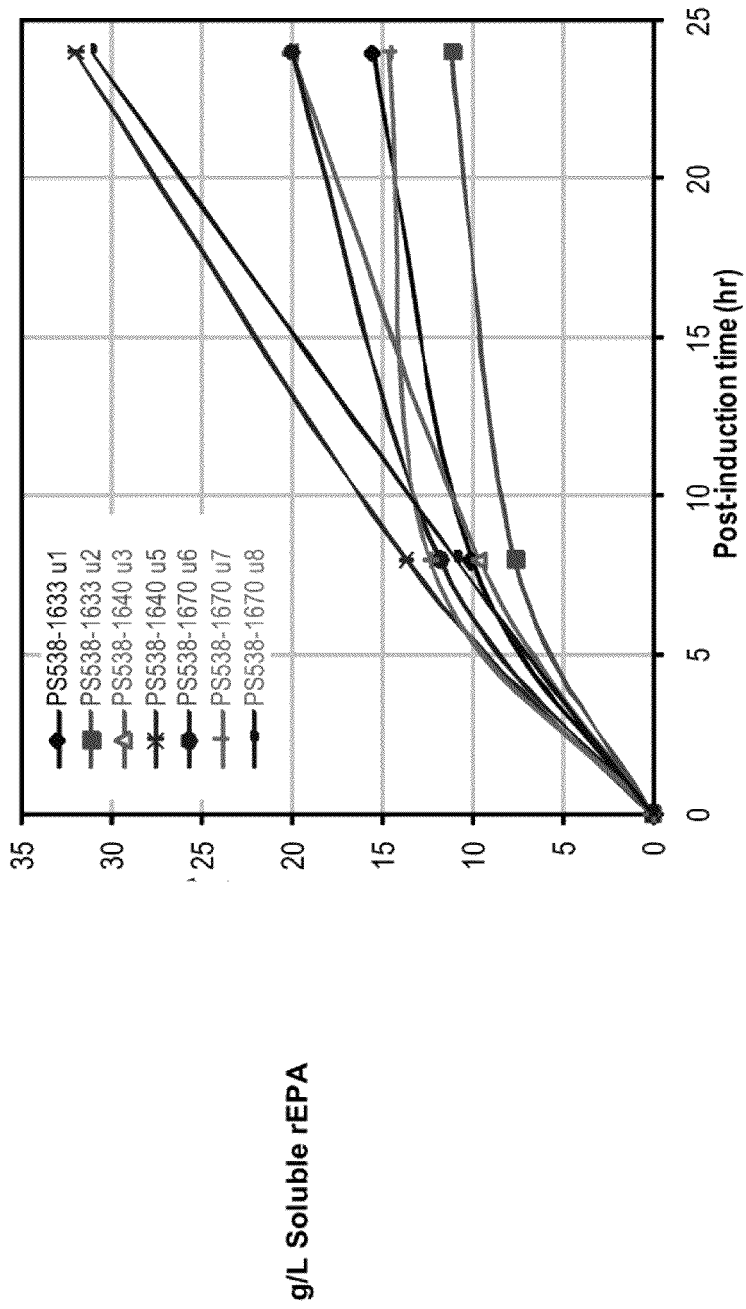
Figure 22:
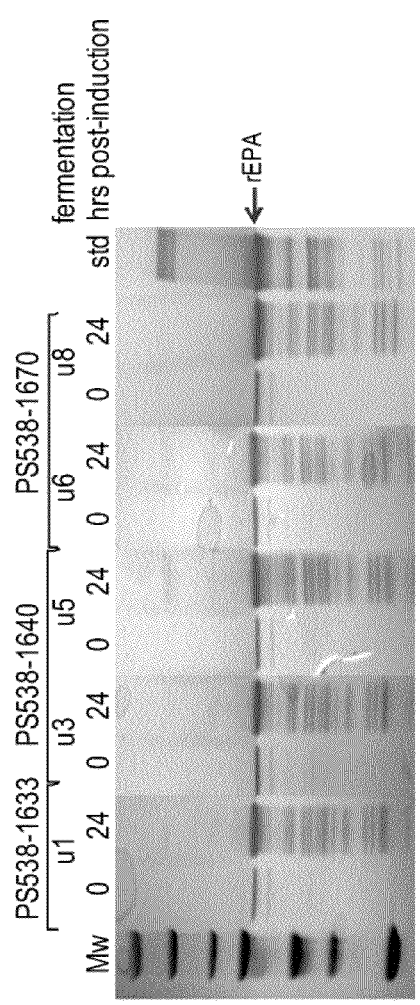

Multiple fermentation conditions were evaluated resulting in top rEPA expression as determined by SDS-CGE of up to 32 g/L (FIGS. 20 and 21). The identity of the induced protein was confirmed by Western blot analysis using an antibody specific for P. aeruginosa exotoxin A (FIG. 22). The yields obtained are shown in Table 22.

TABLE 22 rEPA Fermentation Analysis

| Strain Number | Fermentation | Yield (g/L) |
|---|---|---|
| PS538-1633 | U1 | 15.5 ± 0.7 |
| PS538-1633 | U2 | 11.1 ± 0.6 |
| PS538-1640 | U3 | 20.1 ± 1.7 |
| PS538-1640 | U5 | 31.9 ± 1.6 |
| PS538-1670 | U6 | 20.0 ± 0.7 |
| PS538-1670 | U7 | 14.6 ± 1.1 |
| PS538-1670 | U8 | 31.0 ± 1.7 |

Example 14

High Throughput Expression of a Recombinant Wild-Type Diphtheria Toxin Protein Construction and Growth of Wild-Type Diphtheria Toxin Expression Strains A Diphtheria Toxin coding sequence is constructed using P. fluorescens preferred codons to encode the wild-type Diphtheria Toxin amino acid sequence. FIG. 18 shows the amino acid and DNA sequences of the expressed synthetic Diphtheria Toxin gene.

Plasmids carrying the optimized sequences encoding Diphtheria Toxin, fused to the ten *P. fluorescens* secretion leader coding sequences used with CRM197 (shown in Table 8) are constructed. The secretion leader coding sequences are included to target the protein to the periplasm for recovery in the properly folded and active form.

Constructs expressing the ten secretion leaders fused to the recombinant Diphtheria Toxin proteins are tested in *P. fluorescens* hosts. The four hosts listed in Table 9 are tested with each leader. Host cells are electroporated with the indicated plasmids, and grown and induced in 96-well format as described above for the CRM197 high throughput expression. Samples are prepared and analyzed by SDS-CGE as described above for the CRM197 high throughput expression samples.

Example 15

Large-Scale Expression of a Recombinant Wild-Type Diphtheria Toxin Protein

Recombinant Wild-Type Diphtheria Toxin protein is produced in selected *Pseudomonas fluorescens* Pfēnex Expression Technology™ strains. The selected strains are grown in 2 liter fermentors, induced with IPTG, and samples prepared for analysis, as described above for CRM197 large-scale expression. The samples are analyzed by SDS-CGE.

Example 16

High Throughput Expression of a Recombinant Cholera Holotoxin Protein

Construction and Growth of CTX Expression Strains

The CTX coding sequence is constructed using *P. fluorescens* preferred codons to encode the CTX amino acid sequence. The coding sequence is based on the amino acid and DNA sequences of the CTX gene shown in FIG. 19.

Plasmids carrying the optimized CTX sequence, fused to the ten *P. fluorescens* secretion leader coding sequences used with CRM197 (shown in Table 8) are constructed. The secretion leaders are included to target the protein to the periplasm for recovery in the properly folded and active form.

Constructs expressing the ten secretion leaders fused to the recombinant CTX protein are tested in *P. fluorescens* hosts. The four hosts listed in Table 9 are tested with each expression plasmid. Host cells are electroporated with the indicated plasmids, and grown and induced in 96-well format as described above for the CRM197 high throughput expression. Samples are prepared and analyzed by SDS-CGE as described above for the CRM197 high throughput expression samples.

Example 17

Large-Scale Expression of a Recombinant Cholera Holotoxin Protein

Recombinant Cholera Holotoxin protein is produced in selected *Pseudomonas fluorescens* Pfēnex Expression Technology™ strains. The selected strains are grown in 2 liter fermentors, induced with IPTG, and samples prepared for analysis, as described above for CRM197 large-scale expression. The samples are analyzed by SDS-CGE.

TABLE 23

Sequence Listings

| SEQ ID NO | DESCRIPTION |
|---|---|
| 1 | CRM197 Amino Acid Sequence |
| 2 | CRM197 DNA Sequence, optimized |
| 3 | DsbA Secretion Leader |
| 4 | Azu |
| 5 | Ibp-S31A |
| 6 | Tpr |
| 7 | CupB2 |
| 8 | CupA2 |
| 9 | NikA |
| 10 | Pbp A20V |
| 11 | DsbC |
| 12 | TolB |
| 13 | Pbp |
| 14 | Lao |
| 15 | CupC2 |
| 16 | PorE |
| 17 | Pbp |
| 18 | FlgI |
| 19 | ttg2C |
| 20 | CRM197 native leader |
| 21 | Cleavage product GADD |
| 22 | Cholera Toxin B Amino Acid Sequence |
| 23 | Cholera Toxin B DNA Sequence, optimized |
| 24 | Pertussis toxin S1 R9K E129A DNA sequence |
| 25 | Pertussis toxin S1 R9K E129A Amino Acid Sequence |
| 26 | Pertussis toxin S2 Amino Acid Sequence |
| 27 | Pertussis toxin S3 Amino Acid Sequence |
| 28 | Pertussis toxin S4 Amino Acid Sequence |
| 29 | Pertussis toxin S5 Amino Acid Sequence |
| 30 | Tetanus Toxin C Amino Acid Sequence |
| 31 | Tetanus Toxin C DNA Sequence, optimized |
| 32 | TcdB Amino Acid Sequence |
| 33 | TcdB DNA Sequence, optimized |
| 34 | Exotoxin A Amino Acid Sequence |
| 35 | DNA Sequence of Wild-Type Pertussis Toxoid |
| 36 | Wild-Type Diphtheria Toxin Amino Acid Sequence |
| 37 | Wild-Type Diphtheria Toxin DNA Sequence, optimized |
| 38 | Cholera Toxin A Amino Acid Sequence |
| 39 | Cholera Toxin B Amino Acid Sequence |
| 40 | Cholera Holotoxin (CTX) DNA Sequence |
| 41 | Wild Type Pertussis toxin 51 Amino Acid Sequence |
| 42 | Pertussis toxin S2 Amino Acid Sequence |
| 43 | Pertussis toxin S4 Amino Acid Sequence |
| 44 | Pertussis toxin S5 Amino Acid Sequence |
| 45 | Pertussis toxin S3 Amino Acid Sequence |
| 46 | Hexa-histidine affinity tag |

SEQUENCE LISTING

<160> NUMBER OF SEQ ID NOS: 46

<210> SEQ ID NO 1
<211> LENGTH: 535
<212> TYPE: PRT
<213> ORGANISM: Corynebacterium diphtheriae

```
<400> SEQUENCE: 1

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Glu Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr Gln Pro Phe Leu His Asp Gly Tyr Ala Val Ser Trp Asn Thr
385                 390                 395                 400

Val Glu Asp Ser Ile Ile Arg Thr Gly Phe Gln Gly Glu Ser Gly His
                405                 410                 415
```

```
Asp Ile Lys Ile Thr Ala Glu Asn Thr Pro Leu Pro Ile Ala Gly Val
        420                 425                 430

Leu Leu Pro Thr Ile Pro Gly Lys Leu Asp Val Asn Lys Ser Lys Thr
            435                 440                 445

His Ile Ser Val Asn Gly Arg Lys Ile Arg Met Arg Cys Arg Ala Ile
        450                 455                 460

Asp Gly Asp Val Thr Phe Cys Arg Pro Lys Ser Pro Val Tyr Val Gly
465                 470                 475                 480

Asn Gly Val His Ala Asn Leu His Val Ala Phe His Arg Ser Ser Ser
                485                 490                 495

Glu Lys Ile His Ser Asn Glu Ile Ser Ser Asp Ser Ile Gly Val Leu
            500                 505                 510

Gly Tyr Gln Lys Thr Val Asp His Thr Lys Val Asn Ser Lys Leu Ser
        515                 520                 525

Leu Phe Phe Glu Ile Lys Ser
            530                 535

<210> SEQ ID NO 2
<211> LENGTH: 1605
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1605)

<400> SEQUENCE: 2 ggg gcg gac gat gtg gtg gat tcc tcc aag tcg ttt gtc atg gaa aat      48
Gly Ala Asp Asp Val Val Asp Ser Ser Lys Ser Phe Val Met Glu Asn
1               5                   10                  15 ttc tcg tcg tac cat ggc act aag cca ggc tac gtg gat agc att caa      96
Phe Ser Ser Tyr His Gly Thr Lys Pro Gly Tyr Val Asp Ser Ile Gln
                20                  25                  30 aag ggc atc cag aag ccc aag agc ggt act cag ggg aac tat gac gac     144
Lys Gly Ile Gln Lys Pro Lys Ser Gly Thr Gln Gly Asn Tyr Asp Asp
            35                  40                  45 gac tgg aag gaa ttt tac agc acc gac aat aag tac gat gct gcg ggc     192
Asp Trp Lys Glu Phe Tyr Ser Thr Asp Asn Lys Tyr Asp Ala Ala Gly
        50                  55                  60 tat agc gtg gac aac gaa aac cca ttg tcg ggc aag gcc ggt ggc gtg     240
Tyr Ser Val Asp Asn Glu Asn Pro Leu Ser Gly Lys Ala Gly Gly Val
65                  70                  75                  80 gtg aag gtg acc tat cct ggt ctg acg aaa gtt ctg gcg ttg aaa gtg     288
Val Lys Val Thr Tyr Pro Gly Leu Thr Lys Val Leu Ala Leu Lys Val
                85                  90                  95 gac aac gcc gag act atc aag aaa gaa ttg ggc ttg agt ttg acc gag     336
Asp Asn Ala Glu Thr Ile Lys Lys Glu Leu Gly Leu Ser Leu Thr Glu
            100                 105                 110 ccg ctg atg gaa cag gtg ggt acc gaa gaa ttc att aaa cgt ttt ggg     384
Pro Leu Met Glu Gln Val Gly Thr Glu Glu Phe Ile Lys Arg Phe Gly
        115                 120                 125 gac ggc gcg tcg cgc gtg gtc ctg tcg ttg ccg ttc gcc gaa ggg tcg     432
Asp Gly Ala Ser Arg Val Val Leu Ser Leu Pro Phe Ala Glu Gly Ser
130                 135                 140 tcg tcg gtg gaa tat atc aac aac tgg gaa cag gcc aag gcg ctg tcg     480
Ser Ser Val Glu Tyr Ile Asn Asn Trp Glu Gln Ala Lys Ala Leu Ser
145                 150                 155                 160 gtg gaa ctg gaa att aac ttc gaa acg cgg ggc aaa cgg ggc cag gac     528
Val Glu Leu Glu Ile Asn Phe Glu Thr Arg Gly Lys Arg Gly Gln Asp
```

|  |  |  |  |  |  |  |  |  |  |  |  |  |
|---|---|---|---|---|---|---|---|---|---|---|---|---|
|  |  | 165 |  |  |  | 170 |  |  |  | 175 |  |  |
| gcc | atg | tac | gaa | tac | atg | gcg | cag | gcg | tgc | gcc | ggg | aac | cgg | gtg | cgg | 576 |
| Ala | Met | Tyr | Glu | Tyr | Met | Ala | Gln | Ala | Cys | Ala | Gly | Asn | Arg | Val | Arg |
|  |  | 180 |  |  |  | 185 |  |  |  | 190 |  |  | cgc agc gtg ggc agt tcc ttg agt tgc atc aat ctg gac tgg gac gtc   624
Arg Ser Val Gly Ser Ser Leu Ser Cys Ile Asn Leu Asp Trp Asp Val
        195                 200                 205 atc cgc gat aag acg aag acg aaa atc gag tcg ctc aaa gag cac ggc   672
Ile Arg Asp Lys Thr Lys Thr Lys Ile Glu Ser Leu Lys Glu His Gly
    210                 215                 220 ccg atc aaa aac aaa atg agc gag tcg ccg aat aaa acg gtg tcc gag   720
Pro Ile Lys Asn Lys Met Ser Glu Ser Pro Asn Lys Thr Val Ser Glu
225                 230                 235                 240 gag aag gcg aag caa tac ctg gag gaa ttc cac cag acg gct ctg gag   768
Glu Lys Ala Lys Gln Tyr Leu Glu Glu Phe His Gln Thr Ala Leu Glu
                245                 250                 255 cac ccg gag ctg agc gaa ctc aaa acc gtt acc ggt acg aac ccg gtg   816
His Pro Glu Leu Ser Glu Leu Lys Thr Val Thr Gly Thr Asn Pro Val
            260                 265                 270 ttt gcc ggg gca aac tat gca gct tgg gcc gtc aac gtg gcc caa gtg   864
Phe Ala Gly Ala Asn Tyr Ala Ala Trp Ala Val Asn Val Ala Gln Val
        275                 280                 285 atc gac tcc gaa acg gcc gac aac ctg gaa aag act acc gcc gcg ttg   912
Ile Asp Ser Glu Thr Ala Asp Asn Leu Glu Lys Thr Thr Ala Ala Leu
    290                 295                 300 tcg atc ctc ccg ggc atc ggg agc gtc atg ggt att gcc gat ggt gcg   960
Ser Ile Leu Pro Gly Ile Gly Ser Val Met Gly Ile Ala Asp Gly Ala
305                 310                 315                 320 gtg cat cac aac acc gaa gag atc gtc gcg cag tcg atc gca ttg tcc   1008
Val His His Asn Thr Glu Glu Ile Val Ala Gln Ser Ile Ala Leu Ser
                325                 330                 335 tcc ctg atg gtc gcc caa gct atc ccg ctg gtc ggc gag ctg gtc gat   1056
Ser Leu Met Val Ala Gln Ala Ile Pro Leu Val Gly Glu Leu Val Asp
            340                 345                 350 atc ggc ttt gcc gct tat aac ttt gtt gaa tcg atc att aac ctg ttc   1104
Ile Gly Phe Ala Ala Tyr Asn Phe Val Glu Ser Ile Ile Asn Leu Phe
        355                 360                 365 cag gtg gtg cat aac agc tac aac cgg cca gcg tac tcg ccc ggt cac   1152
Gln Val Val His Asn Ser Tyr Asn Arg Pro Ala Tyr Ser Pro Gly His
    370                 375                 380 aag acc cag ccc ttt ctc cac gac ggc tat gcc gtg tcg tgg aac acc   1200
Lys Thr Gln Pro Phe Leu His Asp Gly Tyr Ala Val Ser Trp Asn Thr
385                 390                 395                 400 gtg gag gac agc atc atc cgc acc ggt ttc cag ggc gag agc ggc cat   1248
Val Glu Asp Ser Ile Ile Arg Thr Gly Phe Gln Gly Glu Ser Gly His
                405                 410                 415 gac atc aaa att acc gcg gaa aac acg ccc ttg ccg atc gct ggc gtg   1296
Asp Ile Lys Ile Thr Ala Glu Asn Thr Pro Leu Pro Ile Ala Gly Val
            420                 425                 430 ttg ctc ccg acg atc ccg ggt aag ctc gac gtc aac aag tcc aag acc   1344
Leu Leu Pro Thr Ile Pro Gly Lys Leu Asp Val Asn Lys Ser Lys Thr
        435                 440                 445 cat atc agc gtc aat ggc cgc aag atc cgc atg cgc tgt cgg gcc att   1392
His Ile Ser Val Asn Gly Arg Lys Ile Arg Met Arg Cys Arg Ala Ile
    450                 455                 460 gat ggc gac gtc acg ttt tgc cgg ccg aag agt ccc gtc tat gtc ggg   1440
Asp Gly Asp Val Thr Phe Cys Arg Pro Lys Ser Pro Val Tyr Val Gly
465                 470                 475                 480 aac ggt gtc cat gcc aac ctg cac gtc gca ttc cac cgg agc agc tcg   1488
Asn Gly Val His Ala Asn Leu His Val Ala Phe His Arg Ser Ser Ser

```
                                485                 490                 495
gaa aag atc cac agc aat gag atc agc agc gac agc atc ggc gtg ctg        1536
Glu Lys Ile His Ser Asn Glu Ile Ser Ser Asp Ser Ile Gly Val Leu
            500                 505                 510 ggg tat caa aag acg gtc gat cac acc aag gtg aac agt aaa ctg agc        1584
Gly Tyr Gln Lys Thr Val Asp His Thr Lys Val Asn Ser Lys Leu Ser
        515                 520                 525 ttg ttc ttt gaa atc aag tcg                                            1605
Leu Phe Phe Glu Ile Lys Ser
        530             535

<210> SEQ ID NO 3
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Met Arg Asn Leu Ile Leu Ser Ala Ala Leu Val Thr Ala Ser Leu Phe
1               5                   10                  15

Gly Met Thr Ala Gln Ala
            20

<210> SEQ ID NO 4
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Met Phe Ala Lys Leu Val Ala Val Ser Leu Leu Thr Leu Ala Ser Gly
1               5                   10                  15

Gln Leu Leu Ala
            20

<210> SEQ ID NO 5
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Ile Arg Asp Asn Arg Leu Lys Thr Ser Leu Leu Arg Gly Leu Thr
1               5                   10                  15

Leu Thr Leu Leu Ser Leu Thr Leu Leu Ser Pro Ala Ala His Ala
            20                  25                  30

<210> SEQ ID NO 6
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Met Asn Arg Ser Ser Ala Leu Leu Leu Ala Phe Val Phe Leu Ser Gly
1               5                   10                  15

Cys Gln Ala Met Ala
```

<210> SEQ ID NO 7
<211> LENGTH: 24
<212> TYPE: PRT
<213> ORGANISM: Artificial Sequence
<220> FEATURE:
<223> OTHER INFORMATION: Description of Artificial Sequence: Synthetic peptide

<400> SEQUENCE: 7

Met Leu Phe Arg Thr Leu Leu Ala Ser Leu Thr Phe Ala Val Ile Ala
1               5                   10                  15

Gly Leu Pro Ser Thr Ala His Ala
            20

<210> SEQ ID NO 8
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 8

Met Ser Cys Thr Arg Ala Phe Lys Pro Leu Leu Leu Ile Gly Leu Ala
1               5                   10                  15

Thr Leu Met Cys Ser His Ala Phe Ala
            20                  25

<210> SEQ ID NO 9
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 9

Met Arg Leu Ala Ala Leu Pro Leu Leu Leu Ala Pro Leu Phe Ile Ala
1               5                   10                  15

Pro Met Ala Val Ala
            20

<210> SEQ ID NO 10
<211> LENGTH: 24
<212> TYPE: PRT
<213> ORGANISM: Artificial Sequence
<220> FEATURE:
<223> OTHER INFORMATION: Description of Artificial Sequence: Synthetic peptide

<400> SEQUENCE: 10

Met Lys Leu Lys Arg Leu Met Ala Ala Met Thr Phe Val Ala Ala Gly
1               5                   10                  15

Val Ala Thr Val Asn Ala Val Ala
            20

<210> SEQ ID NO 11
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 11

```
Met Arg Leu Thr Gln Ile Ile Ala Ala Ala Ala Ile Ala Leu Val Ser
1               5                   10                  15

Thr Phe Ala Leu Ala
            20

<210> SEQ ID NO 12
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Met Arg Asn Leu Leu Arg Gly Met Leu Val Val Ile Cys Cys Met Ala
1               5                   10                  15

Gly Ile Ala Ala Ala
            20

<210> SEQ ID NO 13
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Met Lys Leu Lys Arg Leu Met Ala Ala Met Thr Phe Val Ala Ala Gly
1               5                   10                  15

Val Ala Thr Ala Asn Ala Val Ala
            20

<210> SEQ ID NO 14
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Met Gln Asn Tyr Lys Lys Phe Leu Leu Ala Ala Val Ser Met Ala
1               5                   10                  15

Phe Ser Ala Thr Ala Met Ala
            20

<210> SEQ ID NO 15
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Met Pro Pro Arg Ser Ile Ala Ala Cys Leu Gly Leu Leu Gly Leu Leu
1               5                   10                  15

Met Ala Thr Gln Ala Ala Ala
            20

<210> SEQ ID NO 16
<211> LENGTH: 21
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 16

Met Lys Lys Ser Thr Leu Ala Val Ala Val Thr Leu Gly Ala Ile Ala
1               5                   10                  15

Gln Gln Ala Gly Ala
            20

<210> SEQ ID NO 17
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Met Lys Leu Lys Arg Leu Met Ala Ala Met Thr Phe Val Ala Ala Gly
1               5                   10                  15

Val Ala Thr Ala Asn Ala Val Ala
            20

<210> SEQ ID NO 18
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Met Lys Phe Lys Gln Leu Met Ala Met Ala Leu Leu Leu Ala Leu Ser
1               5                   10                  15

Ala Val Ala Gln Ala
            20

<210> SEQ ID NO 19
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Gln Asn Arg Thr Val Glu Ile Gly Val Gly Leu Phe Leu Leu Ala
1               5                   10                  15

Gly Ile Leu Ala Leu Leu Leu Leu Ala Leu Arg Val Ser Gly Leu Ser
            20                  25                  30

Ala

<210> SEQ ID NO 20
<211> LENGTH: 25
<212> TYPE: PRT
<213> ORGANISM: Corynebacterium diphtheriae
<220> FEATURE:
<221> NAME/KEY: MOD_RES
<222> LOCATION: (9)..(9)
<223> OTHER INFORMATION: Any amino acid

<400> SEQUENCE: 20

Met Ser Arg Lys Leu Phe Ala Ser Xaa Leu Ile Gly Ala Leu Leu Gly
1               5                   10                  15
```

```
Ile Gly Ala Pro Pro Ser Ala His Ala
            20                  25
```

<210> SEQ ID NO 21
<211> LENGTH: 4
<212> TYPE: PRT
<213> ORGANISM: Corynebacterium diphtheriae

<400> SEQUENCE: 21

```
Gly Ala Asp Asp
1
```

<210> SEQ ID NO 22
<211> LENGTH: 102
<212> TYPE: PRT
<213> ORGANISM: Vibrio cholerae

<400> SEQUENCE: 22

```
Thr Pro Gln Asn Ile Thr Asp Leu Cys Ala Glu Tyr His Asn Thr Gln
1               5                   10                  15

Ile His Thr Leu Asn Asp Lys Ile Phe Ser Tyr Thr Glu Ser Leu Ala
            20                  25                  30

Gly Lys Arg Glu Met Ala Ile Ile Thr Phe Lys Asn Gly Ala Thr Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Ala Tyr Leu Thr Glu Ala
65                  70                  75                  80

Lys Val Glu Lys Leu Cys Val Trp Asn Asn Lys Thr Pro His Ala Ile
                85                  90                  95

Ala Ala Ile Ser Met Ala
            100
```

<210> SEQ ID NO 23
<211> LENGTH: 306
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(306)

<400> SEQUENCE: 23

```
acg ccg caa aat atc acc gac ctg tgc gca gaa tat cac aat acc caa      48
Thr Pro Gln Asn Ile Thr Asp Leu Cys Ala Glu Tyr His Asn Thr Gln
1               5                   10                  15 atc cat act ctg aac gac aaa atc ttc agc tac acc gag agc ctg gct      96
Ile His Thr Leu Asn Asp Lys Ile Phe Ser Tyr Thr Glu Ser Leu Ala
            20                  25                  30 ggc aag cgc gag atg gcg atc att acg ttc aaa aac ggt gcg acc ttt     144
Gly Lys Arg Glu Met Ala Ile Ile Thr Phe Lys Asn Gly Ala Thr Phe
        35                  40                  45 cag gtg gaa gtc ccc ggc agt cag cac atc gat tcc cag aaa aag gcc     192
Gln Val Glu Val Pro Gly Ser Gln His Ile Asp Ser Gln Lys Lys Ala
    50                  55                  60 att gaa cgg atg aag gac acc ctc cgt atc gcc tac ttg acc gaa gcc     240
Ile Glu Arg Met Lys Asp Thr Leu Arg Ile Ala Tyr Leu Thr Glu Ala
65                  70                  75                  80 aag gtg gag aag ctg tgc gtt tgg aac aac aaa acc ccg cac gcc atc     288
Lys Val Glu Lys Leu Cys Val Trp Asn Asn Lys Thr Pro His Ala Ile
                85                  90                  95
```

-continued

```
gcg gcc atc tcg atg gcc                                              306
Ala Ala Ile Ser Met Ala
            100

<210> SEQ ID NO 24
<211> LENGTH: 3119
<212> TYPE: DNA
<213> ORGANISM: Bordetella pertussis
<220> FEATURE:
<221> NAME/KEY: CDS
<222> LOCATION: (1)..(807)
<220> FEATURE:
<221> NAME/KEY: CDS
<222> LOCATION: (850)..(1527)
<220> FEATURE:
<221> NAME/KEY: CDS
<222> LOCATION: (1587)..(1979)
<220> FEATURE:
<221> NAME/KEY: CDS
<222> LOCATION: (1994)..(2353)
<220> FEATURE:
<221> NAME/KEY: CDS
<222> LOCATION: (2439)..(3119)

<400> SEQUENCE: 24 atg cgt tgc act cgg gca att cgc caa acc gca aga aca ggc tgg ctg    48
Met Arg Cys Thr Arg Ala Ile Arg Gln Thr Ala Arg Thr Gly Trp Leu
1               5                   10                  15 acg tgg ctg gcg att ctt gcc gtc acg gcg ccc gtg act tcg ccg gca    96
Thr Trp Leu Ala Ile Leu Ala Val Thr Ala Pro Val Thr Ser Pro Ala
                20                  25                  30 tgg gcc gac gat cct ccc gcc acc gta tac aaa tat gac tcc cgc ccg   144
Trp Ala Asp Asp Pro Pro Ala Thr Val Tyr Lys Tyr Asp Ser Arg Pro
            35                  40                  45 ccg gag gac gtt ttc cag aac gga ttc acg gcg tgg gga aac aac gac   192
Pro Glu Asp Val Phe Gln Asn Gly Phe Thr Ala Trp Gly Asn Asn Asp
        50                  55                  60 aat gtg ctc gac cat ctg acc gga cgt tcc tgc cag gtc ggc agc agc   240
Asn Val Leu Asp His Leu Thr Gly Arg Ser Cys Gln Val Gly Ser Ser
65                  70                  75                  80 aac agc gct ttc gtc tcc acc agc agc agc cgg cgc tat acc gag gtc   288
Asn Ser Ala Phe Val Ser Thr Ser Ser Ser Arg Arg Tyr Thr Glu Val
                85                  90                  95 tat ctc gaa cat cgc atg cag gaa gcg gtc gag gcc gaa cgc gcc ggc   336
Tyr Leu Glu His Arg Met Gln Glu Ala Val Glu Ala Glu Arg Ala Gly
            100                 105                 110 agg ggc acc ggc cac ttc atc ggc tac atc tac gaa gtc cgc gcc gac   384
Arg Gly Thr Gly His Phe Ile Gly Tyr Ile Tyr Glu Val Arg Ala Asp
        115                 120                 125 aac aat ttc tac ggc gcc gcc agc tcg tac ttc gaa tac gtc gac act   432
Asn Asn Phe Tyr Gly Ala Ala Ser Ser Tyr Phe Glu Tyr Val Asp Thr
    130                 135                 140 tat ggc gac aat gcc ggc cgt atc ctc gcc ggc gcg ctg gcc acc tac   480
Tyr Gly Asp Asn Ala Gly Arg Ile Leu Ala Gly Ala Leu Ala Thr Tyr
145                 150                 155                 160 cag agc gca tat ctg gca cac cgg cgc att ccg ccc gaa aac atc cgc   528
Gln Ser Ala Tyr Leu Ala His Arg Arg Ile Pro Pro Glu Asn Ile Arg
                165                 170                 175 agg gta acg cgg gtc tat cac aac ggc atc acc ggc gag acc acg acc   576
Arg Val Thr Arg Val Tyr His Asn Gly Ile Thr Gly Glu Thr Thr Thr
            180                 185                 190 acg gag tat tcc aac gct cgc tac gtc agc cag cag act cgc gcc aat   624
Thr Glu Tyr Ser Asn Ala Arg Tyr Val Ser Gln Gln Thr Arg Ala Asn
        195                 200                 205
```

| | | |
|---|---|---|
| ccc aac ccc tac aca tcg cga agg tcc gta gcg tcg atc gtc ggc aca<br>Pro Asn Pro Tyr Thr Ser Arg Arg Ser Val Ala Ser Ile Val Gly Thr<br>210                           215                         220 | 672 |
| ttg gtg cgc atg gcg ccg gtg ata ggc gct tgc atg gcg cgg cag gcc<br>Leu Val Arg Met Ala Pro Val Ile Gly Ala Cys Met Ala Arg Gln Ala<br>225                       230                     235                 240 | 720 |
| gaa agc tcc gag gcc atg gca gcc tgg tcc gaa cgc gcc ggc gag gcg<br>Glu Ser Ser Glu Ala Met Ala Ala Trp Ser Glu Arg Ala Gly Glu Ala<br>                    245                     250                     255 | 768 |
| atg gtt ctc gtg tac tac gaa agc atc gcg tat tcg ttc tagacctggc<br>Met Val Leu Val Tyr Tyr Glu Ser Ile Ala Tyr Ser Phe<br>260                       265 | 817 |
| ccagccccgc ccaactccgg taattgaaca gc atg ccg atc gac cgc aag acg<br>                                          Met Pro Ile Asp Arg Lys Thr<br>                                                270                     275 | 870 |
| ctc tgc cat ctc ctg tcc gtt ctg ccg ttg gcc ctc ctc gga tct cac<br>Leu Cys His Leu Leu Ser Val Leu Pro Leu Ala Leu Leu Gly Ser His<br>                 280                     285                     290 | 918 |
| gtg gcg cgg gcc tcc acg cca ggc atc gtc att ccg ccg cag gaa cag<br>Val Ala Arg Ala Ser Thr Pro Gly Ile Val Ile Pro Pro Gln Glu Gln<br>         295                     300 | 966 |
| att acc cag cat ggc agc ccc tat gga cgc tgc gcg aac aag acc cgt<br>Ile Thr Gln His Gly Ser Pro Tyr Gly Arg Cys Ala Asn Lys Thr Arg<br>310                       315                     320 | 1014 |
| gcc ctg acc gtg gcg gaa ttg cgc ggc agc ggc gat ctg cag gag tac<br>Ala Leu Thr Val Ala Glu Leu Arg Gly Ser Gly Asp Leu Gln Glu Tyr<br>325                       330                     335                 340 | 1062 |
| ctg cgt cat gtg acg cgc ggc tgg tca ata ttt gcg ctc tac gat ggc<br>Leu Arg His Val Thr Arg Gly Trp Ser Ile Phe Ala Leu Tyr Asp Gly<br>                 345                     350                     355 | 1110 |
| acc tat ctc ggc ggc gaa tat ggc ggc gtg atc aag gac gga aca ccc<br>Thr Tyr Leu Gly Gly Glu Tyr Gly Gly Val Ile Lys Asp Gly Thr Pro<br>             360                     365                     370 | 1158 |
| ggc ggc gca ttc gac ctg aaa acg acg ttc tgc atc atg acc acg cgc<br>Gly Gly Ala Phe Asp Leu Lys Thr Thr Phe Cys Ile Met Thr Thr Arg<br>375                       380                     385 | 1206 |
| aat acg ggt caa ccc gca acg gat cac tac tac agc aac gtc acc gcc<br>Asn Thr Gly Gln Pro Ala Thr Asp His Tyr Tyr Ser Asn Val Thr Ala<br>390                       395                     400 | 1254 |
| act cgc ctg ctc tcc agc acc aac agc agg cta tgc gcg gtc ttc gtc<br>Thr Arg Leu Leu Ser Ser Thr Asn Ser Arg Leu Cys Ala Val Phe Val<br>405                       410                     415                 420 | 1302 |
| aga agc ggg caa ccg gtc att ggc gcc tgc acc agc ccg tat gac ggc<br>Arg Ser Gly Gln Pro Val Ile Gly Ala Cys Thr Ser Pro Tyr Asp Gly<br>                 425                     430                     435 | 1350 |
| aag tac tgg agc atg tac agc cgg ctg cgg aaa atg ctt tac ctg atc<br>Lys Tyr Trp Ser Met Tyr Ser Arg Leu Arg Lys Met Leu Tyr Leu Ile<br>             440                     445                     450 | 1398 |
| tac gtg gcc ggc atc tcc gta cgc gtc cat gtc agc aag gaa gaa cag<br>Tyr Val Ala Gly Ile Ser Val Arg Val His Val Ser Lys Glu Glu Gln<br>455                       460                     465 | 1446 |
| tat tac gac tat gag gac gca acg ttc gag act tac gcc ctt acc ggc<br>Tyr Tyr Asp Tyr Glu Asp Ala Thr Phe Glu Thr Tyr Ala Leu Thr Gly<br>470                       475                     480 | 1494 |
| atc tcc atc tgc aat cct gga tca tcc tta tgc tgagacgctt ccccactcga<br>Ile Ser Ile Cys Asn Pro Gly Ser Ser Leu Cys<br>485                       490                     495 | 1547 |
| accaccgccc cgggacaggg cggcgcccgg cggtcgcgc gtg cgc gcc ctg gcg<br>                                                    Val Arg Ala Leu Ala<br>                                                      500 | 1601 |

```
                                      -continued
tgg ttg ctg gca tcc ggc gcg atg acg cat ctt tcc ccc gcc ctg gcc    1649
Trp Leu Leu Ala Ser Gly Ala Met Thr His Leu Ser Pro Ala Leu Ala
            505                 510                 515 gac gtt cct tat gtg ctg gtg aag acc aat atg gtg gtc acc agc gta    1697
Asp Val Pro Tyr Val Leu Val Lys Thr Asn Met Val Val Thr Ser Val
        520                 525                 530 gcc atg aag ccg tat gaa gtc acc ccg acg cgc atg ctg gtc tgc ggc    1745
Ala Met Lys Pro Tyr Glu Val Thr Pro Thr Arg Met Leu Val Cys Gly
    535                 540                 545 atc gcc gcc aaa ctg ggc gcc gcg gcc agc agc ccg gac gcg cac gtg    1793
Ile Ala Ala Lys Leu Gly Ala Ala Ala Ser Ser Pro Asp Ala His Val
550                 555                 560 ccg ttc tgc ttc ggc aag gat ctc aag cgt ccc ggc agc agt ccc atg    1841
Pro Phe Cys Phe Gly Lys Asp Leu Lys Arg Pro Gly Ser Ser Pro Met
565                 570                 575                 580 gaa gtc atg ttg cgc gcc gtc ttc atg caa caa cgg ccg ctg cgc atg    1889
Glu Val Met Leu Arg Ala Val Phe Met Gln Gln Arg Pro Leu Arg Met
            585                 590                 595 ttt ctg ggt ccc aag caa ctc act ttc gaa ggc aag ccc gcg ctc gaa    1937
Phe Leu Gly Pro Lys Gln Leu Thr Phe Glu Gly Lys Pro Ala Leu Glu
        600                 605                 610 ctg atc cgg atg gtc gaa tgc agc ggc aag cag gat tgc ccc               1979
Leu Ile Arg Met Val Glu Cys Ser Gly Lys Gln Asp Cys Pro
    615                 620                 625 tgaaggcgaa cccc atg cat acc atc gca tcc atc ctg ttg tcc gtg ctc    2029
              Met His Thr Ile Ala Ser Ile Leu Leu Ser Val Leu
                              630                 635 ggc ata tac agc ccg gct gac gtc gcc ggc ttg ccg acc cat ctg tac    2077
Gly Ile Tyr Ser Pro Ala Asp Val Ala Gly Leu Pro Thr His Leu Tyr
        640                 645                 650 aag aac ttc act gtc cag gag ctg gcc ttg aaa ctg aag ggc aag aat    2125
Lys Asn Phe Thr Val Gln Glu Leu Ala Leu Lys Leu Lys Gly Lys Asn
655                 660                 665                 670 cag gag ttc tgc ctg acc gcc ttc atg tcg ggc aga agc ctg gtc cgg    2173
Gln Glu Phe Cys Leu Thr Ala Phe Met Ser Gly Arg Ser Leu Val Arg
            675                 680                 685 gcg tgc ctg tcc gac gcg gga cac gag cac gac acg tgg ttc gac acc    2221
Ala Cys Leu Ser Asp Ala Gly His Glu His Asp Thr Trp Phe Asp Thr
        690                 695                 700 atg ctt ggc ttt gcc ata tcc gcg tat gcg ctc aag agc cgg atc gcg    2269
Met Leu Gly Phe Ala Ile Ser Ala Tyr Ala Leu Lys Ser Arg Ile Ala
    705                 710                 715 ctg acg gtg gaa gac tcg ccg tat ccg ggc act ccc ggc gat ctg ctc    2317
Leu Thr Val Glu Asp Ser Pro Tyr Pro Gly Thr Pro Gly Asp Leu Leu
720                 725                 730 gaa ctg cag atc tgc ccg ctc aac gga tat tgc gaa tgaacccttc         2363
Glu Leu Gln Ile Cys Pro Leu Asn Gly Tyr Cys Glu
735                 740                 745 cggaggtttc gacgtttccg cgcaatccgc ttgagacgat cttccgccct ggttccattc   2423
cgggaacacc gcaac atg ctg atc aac aac aag aag ctg ctt cat cac att    2474
              Met Leu Ile Asn Asn Lys Lys Leu Leu His His Ile
                              750                 755 ctg ccc atc ctg gtg ctc gcc ctg ctg ggc atg cgc acg gcc cag gcc    2522
Leu Pro Ile Leu Val Leu Ala Leu Leu Gly Met Arg Thr Ala Gln Ala
    760                 765                 770 gtt gcg cca ggc atc gtc atc ccg ccg aag gca ctg ttc acc caa cag    2570
Val Ala Pro Gly Ile Val Ile Pro Pro Lys Ala Leu Phe Thr Gln Gln
775                 780                 785                 790 ggc ggc gcc tat gga cgc tgc ccg aac gga acc cgc gcc ttg acc gtg    2618
Gly Gly Ala Tyr Gly Arg Cys Pro Asn Gly Thr Arg Ala Leu Thr Val
```

```
                              795                 800                 805
gcc gaa ctg cgc ggc aac gcc gaa ttg cag acg tat ttg cgc cag ata          2666
Ala Glu Leu Arg Gly Asn Ala Glu Leu Gln Thr Tyr Leu Arg Gln Ile
            810                 815                 820 acg ccc ggc tgg tcc ata tac ggt ctc tat gac ggt acg tac ctg ggc          2714
Thr Pro Gly Trp Ser Ile Tyr Gly Leu Tyr Asp Gly Thr Tyr Leu Gly
        825                 830                 835 cag gcg tac ggc ggc atc atc aag gac gcg ccg cca ggc gcg ggg ttc          2762
Gln Ala Tyr Gly Gly Ile Ile Lys Asp Ala Pro Pro Gly Ala Gly Phe
    840                 845                 850 att tat cgc gaa act ttc tgc atc acg acc ata tac aag acc ggg caa          2810
Ile Tyr Arg Glu Thr Phe Cys Ile Thr Thr Ile Tyr Lys Thr Gly Gln
855                 860                 865                 870 ccg gct gcg gat cac tac tac agc aag gtc acg gcc acg cgc ctg ctc          2858
Pro Ala Ala Asp His Tyr Tyr Ser Lys Val Thr Ala Thr Arg Leu Leu
                875                 880                 885 gcc agc acc aac agc agg ctg tgc gcg gta ttc gtc agg gac ggg caa          2906
Ala Ser Thr Asn Ser Arg Leu Cys Ala Val Phe Val Arg Asp Gly Gln
            890                 895                 900 tcg gtc atc gga gcc tgc gcc agc ccg tat gaa ggc agg tac aga gac          2954
Ser Val Ile Gly Ala Cys Ala Ser Pro Tyr Glu Gly Arg Tyr Arg Asp
        905                 910                 915 atg tac gac gcg ctg cgg cgc ctg ctg tac atg atc tat atg tcc ggc          3002
Met Tyr Asp Ala Leu Arg Arg Leu Leu Tyr Met Ile Tyr Met Ser Gly
    920                 925                 930 ctt gcc gta cgc gtc cac gtc agc aag gag gaa cag tat tac gac tac          3050
Leu Ala Val Arg Val His Val Ser Lys Glu Glu Gln Tyr Tyr Asp Tyr
935                 940                 945                 950 gag gac gcc aca ttc cag acc tat gcc ctc acc ggc att tcc ctc tgc          3098
Glu Asp Ala Thr Phe Gln Thr Tyr Ala Leu Thr Gly Ile Ser Leu Cys
                955                 960                 965 aac ccg gca gcg tcg ata tgc                                              3119
Asn Pro Ala Ala Ser Ile Cys
            970

<210> SEQ ID NO 25
<211> LENGTH: 269
<212> TYPE: PRT
<213> ORGANISM: Bordetella pertussis

<400> SEQUENCE: 25

Met Arg Cys Thr Arg Ala Ile Arg Gln Thr Ala Arg Thr Gly Trp Leu
1               5                   10                  15

Thr Trp Leu Ala Ile Leu Ala Val Thr Ala Pro Val Thr Ser Pro Ala
            20                  25                  30

Trp Ala Asp Asp Pro Pro Ala Thr Val Tyr Lys Tyr Asp Ser Arg Pro
        35                  40                  45

Pro Glu Asp Val Phe Gln Asn Gly Phe Thr Ala Trp Gly Asn Asn Asp
    50                  55                  60

Asn Val Leu Asp His Leu Thr Gly Arg Ser Cys Gln Val Gly Ser Ser
65                  70                  75                  80

Asn Ser Ala Phe Val Ser Thr Ser Ser Arg Arg Tyr Thr Glu Val
            85                  90                  95

Tyr Leu Glu His Arg Met Gln Glu Ala Val Glu Ala Glu Arg Ala Gly
                100                 105                 110

Arg Gly Thr Gly His Phe Ile Gly Tyr Ile Tyr Glu Val Arg Ala Asp
        115                 120                 125

Asn Asn Phe Tyr Gly Ala Ala Ser Ser Tyr Phe Glu Tyr Val Asp Thr
    130                 135                 140
```

```
Tyr Gly Asp Asn Ala Gly Arg Ile Leu Ala Gly Ala Leu Ala Thr Tyr
145                 150                 155                 160

Gln Ser Ala Tyr Leu Ala His Arg Arg Ile Pro Pro Glu Asn Ile Arg
            165                 170                 175

Arg Val Thr Arg Val Tyr His Asn Gly Ile Thr Gly Glu Thr Thr Thr
        180                 185                 190

Thr Glu Tyr Ser Asn Ala Arg Tyr Val Ser Gln Gln Thr Arg Ala Asn
    195                 200                 205

Pro Asn Pro Tyr Thr Ser Arg Arg Ser Val Ala Ser Ile Val Gly Thr
    210                 215                 220

Leu Val Arg Met Ala Pro Val Ile Gly Ala Cys Met Ala Arg Gln Ala
225                 230                 235                 240

Glu Ser Ser Glu Ala Met Ala Ala Trp Ser Glu Arg Ala Gly Glu Ala
            245                 250                 255

Met Val Leu Val Tyr Tyr Glu Ser Ile Ala Tyr Ser Phe
            260                 265
```

<210> SEQ ID NO 26
<211> LENGTH: 226
<212> TYPE: PRT
<213> ORGANISM: Bordetella pertussis

<400> SEQUENCE: 26

```
Met Pro Ile Asp Arg Lys Thr Leu Cys His Leu Ser Val Leu Pro
1               5                   10                  15

Leu Ala Leu Leu Gly Ser His Val Ala Arg Ala Ser Thr Pro Gly Ile
            20                  25                  30

Val Ile Pro Pro Gln Glu Gln Ile Thr Gln His Gly Ser Pro Tyr Gly
        35                  40                  45

Arg Cys Ala Asn Lys Thr Arg Ala Leu Thr Val Ala Glu Leu Arg Gly
    50                  55                  60

Ser Gly Asp Leu Gln Glu Tyr Leu Arg His Val Thr Arg Gly Trp Ser
65                  70                  75                  80

Ile Phe Ala Leu Tyr Asp Gly Thr Tyr Leu Gly Gly Glu Tyr Gly Gly
            85                  90                  95

Val Ile Lys Asp Gly Thr Pro Gly Gly Ala Phe Asp Leu Lys Thr Thr
        100                 105                 110

Phe Cys Ile Met Thr Thr Arg Asn Thr Gly Gln Pro Ala Thr Asp His
    115                 120                 125

Tyr Tyr Ser Asn Val Thr Ala Thr Arg Leu Leu Ser Ser Thr Asn Ser
130                 135                 140

Arg Leu Cys Ala Val Phe Val Arg Ser Gly Gln Pro Val Ile Gly Ala
145                 150                 155                 160

Cys Thr Ser Pro Tyr Asp Gly Lys Tyr Trp Ser Met Tyr Ser Arg Leu
            165                 170                 175

Arg Lys Met Leu Tyr Leu Ile Tyr Val Ala Gly Ile Ser Val Arg Val
        180                 185                 190

His Val Ser Lys Glu Glu Gln Tyr Tyr Asp Tyr Glu Asp Ala Thr Phe
    195                 200                 205

Glu Thr Tyr Ala Leu Thr Gly Ile Ser Ile Cys Asn Pro Gly Ser Ser
210                 215                 220

Leu Cys
225
```

<210> SEQ ID NO 27

```
<211> LENGTH: 227
<212> TYPE: PRT
<213> ORGANISM: Bordetella pertussis

<400> SEQUENCE: 27

Met Leu Ile Asn Asn Lys Lys Leu Leu His His Ile Leu Pro Ile Leu
1               5                   10                  15

Val Leu Ala Leu Leu Gly Met Arg Thr Ala Gln Ala Val Ala Pro Gly
            20                  25                  30

Ile Val Ile Pro Pro Lys Ala Leu Phe Thr Gln Gln Gly Gly Ala Tyr
        35                  40                  45

Gly Arg Cys Pro Asn Gly Thr Arg Ala Leu Thr Val Ala Glu Leu Arg
    50                  55                  60

Gly Asn Ala Glu Leu Gln Thr Tyr Leu Arg Gln Ile Thr Pro Gly Trp
65                  70                  75                  80

Ser Ile Tyr Gly Leu Tyr Asp Gly Thr Tyr Leu Gly Gln Ala Tyr Gly
                85                  90                  95

Gly Ile Ile Lys Asp Ala Pro Pro Gly Ala Gly Phe Ile Tyr Arg Glu
            100                 105                 110

Thr Phe Cys Ile Thr Thr Ile Tyr Lys Thr Gly Gln Pro Ala Ala Asp
        115                 120                 125

His Tyr Tyr Ser Lys Val Thr Ala Thr Arg Leu Leu Ala Ser Thr Asn
    130                 135                 140

Ser Arg Leu Cys Ala Val Phe Val Arg Asp Gly Gln Ser Val Ile Gly
145                 150                 155                 160

Ala Cys Ala Ser Pro Tyr Glu Gly Arg Tyr Arg Asp Met Tyr Asp Ala
                165                 170                 175

Leu Arg Arg Leu Leu Tyr Met Ile Tyr Met Ser Gly Leu Ala Val Arg
            180                 185                 190

Val His Val Ser Lys Glu Glu Gln Tyr Tyr Asp Tyr Glu Asp Ala Thr
        195                 200                 205

Phe Gln Thr Tyr Ala Leu Thr Gly Ile Ser Leu Cys Asn Pro Ala Ala
    210                 215                 220

Ser Ile Cys
225

<210> SEQ ID NO 28
<211> LENGTH: 131
<212> TYPE: PRT
<213> ORGANISM: Bordetella pertussis

<400> SEQUENCE: 28

Val Arg Ala Leu Ala Trp Leu Leu Ala Ser Gly Ala Met Thr His Leu
1               5                   10                  15

Ser Pro Ala Leu Ala Asp Val Pro Tyr Val Leu Val Lys Thr Asn Met
            20                  25                  30

Val Val Thr Ser Val Ala Met Lys Pro Tyr Glu Val Thr Pro Thr Arg
        35                  40                  45

Met Leu Val Cys Gly Ile Ala Ala Lys Leu Gly Ala Ala Ala Ser Ser
    50                  55                  60

Pro Asp Ala His Val Pro Phe Cys Phe Gly Lys Asp Leu Lys Arg Pro
65                  70                  75                  80

Gly Ser Ser Pro Met Glu Val Met Leu Arg Ala Val Phe Met Gln Gln
                85                  90                  95

Arg Pro Leu Arg Met Phe Leu Gly Pro Lys Gln Leu Thr Phe Glu Gly
            100                 105                 110
```

```
Lys Pro Ala Leu Glu Leu Ile Arg Met Val Glu Cys Ser Gly Lys Gln
            115                 120                 125

Asp Cys Pro
        130
```

<210> SEQ ID NO 29
<211> LENGTH: 120
<212> TYPE: PRT
<213> ORGANISM: Bordetella pertussis

<400> SEQUENCE: 29

```
Met His Thr Ile Ala Ser Ile Leu Leu Ser Val Leu Gly Ile Tyr Ser
1               5                   10                  15

Pro Ala Asp Val Ala Gly Leu Pro Thr His Leu Tyr Lys Asn Phe Thr
            20                  25                  30

Val Gln Glu Leu Ala Leu Lys Leu Lys Gly Lys Asn Gln Glu Phe Cys
        35                  40                  45

Leu Thr Ala Phe Met Ser Gly Arg Ser Leu Val Arg Ala Cys Leu Ser
    50                  55                  60

Asp Ala Gly His Glu His Asp Thr Trp Phe Asp Thr Met Leu Gly Phe
65                  70                  75                  80

Ala Ile Ser Ala Tyr Ala Leu Lys Ser Arg Ile Ala Leu Thr Val Glu
                85                  90                  95

Asp Ser Pro Tyr Pro Gly Thr Pro Gly Asp Leu Leu Glu Leu Gln Ile
            100                 105                 110

Cys Pro Leu Asn Gly Tyr Cys Glu
        115                 120
```

<210> SEQ ID NO 30
<211> LENGTH: 451
<212> TYPE: PRT
<213> ORGANISM: Clostridium tetani

<400> SEQUENCE: 30

```
Lys Asn Leu Asp Cys Trp Val Asp Asn Glu Glu Asp Ile Asp Val Ile
1               5                   10                  15

Leu Lys Lys Ser Thr Ile Leu Asn Leu Asp Ile Asn Asn Asp Ile Ile
            20                  25                  30

Ser Asp Ile Ser Gly Phe Asn Ser Ser Val Ile Thr Tyr Pro Asp Ala
        35                  40                  45

Gln Leu Val Pro Gly Ile Asn Gly Lys Ala Ile His Leu Val Asn Asn
    50                  55                  60

Glu Ser Ser Glu Val Ile Val His Lys Ala Met Asp Ile Glu Tyr Asn
65                  70                  75                  80

Asp Met Phe Asn Asn Phe Thr Val Ser Phe Trp Leu Arg Val Pro Lys
                85                  90                  95

Val Ser Ala Ser His Leu Glu Gln Tyr Gly Thr Asn Glu Tyr Ser Ile
            100                 105                 110

Ile Ser Ser Met Lys Lys His Ser Leu Ser Ile Gly Ser Gly Trp Ser
        115                 120                 125

Val Ser Leu Lys Gly Asn Asn Leu Ile Trp Thr Leu Lys Asp Ser Ala
    130                 135                 140

Gly Glu Val Arg Gln Ile Thr Phe Arg Asp Leu Pro Asp Lys Phe Asn
145                 150                 155                 160

Ala Tyr Leu Ala Asn Lys Trp Val Phe Ile Thr Ile Thr Asn Asp Arg
                165                 170                 175

Leu Ser Ser Ala Asn Leu Tyr Ile Asn Gly Val Leu Met Gly Ser Ala
```

```
                     180                 185                 190
Glu Ile Thr Gly Leu Gly Ala Ile Arg Glu Asp Asn Asn Ile Thr Leu
                 195                 200                 205

Lys Leu Asp Arg Cys Asn Asn Asn Gln Tyr Val Ser Ile Asp Lys
            210                 215                 220

Phe Arg Ile Phe Cys Lys Ala Leu Asn Pro Lys Glu Ile Glu Lys Leu
225                 230                 235                 240

Tyr Thr Ser Tyr Leu Ser Ile Thr Phe Leu Arg Asp Phe Trp Gly Asn
                245                 250                 255

Pro Leu Arg Tyr Asp Thr Glu Tyr Tyr Leu Ile Pro Val Ala Ser Ser
            260                 265                 270

Ser Lys Asp Val Gln Leu Lys Asn Ile Thr Asp Tyr Met Tyr Leu Thr
        275                 280                 285

Asn Ala Pro Ser Tyr Thr Asn Gly Lys Leu Asn Ile Tyr Tyr Arg Arg
    290                 295                 300

Leu Tyr Asn Gly Leu Lys Phe Ile Ile Lys Arg Tyr Thr Pro Asn Asn
305                 310                 315                 320

Glu Ile Asp Ser Phe Val Lys Ser Gly Asp Phe Ile Lys Leu Tyr Val
                325                 330                 335

Ser Tyr Asn Asn Asn Glu His Ile Val Gly Tyr Pro Lys Asp Gly Asn
            340                 345                 350

Ala Phe Asn Asn Leu Asp Arg Ile Leu Arg Val Gly Tyr Asn Ala Pro
        355                 360                 365

Gly Ile Pro Leu Tyr Lys Lys Met Glu Ala Val Lys Leu Arg Asp Leu
    370                 375                 380

Lys Thr Tyr Ser Val Gln Leu Lys Leu Tyr Asp Asp Lys Asn Ala Ser
385                 390                 395                 400

Leu Gly Leu Val Gly Thr His Asn Gly Gln Ile Gly Asn Asp Pro Asn
                405                 410                 415

Arg Asp Ile Leu Ile Ala Ser Asn Trp Tyr Phe Asn His Leu Lys Asp
            420                 425                 430

Lys Ile Leu Gly Cys Asp Trp Tyr Phe Val Pro Thr Asp Glu Gly Trp
        435                 440                 445

Thr Asn Asp
    450

<210> SEQ ID NO 31
<211> LENGTH: 1353
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1353)

<400> SEQUENCE: 31 aaa aac ctg gac tgt tgg gtt gac aac gaa gaa gat atc gat gtc atc    48
Lys Asn Leu Asp Cys Trp Val Asp Asn Glu Glu Asp Ile Asp Val Ile
1               5                   10                  15 ctg aag aaa tcc acc att ttg aac ctc gac atc aac aat gac atc att    96
Leu Lys Lys Ser Thr Ile Leu Asn Leu Asp Ile Asn Asn Asp Ile Ile
            20                  25                  30 tcc gac att agc ggt ttc aac tcg tcc gtg att acg tac cca gat gct   144
Ser Asp Ile Ser Gly Phe Asn Ser Ser Val Ile Thr Tyr Pro Asp Ala
        35                  40                  45 cag ctg gtg ccc ggg att aac ggc aag gct atc cac ctc gtc aac aac   192
```

```
       Gln Leu Val Pro Gly Ile Asn Gly Lys Ala Ile His Leu Val Asn Asn
           50                  55                  60 gag tcg tcg gaa gtc atc gtc cat aaa gcg atg gac atc gag tat aac         240
Glu Ser Ser Glu Val Ile Val His Lys Ala Met Asp Ile Glu Tyr Asn
 65                  70                  75                  80 gac atg ttt aat aat ttc acc gtg tcc ttt tgg ctg cgc gtg ccc aag         288
Asp Met Phe Asn Asn Phe Thr Val Ser Phe Trp Leu Arg Val Pro Lys
                     85                  90                  95 gtg tcc gcc tcc cac ctg gaa cag tac ggg acc aac gag tac agc atc         336
Val Ser Ala Ser His Leu Glu Gln Tyr Gly Thr Asn Glu Tyr Ser Ile
                100                 105                 110 atc agc tcg atg aag aag cac tcg ttg agc atc ggc agc ggc tgg tcg         384
Ile Ser Ser Met Lys Lys His Ser Leu Ser Ile Gly Ser Gly Trp Ser
            115                 120                 125 gtt agt ctc aaa ggg aac aac ctg att tgg acc ctg aaa gat agc gcc         432
Val Ser Leu Lys Gly Asn Asn Leu Ile Trp Thr Leu Lys Asp Ser Ala
        130                 135                 140 ggc gag gtg cgt cag atc act ttc cgg gac ctg ccg gat aag ttc aac         480
Gly Glu Val Arg Gln Ile Thr Phe Arg Asp Leu Pro Asp Lys Phe Asn
145                 150                 155                 160 gcc tac ctg gca aac aaa tgg gtg ttc att acc atc acg aac gac cgc         528
Ala Tyr Leu Ala Asn Lys Trp Val Phe Ile Thr Ile Thr Asn Asp Arg
                165                 170                 175 ctg agt agc gcg aat ctc tac atc aat ggc gtg ctg atg ggc agc gcg         576
Leu Ser Ser Ala Asn Leu Tyr Ile Asn Gly Val Leu Met Gly Ser Ala
                180                 185                 190 gaa atc acg ggc ttg ggt gcc atc cgc gaa gat aac aat atc acc ttg         624
Glu Ile Thr Gly Leu Gly Ala Ile Arg Glu Asp Asn Asn Ile Thr Leu
            195                 200                 205 aag ctg gac cgc tgc aac aac aac aac caa tac gtg tcc att gat aag         672
Lys Leu Asp Arg Cys Asn Asn Asn Asn Gln Tyr Val Ser Ile Asp Lys
        210                 215                 220 ttc cgc atc ttt tgc aag gcc ctg aac ccg aaa gag atc gaa aag ctc         720
Phe Arg Ile Phe Cys Lys Ala Leu Asn Pro Lys Glu Ile Glu Lys Leu
225                 230                 235                 240 tac acc agc tac ttg agt atc acc ttc ctg cgc gac ttt tgg ggt aat         768
Tyr Thr Ser Tyr Leu Ser Ile Thr Phe Leu Arg Asp Phe Trp Gly Asn
                245                 250                 255 ccg ttg cgt tat gac acc gag tat tat ctg atc ccc gtg gcc agc agc         816
Pro Leu Arg Tyr Asp Thr Glu Tyr Tyr Leu Ile Pro Val Ala Ser Ser
                260                 265                 270 agc aag gac gtc cag ctg aag aac atc acc gac tac atg tac ttg act         864
Ser Lys Asp Val Gln Leu Lys Asn Ile Thr Asp Tyr Met Tyr Leu Thr
            275                 280                 285 aac gcg ccc tcg tat acc aat ggc aaa ctg aac att tac tac cgc cgg         912
Asn Ala Pro Ser Tyr Thr Asn Gly Lys Leu Asn Ile Tyr Tyr Arg Arg
        290                 295                 300 ctc tac aac ggg ctc aag ttc atc atc aaa cgc tat acg ccg aat aat         960
Leu Tyr Asn Gly Leu Lys Phe Ile Ile Lys Arg Tyr Thr Pro Asn Asn
305                 310                 315                 320 gaa atc gac agt ttt gtc aag agc ggc gac ttc atc aag ttg tac gtg        1008
Glu Ile Asp Ser Phe Val Lys Ser Gly Asp Phe Ile Lys Leu Tyr Val
                325                 330                 335 agc tac aat aac aac gag cac atc gtt ggt tac cct aag gat ggc aac        1056
Ser Tyr Asn Asn Asn Glu His Ile Val Gly Tyr Pro Lys Asp Gly Asn
                340                 345                 350 gct ttc aac aac ctc gat cgt atc ctg cgg gtt ggc tac aac gca cca        1104
Ala Phe Asn Asn Leu Asp Arg Ile Leu Arg Val Gly Tyr Asn Ala Pro
            355                 360                 365 ggc att ccg ctg tat aag aag atg gaa gcg gtc aaa ctg cgt gac ctg        1152
```

-continued

| | | | | | | | | | | | | |
|---|---|---|---|---|---|---|---|---|---|---|---|---|
| Gly | Ile | Pro | Leu | Tyr | Lys | Lys | Met | Glu | Ala | Val | Lys | Leu | Arg | Asp | Leu |
| | 370 | | | | 375 | | | | 380 | | | | | | |

```
aaa acc tac tcc gtg caa ctg aag ctg tac gac gac aag aat gcc tcg      1200
Lys Thr Tyr Ser Val Gln Leu Lys Leu Tyr Asp Asp Lys Asn Ala Ser
385             390                 395                 400 ttg ggt ctg gtc ggc acg cat aat ggt cag att ggc aac gac ccg aac      1248
Leu Gly Leu Val Gly Thr His Asn Gly Gln Ile Gly Asn Asp Pro Asn
            405                 410                 415 cgg gac atc ctg atc gcc agc aac tgg tat ttc aat cac ctg aag gat      1296
Arg Asp Ile Leu Ile Ala Ser Asn Trp Tyr Phe Asn His Leu Lys Asp
        420                 425                 430 aag atc ttg ggc tgc gat tgg tat ttc gtc cct acc gat gag ggc tgg      1344
Lys Ile Leu Gly Cys Asp Trp Tyr Phe Val Pro Thr Asp Glu Gly Trp
    435                 440                 445 act aat gac                                                           1353
Thr Asn Asp
    450

<210> SEQ ID NO 32
<211> LENGTH: 2366
<212> TYPE: PRT
<213> ORGANISM: Clostridium difficile

<400> SEQUENCE: 32

Met Ser Leu Val Asn Arg Lys Gln Leu Glu Lys Met Ala Asn Val Arg
1               5                   10                  15

Phe Arg Thr Gln Glu Asp Glu Tyr Val Ala Ile Leu Asp Ala Leu Glu
            20                  25                  30

Glu Tyr His Asn Met Ser Glu Asn Thr Val Val Glu Lys Tyr Leu Lys
        35                  40                  45

Leu Lys Asp Ile Asn Ser Leu Thr Asp Ile Tyr Ile Asp Thr Tyr Lys
    50                  55                  60

Lys Ser Gly Arg Asn Lys Ala Leu Lys Lys Phe Lys Glu Tyr Leu Val
65                  70                  75                  80

Thr Glu Val Leu Glu Leu Lys Asn Asn Asn Leu Thr Pro Val Glu Lys
                85                  90                  95

Asn Leu His Phe Val Trp Ile Gly Gly Gln Ile Asn Asp Thr Ala Ile
            100                 105                 110

Asn Tyr Ile Asn Gln Trp Lys Asp Val Asn Ser Asp Tyr Asn Val Asn
        115                 120                 125

Val Phe Tyr Asp Ser Asn Ala Phe Leu Ile Asn Thr Leu Lys Lys Thr
    130                 135                 140

Val Val Glu Ser Ala Ile Asn Asp Thr Leu Glu Ser Phe Arg Glu Asn
145                 150                 155                 160

Leu Asn Asp Pro Arg Phe Asp Tyr Asn Lys Phe Phe Arg Lys Arg Met
                165                 170                 175

Glu Ile Ile Tyr Asp Lys Gln Lys Asn Phe Ile Asn Tyr Tyr Lys Ala
            180                 185                 190

Gln Arg Glu Glu Asn Pro Glu Leu Ile Ile Asp Asp Ile Val Lys Thr
        195                 200                 205

Tyr Leu Ser Asn Glu Tyr Ser Lys Glu Ile Asp Glu Leu Asn Thr Tyr
    210                 215                 220

Ile Glu Glu Ser Leu Asn Lys Ile Thr Gln Asn Ser Gly Asn Asp Val
225                 230                 235                 240

Arg Asn Phe Glu Glu Phe Lys Asn Gly Glu Ser Phe Asn Leu Tyr Glu
                245                 250                 255

Gln Glu Leu Val Glu Arg Trp Asn Leu Ala Ala Ala Ser Asp Ile Leu
```

```
                260                 265                 270
Arg Ile Ser Ala Leu Lys Glu Ile Gly Gly Met Tyr Leu Asp Val Asp
                275                 280                 285

Met Leu Pro Gly Ile Gln Pro Asp Leu Phe Glu Ser Ile Glu Lys Pro
            290                 295                 300

Ser Ser Val Thr Val Asp Phe Trp Glu Met Thr Lys Leu Glu Ala Ile
305                 310                 315                 320

Met Lys Tyr Lys Glu Tyr Ile Pro Glu Tyr Thr Ser Glu His Phe Asp
                325                 330                 335

Met Leu Asp Glu Glu Val Gln Ser Ser Phe Glu Ser Val Leu Ala Ser
            340                 345                 350

Lys Ser Asp Lys Ser Glu Ile Phe Ser Ser Leu Gly Asp Met Glu Ala
        355                 360                 365

Ser Pro Leu Glu Val Lys Ile Ala Phe Asn Ser Lys Gly Ile Ile Asn
        370                 375                 380

Gln Gly Leu Ile Ser Val Lys Asp Ser Tyr Cys Ser Asn Leu Ile Val
385                 390                 395                 400

Lys Gln Ile Glu Asn Arg Tyr Lys Ile Leu Asn Asn Ser Leu Asn Pro
                405                 410                 415

Ala Ile Ser Glu Asp Asn Asp Phe Asn Thr Thr Thr Asn Thr Phe Ile
            420                 425                 430

Asp Ser Ile Met Ala Glu Ala Asn Ala Asp Asn Gly Arg Phe Met Met
        435                 440                 445

Glu Leu Gly Lys Tyr Leu Arg Val Gly Phe Phe Pro Asp Val Lys Thr
        450                 455                 460

Thr Ile Asn Leu Ser Gly Pro Glu Ala Tyr Ala Ala Ala Tyr Gln Asp
465                 470                 475                 480

Leu Leu Met Phe Lys Glu Gly Ser Met Asn Ile His Leu Ile Glu Ala
                485                 490                 495

Asp Leu Arg Asn Phe Glu Ile Ser Lys Thr Asn Ile Ser Gln Ser Thr
            500                 505                 510

Glu Gln Glu Met Ala Ser Leu Trp Ser Phe Asp Asp Ala Arg Ala Lys
        515                 520                 525

Ala Gln Phe Glu Glu Tyr Lys Arg Asn Tyr Phe Glu Gly Ser Leu Gly
        530                 535                 540

Glu Asp Asp Asn Leu Asp Phe Ser Gln Asn Ile Val Val Asp Lys Glu
545                 550                 555                 560

Tyr Leu Leu Glu Lys Ile Ser Ser Leu Ala Arg Ser Ser Glu Arg Gly
                565                 570                 575

Tyr Ile His Tyr Ile Val Gln Leu Gln Gly Asp Lys Ile Ser Tyr Glu
            580                 585                 590

Ala Ala Cys Asn Leu Phe Ala Lys Thr Pro Tyr Asp Ser Val Leu Phe
        595                 600                 605

Gln Lys Asn Ile Glu Asp Ser Glu Ile Ala Tyr Tyr Tyr Asn Pro Gly
        610                 615                 620

Asp Gly Glu Ile Gln Glu Ile Asp Lys Tyr Lys Ile Pro Ser Ile Ile
625                 630                 635                 640

Ser Asp Arg Pro Lys Ile Lys Leu Thr Phe Ile Gly His Gly Lys Asp
                645                 650                 655

Glu Phe Asn Thr Asp Ile Phe Ala Gly Phe Asp Val Asp Ser Leu Ser
            660                 665                 670

Thr Glu Ile Glu Ala Ala Ile Asp Leu Ala Lys Glu Asp Ile Ser Pro
        675                 680                 685
```

-continued

```
Lys Ser Ile Glu Ile Asn Leu Leu Gly Cys Asn Met Phe Ser Tyr Ser
690                 695                 700

Ile Asn Val Glu Glu Thr Tyr Pro Gly Lys Leu Leu Lys Val Lys
705                 710                 715                 720

Asp Lys Ile Ser Glu Leu Met Pro Ser Ile Ser Gln Asp Ser Ile Ile
                    725                 730                 735

Val Ser Ala Asn Gln Tyr Glu Val Arg Ile Asn Ser Glu Gly Arg Arg
                740                 745                 750

Glu Leu Leu Asp His Ser Gly Glu Trp Ile Asn Lys Glu Ser Ile
            755                 760                 765

Ile Lys Asp Ile Ser Ser Lys Gly Tyr Ile Ser Phe Asn Pro Lys Glu
770                 775                 780

Asn Lys Ile Thr Val Lys Ser Lys Asn Leu Pro Glu Leu Ser Thr Leu
785                 790                 795                 800

Leu Gln Glu Ile Arg Asn Asn Ser Asn Ser Ser Asp Ile Glu Leu Glu
                805                 810                 815

Glu Lys Val Met Leu Thr Glu Cys Glu Ile Asn Val Ile Ser Asn Ile
                820                 825                 830

Asp Thr Gln Ile Val Glu Glu Arg Ile Glu Glu Ala Lys Asn Leu Thr
                835                 840                 845

Ser Asp Ser Ile Asn Tyr Ile Lys Asp Glu Phe Lys Leu Ile Glu Ser
850                 855                 860

Ile Ser Asp Ala Leu Cys Asp Leu Lys Gln Gln Asn Glu Leu Glu Asp
865                 870                 875                 880

Ser His Phe Ile Ser Phe Glu Asp Ile Ser Glu Thr Asp Glu Gly Phe
                885                 890                 895

Ser Ile Arg Phe Ile Asn Lys Glu Thr Gly Glu Ser Ile Phe Val Glu
                900                 905                 910

Thr Glu Lys Thr Ile Phe Ser Glu Tyr Ala Asn His Ile Thr Glu Glu
                915                 920                 925

Ile Ser Lys Ile Lys Gly Thr Ile Phe Asp Thr Val Asn Gly Lys Leu
930                 935                 940

Val Lys Lys Val Asn Leu Asp Thr Thr His Glu Val Asn Thr Leu Asn
945                 950                 955                 960

Ala Ala Phe Phe Ile Gln Ser Leu Ile Glu Tyr Asn Ser Ser Lys Glu
                965                 970                 975

Ser Leu Ser Asn Leu Ser Val Ala Met Lys Val Gln Val Tyr Ala Gln
                980                 985                 990

Leu Phe Ser Thr Gly Leu Asn Thr Ile Thr Asp Ala Ala Lys Val Val
                995                 1000                1005

Glu Leu Val Ser Thr Ala Leu Asp Glu Thr Ile Asp Leu Leu Pro
    1010                1015                1020

Thr Leu Ser Glu Gly Leu Pro Ile Ile Ala Thr Ile Ile Asp Gly
    1025                1030                1035

Val Ser Leu Gly Ala Ala Ile Lys Glu Leu Ser Glu Thr Ser Asp
    1040                1045                1050

Pro Leu Leu Arg Gln Glu Ile Glu Ala Lys Ile Gly Ile Met Ala
    1055                1060                1065

Val Asn Leu Thr Thr Ala Thr Thr Ala Ile Ile Thr Ser Ser Leu
    1070                1075                1080

Gly Ile Ala Ser Gly Phe Ser Ile Leu Leu Val Pro Leu Ala Gly
    1085                1090                1095

Ile Ser Ala Gly Ile Pro Ser Leu Val Asn Asn Glu Leu Val Leu
    1100                1105                1110
```

```
Arg Asp Lys Ala Thr Lys Val Val Asp Tyr Phe Lys His Val Ser
1115                1120                1125

Leu Val Glu Thr Glu Gly Val Phe Thr Leu Leu Asp Asp Lys Ile
1130                1135                1140

Met Met Pro Gln Asp Asp Leu Val Ile Ser Glu Ile Asp Phe Asn
1145                1150                1155

Asn Asn Ser Ile Val Leu Gly Lys Cys Glu Ile Trp Arg Met Glu
1160                1165                1170

Gly Gly Ser Gly His Thr Val Thr Asp Asp Ile Asp His Phe Phe
1175                1180                1185

Ser Ala Pro Ser Ile Thr Tyr Arg Glu Pro His Leu Ser Ile Tyr
1190                1195                1200

Asp Val Leu Glu Val Gln Lys Glu Glu Leu Asp Leu Ser Lys Asp
1205                1210                1215

Leu Met Val Leu Pro Asn Ala Pro Asn Arg Val Phe Ala Trp Glu
1220                1225                1230

Thr Gly Trp Thr Pro Gly Leu Arg Ser Leu Glu Asn Asp Gly Thr
1235                1240                1245

Lys Leu Leu Asp Arg Ile Arg Asp Asn Tyr Glu Gly Glu Phe Tyr
1250                1255                1260

Trp Arg Tyr Phe Ala Phe Ile Ala Asp Ala Leu Ile Thr Thr Leu
1265                1270                1275

Lys Pro Arg Tyr Glu Asp Thr Asn Ile Arg Ile Asn Leu Asp Ser
1280                1285                1290

Asn Thr Arg Ser Phe Ile Val Pro Ile Ile Thr Thr Glu Tyr Ile
1295                1300                1305

Arg Glu Lys Leu Ser Tyr Ser Phe Tyr Gly Ser Gly Gly Thr Tyr
1310                1315                1320

Ala Leu Ser Leu Ser Gln Tyr Asn Met Gly Ile Asn Ile Glu Leu
1325                1330                1335

Ser Glu Ser Asp Val Trp Ile Ile Asp Val Asp Asn Val Val Arg
1340                1345                1350

Asp Val Thr Ile Glu Ser Asp Lys Ile Lys Lys Gly Asp Leu Ile
1355                1360                1365

Glu Gly Ile Leu Ser Thr Leu Ser Ile Glu Glu Asn Lys Ile Ile
1370                1375                1380

Leu Asn Ser His Glu Ile Asn Phe Ser Gly Glu Val Asn Gly Ser
1385                1390                1395

Asn Gly Phe Val Ser Leu Thr Phe Ser Ile Leu Glu Gly Ile Asn
1400                1405                1410

Ala Ile Ile Glu Val Asp Leu Leu Ser Lys Ser Tyr Lys Leu Leu
1415                1420                1425

Ile Ser Gly Glu Leu Lys Ile Leu Met Leu Asn Ser Asn His Ile
1430                1435                1440

Gln Gln Lys Ile Asp Tyr Ile Gly Phe Asn Ser Glu Leu Gln Lys
1445                1450                1455

Asn Ile Pro Tyr Ser Phe Val Asp Ser Glu Gly Lys Glu Asn Gly
1460                1465                1470

Phe Ile Asn Gly Ser Thr Lys Glu Gly Leu Phe Val Ser Glu Leu
1475                1480                1485

Pro Asp Val Val Leu Ile Ser Lys Val Tyr Met Asp Asp Ser Lys
1490                1495                1500

Pro Ser Phe Gly Tyr Tyr Ser Asn Asn Leu Lys Asp Val Lys Val
```

-continued

```
            1505                1510                1515

Ile Thr Lys Asp Asn Val Asn Ile Leu Thr Gly Tyr Tyr Leu Lys
    1520                1525                1530

Asp Asp Ile Lys Ile Ser Leu Ser Leu Thr Leu Gln Asp Glu Lys
    1535                1540                1545

Thr Ile Lys Leu Asn Ser Val His Leu Asp Glu Ser Gly Val Ala
    1550                1555                1560

Glu Ile Leu Lys Phe Met Asn Arg Lys Gly Asn Thr Asn Thr Ser
    1565                1570                1575

Asp Ser Leu Met Ser Phe Leu Glu Ser Met Asn Ile Lys Ser Ile
    1580                1585                1590

Phe Val Asn Phe Leu Gln Ser Asn Ile Lys Phe Ile Leu Asp Ala
    1595                1600                1605

Asn Phe Ile Ile Ser Gly Thr Thr Ser Ile Gly Gln Phe Glu Phe
    1610                1615                1620

Ile Cys Asp Glu Asn Asp Asn Ile Gln Pro Tyr Phe Ile Lys Phe
    1625                1630                1635

Asn Thr Leu Glu Thr Asn Tyr Thr Leu Tyr Val Gly Asn Arg Gln
    1640                1645                1650

Asn Met Ile Val Glu Pro Asn Tyr Asp Leu Asp Asp Ser Gly Asp
    1655                1660                1665

Ile Ser Ser Thr Val Ile Asn Phe Ser Gln Lys Tyr Leu Tyr Gly
    1670                1675                1680

Ile Asp Ser Cys Val Asn Lys Val Val Ile Ser Pro Asn Ile Tyr
    1685                1690                1695

Thr Asp Glu Ile Asn Ile Thr Pro Val Tyr Glu Thr Asn Asn Thr
    1700                1705                1710

Tyr Pro Glu Val Ile Val Leu Asp Ala Asn Tyr Ile Asn Glu Lys
    1715                1720                1725

Ile Asn Val Asn Ile Asn Asp Leu Ser Ile Arg Tyr Val Trp Ser
    1730                1735                1740

Asn Asp Gly Asn Asp Phe Ile Leu Met Ser Thr Ser Glu Glu Asn
    1745                1750                1755

Lys Val Ser Gln Val Lys Ile Arg Phe Val Asn Val Phe Lys Asp
    1760                1765                1770

Lys Thr Leu Ala Asn Lys Leu Ser Phe Asn Phe Ser Asp Lys Gln
    1775                1780                1785

Asp Val Pro Val Ser Glu Ile Ile Leu Ser Phe Thr Pro Ser Tyr
    1790                1795                1800

Tyr Glu Asp Gly Leu Ile Gly Tyr Asp Leu Gly Leu Val Ser Leu
    1805                1810                1815

Tyr Asn Glu Lys Phe Tyr Ile Asn Asn Phe Gly Met Met Val Ser
    1820                1825                1830

Gly Leu Ile Tyr Ile Asn Asp Ser Leu Tyr Tyr Phe Lys Pro Pro
    1835                1840                1845

Val Asn Asn Leu Ile Thr Gly Phe Val Thr Val Gly Asp Asp Lys
    1850                1855                1860

Tyr Tyr Phe Asn Pro Ile Asn Gly Gly Ala Ala Ser Ile Gly Glu
    1865                1870                1875

Thr Ile Ile Asp Asp Lys Asn Tyr Tyr Phe Asn Gln Ser Gly Val
    1880                1885                1890

Leu Gln Thr Gly Val Phe Ser Thr Glu Asp Gly Phe Lys Tyr Phe
    1895                1900                1905
```

```
Ala Pro Ala Asn Thr Leu Asp Glu Asn Leu Glu Gly Glu Ala Ile
    1910            1915                1920
Asp Phe Thr Gly Lys Leu Ile Ile Asp Glu Asn Ile Tyr Tyr Phe
    1925            1930                1935
Asp Asp Asn Tyr Arg Gly Ala Val Glu Trp Lys Glu Leu Asp Gly
    1940            1945                1950
Glu Met His Tyr Phe Ser Pro Glu Thr Gly Lys Ala Phe Lys Gly
    1955            1960                1965
Leu Asn Gln Ile Gly Asp Tyr Lys Tyr Phe Asn Ser Asp Gly
    1970            1975                1980
Val Met Gln Lys Gly Phe Val Ser Ile Asn Asp Asn Lys His Tyr
    1985            1990                1995
Phe Asp Asp Ser Gly Val Met Lys Val Gly Tyr Thr Glu Ile Asp
    2000            2005                2010
Gly Lys His Phe Tyr Phe Ala Glu Asn Gly Glu Met Gln Ile Gly
    2015            2020                2025
Val Phe Asn Thr Glu Asp Gly Phe Lys Tyr Phe Ala His His Asn
    2030            2035                2040
Glu Asp Leu Gly Asn Glu Glu Gly Glu Glu Ile Ser Tyr Ser Gly
    2045            2050                2055
Ile Leu Asn Phe Asn Asn Lys Ile Tyr Tyr Phe Asp Asp Ser Phe
    2060            2065                2070
Thr Ala Val Val Gly Trp Lys Asp Leu Glu Asp Gly Ser Lys Tyr
    2075            2080                2085
Tyr Phe Asp Glu Asp Thr Ala Glu Ala Tyr Ile Gly Leu Ser Leu
    2090            2095                2100
Ile Asn Asp Gly Gln Tyr Tyr Phe Asn Asp Asp Gly Ile Met Gln
    2105            2110                2115
Val Gly Phe Val Thr Ile Asn Asp Lys Val Phe Tyr Phe Ser Asp
    2120            2125                2130
Ser Gly Ile Ile Glu Ser Gly Val Gln Asn Ile Asp Asp Asn Tyr
    2135            2140                2145
Phe Tyr Ile Asp Asp Asn Gly Ile Val Gln Ile Gly Val Phe Asp
    2150            2155                2160
Thr Ser Asp Gly Tyr Lys Tyr Phe Ala Pro Ala Asn Thr Val Asn
    2165            2170                2175
Asp Asn Ile Tyr Gly Gln Ala Val Glu Tyr Ser Gly Leu Val Arg
    2180            2185                2190
Val Gly Glu Asp Val Tyr Tyr Phe Gly Glu Thr Tyr Thr Ile Glu
    2195            2200                2205
Thr Gly Trp Ile Tyr Asp Met Glu Asn Glu Ser Asp Lys Tyr Tyr
    2210            2215                2220
Phe Asn Pro Glu Thr Lys Lys Ala Cys Lys Gly Ile Asn Leu Ile
    2225            2230                2235
Asp Asp Ile Lys Tyr Tyr Phe Asp Glu Lys Gly Ile Met Arg Thr
    2240            2245                2250
Gly Leu Ile Ser Phe Glu Asn Asn Asn Tyr Tyr Phe Asn Glu Asn
    2255            2260                2265
Gly Glu Met Gln Phe Gly Tyr Ile Asn Ile Glu Asp Lys Met Phe
    2270            2275                2280
Tyr Phe Gly Glu Asp Gly Val Met Gln Ile Gly Val Phe Asn Thr
    2285            2290                2295
Pro Asp Gly Phe Lys Tyr Phe Ala His Gln Asn Thr Leu Asp Glu
    2300            2305                2310
```

-continued

```
Asn Phe Glu Gly Glu Ser Ile Asn Tyr Thr Gly Trp Leu Asp Leu
    2315                2320                2325

Asp Glu Lys Arg Tyr Tyr Phe Thr Asp Glu Tyr Ile Ala Ala Thr
    2330                2335                2340

Gly Ser Val Ile Ile Asp Gly Glu Glu Tyr Phe Asp Pro Asp
    2345                2350                2355

Thr Ala Gln Leu Val Ile Ser Glu
    2360                2365

<210> SEQ ID NO 33
<211> LENGTH: 7098
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(7098)

<400> SEQUENCE: 33 atg tcc ctc gtc aat cgc aag cag ctg gag aag atg gcc aac gtt cgt      48
Met Ser Leu Val Asn Arg Lys Gln Leu Glu Lys Met Ala Asn Val Arg
1               5                   10                  15 ttc cgc acc caa gag gac gaa tac gtc gcc atc ctc gac gcc ctg gaa      96
Phe Arg Thr Gln Glu Asp Glu Tyr Val Ala Ile Leu Asp Ala Leu Glu
            20                  25                  30 gaa tac cat aac atg agc gaa aac acc gtt gtc gag aag tac ctc aag     144
Glu Tyr His Asn Met Ser Glu Asn Thr Val Val Glu Lys Tyr Leu Lys
        35                  40                  45 ctg aag gac atc aac agc ctg acg gac atc tat atc gac acg tac aag     192
Leu Lys Asp Ile Asn Ser Leu Thr Asp Ile Tyr Ile Asp Thr Tyr Lys
    50                  55                  60 aag tcc ggt cgc aac aag gca ctc aag aag ttc aaa gag tac ctg gtc     240
Lys Ser Gly Arg Asn Lys Ala Leu Lys Lys Phe Lys Glu Tyr Leu Val
65                  70                  75                  80 acc gaa gtg ttg gaa ctc aag aac aac aac ctc acg ccg gtg gaa aag     288
Thr Glu Val Leu Glu Leu Lys Asn Asn Asn Leu Thr Pro Val Glu Lys
                85                  90                  95 aac ctg cat ttc gtg tgg att ggc ggc cag atc aac gac acc gcc atc     336
Asn Leu His Phe Val Trp Ile Gly Gly Gln Ile Asn Asp Thr Ala Ile
            100                 105                 110 aac tac att aac cag tgg aaa gac gtc aac tcg gac tac aat gtg aat     384
Asn Tyr Ile Asn Gln Trp Lys Asp Val Asn Ser Asp Tyr Asn Val Asn
        115                 120                 125 gtg ttc tat gac tcg aac gcc ttt ttg atc aac acg ctg aag aaa acc     432
Val Phe Tyr Asp Ser Asn Ala Phe Leu Ile Asn Thr Leu Lys Lys Thr
    130                 135                 140 gtc gtg gaa tcg gcc atc aat gac acc ctg gaa agc ttc cgt gaa aac     480
Val Val Glu Ser Ala Ile Asn Asp Thr Leu Glu Ser Phe Arg Glu Asn
145                 150                 155                 160 ctc aac gat cct cgg ttt gac tac aac aag ttt ttc cgc aag cgc atg     528
Leu Asn Asp Pro Arg Phe Asp Tyr Asn Lys Phe Phe Arg Lys Arg Met
                165                 170                 175 gag atc atc tat gac aag cag aaa aac ttt atc aac tac tac aaa gcg     576
Glu Ile Ile Tyr Asp Lys Gln Lys Asn Phe Ile Asn Tyr Tyr Lys Ala
            180                 185                 190 cag cgc gaa gag aac ccg gag ctg atc atc gac gat atc gtg aaa acc     624
Gln Arg Glu Glu Asn Pro Glu Leu Ile Ile Asp Asp Ile Val Lys Thr
        195                 200                 205 tat ctg tcc aac gag tat agt aaa gaa atc gat gag ctg aac acg tat     672
```

```
                Tyr Leu Ser Asn Glu Tyr Ser Lys Glu Ile Asp Glu Leu Asn Thr Tyr
                    210                 215                 220 atc gaa gag agt ctg aac aag atc act cag aac agc ggt aac gac gtc        720
Ile Glu Glu Ser Leu Asn Lys Ile Thr Gln Asn Ser Gly Asn Asp Val
225                 230                 235                 240 cgg aac ttt gaa gag ttc aaa aac ggc gag tcg ttc aac ctc tac gaa        768
Arg Asn Phe Glu Glu Phe Lys Asn Gly Glu Ser Phe Asn Leu Tyr Glu
                245                 250                 255 cag gag ctg gtc gag cgc tgg aac ctg gca gcg gcg tcg gac atc ctg        816
Gln Glu Leu Val Glu Arg Trp Asn Leu Ala Ala Ala Ser Asp Ile Leu
                260                 265                 270 cgt atc agc gct ctg aaa gag atc ggc ggc atg tac ctg gac gtg gat        864
Arg Ile Ser Ala Leu Lys Glu Ile Gly Gly Met Tyr Leu Asp Val Asp
        275                 280                 285 atg ctc cct ggc atc cag cct gat ctg ttt gaa tcg att gaa aag cca        912
Met Leu Pro Gly Ile Gln Pro Asp Leu Phe Glu Ser Ile Glu Lys Pro
        290                 295                 300 tcg agc gtg acc gtc gac ttt tgg gag atg acc aag ctg gag gcg atc        960
Ser Ser Val Thr Val Asp Phe Trp Glu Met Thr Lys Leu Glu Ala Ile
305                 310                 315                 320 atg aag tac aaa gaa tac atc ccg gag tat acg agt gaa cac ttt gat       1008
Met Lys Tyr Lys Glu Tyr Ile Pro Glu Tyr Thr Ser Glu His Phe Asp
                325                 330                 335 atg ctg gac gaa gaa gtg caa tcc tcg ttt gaa agc gtc ctg gcg agc       1056
Met Leu Asp Glu Glu Val Gln Ser Ser Phe Glu Ser Val Leu Ala Ser
                340                 345                 350 aag agt gat aag agc gaa atc ttc tcg tcc ttg ggc gat atg gag gcg       1104
Lys Ser Asp Lys Ser Glu Ile Phe Ser Ser Leu Gly Asp Met Glu Ala
                355                 360                 365 tcc cca ctg gag gtc aaa atc gcc ttc aac agc aag ggc att atc aat       1152
Ser Pro Leu Glu Val Lys Ile Ala Phe Asn Ser Lys Gly Ile Ile Asn
370                 375                 380 cag ggc ctg att tcg gtc aag gat agc tac tgc agc aac ctg atc gtc       1200
Gln Gly Leu Ile Ser Val Lys Asp Ser Tyr Cys Ser Asn Leu Ile Val
385                 390                 395                 400 aag cag atc gag aac cgt tac aag atc ctg aac aac agt ctg aac ccc       1248
Lys Gln Ile Glu Asn Arg Tyr Lys Ile Leu Asn Asn Ser Leu Asn Pro
                405                 410                 415 gcc atc agc gaa gat aat gac ttc aat acc acg acg aac acg ttt atc       1296
Ala Ile Ser Glu Asp Asn Asp Phe Asn Thr Thr Thr Asn Thr Phe Ile
                420                 425                 430 gac tcc atc atg gcc gaa gcc aac gcg gac aac ggc cgc ttt atg atg       1344
Asp Ser Ile Met Ala Glu Ala Asn Ala Asp Asn Gly Arg Phe Met Met
            435                 440                 445 gag ttg ggg aag tac ctg cgc gtg ggc ttc ttc ccg gac gtg aaa acc       1392
Glu Leu Gly Lys Tyr Leu Arg Val Gly Phe Phe Pro Asp Val Lys Thr
450                 455                 460 acg atc aat ctc tcc ggc cca gaa gcg tat gca gcc gca tac caa gat       1440
Thr Ile Asn Leu Ser Gly Pro Glu Ala Tyr Ala Ala Ala Tyr Gln Asp
465                 470                 475                 480 ctg ctc atg ttc aaa gag ggc tcg atg aac atc cat ctg att gag gcg       1488
Leu Leu Met Phe Lys Glu Gly Ser Met Asn Ile His Leu Ile Glu Ala
                485                 490                 495 gac ttg cgc aac ttc gaa atc tcg aaa acg aac atc agc caa tcg acg       1536
Asp Leu Arg Asn Phe Glu Ile Ser Lys Thr Asn Ile Ser Gln Ser Thr
                500                 505                 510 gag cag gaa atg gcg agc ctg tgg tcc ttc gac gat gct cgc gcc aag       1584
Glu Gln Glu Met Ala Ser Leu Trp Ser Phe Asp Asp Ala Arg Ala Lys
            515                 520                 525 gcc caa ttt gaa gag tac aaa cgg aac tac ttc gaa ggc tcg ctg ggt       1632
Ala Gln Phe Glu Glu Tyr Lys Arg Asn Tyr Phe Glu Gly Ser Leu Gly
```

|     |     |     |     |     |     |     |     |     |     |     |     |     |     |      |
|-----|-----|-----|-----|-----|-----|-----|-----|-----|-----|-----|-----|-----|-----|------|
| Ala | Gln | Phe | Glu | Glu | Tyr | Lys | Arg | Asn | Tyr | Phe | Glu | Gly | Ser | Leu Gly |
|     | 530 |     |     |     | 535 |     |     |     | 540 |     |     |     |     |      |

```
gag gat gac aac ttg gac ttc tcg caa aac atc gtc gtg gac aaa gaa    1680
Glu Asp Asp Asn Leu Asp Phe Ser Gln Asn Ile Val Val Asp Lys Glu
545                 550                 555                 560 tac ctg ttg gaa aag atc agc tcc ctg gcc cgg agc tcg gaa cgg ggc    1728
Tyr Leu Leu Glu Lys Ile Ser Ser Leu Ala Arg Ser Ser Glu Arg Gly
                565                 570                 575 tac atc cac tac att gtt cag ctg caa ggg gat aag atc tcg tat gaa    1776
Tyr Ile His Tyr Ile Val Gln Leu Gln Gly Asp Lys Ile Ser Tyr Glu
            580                 585                 590 gcg gcg tgc aat ctc ttc gcc aag acg ccg tac gac tcc gtg ctg ttc    1824
Ala Ala Cys Asn Leu Phe Ala Lys Thr Pro Tyr Asp Ser Val Leu Phe
        595                 600                 605 cag aag aac atc gag gac agt gaa atc gcc tac tat tac aac ccc ggt    1872
Gln Lys Asn Ile Glu Asp Ser Glu Ile Ala Tyr Tyr Tyr Asn Pro Gly
    610                 615                 620 gac ggc gaa atc caa gaa att gat aag tac aag atc ccg tcc att atc    1920
Asp Gly Glu Ile Gln Glu Ile Asp Lys Tyr Lys Ile Pro Ser Ile Ile
625                 630                 635                 640 tcc gat cgt ccg aag atc aaa ctc acc ttc att ggc cac ggg aag gac    1968
Ser Asp Arg Pro Lys Ile Lys Leu Thr Phe Ile Gly His Gly Lys Asp
                645                 650                 655 gag ttc aac acc gat atc ttc gca ggt ttt gac gtg gat agt ctc tcg    2016
Glu Phe Asn Thr Asp Ile Phe Ala Gly Phe Asp Val Asp Ser Leu Ser
            660                 665                 670 acc gag atc gag gcc gcg atc gac ctg gcg aaa gag gac att tcg cca    2064
Thr Glu Ile Glu Ala Ala Ile Asp Leu Ala Lys Glu Asp Ile Ser Pro
        675                 680                 685 aag tcg atc gaa atc aac ctg ctg ggc tgc aat atg ttt tcg tat agt    2112
Lys Ser Ile Glu Ile Asn Leu Leu Gly Cys Asn Met Phe Ser Tyr Ser
    690                 695                 700 atc aac gtt gaa gaa acc tat ccg ggc aaa ctc ctg ctg aag gtc aag    2160
Ile Asn Val Glu Glu Thr Tyr Pro Gly Lys Leu Leu Leu Lys Val Lys
705                 710                 715                 720 gac aag att agc gaa ctg atg ccg agc atc tcg cag gat agc atc atc    2208
Asp Lys Ile Ser Glu Leu Met Pro Ser Ile Ser Gln Asp Ser Ile Ile
                725                 730                 735 gtg agt gct aac cag tat gag gtg cgt atc aac agc gag ggt cgc cgc    2256
Val Ser Ala Asn Gln Tyr Glu Val Arg Ile Asn Ser Glu Gly Arg Arg
            740                 745                 750 gag ctg ctc gat cac tcg ggc gag tgg atc aac aaa gaa gag agc atc    2304
Glu Leu Leu Asp His Ser Gly Glu Trp Ile Asn Lys Glu Glu Ser Ile
        755                 760                 765 atc aaa gat atc agc agt aaa gaa tac att agt ttc aac ccg aaa gag    2352
Ile Lys Asp Ile Ser Ser Lys Glu Tyr Ile Ser Phe Asn Pro Lys Glu
    770                 775                 780 aac aag atc acg gtg aaa tcg aag aat ttg ccg gag ttg agt acc ctg    2400
Asn Lys Ile Thr Val Lys Ser Lys Asn Leu Pro Glu Leu Ser Thr Leu
785                 790                 795                 800 ctg cag gag atc cgt aac aat tcc aac tcc agt gat atc gaa ctc gaa    2448
Leu Gln Glu Ile Arg Asn Asn Ser Asn Ser Ser Asp Ile Glu Leu Glu
                805                 810                 815 gaa aag gtc atg ctg acc gag tgc gag atc aat gtc atc agc aac atc    2496
Glu Lys Val Met Leu Thr Glu Cys Glu Ile Asn Val Ile Ser Asn Ile
            820                 825                 830 gac act cag atc gtg gaa gaa cgc att gaa gag gcc aag aac ctg acc    2544
Asp Thr Gln Ile Val Glu Glu Arg Ile Glu Glu Ala Lys Asn Leu Thr
        835                 840                 845 tcg gac tcg atc aac tat atc aaa gac gag ttc aag ctg att gaa tcc    2592
```

```
                Ser Asp Ser Ile Asn Tyr Ile Lys Asp Glu Phe Lys Leu Ile Glu Ser
                    850                 855                 860 atc tcg gat gcc ctg tgc gac ctg aag cag cag aac gag ttg gag gat        2640
Ile Ser Asp Ala Leu Cys Asp Leu Lys Gln Gln Asn Glu Leu Glu Asp
865                 870                 875                 880 agc cac ttc atc agt ttc gag gat atc tcg gag act gac gag ggc ttc        2688
Ser His Phe Ile Ser Phe Glu Asp Ile Ser Glu Thr Asp Glu Gly Phe
                885                 890                 895 agc atc cgt ttc atc aac aaa gaa acc ggt gaa tcc att ttc gtt gaa        2736
Ser Ile Arg Phe Ile Asn Lys Glu Thr Gly Glu Ser Ile Phe Val Glu
            900                 905                 910 acg gag aaa acc att ttc agc gaa tac gcc aat cac atc acc gaa gag        2784
Thr Glu Lys Thr Ile Phe Ser Glu Tyr Ala Asn His Ile Thr Glu Glu
        915                 920                 925 atc agc aag atc aag ggt act atc ttt gac acg gtg aat ggc aaa ctg        2832
Ile Ser Lys Ile Lys Gly Thr Ile Phe Asp Thr Val Asn Gly Lys Leu
    930                 935                 940 gtg aag aaa gtc aac ctg gac acc acc cac gag gtc aac acc ctg aac        2880
Val Lys Lys Val Asn Leu Asp Thr Thr His Glu Val Asn Thr Leu Asn
945                 950                 955                 960 gcc gcg ttc ttc atc caa agc ctg atc gaa tac aac agc tcc aaa gaa        2928
Ala Ala Phe Phe Ile Gln Ser Leu Ile Glu Tyr Asn Ser Ser Lys Glu
                965                 970                 975 tcc ttg agc aac ttg agc gtg gcc atg aaa gtg cag gtg tat gcc cag        2976
Ser Leu Ser Asn Leu Ser Val Ala Met Lys Val Gln Val Tyr Ala Gln
            980                 985                 990 ttg ttc tcg acc ggc ctg aac acc att acg gac gcg gca aag gtg gtt        3024
Leu Phe Ser Thr Gly Leu Asn Thr Ile Thr Asp Ala Ala Lys Val Val
        995                 1000                1005 gaa ctg gtc agc acc gcc ttg gac gaa acc atc gac ctg ctg ccg            3069
Glu Leu Val Ser Thr Ala Leu Asp Glu Thr Ile Asp Leu Leu Pro
    1010                1015                1020 acc ctg agc gag ggc ctg ccc atc atc gcc acg atc att gac ggg            3114
Thr Leu Ser Glu Gly Leu Pro Ile Ile Ala Thr Ile Ile Asp Gly
    1025                1030                1035 gtc agc ctg ggc gca gcc atc aaa gag ttg agc gag act tcc gac            3159
Val Ser Leu Gly Ala Ala Ile Lys Glu Leu Ser Glu Thr Ser Asp
    1040                1045                1050 ccg ctg ctg cgc cag gaa atc gaa gct aag atc ggg atc atg gcc            3204
Pro Leu Leu Arg Gln Glu Ile Glu Ala Lys Ile Gly Ile Met Ala
    1055                1060                1065 gtg aat ctg acc acc gcg acc acc gcg atc att acc tcc agc ctc            3249
Val Asn Leu Thr Thr Ala Thr Thr Ala Ile Ile Thr Ser Ser Leu
    1070                1075                1080 ggc att gcg tcc ggc ttc tcc atc ctg ctg gtc ccc ttg gcg ggc            3294
Gly Ile Ala Ser Gly Phe Ser Ile Leu Leu Val Pro Leu Ala Gly
    1085                1090                1095 atc agc gcc ggt atc cct agc ttg gtg aac aac gag ttg gtc ctg            3339
Ile Ser Ala Gly Ile Pro Ser Leu Val Asn Asn Glu Leu Val Leu
    1100                1105                1110 cgt gat aaa gcg acc aag gtt gtg gat tac ttc aag cat gtc tcc            3384
Arg Asp Lys Ala Thr Lys Val Val Asp Tyr Phe Lys His Val Ser
    1115                1120                1125 ctg gtc gaa acg gaa ggg gtg ttc acc ctg ctg gac gat aag att            3429
Leu Val Glu Thr Glu Gly Val Phe Thr Leu Leu Asp Asp Lys Ile
    1130                1135                1140 atg atg ccc caa gac gat ttg gtc atc agc gaa att gac ttt aac            3474
Met Met Pro Gln Asp Asp Leu Val Ile Ser Glu Ile Asp Phe Asn
    1145                1150                1155 aac aat tcg atc gtc ctc ggg aag tgt gaa atc tgg cgg atg gag            3519
```

```
                Asn Asn Ser Ile Val Leu Gly Lys Cys Glu Ile Trp Arg Met Glu
                    1160            1165                1170 ggc ggt tcg ggc cac acc gtg acc gat gat atc gac cat ttc ttt       3564
Gly Gly Ser Gly His Thr Val Thr Asp Asp Ile Asp His Phe Phe
1175            1180                1185 agt gcg ccc tcc atc acg tac cgc gag ccg cac ctg agc atc tac       3609
Ser Ala Pro Ser Ile Thr Tyr Arg Glu Pro His Leu Ser Ile Tyr
    1190            1195                1200 gac gtg ctc gag gtg cag aaa gaa gaa ctg gat ctg tcc aaa gat       3654
Asp Val Leu Glu Val Gln Lys Glu Glu Leu Asp Leu Ser Lys Asp
1205            1210                1215 ctg atg gtt ctg ccg aac gct ccc aat cgg gtg ttc gct tgg gaa       3699
Leu Met Val Leu Pro Asn Ala Pro Asn Arg Val Phe Ala Trp Glu
    1220            1225                1230 acg ggc tgg acg cca ggc ctc cgc tcg ctg gag aac gac ggg act       3744
Thr Gly Trp Thr Pro Gly Leu Arg Ser Leu Glu Asn Asp Gly Thr
1235            1240                1245 aag ttg ctg gat cgc att cgc gac aat tac gaa ggc gaa ttc tac       3789
Lys Leu Leu Asp Arg Ile Arg Asp Asn Tyr Glu Gly Glu Phe Tyr
    1250            1255                1260 tgg cgc tac ttt gcg ttt atc gcc gac gct ctg att acc acc ctg       3834
Trp Arg Tyr Phe Ala Phe Ile Ala Asp Ala Leu Ile Thr Thr Leu
1265            1270                1275 aag ccg cgg tac gag gac act aac atc cgc atc aat ctg gat agc       3879
Lys Pro Arg Tyr Glu Asp Thr Asn Ile Arg Ile Asn Leu Asp Ser
    1280            1285                1290 aac act cgc agc ttc att gtc ccg atc atc acc act gaa tac att       3924
Asn Thr Arg Ser Phe Ile Val Pro Ile Ile Thr Thr Glu Tyr Ile
1295            1300                1305 cgc gaa aag ctg agc tac agc ttt tac ggt agc ggt ggt acc tat       3969
Arg Glu Lys Leu Ser Tyr Ser Phe Tyr Gly Ser Gly Gly Thr Tyr
    1310            1315                1320 gcc ctg agc ctg tcc cag tac aac atg ggc atc aac att gaa ttg       4014
Ala Leu Ser Leu Ser Gln Tyr Asn Met Gly Ile Asn Ile Glu Leu
1325            1330                1335 tcg gag agc gat gtg tgg atc att gac gtg gat aat gtc gtc cgc       4059
Ser Glu Ser Asp Val Trp Ile Ile Asp Val Asp Asn Val Val Arg
    1340            1345                1350 gat gtg acc att gag agc gac aaa atc aag aaa ggg gat ttg atc       4104
Asp Val Thr Ile Glu Ser Asp Lys Ile Lys Lys Gly Asp Leu Ile
1355            1360                1365 gaa ggc atc ctg tcg acc ttg agc atc gaa gag aat aag atc atc       4149
Glu Gly Ile Leu Ser Thr Leu Ser Ile Glu Glu Asn Lys Ile Ile
    1370            1375                1380 ctg aat agc cac gaa atc aac ttc tcc ggc gaa gtg aac ggc agc       4194
Leu Asn Ser His Glu Ile Asn Phe Ser Gly Glu Val Asn Gly Ser
1385            1390                1395 aac ggc ttc gtc agc ctg acc ttt tcc atc ctg gaa ggt atc aac       4239
Asn Gly Phe Val Ser Leu Thr Phe Ser Ile Leu Glu Gly Ile Asn
    1400            1405                1410 gcc atc att gag gtc gat ctg ctc agc aaa agc tac aag ctg ctc       4284
Ala Ile Ile Glu Val Asp Leu Leu Ser Lys Ser Tyr Lys Leu Leu
1415            1420                1425 atc tcg ggc gag ctg aaa atc ctc atg ttg aat tcg aat cac atc       4329
Ile Ser Gly Glu Leu Lys Ile Leu Met Leu Asn Ser Asn His Ile
    1430            1435                1440 caa cag aaa atc gac tat atc ggc ttc aac agc gag ctg caa aag       4374
Gln Gln Lys Ile Asp Tyr Ile Gly Phe Asn Ser Glu Leu Gln Lys
1445            1450                1455 aac atc ccc tac tcg ttt gtg gac agc gaa ggc aaa gag aac ggc       4419
```

```
Asn Ile Pro Tyr Ser Phe Val Asp Ser Glu Gly Lys Glu Asn Gly
    1460            1465            1470 ttc atc aac ggc tcc acc aaa gag ggg ctg ttc gtg agc gag ctg         4464
Phe Ile Asn Gly Ser Thr Lys Glu Gly Leu Phe Val Ser Glu Leu
1475            1480            1485 ccg gac gtg gtg ctc atc agc aaa gtg tat atg gac gac agc aag         4509
Pro Asp Val Val Leu Ile Ser Lys Val Tyr Met Asp Asp Ser Lys
1490            1495            1500 cct agt ttt ggc tac tac tcc aat aac ctg aaa gat gtt aaa gtg         4554
Pro Ser Phe Gly Tyr Tyr Ser Asn Asn Leu Lys Asp Val Lys Val
1505            1510            1515 att acc aag gat aac gtg aac atc ctc acc ggt tac tac ctg aag         4599
Ile Thr Lys Asp Asn Val Asn Ile Leu Thr Gly Tyr Tyr Leu Lys
1520            1525            1530 gac gac att aag atc agc ctg tcc ctg acc ctg caa gat gaa aag         4644
Asp Asp Ile Lys Ile Ser Leu Ser Leu Thr Leu Gln Asp Glu Lys
1535            1540            1545 acc atc aaa ttg aat agc gtc cat ctc gac gag agt ggt gtc gcc         4689
Thr Ile Lys Leu Asn Ser Val His Leu Asp Glu Ser Gly Val Ala
1550            1555            1560 gag atc ttg aag ttc atg aat cgc aag ggt aat acc aac acg agc         4734
Glu Ile Leu Lys Phe Met Asn Arg Lys Gly Asn Thr Asn Thr Ser
1565            1570            1575 gac tcg ttg atg tcc ttc ctg gaa agc atg aac atc aag agc att         4779
Asp Ser Leu Met Ser Phe Leu Glu Ser Met Asn Ile Lys Ser Ile
1580            1585            1590 ttc gtg aac ttc ctg caa agc aat atc aag ttc att ttg gac gcg         4824
Phe Val Asn Phe Leu Gln Ser Asn Ile Lys Phe Ile Leu Asp Ala
1595            1600            1605 aac ttt atc atc tcc ggg acc acg tcc atc ggc cag ttt gag ttc         4869
Asn Phe Ile Ile Ser Gly Thr Thr Ser Ile Gly Gln Phe Glu Phe
1610            1615            1620 atc tgt gac gag aac gac aac att cag ccg tat ttc atc aag ttc         4914
Ile Cys Asp Glu Asn Asp Asn Ile Gln Pro Tyr Phe Ile Lys Phe
1625            1630            1635 aat acc ttg gaa act aac tac acc ctg tac gtt ggc aac cgg caa         4959
Asn Thr Leu Glu Thr Asn Tyr Thr Leu Tyr Val Gly Asn Arg Gln
1640            1645            1650 aac atg att gtc gaa ccc aac tat gac ttg gat gac agt ggt gat         5004
Asn Met Ile Val Glu Pro Asn Tyr Asp Leu Asp Asp Ser Gly Asp
1655            1660            1665 atc agt agc acc gtg att aac ttt tcc cag aag tac ctg tat ggc         5049
Ile Ser Ser Thr Val Ile Asn Phe Ser Gln Lys Tyr Leu Tyr Gly
1670            1675            1680 atc gac tcc tgc gtg aac aaa gtg gtg atc tcg ccg aat atc tac         5094
Ile Asp Ser Cys Val Asn Lys Val Val Ile Ser Pro Asn Ile Tyr
1685            1690            1695 acg gac gaa atc aat atc act ccc gtc tat gaa acc aac aac acc         5139
Thr Asp Glu Ile Asn Ile Thr Pro Val Tyr Glu Thr Asn Asn Thr
1700            1705            1710 tac ccc gag gtg att gtc ttg gat gcg aac tac att aac gaa aag         5184
Tyr Pro Glu Val Ile Val Leu Asp Ala Asn Tyr Ile Asn Glu Lys
1715            1720            1725 att aac gtg aac att aac gac ctg agc atc cgg tat gtg tgg agt         5229
Ile Asn Val Asn Ile Asn Asp Leu Ser Ile Arg Tyr Val Trp Ser
1730            1735            1740 aat gac ggg aac gac ttc att ctg atg agc acc tcc gaa gaa aac         5274
Asn Asp Gly Asn Asp Phe Ile Leu Met Ser Thr Ser Glu Glu Asn
1745            1750            1755 aaa gtc tcg caa gtc aag atc cgc ttc gtt aac gtt ttc aaa gac         5319
```

```
Lys Val Ser Gln Val Lys Ile Arg Phe Val Asn Val Phe Lys Asp
        1760            1765            1770 aag acc ttg gcc aac aaa ctc agc ttc aat ttc tcg gac aaa cag     5364
Lys Thr Leu Ala Asn Lys Leu Ser Phe Asn Phe Ser Asp Lys Gln
    1775            1780            1785 gac gtg cct gtg tcg gag atc att ctc agt ttc acc ccg agc tac     5409
Asp Val Pro Val Ser Glu Ile Ile Leu Ser Phe Thr Pro Ser Tyr
    1790            1795            1800 tac gag gac ggc ctg atc ggt tac gac ctg ggc ctg gtt agc ctc     5454
Tyr Glu Asp Gly Leu Ile Gly Tyr Asp Leu Gly Leu Val Ser Leu
    1805            1810            1815 tac aac gaa aag ttc tat atc aac aat ttc ggg atg atg gtt tcg     5499
Tyr Asn Glu Lys Phe Tyr Ile Asn Asn Phe Gly Met Met Val Ser
    1820            1825            1830 ggt ctg atc tat atc aat gac agc ttg tac tac ttc aaa cct ccg     5544
Gly Leu Ile Tyr Ile Asn Asp Ser Leu Tyr Tyr Phe Lys Pro Pro
    1835            1840            1845 gtg aac aat ttg atc acc ggc ttc gtg acc gtg ggc gat gac aag     5589
Val Asn Asn Leu Ile Thr Gly Phe Val Thr Val Gly Asp Asp Lys
    1850            1855            1860 tac tat ttc aac ccg att aac ggt ggc gct gcg tcg att ggc gaa     5634
Tyr Tyr Phe Asn Pro Ile Asn Gly Gly Ala Ala Ser Ile Gly Glu
    1865            1870            1875 acc atc atc gac gac aag aac tac tat ttc aac cag agc ggt gtg     5679
Thr Ile Ile Asp Asp Lys Asn Tyr Tyr Phe Asn Gln Ser Gly Val
    1880            1885            1890 ctg caa acc ggg gtc ttt agc acg gag gat ggg ttt aag tat ttc     5724
Leu Gln Thr Gly Val Phe Ser Thr Glu Asp Gly Phe Lys Tyr Phe
    1895            1900            1905 gcg cct gcc aat acc ctg gac gag aat ttg gag ggc gaa gcc att     5769
Ala Pro Ala Asn Thr Leu Asp Glu Asn Leu Glu Gly Glu Ala Ile
    1910            1915            1920 gac ttc acc ggc aaa ctg att atc gac gaa aac atc tac tat ttc     5814
Asp Phe Thr Gly Lys Leu Ile Ile Asp Glu Asn Ile Tyr Tyr Phe
    1925            1930            1935 gat gac aac tac cgc ggt gcg gtc gaa tgg aaa gag ttg gac ggg     5859
Asp Asp Asn Tyr Arg Gly Ala Val Glu Trp Lys Glu Leu Asp Gly
    1940            1945            1950 gag atg cac tat ttc tcg cca gag act ggt aag gcc ttc aag ggc     5904
Glu Met His Tyr Phe Ser Pro Glu Thr Gly Lys Ala Phe Lys Gly
    1955            1960            1965 ctg aac cag atc ggc gac tac aag tac tat ttc aat agc gac ggc     5949
Leu Asn Gln Ile Gly Asp Tyr Lys Tyr Tyr Phe Asn Ser Asp Gly
    1970            1975            1980 gtg atg cag aag ggg ttc gtc agc atc aac gac aac aag cat tac     5994
Val Met Gln Lys Gly Phe Val Ser Ile Asn Asp Asn Lys His Tyr
    1985            1990            1995 ttc gac gat agc ggc gtt atg aag gtg ggc tat act gag atc gac     6039
Phe Asp Asp Ser Gly Val Met Lys Val Gly Tyr Thr Glu Ile Asp
    2000            2005            2010 ggc aag cac ttc tat ttc gcc gag aac ggc gag atg caa atc ggc     6084
Gly Lys His Phe Tyr Phe Ala Glu Asn Gly Glu Met Gln Ile Gly
    2015            2020            2025 gtg ttc aac acc gag gac ggc ttc aaa tac ttc gct cat cac aac     6129
Val Phe Asn Thr Glu Asp Gly Phe Lys Tyr Phe Ala His His Asn
    2030            2035            2040 gaa gat ctc ggt aat gaa gaa ggt gaa gag att tcc tat tcg ggc     6174
Glu Asp Leu Gly Asn Glu Glu Gly Glu Glu Ile Ser Tyr Ser Gly
    2045            2050            2055 atc ctg aac ttc aac aat aag atc tac tac ttt gat gac tcg ttc     6219
```

```
Ile Leu Asn Phe Asn Asn Lys Ile Tyr Tyr Phe Asp Asp Ser Phe
    2060                2065            2070 acc gcc gtg gtg ggt tgg aag gac ttg gag gac ggg agc aag tat      6264
Thr Ala Val Val Gly Trp Lys Asp Leu Glu Asp Gly Ser Lys Tyr
    2075                2080            2085 tac ttc gac gaa gat acc gcc gag gca tac atc ggc ttg tcg ctc      6309
Tyr Phe Asp Glu Asp Thr Ala Glu Ala Tyr Ile Gly Leu Ser Leu
    2090                2095            2100 atc aac gac ggt cag tac tac ttc aac gac gat ggc atc atg cag      6354
Ile Asn Asp Gly Gln Tyr Tyr Phe Asn Asp Asp Gly Ile Met Gln
    2105                2110            2115 gtg ggc ttc gtg act atc aac gac aag gtg ttc tac ttc agt gac      6399
Val Gly Phe Val Thr Ile Asn Asp Lys Val Phe Tyr Phe Ser Asp
    2120                2125            2130 agt ggc atc att gag tcg ggc gtg cag aat atc gac gat aac tat      6444
Ser Gly Ile Ile Glu Ser Gly Val Gln Asn Ile Asp Asp Asn Tyr
    2135                2140            2145 ttc tat atc gat gac aat ggc att gtg cag atc ggc gtg ttt gat      6489
Phe Tyr Ile Asp Asp Asn Gly Ile Val Gln Ile Gly Val Phe Asp
    2150                2155            2160 acc tcc gat ggg tat aag tat ttc gca cca gca aat acc gtc aat      6534
Thr Ser Asp Gly Tyr Lys Tyr Phe Ala Pro Ala Asn Thr Val Asn
    2165                2170            2175 gac aac atc tac ggc cag gcc gtg gag tac agc ggg ctg gtt cgt      6579
Asp Asn Ile Tyr Gly Gln Ala Val Glu Tyr Ser Gly Leu Val Arg
    2180                2185            2190 gtg ggc gag gac gtt tac tat ttc ggt gag act tat act atc gaa      6624
Val Gly Glu Asp Val Tyr Tyr Phe Gly Glu Thr Tyr Thr Ile Glu
    2195                2200            2205 acc ggc tgg atc tat gat atg gaa aac gaa tcg gat aag tac tac      6669
Thr Gly Trp Ile Tyr Asp Met Glu Asn Glu Ser Asp Lys Tyr Tyr
    2210                2215            2220 ttt aac cca gaa acg aag aaa gcc tgc aag ggc atc aac ctc att      6714
Phe Asn Pro Glu Thr Lys Lys Ala Cys Lys Gly Ile Asn Leu Ile
    2225                2230            2235 gat gac atc aag tat tac ttt gac gaa aag ggt atc atg cgc acc      6759
Asp Asp Ile Lys Tyr Tyr Phe Asp Glu Lys Gly Ile Met Arg Thr
    2240                2245            2250 ggc ctg atc tcg ttt gag aac aac aac tac tat ttc aac gag aat      6804
Gly Leu Ile Ser Phe Glu Asn Asn Asn Tyr Tyr Phe Asn Glu Asn
    2255                2260            2265 ggc gaa atg cag ttt ggg tac atc aat atc gag gat aag atg ttc      6849
Gly Glu Met Gln Phe Gly Tyr Ile Asn Ile Glu Asp Lys Met Phe
    2270                2275            2280 tac ttt ggg gag gac ggc gtc atg cag att ggt gtg ttt aac acc      6894
Tyr Phe Gly Glu Asp Gly Val Met Gln Ile Gly Val Phe Asn Thr
    2285                2290            2295 ccg gat ggc ttc aag tac ttc gcc cat cag aac act ctg gac gaa      6939
Pro Asp Gly Phe Lys Tyr Phe Ala His Gln Asn Thr Leu Asp Glu
    2300                2305            2310 aac ttc gag ggc gaa agc atc aat tac act ggc tgg ctg gac ctg      6984
Asn Phe Glu Gly Glu Ser Ile Asn Tyr Thr Gly Trp Leu Asp Leu
    2315                2320            2325 gat gag aaa cgc tac tac ttc acc gac gag tac att gcc gcc acg      7029
Asp Glu Lys Arg Tyr Tyr Phe Thr Asp Glu Tyr Ile Ala Ala Thr
    2330                2335            2340 ggc tcc gtg att atc gac ggc gaa gaa tac tat ttc gat ccc gac      7074
Gly Ser Val Ile Ile Asp Gly Glu Glu Tyr Tyr Phe Asp Pro Asp
    2345                2350            2355 acc gcc cag ttg gtc att agc gaa                                   7098
Thr Ala Gln Leu Val Ile Ser Glu
```

```
Thr Ala Gln Leu Val Ile Ser Glu
    2360            2365

<210> SEQ ID NO 34
<211> LENGTH: 613
<212> TYPE: PRT
<213> ORGANISM: Pseudomonas aeruginosa
<220> FEATURE:
<221> NAME/KEY: MOD_RES
<222> LOCATION: (426)..(426)
<223> OTHER INFORMATION: His or Tyr
<220> FEATURE:
<221> NAME/KEY: MOD_RES
<222> LOCATION: (553)..(553)
<223> OTHER INFORMATION: May or may not be present

<400> SEQUENCE: 34

Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
            20                  25                  30

Ala Ile Ala Asp Thr Asn Gly Gln Gly Val Leu His Tyr Ser Met Val
        35                  40                  45

Leu Glu Gly Gly Asn Asp Ala Leu Lys Leu Ala Ile Asp Asn Ala Leu
50                  55                  60

Ser Ile Thr Ser Asp Gly Leu Thr Ile Arg Leu Glu Gly Gly Val Glu
65                  70                  75                  80

Pro Asn Lys Pro Val Arg Tyr Ser Tyr Thr Arg Gln Ala Arg Gly Ser
                85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
        115                 120                 125

Met Ser Pro Ile Tyr Thr Ile Glu Met Gly Asp Glu Leu Leu Ala Lys
130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Ala Gln Pro Arg Arg Glu Lys Arg Trp Ser Glu Trp Ala Ser
            180                 185                 190

Gly Lys Val Leu Cys Leu Leu Asp Pro Leu Asp Gly Val Tyr Asn Tyr
        195                 200                 205

Leu Ala Gln Gln Arg Cys Asn Leu Asp Asp Thr Trp Glu Gly Lys Ile
210                 215                 220

Tyr Arg Val Leu Ala Gly Asn Pro Ala Lys His Asp Leu Asp Ile Lys
225                 230                 235                 240

Pro Thr Val Ile Ser His Arg Leu His Phe Pro Glu Gly Gly Ser Leu
                245                 250                 255

Ala Ala Leu Thr Ala His Gln Ala Cys His Leu Pro Leu Glu Thr Phe
            260                 265                 270

Thr Arg His Arg Gln Pro Arg Gly Trp Glu Gln Leu Glu Gln Cys Gly
        275                 280                 285

Tyr Pro Val Gln Arg Leu Val Ala Leu Tyr Leu Ala Ala Arg Leu Ser
290                 295                 300

Trp Asn Gln Val Asp Gln Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
```

```
                325                 330                 335

Arg Leu Ala Leu Thr Leu Ala Ala Ala Glu Ser Glu Arg Phe Val Arg
            340                 345                 350

Gln Gly Thr Gly Asn Asp Glu Ala Gly Ala Ala Ser Ala Asp Val Val
        355                 360                 365
Ser Leu Thr Cys Pro Val Ala Ala Gly Glu Cys Ala Gly Pro Ala Asp
    370                 375                 380
Ser Gly Asp Ala Leu Leu Glu Arg Asn Tyr Pro Thr Gly Ala Glu Phe
385                 390                 395                 400
Leu Gly Asp Gly Gly Asp Ile Ser Phe Ser Thr Arg Gly Thr Gln Asn
                405                 410                 415
Trp Thr Val Glu Arg Leu Leu Gln Ala Xaa Arg Gln Leu Glu Glu Arg
            420                 425                 430
Gly Tyr Val Phe Val Gly Tyr His Gly Thr Phe Leu Glu Ala Ala Gln
        435                 440                 445

Ser Ile Val Phe Gly Gly Val Arg Ala Arg Ser Gln Asp Leu Asp Ala
    450                 455                 460

Ile Trp Arg Gly Phe Tyr Ile Ala Gly Asp Pro Ala Leu Ala Tyr Gly
465                 470                 475                 480
Tyr Ala Gln Asp Gln Glu Pro Asp Ala Arg Gly Arg Ile Arg Asn Gly
                485                 490                 495
Ala Leu Leu Arg Val Tyr Val Pro Arg Ser Ser Leu Pro Gly Phe Tyr
            500                 505                 510
Arg Thr Gly Leu Thr Leu Ala Ala Pro Glu Ala Ala Gly Glu Val Glu
        515                 520                 525
Arg Leu Ile Gly His Pro Leu Pro Leu Arg Leu Asp Ala Ile Thr Gly
    530                 535                 540
Pro Glu Glu Glu Gly Gly Arg Leu Glu Thr Ile Leu Gly Trp Pro Leu
545                 550                 555                 560
Ala Glu Arg Thr Val Val Ile Pro Ser Ala Ile Pro Thr Asp Pro Arg
                565                 570                 575
Asn Val Gly Gly Asp Leu Asp Pro Ser Ser Ile Pro Asp Lys Glu Gln
            580                 585                 590
Ala Ile Ser Ala Leu Pro Asp Tyr Ala Ser Gln Pro Gly Lys Pro Pro
        595                 600                 605
Arg Glu Asp Leu Lys
    610

<210> SEQ ID NO 35
<211> LENGTH: 3119
<212> TYPE: DNA
<213> ORGANISM: Bordetella pertussis
<220> FEATURE:
<221> NAME/KEY: CDS
<222> LOCATION: (1)..(807)
<220> FEATURE:
<221> NAME/KEY: CDS
<222> LOCATION: (850)..(1527)
<220> FEATURE:
<221> NAME/KEY: CDS
<222> LOCATION: (1587)..(1979)
<220> FEATURE:
<221> NAME/KEY: CDS
<222> LOCATION: (1994)..(2353)
<220> FEATURE:
<221> NAME/KEY: CDS
<222> LOCATION: (2439)..(3119)

<400> SEQUENCE: 35 atg cgt tgc act cgg gca att cgc caa acc gca aga aca ggc tgg ctg       48

```
Met Arg Cys Thr Arg Ala Ile Arg Gln Thr Ala Arg Thr Gly Trp Leu
1               5                   10                  15 acg tgg ctg gcg att ctt gcc gtc acg gcg ccc gtg act tcg ccg gca      96
Thr Trp Leu Ala Ile Leu Ala Val Thr Ala Pro Val Thr Ser Pro Ala
            20                  25                  30 tgg gcc gac gat cct ccc gcc acc gta tac cgc tat gac tcc cgc ccg     144
Trp Ala Asp Asp Pro Pro Ala Thr Val Tyr Arg Tyr Asp Ser Arg Pro
        35                  40                  45 ccg gag gac gtt ttc cag aac gga ttc acg gcg tgg gga aac aac gac     192
Pro Glu Asp Val Phe Gln Asn Gly Phe Thr Ala Trp Gly Asn Asn Asp
    50                  55                  60 aat gtg ctc gac cat ctg acc gga cgt tcc tgc cag gtc ggc agc agc     240
Asn Val Leu Asp His Leu Thr Gly Arg Ser Cys Gln Val Gly Ser Ser
65              70                  75                  80 aac agc gct ttc gtc tcc acc agc agc agc cgg cgc tat acc gag gtc     288
Asn Ser Ala Phe Val Ser Thr Ser Ser Ser Arg Arg Tyr Thr Glu Val
                85                  90                  95 tat ctc gaa cat cgc atg cag gaa gcg gtc gag gcc gaa cgc gcc ggc     336
Tyr Leu Glu His Arg Met Gln Glu Ala Val Glu Ala Glu Arg Ala Gly
            100                 105                 110 agg ggc acc ggc cac ttc atc ggc tac atc tac gaa gtc cgc gcc gac     384
Arg Gly Thr Gly His Phe Ile Gly Tyr Ile Tyr Glu Val Arg Ala Asp
        115                 120                 125 aac aat ttc tac ggc gcc gcc agc tcg tac ttc gaa tac gtc gac act     432
Asn Asn Phe Tyr Gly Ala Ala Ser Ser Tyr Phe Glu Tyr Val Asp Thr
    130                 135                 140 tat ggc gac aat gcc ggc cgt atc ctc gcc ggc gcg ctg gcc acc tac     480
Tyr Gly Asp Asn Ala Gly Arg Ile Leu Ala Gly Ala Leu Ala Thr Tyr
145                 150                 155                 160 cag agc gaa tat ctg gca cac cgg cgc att ccg ccc gaa aac atc cgc     528
Gln Ser Glu Tyr Leu Ala His Arg Arg Ile Pro Pro Glu Asn Ile Arg
                165                 170                 175 agg gta acg cgg gtc tat cac aac ggc atc acc ggc gag acc acg acc     576
Arg Val Thr Arg Val Tyr His Asn Gly Ile Thr Gly Glu Thr Thr Thr
            180                 185                 190 acg gag tat tcc aac gct cgc tac gtc agc cag cag act cgc gcc aat     624
Thr Glu Tyr Ser Asn Ala Arg Tyr Val Ser Gln Gln Thr Arg Ala Asn
        195                 200                 205 ccc aac ccc tac aca tcg cga agg tcc gta gcg tcg atc gtc ggc aca     672
Pro Asn Pro Tyr Thr Ser Arg Arg Ser Val Ala Ser Ile Val Gly Thr
    210                 215                 220 ttg gtg cgc atg gcg ccg gtg ata ggc gct tgc atg gcg cgg cag gcc     720
Leu Val Arg Met Ala Pro Val Ile Gly Ala Cys Met Ala Arg Gln Ala
225                 230                 235                 240 gaa agc tcc gag gcc atg gca gcc tgg tcc gaa cgc gcc ggc gag gcg     768
Glu Ser Ser Glu Ala Met Ala Ala Trp Ser Glu Arg Ala Gly Glu Ala
                245                 250                 255 atg gtt ctc gtg tac tac gaa agc atc gcg tat tcg ttc tagacctggc     817
Met Val Leu Val Tyr Tyr Glu Ser Ile Ala Tyr Ser Phe
            260                 265 ccagccccgc ccaactccgg taattgaaca gc atg ccg atc gac cgc aag acg     870
                                     Met Pro Ile Asp Arg Lys Thr
                                     270                 275 ctc tgc cat ctc ctg tcc gtt ctg ccg ttg gcc ctc ctc gga tct cac     918
Leu Cys His Leu Leu Ser Val Leu Pro Leu Ala Leu Leu Gly Ser His
            280                 285                 290 gtg gcg cgg gcc tcc acg cca ggc atc gtc att ccg ccg cag gaa cag     966
Val Ala Arg Ala Ser Thr Pro Gly Ile Val Ile Pro Pro Gln Glu Gln
        295                 300                 305 att acc cag cat ggc agc ccc tat gga cgc tgc gcg aac aag acc cgt    1014
Ile Thr Gln His Gly Ser Pro Tyr Gly Arg Cys Ala Asn Lys Thr Arg
```

-continued

```
Ile Thr Gln His Gly Ser Pro Tyr Gly Arg Cys Ala Asn Lys Thr Arg
    310                 315                 320 gcc ctg acc gtg gcg gaa ttg cgc ggc agc ggc gat ctg cag gag tac      1062
Ala Leu Thr Val Ala Glu Leu Arg Gly Ser Gly Asp Leu Gln Glu Tyr
325                 330                 335                 340 ctg cgt cat gtg acg cgc ggc tgg tca ata ttt gcg ctc tac gat ggc      1110
Leu Arg His Val Thr Arg Gly Trp Ser Ile Phe Ala Leu Tyr Asp Gly
                345                 350                 355 acc tat ctc ggc ggc gaa tat ggc ggc gtg atc aag gac gga aca ccc      1158
Thr Tyr Leu Gly Gly Glu Tyr Gly Gly Val Ile Lys Asp Gly Thr Pro
            360                 365                 370 ggc ggc gca ttc gac ctg aaa acg acg ttc tgc atc atg acc acg cgc      1206
Gly Gly Ala Phe Asp Leu Lys Thr Thr Phe Cys Ile Met Thr Thr Arg
        375                 380                 385 aat acg ggt caa ccc gca acg gat cac tac tac agc aac gtc acc gcc      1254
Asn Thr Gly Gln Pro Ala Thr Asp His Tyr Tyr Ser Asn Val Thr Ala
    390                 395                 400 act cgc ctg ctc tcc agc acc aac agc agg cta tgc gcg gtc ttc gtc      1302
Thr Arg Leu Leu Ser Ser Thr Asn Ser Arg Leu Cys Ala Val Phe Val
405                 410                 415                 420 aga agc ggg caa ccg gtc att ggc gcc tgc acc agc ccg tat gac ggc      1350
Arg Ser Gly Gln Pro Val Ile Gly Ala Cys Thr Ser Pro Tyr Asp Gly
                425                 430                 435 aag tac tgg agc atg tac agc cgg ctg cgg aaa atg ctt tac ctg atc      1398
Lys Tyr Trp Ser Met Tyr Ser Arg Leu Arg Lys Met Leu Tyr Leu Ile
            440                 445                 450 tac gtg gcc ggc atc tcc gta cgc gtc cat gtc agc aag gaa gaa cag      1446
Tyr Val Ala Gly Ile Ser Val Arg Val His Val Ser Lys Glu Glu Gln
        455                 460                 465 tat tac gac tat gag gac gca acg ttc gag act tac gcc ctt acc ggc      1494
Tyr Tyr Asp Tyr Glu Asp Ala Thr Phe Glu Thr Tyr Ala Leu Thr Gly
    470                 475                 480 atc tcc atc tgc aat cct gga tca tcc tta tgc tgagacgctt ccccactcga   1547
Ile Ser Ile Cys Asn Pro Gly Ser Ser Leu Cys
485                 490                 495 accaccgccc cgggacaggg cggcgcccgg cggtcgcgc gtg cgc gcc ctg gcg       1601
                                          Val Arg Ala Leu Ala
                                                          500 tgg ttg ctg gca tcc ggc gcg atg acg cat ctt tcc ccc gcc ctg gcc      1649
Trp Leu Leu Ala Ser Gly Ala Met Thr His Leu Ser Pro Ala Leu Ala
            505                 510                 515 gac gtt cct tat gtg ctg gtg aag acc aat atg gtg gtc acc agc gta      1697
Asp Val Pro Tyr Val Leu Val Lys Thr Asn Met Val Val Thr Ser Val
        520                 525                 530 gcc atg aag ccg tat gaa gtc acc ccg acg cgc atg ctg gtc tgc ggc      1745
Ala Met Lys Pro Tyr Glu Val Thr Pro Thr Arg Met Leu Val Cys Gly
    535                 540                 545 atc gcc gcc aaa ctg ggc gcc gcg gcc agc agc ccg gac gcg cac gtg      1793
Ile Ala Ala Lys Leu Gly Ala Ala Ala Ser Ser Pro Asp Ala His Val
550                 555                 560 ccg ttc tgc ttc ggc aag gat ctc aag cgt ccc ggc agc agt ccc atg      1841
Pro Phe Cys Phe Gly Lys Asp Leu Lys Arg Pro Gly Ser Ser Pro Met
565                 570                 575                 580 gaa gtc atg ttg cgc gcc gtc ttc atg caa caa cgg ccg ctg cgc atg      1889
Glu Val Met Leu Arg Ala Val Phe Met Gln Gln Arg Pro Leu Arg Met
                585                 590                 595 ttt ctg ggt ccc aag caa ctc act ttc gaa ggc aag ccc gcg ctc gaa      1937
Phe Leu Gly Pro Lys Gln Leu Thr Phe Glu Gly Lys Pro Ala Leu Glu
            600                 605                 610 ctg atc cgg atg gtc gaa tgc agc ggc aag cag gat tgc ccc                1979
```

```
Leu Ile Arg Met Val Glu Cys Ser Gly Lys Gln Asp Cys Pro
        615                 620                 625 tgaaggcgaa cccc atg cat acc atc gca tcc atc ctg ttg tcc gtg ctc          2029
                Met His Thr Ile Ala Ser Ile Leu Leu Ser Val Leu
                        630                 635 ggc ata tac agc ccg gct gac gtc gcc ggc ttg ccg acc cat ctg tac          2077
Gly Ile Tyr Ser Pro Ala Asp Val Ala Gly Leu Pro Thr His Leu Tyr
        640                 645                 650 aag aac ttc act gtc cag gag ctg gcc ttg aaa ctg aag ggc aag aat          2125
Lys Asn Phe Thr Val Gln Glu Leu Ala Leu Lys Leu Lys Gly Lys Asn
655                 660                 665                 670 cag gag ttc tgc ctg acc gcc ttc atg tcg ggc aga agc ctg gtc cgg          2173
Gln Glu Phe Cys Leu Thr Ala Phe Met Ser Gly Arg Ser Leu Val Arg
                675                 680                 685 gcg tgc ctg tcc gac gcg gga cac gag cac gac acg tgg ttc gac acc          2221
Ala Cys Leu Ser Asp Ala Gly His Glu His Asp Thr Trp Phe Asp Thr
        690                 695                 700 atg ctt ggc ttt gcc ata tcc gcg tat gcg ctc aag agc cgg atc gcg          2269
Met Leu Gly Phe Ala Ile Ser Ala Tyr Ala Leu Lys Ser Arg Ile Ala
        705                 710                 715 ctg acg gtg gaa gac tcg ccg tat ccg ggc act ccc ggc gat ctg ctc          2317
Leu Thr Val Glu Asp Ser Pro Tyr Pro Gly Thr Pro Gly Asp Leu Leu
720                 725                 730 gaa ctg cag atc tgc ccg ctc aac gga tat tgc gaa tgaacccttc               2363
Glu Leu Gln Ile Cys Pro Leu Asn Gly Tyr Cys Glu
735                 740                 745 cggaggtttc gacgtttccg cgcaatccgc ttgagacgat cttccgccct ggttccattc        2423
cgggaacacc gcaac atg ctg atc aac aac aag aag ctg ctt cat cac att        2474
                Met Leu Ile Asn Asn Lys Lys Leu Leu His His Ile
                        750                 755 ctg ccc atc ctg gtg ctc gcc ctg ctg ggc atg cgc acg gcc cag gcc          2522
Leu Pro Ile Leu Val Leu Ala Leu Leu Gly Met Arg Thr Ala Gln Ala
        760                 765                 770 gtt gcg cca ggc atc gtc atc ccg ccg aag gca ctg ttc acc caa cag          2570
Val Ala Pro Gly Ile Val Ile Pro Pro Lys Ala Leu Phe Thr Gln Gln
775                 780                 785                 790 ggc ggc gcc tat gga cgc tgc ccg aac gga acc cgc gcc ttg acc gtg          2618
Gly Gly Ala Tyr Gly Arg Cys Pro Asn Gly Thr Arg Ala Leu Thr Val
                795                 800                 805 gcc gaa ctg cgc ggc aac gcc gaa ttg cag acg tat ttg cgc cag ata          2666
Ala Glu Leu Arg Gly Asn Ala Glu Leu Gln Thr Tyr Leu Arg Gln Ile
        810                 815                 820 acg ccc ggc tgg tcc ata tac ggt ctc tat gac ggt acg tac ctg ggc          2714
Thr Pro Gly Trp Ser Ile Tyr Gly Leu Tyr Asp Gly Thr Tyr Leu Gly
        825                 830                 835 cag gcg tac ggc ggc atc atc aag gac gcg ccg cca ggc gcg ggg ttc          2762
Gln Ala Tyr Gly Gly Ile Ile Lys Asp Ala Pro Pro Gly Ala Gly Phe
        840                 845                 850 att tat cgc gaa act ttc tgc atc acg acc ata tac aag acc ggg caa          2810
Ile Tyr Arg Glu Thr Phe Cys Ile Thr Thr Ile Tyr Lys Thr Gly Gln
855                 860                 865                 870 ccg gct gcg gat cac tac tac agc aag gtc acg gcc acg cgc ctg ctc          2858
Pro Ala Ala Asp His Tyr Tyr Ser Lys Val Thr Ala Thr Arg Leu Leu
                875                 880                 885 gcc agc acc aac agc agg ctg tgc gcg gta ttc gtc agg gac ggg caa          2906
Ala Ser Thr Asn Ser Arg Leu Cys Ala Val Phe Val Arg Asp Gly Gln
        890                 895                 900 tcg gtc atc gga gcc tgc gcc agc ccg tat gaa ggc agg tac aga gac          2954
Ser Val Ile Gly Ala Cys Ala Ser Pro Tyr Glu Gly Arg Tyr Arg Asp
        905                 910                 915
```

```
atg tac gac gcg ctg cgg cgc ctg ctg tac atg atc tat atg tcc ggc        3002
Met Tyr Asp Ala Leu Arg Arg Leu Leu Tyr Met Ile Tyr Met Ser Gly
920             925                 930 ctt gcc gta cgc gtc cac gtc agc aag gag gaa cag tat tac gac tac        3050
Leu Ala Val Arg Val His Val Ser Lys Glu Glu Gln Tyr Tyr Asp Tyr
935             940                 945                 950 gag gac gcc aca ttc cag acc tat gcc ctc acc ggc att tcc ctc tgc        3098
Glu Asp Ala Thr Phe Gln Thr Tyr Ala Leu Thr Gly Ile Ser Leu Cys
            955                 960                 965 aac ccg gca gcg tcg ata tgc                                            3119
Asn Pro Ala Ala Ser Ile Cys
            970

<210> SEQ ID NO 36
<211> LENGTH: 535
<212> TYPE: PRT
<213> ORGANISM: Corynebacterium diphtheriae

<400> SEQUENCE: 36

Gly Ala Asp Asp Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
```

```
                   290                 295                 300
Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr Gln Pro Phe Leu His Asp Gly Tyr Ala Val Ser Trp Asn Thr
385                 390                 395                 400

Val Glu Asp Ser Ile Ile Arg Thr Gly Phe Gln Gly Glu Ser Gly His
                405                 410                 415

Asp Ile Lys Ile Thr Ala Glu Asn Thr Pro Leu Pro Ile Ala Gly Val
            420                 425                 430

Leu Leu Pro Thr Ile Pro Gly Lys Leu Asp Val Asn Lys Ser Lys Thr
        435                 440                 445

His Ile Ser Val Asn Gly Arg Lys Ile Arg Met Arg Cys Arg Ala Ile
    450                 455                 460

Asp Gly Asp Val Thr Phe Cys Arg Pro Lys Ser Pro Val Tyr Val Gly
465                 470                 475                 480

Asn Gly Val His Ala Asn Leu His Val Ala Phe His Arg Ser Ser
                485                 490                 495

Glu Lys Ile His Ser Asn Glu Ile Ser Ser Asp Ser Ile Gly Val Leu
            500                 505                 510

Gly Tyr Gln Lys Thr Val Asp His Thr Lys Val Asn Ser Lys Leu Ser
        515                 520                 525

Leu Phe Phe Glu Ile Lys Ser
    530                 535

<210> SEQ ID NO 37
<211> LENGTH: 960
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(960)

<400> SEQUENCE: 37 ggg gcg gac gat gtg gtg gat tcc tcc aag tcg ttt gtc atg gaa aat    48
Gly Ala Asp Asp Val Val Asp Ser Ser Lys Ser Phe Val Met Glu Asn
1               5                   10                  15 ttc tcg tcg tac cat ggc act aag cca ggc tac gtg gat agc att caa    96
Phe Ser Ser Tyr His Gly Thr Lys Pro Gly Tyr Val Asp Ser Ile Gln
            20                  25                  30 aag ggc atc cag aag ccc aag agc ggt act cag ggg aac tat gac gac   144
Lys Gly Ile Gln Lys Pro Lys Ser Gly Thr Gln Gly Asn Tyr Asp Asp
        35                  40                  45 gac tgg aag gga ttt tac agc acc gac aat aag tac gat gct gcg ggc   192
Asp Trp Lys Gly Phe Tyr Ser Thr Asp Asn Lys Tyr Asp Ala Ala Gly
    50                  55                  60 tat agc gtg gac aac gaa aac cca ttg tcg ggc aag gcc ggt ggc gtg   240
Tyr Ser Val Asp Asn Glu Asn Pro Leu Ser Gly Lys Ala Gly Gly Val
65                  70                  75                  80
```

```
gtg aag gtg acc tat cct ggt ctg acg aaa gtt ctg gcg ttg aaa gtg      288
Val Lys Val Thr Tyr Pro Gly Leu Thr Lys Val Leu Ala Leu Lys Val
                85                  90                  95 gac aac gcc gag act atc aag aaa gaa ttg ggc ttg agt ttg acc gag      336
Asp Asn Ala Glu Thr Ile Lys Lys Glu Leu Gly Leu Ser Leu Thr Glu
            100                 105                 110 ccg ctg atg gaa cag gtg ggt acc gaa gaa ttc att aaa cgt ttt ggg      384
Pro Leu Met Glu Gln Val Gly Thr Glu Glu Phe Ile Lys Arg Phe Gly
        115                 120                 125 gac ggc gcg tcg cgc gtg gtc ctg tcg ttg ccg ttc gcc gaa ggg tcg      432
Asp Gly Ala Ser Arg Val Val Leu Ser Leu Pro Phe Ala Glu Gly Ser
    130                 135                 140 tcg tcg gtg gaa tat atc aac aac tgg gaa cag gcc aag gcg ctg tcg      480
Ser Ser Val Glu Tyr Ile Asn Asn Trp Glu Gln Ala Lys Ala Leu Ser
145                 150                 155                 160 gtg gaa ctg gaa att aac ttc gaa acg cgg ggc aaa cgg ggc cag gac      528
Val Glu Leu Glu Ile Asn Phe Glu Thr Arg Gly Lys Arg Gly Gln Asp
                165                 170                 175 gcc atg tac gaa tac atg gcg cag gcg tgc gcc ggg aac cgg gtg cgg      576
Ala Met Tyr Glu Tyr Met Ala Gln Ala Cys Ala Gly Asn Arg Val Arg
            180                 185                 190 cgc agc gtg ggc agt tcc ttg agt tgc atc aat ctg gac tgg gac gtc      624
Arg Ser Val Gly Ser Ser Leu Ser Cys Ile Asn Leu Asp Trp Asp Val
        195                 200                 205 atc cgc gat aag acg aag acg aaa atc gag tcg ctc aaa gag cac ggc      672
Ile Arg Asp Lys Thr Lys Thr Lys Ile Glu Ser Leu Lys Glu His Gly
    210                 215                 220 ccg atc aaa aac aaa atg agc gag tcg ccg aat aaa acg gtg tcc gag      720
Pro Ile Lys Asn Lys Met Ser Glu Ser Pro Asn Lys Thr Val Ser Glu
225                 230                 235                 240 gag aag gcg aag caa tac ctg gag gaa ttc cac cag acg gct ctg gag      768
Glu Lys Ala Lys Gln Tyr Leu Glu Glu Phe His Gln Thr Ala Leu Glu
                245                 250                 255 cac ccg gag ctg agc gaa ctc aaa acc gtt acc ggt acg aac ccg gtg      816
His Pro Glu Leu Ser Glu Leu Lys Thr Val Thr Gly Thr Asn Pro Val
            260                 265                 270 ttt gcc ggg gca aac tat gca gct tgg gcc gtc aac gtg gcc caa gtg      864
Phe Ala Gly Ala Asn Tyr Ala Ala Trp Ala Val Asn Val Ala Gln Val
        275                 280                 285 atc gac tcc gaa acg gcc gac aac ctg gaa aag act acc gcc gcg ttg      912
Ile Asp Ser Glu Thr Ala Asp Asn Leu Glu Lys Thr Thr Ala Ala Leu
    290                 295                 300 tcg atc ctc ccg ggc atc ggg agc gtc atg ggt att gcc gat ggt gcg      960
Ser Ile Leu Pro Gly Ile Gly Ser Val Met Gly Ile Ala Asp Gly Ala
305                 310                 315                 320

<210> SEQ ID NO 38
<211> LENGTH: 258
<212> TYPE: PRT
<213> ORGANISM: Vibrio cholerae

<400> SEQUENCE: 38

Met Val Lys Ile Ile Phe Val Phe Phe Ile Phe Leu Ser Ser Phe Ser
1               5                   10                  15

Tyr Ala Asn Asp Asp Lys Leu Tyr Arg Ala Asp Ser Arg Pro Pro Asp
                20                  25                  30

Glu Ile Lys Gln Ser Gly Gly Leu Met Pro Arg Gly Gln Ser Glu Tyr
            35                  40                  45

Phe Asp Arg Gly Thr Gln Met Asn Ile Asn Leu Tyr Asp His Ala Arg
        50                  55                  60
```

Gly Thr Gln Thr Gly Phe Val Arg His Asp Asp Gly Tyr Val Ser Thr
65                  70                  75                  80

Ser Ile Ser Leu Arg Ser Ala His Leu Val Gly Gln Thr Ile Leu Ser
            85                  90                  95

Gly His Ser Thr Tyr Tyr Ile Tyr Val Ile Ala Thr Ala Pro Asn Met
        100                 105                 110

Phe Asn Val Asn Asp Val Leu Gly Ala Tyr Ser Pro His Pro Asp Glu
    115                 120                 125

Gln Glu Val Ser Ala Leu Gly Gly Ile Pro Tyr Ser Gln Ile Tyr Gly
130                 135                 140

Trp Tyr Arg Val His Phe Gly Val Leu Asp Glu Gln Leu His Arg Asn
145                 150                 155                 160

Arg Gly Tyr Arg Asp Arg Tyr Tyr Ser Asn Leu Asp Ile Ala Pro Ala
                165                 170                 175

Ala Asp Gly Tyr Gly Leu Ala Gly Phe Pro Pro Glu His Arg Ala Trp
            180                 185                 190

Arg Glu Glu Pro Trp Ile His His Ala Pro Pro Gly Cys Gly Asn Ala
        195                 200                 205

Pro Arg Ser Ser Met Ser Asn Thr Cys Asp Glu Lys Thr Gln Ser Leu
    210                 215                 220

Gly Val Lys Phe Leu Asp Glu Tyr Gln Ser Lys Val Lys Arg Gln Ile
225                 230                 235                 240

Phe Ser Gly Tyr Gln Ser Asp Ile Asp Thr His Asn Arg Ile Lys Asp
                245                 250                 255

Glu Leu

<210> SEQ ID NO 39
<211> LENGTH: 124
<212> TYPE: PRT
<213> ORGANISM: Vibrio cholerae

<400> SEQUENCE: 39

Met Ile Lys Leu Lys Phe Gly Val Phe Phe Thr Val Leu Leu Ser Ser
1               5                   10                  15

Ala Tyr Ala His Gly Thr Pro Gln Asn Ile Thr Asp Leu Cys Ala Glu
            20                  25                  30

Tyr His Asn Thr Gln Ile Tyr Thr Leu Asn Asp Lys Ile Phe Ser Tyr
        35                  40                  45

Thr Glu Ser Leu Ala Gly Lys Arg Glu Met Ala Ile Ile Thr Phe Lys
    50                  55                  60

Asn Gly Ala Ile Phe Gln Val Glu Val Pro Gly Ser Gln His Ile Asp
65                  70                  75                  80

Ser Gln Lys Lys Ala Ile Glu Arg Met Lys Asp Thr Leu Arg Ile Ala
                85                  90                  95

Tyr Leu Thr Glu Ala Lys Val Glu Lys Leu Cys Val Trp Asn Asn Lys
            100                 105                 110

Thr Pro His Ala Ile Ala Ala Ile Ser Met Ala Asn
        115                 120

<210> SEQ ID NO 40
<211> LENGTH: 1148
<212> TYPE: DNA
<213> ORGANISM: Vibrio cholerae

<400> SEQUENCE: 40
atggtaaaga taatatttgt gttttttatt ttcttatcat cattttcata tgcaaatgat    60

```
gataagttat atcgggcaga ttctagacct cctgatgaaa taaagcagtc aggtggtctt      120
atgccaagag gacagagtga gtactttgac cgaggtactc aaatgaatat caacctttat      180
gatcatgcaa gaggaactca gacgggattt gttaggcacg atgatggata tgtttccacc      240
tcaattagtt tgagaagtgc ccacttagtg ggtcaaacta tattgtctgg tcattctact      300
tattatatat atgttatagc cactgcaccc aacatgttta acgttaatga tgtattaggg      360
gcatacagtc ctcatccaga tgaacaagaa gtttctgctt taggtgggat tccatactcc      420
caaatatatg gatggtatcg agttcatttt ggggtgcttg atgaacaatt acatcgtaat      480
aggggctaca gagatagata ttacagtaac ttagatattg ctccagcagc agatggttat      540
ggattggcag gtttccctcc ggagcataga gcttggaggg aagagccgtg gattcatcat      600
gcaccgccgg gttgtgggaa tgctccaaga tcatcgatga gtaatacttg cgatgaaaaa      660
acccaaagtc taggtgtaaa attccttgac gaataccaat ctaaagttaa aagacaaata      720
ttttcaggct atcaatctga tattgataca cataatagaa ttaaggatga attatgatta      780
aattaaaatt tggtgttttt tttacagttt tactatcttc agcatatgca catggaacac      840
ctcaaaatat tactgatttg tgtgcagaat accacaacac acaaatatat acgctaaatg      900
ataagatatt ttcgtataca gaatctctag ctggaaaaag agagatggct atcattactt      960
ttaagaatgg tgcaattttt caagtagaag taccaggtag tcaacatata gattcacaaa     1020
aaaaagcgat tgaaaggatg aaggataccc tgaggattgc atatcttact gaagctaaag     1080
tcgaaaagtt atgtgtatgg aataataaaa cgcctcatgc gattgccgca attagtatgg     1140
caaattaa                                                              1148
```

<210> SEQ ID NO 41
<211> LENGTH: 269
<212> TYPE: PRT
<213> ORGANISM: Bordetella pertussis

<400> SEQUENCE: 41

```
Met Arg Cys Thr Arg Ala Ile Arg Gln Thr Ala Arg Thr Gly Trp Leu
1               5                   10                  15

Thr Trp Leu Ala Ile Leu Ala Val Thr Ala Pro Val Thr Ser Pro Ala
            20                  25                  30

Trp Ala Asp Asp Pro Pro Ala Thr Val Tyr Arg Tyr Asp Ser Arg Pro
        35                  40                  45

Pro Glu Asp Val Phe Gln Asn Gly Phe Thr Ala Trp Gly Asn Asn Asp
    50                  55                  60

Asn Val Leu Asp His Leu Thr Gly Arg Ser Cys Gln Val Gly Ser Ser
65                  70                  75                  80

Asn Ser Ala Phe Val Ser Thr Ser Ser Arg Arg Tyr Thr Glu Val
                85                  90                  95

Tyr Leu Glu His Arg Met Gln Glu Ala Val Ala Glu Arg Ala Gly
            100                 105                 110

Arg Gly Thr Gly His Phe Ile Gly Tyr Ile Tyr Glu Val Arg Ala Asp
        115                 120                 125

Asn Asn Phe Tyr Gly Ala Ala Ser Ser Tyr Phe Glu Tyr Val Asp Thr
    130                 135                 140

Tyr Gly Asp Asn Ala Gly Arg Ile Leu Ala Gly Ala Leu Ala Thr Tyr
145                 150                 155                 160

Gln Ser Glu Tyr Leu Ala His Arg Arg Ile Pro Pro Glu Asn Ile Arg
                165                 170                 175
```

```
Arg Val Thr Arg Val Tyr His Asn Gly Ile Thr Gly Glu Thr Thr Thr
            180                 185                 190

Thr Glu Tyr Ser Asn Ala Arg Tyr Val Ser Gln Gln Thr Arg Ala Asn
        195                 200                 205

Pro Asn Pro Tyr Thr Ser Arg Arg Ser Val Ala Ser Ile Val Gly Thr
        210                 215                 220

Leu Val Arg Met Ala Pro Val Ile Gly Ala Cys Met Ala Arg Gln Ala
225                 230                 235                 240

Glu Ser Ser Glu Ala Met Ala Ala Trp Ser Glu Arg Ala Gly Glu Ala
                245                 250                 255

Met Val Leu Val Tyr Tyr Glu Ser Ile Ala Tyr Ser Phe
                260                 265

<210> SEQ ID NO 42
<211> LENGTH: 226
<212> TYPE: PRT
<213> ORGANISM: Bordetella pertussis

<400> SEQUENCE: 42

Met Pro Ile Asp Arg Lys Thr Leu Cys His Leu Leu Ser Val Leu Pro
1               5                   10                  15

Leu Ala Leu Leu Gly Ser His Val Ala Arg Ala Ser Thr Pro Gly Ile
                20                  25                  30

Val Ile Pro Pro Gln Glu Gln Ile Thr Gln His Gly Ser Pro Tyr Gly
            35                  40                  45

Arg Cys Ala Asn Lys Thr Arg Ala Leu Thr Val Ala Glu Leu Arg Gly
        50                  55                  60

Ser Gly Asp Leu Gln Glu Tyr Leu Arg His Val Thr Arg Gly Trp Ser
65                  70                  75                  80

Ile Phe Ala Leu Tyr Asp Gly Thr Tyr Leu Gly Gly Glu Tyr Gly Gly
                85                  90                  95

Val Ile Lys Asp Gly Thr Pro Gly Gly Ala Phe Asp Leu Lys Thr Thr
            100                 105                 110

Phe Cys Ile Met Thr Thr Arg Asn Thr Gly Gln Pro Ala Thr Asp His
        115                 120                 125

Tyr Tyr Ser Asn Val Thr Ala Thr Arg Leu Leu Ser Ser Thr Asn Ser
    130                 135                 140

Arg Leu Cys Ala Val Phe Val Arg Ser Gly Gln Pro Val Ile Gly Ala
145                 150                 155                 160

Cys Thr Ser Pro Tyr Asp Gly Lys Tyr Trp Ser Met Tyr Ser Arg Leu
                165                 170                 175

Arg Lys Met Leu Tyr Leu Ile Tyr Val Ala Gly Ile Ser Val Arg Val
            180                 185                 190

His Val Ser Lys Glu Glu Gln Tyr Tyr Asp Tyr Glu Asp Ala Thr Phe
        195                 200                 205

Glu Thr Tyr Ala Leu Thr Gly Ile Ser Ile Cys Asn Pro Gly Ser Ser
    210                 215                 220

Leu Cys
225

<210> SEQ ID NO 43
<211> LENGTH: 131
<212> TYPE: PRT
<213> ORGANISM: Bordetella pertussis

<400> SEQUENCE: 43

Val Arg Ala Leu Ala Trp Leu Leu Ala Ser Gly Ala Met Thr His Leu
```

-continued

```
               1               5              10              15
Ser Pro Ala Leu Ala Asp Val Pro Tyr Val Leu Val Lys Thr Asn Met
                    20                  25                  30

Val Val Thr Ser Val Ala Met Lys Pro Tyr Glu Val Thr Pro Thr Arg
                    35                  40                  45

Met Leu Val Cys Gly Ile Ala Ala Lys Leu Gly Ala Ala Ala Ser Ser
 50                      55                  60

Pro Asp Ala His Val Pro Phe Cys Phe Gly Lys Asp Leu Lys Arg Pro
 65                      70                  75                  80

Gly Ser Ser Pro Met Glu Val Met Leu Arg Ala Val Phe Met Gln Gln
                    85                  90                  95

Arg Pro Leu Arg Met Phe Leu Gly Pro Lys Gln Leu Thr Phe Glu Gly
                   100                 105                 110

Lys Pro Ala Leu Glu Leu Ile Arg Met Val Glu Cys Ser Gly Lys Gln
                   115                 120                 125

Asp Cys Pro
        130
```

<210> SEQ ID NO 44
<211> LENGTH: 120
<212> TYPE: PRT
<213> ORGANISM: Bordetella pertussis

<400> SEQUENCE: 44

```
Met His Thr Ile Ala Ser Ile Leu Leu Ser Val Leu Gly Ile Tyr Ser
 1               5              10              15

Pro Ala Asp Val Ala Gly Leu Pro Thr His Leu Tyr Lys Asn Phe Thr
                    20                  25                  30

Val Gln Glu Leu Ala Leu Lys Leu Lys Gly Lys Asn Gln Glu Phe Cys
                    35                  40                  45

Leu Thr Ala Phe Met Ser Gly Arg Ser Leu Val Arg Ala Cys Leu Ser
 50                      55                  60

Asp Ala Gly His Glu His Asp Thr Trp Phe Asp Thr Met Leu Gly Phe
 65                      70                  75                  80

Ala Ile Ser Ala Tyr Ala Leu Lys Ser Arg Ile Ala Leu Thr Val Glu
                    85                  90                  95

Asp Ser Pro Tyr Pro Gly Thr Pro Gly Asp Leu Leu Gly Leu Gln Ile
                   100                 105                 110

Cys Pro Leu Asn Gly Tyr Cys Glu
        115                 120
```

<210> SEQ ID NO 45
<211> LENGTH: 227
<212> TYPE: PRT
<213> ORGANISM: Bordetella pertussis

<400> SEQUENCE: 45

```
Met Leu Ile Asn Asn Lys Lys Leu Leu His Ile Leu Pro Ile Leu
 1               5              10              15

Val Leu Ala Leu Leu Gly Met Arg Thr Ala Gln Ala Val Ala Pro Gly
                    20                  25                  30

Ile Val Ile Pro Pro Lys Ala Leu Phe Thr Gln Gln Gly Gly Ala Tyr
                    35                  40                  45

Gly Arg Cys Pro Asn Gly Thr Arg Ala Leu Val Ala Glu Leu Arg
 50                      55                  60

Gly Asn Ala Glu Leu Gln Thr Tyr Leu Arg Gln Ile Thr Pro Gly Trp
 65                      70                  75                  80
```

```
Ser Ile Tyr Gly Leu Tyr Asp Gly Thr Tyr Leu Gly Gln Ala Tyr Gly
            85                  90                  95

Gly Ile Ile Lys Asp Ala Pro Pro Gly Ala Gly Phe Ile Tyr Arg Glu
            100                 105                 110

Thr Phe Cys Ile Thr Thr Ile Tyr Lys Thr Gly Gln Pro Ala Ala Asp
            115                 120                 125

His Tyr Tyr Ser Lys Val Thr Ala Thr Arg Leu Leu Ala Ser Thr Asn
    130                 135                 140

Ser Arg Leu Cys Ala Val Phe Val Arg Asp Gly Gln Ser Val Ile Gly
145                 150                 155                 160

Ala Cys Ala Ser Pro Tyr Glu Gly Arg Tyr Arg Asp Met Tyr Asp Ala
                165                 170                 175

Leu Arg Arg Leu Leu Tyr Met Ile Tyr Met Ser Gly Leu Ala Val Arg
                180                 185                 190

Val His Val Ser Lys Glu Glu Gln Tyr Tyr Asp Tyr Glu Asp Ala Thr
        195                 200                 205

Phe Gln Thr Tyr Ala Leu Thr Gly Ile Ser Leu Cys Asn Pro Ala Ala
    210                 215                 220

Ser Ile Cys
225

<210> SEQ ID NO 46
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 46

His His His His His His
1               5
```

What is claimed is:

1. A method for producing a recombinant toxin protein in a *Pseudomonad* host cell, said method comprising:
   ligating into an expression vector a nucleotide sequence encoding the toxin protein;
   transforming the *Pseudomonad* host cell with the expression vector; and
   culturing the transformed *Pseudomonad* host cell in a culture media suitable for the expression of the recombinant toxin protein;

wherein the recombinant toxin protein is CRM 197, and wherein the recombinant protein is produced at a yield of soluble or active CRM197 protein of about 0.2 grams per liter to about 12 grams per liter.

2. The method of claim 1, wherein the yield of soluble or active toxin protein is 0.2 grams per liter to about 12 grams per liter, about 0.2 g/L, about 0.3 g/L, about 0.4 g/L, about 0.5 g/L, about 0.6 g/L, about 0.7 g/L, about 0.8 g/L, about 0.9 g/L, about 1 g/L, about 1.5 g/L, about 2 g/L, about 2.5 g/L, about 3 g/L, about 3.5 g/L, about 4 g/L, about 4.5 g/L, about 5 g/L, about 5.5 g/L, about 6 g/L, about 6.5 g/L, about 7 g/L, about 7.5 g/L, about 8 g/L, about 8.5 g/L, about 9 g/L, about 9.5 g/L, about 10 g/L, about 10.5 g/L, about 11 g/L, about 12 g/L, about 0.2 g/L to about 0.5 g/L, about 0.2 g/L to about 1 g/L, about 0.2 to about 2 g/L, about 0.3 g/L to about 0.6 g/L, about 0.3 g/L to about 1 g/L, about 0.3 to about 2 g/L, about 0.4 to about 0.7 g/L, about 0.4 to about 1 g/L, about 0.4 to about 2 g/L, about 0.4 to about 3 g/L, about 0.5 g/L to about 1 g/L, about 0.5 g/L to about 2 g/L, about 0.5 g/L to about 3 g/L, about 0.5 g/L to about 4 g/L, about 0.5 g/L to about 5 g/L, about 0.5 g/L to about 6 g/L, about 0.5 g/L to about 7 g/L, about 0.5 g/L to about 8 g/L, about 0.5 g/L to about 9 g/L, about 0.5 g/L to about 10 g/L, about 0.5 g/L to about 11 g/L, about 0.5 g/L to about 12 g/L, about 1 g/L to about 2 g/L, about 1 g/L to about 3 g/L, about 1 g/L to about 4 g/L, about 1 g/L to about 5 g/L, about 1 g/L to about 6 g/L, about 1 g/L to about 7 g/L, about 1 g/L to about 8 g/L, about 1 g/L to about 9 g/L, about 1 g/L to about 10 g/L, about 1 g/L to about 11 g/L, about 1 g/L to about 12 g/L, about 2 g/L to about 3 g/L, about 2 g/L to about 4 g/L, about 2 g/L to about 5 g/L, about 2 g/L to about 6 g/L, about 2 g/L to about 7 g/L, about 2 g/L to about 8 g/L, about 2 g/L to about 9 g/L, about 2 g/L to about 10 g/L, about 2 g/L to about 11 g/L, about 2 g/L to about 12 g/L, about 3 g/L to about 4 g/L, about 3 g/L to about 5 g/L, about 3 g/L to about 6 g/L, about 3 g/L to about 7 g/L, about 3 g/L to about 8 g/L, about 3 g/L to about 9 g/L, about 3 g/L to about 10 g/L, about 3 g/L to about 11 g/L, about 3 g/L to about 12 g/L, about 4 g/L to about 5 g/L, about 4 g/L to about 6 g/L, about 4 g/L to about 7 g/L, about 4 g/L to about 8 g/L, about 4 g/L to about 9 g/L, about 4 g/L to about 10 g/L, about 4 g/L to about 11 g/L, about 4 g/L to about 12 g/L, about 5 g/L to about 6 g/L, about 5 g/L to about 7 g/L, about 5 g/L to about 8 g/L, about 5 g/L to about 9 g/L, about 5 g/L to about 10 g/L, about 5 g/L to about 11 g/L, about 5 g/L to about 12 g/L, about 6 g/L to about 7 g/L, about 6 g/L to about 8 g/L, about 6 g/L to about 9 g/L, about 6 g/L to about 10 g/L, about 6 g/L to about 11 g/L, about 6 g/L to about 12 g/L, about 7 g/L to about 8 g/L, about 7 g/L to about 9 g/L, about 7 g/L to about 10 g/L, about 7 g/L to about 11 g/L, about 7 g/L to about 12 g/L, about 8 g/L to about 9 g/L, about 8 g/L to about 10 g/L, about 8 g/L to about 11 g/L, about 8 g/L to about 12 g/L, about 9 g/L to about 10 g/L, about 9 g/L to about 11 g/L, about 9 g/L to about 12 g/L, about 10 g/L to about 11 g/L, about 10 g/L to about 12 g/L, or about 11 g/L to about 12 g/L.

3. The method of claim 1, wherein the nucleotide sequence encoding the toxin protein is fused to a secretion signal coding sequence that when expressed directs transfer of the toxin protein to the periplasm.

4. The method of claim 3, wherein the expression vector further comprises a tag sequence adjacent to the coding sequence for the secretion signal.

5. The method of claim 1, wherein the host cell is defective in the expression of at least one protease or wherein the host cell overexpresses at least one folding modulator, or a combination thereof.

6. The method of claim 1, wherein the recombinant toxin protein is CRM197 and the host cell is defective in the expression of the proteases HslU, HslV, Prc1, DegP1, DegP2, and AprA.

7. The method of claim 6, wherein the recombinant toxin protein is fused to a secretion leader that is Azu, IbpS31A, CupA2, PbpA20V, or Pbp.

8. The method of claim 1, wherein the recombinant toxin protein is CRM197 and the host cell is defective in the expression of a protease that is Serralysin, HslU, HslV, Prc1, DegP1, DegP2, or AprA, or a combination thereof, or wherein the host cell overexpresses folding modulators DsbA, DsbB, DsbC, and DsbD, and further wherein the recombinant toxin protein is fused to the Azu, Pbp, or native secretion leader.

9. The method of claim 1, wherein the recombinant toxin protein is CRM197, the host cell is wild-type and wherein the recombinant toxin protein is fused to the secretion leader Pbp or Azu.

10. The method of claim 4, wherein the recombinant toxin protein is CRM197 and wherein the recombinant toxin protein is fused to the secretion leader Azu, Pbp, IbpS31A, CupA2, or PbpA20V.

11. The method of claim 1, further comprising measuring the activity of the recombinant toxin protein in an activity assay, wherein about 40% to about 100% of the soluble toxin protein produced is determined to be active.

12. The method of claim 11, wherein the activity assay is an immunological assay, a receptor-binding assay, or an enzyme assay.

13. The method of claim 1, wherein the expression vector comprises a lac promoter operatively linked to the protein coding sequence, and wherein the culturing comprises induction of the promoter using IPTG at a concentration of about 0.02 to about 1.0 mM, the cell density at induction is an optical density of about 40 to about 200 absorbance units (AU), the pH of the culture is from about 6 to about 7.5, and the growth temperature is about 20 to about 35° C.

14. The method of claim 13, wherein the lac promoter is selected from the following promoters: tac, trc, Ptac16, Ptac17, PtacII, PlacUV5 and T7lac.

15. The method of claim 1, wherein the host cell is a *Pseudomonas* cell.

16. The method of claim 15, wherein the nucleotide sequence has been optimized for expression in the *Pseudomonas* host cell.

17. The method of claim 1, wherein the host cell is *Pseudomonas fluorescens*.

18. The method of claim 17, wherein the nucleotide sequence has been optimized for expression in the *Pseudomonas fluorescens* host cell.

19. The method of claim 1, wherein the nucleotide sequence has been optimized for expression in the *Pseudomonad* host cell.

20. The method of claim 1, wherein the expression vector further comprises a tag sequence adjacent to the coding sequence for the toxin protein.

21. The method of claim 1, wherein the recombinant protein is produced at a yield of soluble and active CRM197 protein of about 0.2 grams per liter to about 12 grams per liter.

22. The method of claim 21, wherein the yield of soluble and active toxin protein is about 0.2 grams per liter to 12 grams per liter, about 0.2 g/L, about 0.3 g/L, about 0.4 g/L, about 0.5 g/L, about 0.6 g/L, about 0.7 g/L, about 0.8 g/L, about 0.9 g/L, about 1 g/L, about 1.5 g/L, about 2 g/L, about 2.5 g/L, about 3 g/L, about 3.5 g/L, about 4 g/L, about 4.5 g/L, about 5 g/L, about 5.5 g/L, about 6 g/L, about 6.5 g/L, about 7 g/L, about 7.5 g/L, about 8 g/L, about 8.5 g/L, about 9 g/L, about 9.5 g/L, about 10 g/L, about 10.5 g/L, about 11 g/L, about 12 g/L, about 0.2 g/L to about 0.5 g/L, about 0.2 g/L to about 1 g/L, about 0.2 to about 2 g/L, about 0.3 g/L to about 0.6 g/L, about 0.3 g/L to about 1 g/L, about 0.3 to about 2 g/L, about 0.4 to about 0.7 g/L, about 0.4 to about 1 g/L, about 0.4 to about 2 g/L, about 0.4 to about 3 g/L, about 0.5 g/L to about 1 g/L, about 0.5 g/L to about 2 g/L, about 0.5 g/L to about 3 g/L, about 0.5 g/L to about 4 g/L, about 0.5 g/L to about 5 g/L, about 0.5 g/L to about 6 g/L, about 0.5 g/L to about 7 g/L, about 0.5 g/L to about 8 g/L, about 0.5 g/L to about 9 g/L, about 0.5 g/L to about 10 g/L, about 0.5 g/L to about 11 g/L, about 0.5 g/L to about 12 g/L, about 1 g/L to about 2 g/L, about 1 g/L to about 3 g/L, about 1 g/L to about 4 g/L, about 1 g/L to about 5 g/L, about 1 g/L to about 6 g/L, about 1 g/L to about 7 g/L, about 1 g/L to about 8 g/L, about 1 g/L to about 9 g/L, about 1 g/L to about 10 g/L, about 1 g/L to about 11 g/L, about 1 g/L to about 12 g/L, about 2 g/L to about 3 g/L, about 2 g/L to about 4 g/L, about 2 g/L to about 5 g/L, about 2 g/L to about 6 g/L, about 2 g/L to about 7 g/L, about 2 g/L to about 8 g/L, about 2 g/L to about 9 g/L, about 2 g/L to about 10 g/L, about 2 g/L to about 11 g/L, about 2 g/L to about 12 g/L, about 3 g/L to about 4 g/L, about 3 g/L to about 5 g/L, about 3 g/L to about 6 g/L, about 3 g/L to about 7 g/L, about 3 g/L to about 8 g/L, about 3 g/L to about 9 g/L, about 3 g/L to about 10 g/L, about 3 g/L to about 11 g/L, about 3 g/L to about 12 g/L, about 4 g/L to about 5 g/L, about 4 g/L to about 6 g/L, about 4 g/L to about 7 g/L, about 4 g/L to about 8 g/L, about 4 g/L to about 9 g/L, about 4 g/L to about 10 g/L, about 4 g/L to about 11 g/L, about 4 g/L to about 12 g/L, about 5 g/L to about 6 g/L, about 5 g/L to about 7 g/L, about 5 g/L to about 8 g/L, about 5 g/L to about 9 g/L, about 5 g/L to about 10 g/L, about 5 g/L to about 11 g/L, about 5 g/L to about 12 g/L, about 6 g/L to about 7 g/L, about 6 g/L to about 8 g/L, about 6 g/L to about 9 g/L, about 6 g/L to about 10 g/L, about 6 g/L to about 11 g/L, about 6 g/L to about 12 g/L, about 7 g/L to about 8 g/L, about 7 g/L to about 9 g/L, about 7 g/L to about 10 g/L, about 7 g/L to about 11 g/L, about 7 g/L to about 12 g/L, about 8 g/L to about 9 g/L, about 8 g/L to about 10 g/L, about 8 g/L to about 11 g/L, about 8 g/L to about 12 g/L, about 9 g/L to about 10 g/L, about 9 g/L to about 11 g/L, about 9 g/L to about 12 g/L, about 10 g/L to about 11 g/L, about 10 g/L to about 12 g/L, or about 11 g/L to about 12 g/L.

23. The method of claim 21, wherein the nucleotide sequence encoding the toxin protein is fused to a secretion signal coding sequence that when expressed directs transfer of the toxin protein to the periplasm.

24. The method of claim 23, wherein the recombinant toxin protein is CRM197 and wherein the recombinant toxin protein is fused to the secretion leader Azu, Pbp, IbpS31A, CupA2, or PbpA20V.

25. The method of claim 21, wherein the host cell is defective in the expression of at least one protease or wherein the host cell overexpresses at least one folding modulator, or a combination thereof.

26. The method of claim 21, wherein the recombinant toxin protein is CRM197 and the host cell is defective in the expression of the proteases Hs1U, Hs1V, Prc1, DegP1, DegP2, and AprA.

27. The method of claim 21, wherein the recombinant toxin protein is fused to a secretion leader that is Azu, IbpS31A, CupA2, PbpA20V, or Pbp.

28. The method of claim 21, wherein the recombinant toxin protein is CRM197 and the host cell is defective in the expression of a protease that is Serralysin, Hs1U, Hs1V, Prc1, DegP1, DegP2, or AprA, or a combination thereof, or wherein the host cell overexpresses folding modulators DsbA, DsbB, DsbC, and DsbD, and further wherein the recombinant toxin protein is fused to the Azu, Pbp, or native secretion leader.

29. The method of claim 21, wherein the recombinant toxin protein is CRM197, the host cell is wild-type and wherein the recombinant toxin protein is fused to the secretion leader Pbp or Azu.

30. The method of claim 21, wherein the expression vector comprises a lac promoter operatively linked to the protein coding sequence, and wherein the culturing comprises induction of the promoter using IPTG at a concentration of about 0.02 to about 1.0 mM, the cell density at induction is an optical density of about 40 to about 200 absorbance units (AU), the pH of the culture is from about 6 to about 7.5, and the growth temperature is about 20 to about 35° C.

31. The method of claim 30, wherein the lac promoter is selected from the following promoters: tac, trc, Ptac16, Ptac17, PtacII, PlacUV5 and T7lac.

32. The method of claim 21, wherein the host cell is a *Pseudomonas* cell.

33. The method of claim 21, wherein the host cell is *Pseudomonas fluorescens*.

34. The method of claim 21, wherein the nucleotide sequence has been optimized for expression in the *Pseudomonad* host cell.

35. The method of claim 34, wherein the nucleotide sequence has been optimized for expression in the *Pseudomonas* host cell.

36. The method of claim 35, wherein the nucleotide sequence has been optimized for expression in the *Pseudomonas fluorescens* host cell.

* * * * *

UNITED STATES PATENT AND TRADEMARK OFFICE
CERTIFICATE OF CORRECTION

PATENT NO. : 8,530,171 B2
APPLICATION NO. : 13/073955
DATED : September 10, 2013
INVENTOR(S) : Diane M. Retallack et al.

Figure 14:
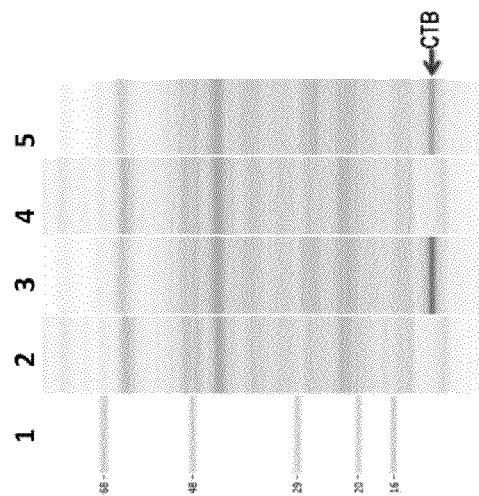
FIG. 14. Soluble Tetanus Toxin C and Cholera Toxin B Production in P. fluorescens Fermentation Cultures. SDS-CGE Analysis. Lane 1-16, 20, 29, 48, 69 and 119 kDa molecular weight markers. Lanes 2 and 4-pre-induction samples and lanes 3 and 5 post-induction samples, respectively, of PS538-088 U5 and U6 fermentations expressing Cholera Toxin B, indicated by arrow at right.

It is certified that error appears in the above-identified patent and that said Letters Patent is hereby corrected as shown below:

In the Specification:

Column 8, lines 15 - 21, replace:

"Fig. 14. Soluble Tetanus Toxin C and Cholera Toxin B Production in P. fluorescens Fermentation Cultures. SDS-CGE Analysis. Lane 1 - 16, 20, 29, 48, 69 and 119 kDa molecular weight markers. Lanes 2 and 4 - pre-induction samples and lanes 3 and 5 post-induction samples, respectively, of PS538-088 U5 and U6 fermentations expressing Cholera Toxin B, indicated by arrow at right."

with

--Fig. 14. Cholera Toxin B Production in P. fluorescens Fermentation Cultures. SDS-CGE Analysis. Lane 1 - 16, 20, 29, 48, 69 and 119 kDa molecular weight markers. Lanes 2 and 4 - pre-induction samples and lanes 3 and 5 post-induction samples, respectively, of PS538-088 U5 and U6 fermentations expressing Cholera Toxin B, indicated by arrow at right.--

Signed and Sealed this
Fourth Day of February, 2014

Michelle K. Lee
*Deputy Director of the United States Patent and Trademark Office*